(12) United States Patent
Park et al.

(10) Patent No.: US 11,844,270 B2
(45) Date of Patent: Dec. 12, 2023

(54) COMPOUND AND ORGANIC LIGHT EMITTING DEVICE INCLUDING THE SAME

(71) Applicant: LG DISPLAY CO., LTD., Seoul (KR)

(72) Inventors: Heejun Park, Paju-si (KR); Jeongdae Seo, Incheon (KR); Seonkeun Yoo, Gunpo-si (KR); Soyoung Jang, Seoul (KR); Sunghoon Kim, Seoul (KR); Sang-Hoon Hong, Seoul (KR); Seong-Min Park, Seoul (KR); Tae Wan Lee, Seoul (KR); Sunjae Kim, Goyang-si (KR); Dong Hun Lee, Seoul (KR); Jeonghoe Heo, Seoul (KR); Gwangyong Kim, Seoul (KR)

(73) Assignee: LG Display Co., Ltd., Seoul (KR)

( * ) Notice: Subject to any disclaimer, the term of this patent is extended or adjusted under 35 U.S.C. 154(b) by 546 days.

(21) Appl. No.: 16/850,348

(22) Filed: Apr. 16, 2020

(65) Prior Publication Data
US 2020/0335698 A1 Oct. 22, 2020

(30) Foreign Application Priority Data
Apr. 17, 2019 (KR) ........................ 10-2019-0044979

(51) Int. Cl.
*H01L 51/00* (2006.01)
*H01L 51/52* (2006.01)
(Continued)

(52) U.S. Cl.
CPC .......... *H10K 85/633* (2023.02); *C07C 211/54* (2013.01); *C07C 2603/18* (2017.05);
(Continued)

(58) Field of Classification Search
CPC ............... H01L 51/006; H01L 27/3248; H01L 29/7869; H01L 51/001; H01L 51/0058;
(Continued)

(56) References Cited

U.S. PATENT DOCUMENTS 9,461,269 B2   10/2016 Lee et al.
9,608,211 B2 *  3/2017 Kim ................... H10K 85/633
(Continued)

FOREIGN PATENT DOCUMENTS

CN   101185177 A   5/2008
CN   101427398 A   5/2009
(Continued)

OTHER PUBLICATIONS

STIC full search report (Year: 2013).*
(Continued)

*Primary Examiner* — Mamadou L Diallo
(74) *Attorney, Agent, or Firm* — Morgan, Lewis & Bockius LLP

(57) ABSTRACT

Disclosed is a novel compound and an organic light-emitting device. The novel compound is represented by the following Chemical Formula 1, and when the novel compound is used
(Continued)

as a material for a hole transport layer of an organic light emitting device, the novel compound allows the device to have lowered drive voltage, and improved efficiency and lifespan characteristics.

[Chemical Formula 1]

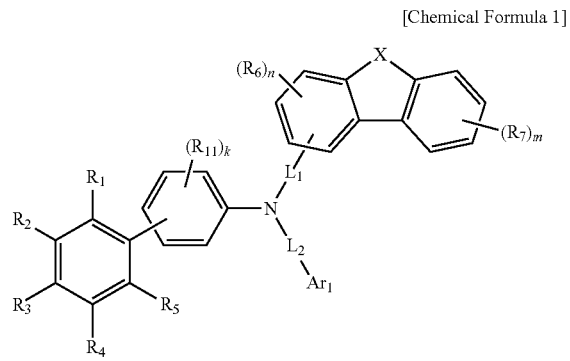

9 Claims, 2 Drawing Sheets

(51) Int. Cl.
*H01L 27/32* (2006.01)
*H01L 29/786* (2006.01)
*H01L 51/05* (2006.01)
*H01L 51/50* (2006.01)
*H10K 85/60* (2023.01)
*C07C 211/54* (2006.01)
*H10K 50/15* (2023.01)
*H10K 50/844* (2023.01)
*H10K 59/123* (2023.01)
*H10K 71/00* (2023.01)
*H10K 71/16* (2023.01)
*H10K 102/00* (2023.01)

(52) U.S. Cl.
CPC ...... *C07C 2603/74* (2017.05); *H01L 29/7869* (2013.01); *H10K 50/156* (2023.02); *H10K 50/844* (2023.02); *H10K 59/123* (2023.02); *H10K 71/00* (2023.02); *H10K 71/164* (2023.02); *H10K 85/626* (2023.02); *H10K 2102/351* (2023.02)

(58) Field of Classification Search
CPC . H01L 51/5064; H01L 51/5253; H01L 51/56; H01L 2251/558; H01L 27/1255; C07C 211/54; C07C 2603/18; C07C 2603/74
See application file for complete search history.

(56) References Cited

U.S. PATENT DOCUMENTS

| 10,615,347 | B2 | 4/2020 | Lee et al. | |
| 10,941,108 | B2 | 3/2021 | Jeong et al. | |
| 2014/0084270 | A1 | 3/2014 | Kato et al. | |
| 2015/0053940 | A1* | 2/2015 | Kim | H10K 85/636 548/425 |
| 2015/0115235 | A1* | 4/2015 | Lee | H10K 50/841 257/40 |
| 2016/0111644 | A1 | 4/2016 | Cho et al. | |
| 2016/0111653 | A1 | 4/2016 | Itoi | |
| 2016/0111658 | A1* | 4/2016 | Ito | H10K 85/6574 252/500 |
| 2017/0084867 | A1* | 3/2017 | Lim | G02B 5/22 |
| 2018/0323397 | A1* | 11/2018 | Ahn | H10K 2101/40 |
| 2019/0006591 | A1* | 1/2019 | Yamaki | C07D 307/91 |
| 2019/0165318 | A1* | 5/2019 | Choi | H10K 50/844 |
| 2019/0241548 | A1* | 8/2019 | Park | H10K 85/626 |
| 2020/0144506 | A1* | 5/2020 | Song | H10K 85/636 |
| 2020/0227683 | A1* | 7/2020 | Wittmann | H10K 50/8445 |
| 2020/0321525 | A1* | 10/2020 | Lee | C07C 211/61 |
| 2020/0392122 | A1* | 12/2020 | Ito | C07D 407/12 |

FOREIGN PATENT DOCUMENTS

| CN | 104576684 A | | 4/2015 | |
| CN | 105529400 A | | 4/2016 | |
| CN | 106749198 A | | 5/2017 | |
| CN | 107148408 A | | 9/2017 | |
| CN | 107880021 A | | 4/2018 | |
| CN | 107892650 A | | 4/2018 | |
| CN | 108003038 A | | 5/2018 | |
| CN | 109485577 A | | 3/2019 | |
| CN | 110218156 A | | 9/2019 | |
| CN | 110317184 A | | 10/2019 | |
| CN | 110577510 A | | 12/2019 | |
| CN | 110885334 A | | 3/2020 | |
| CN | 111146349 A | | 5/2020 | |
| CN | 111606813 A | | 9/2020 | |
| CN | 111662190 A | | 9/2020 | |
| CN | 111793000 A | | 10/2020 | |
| CN | 112601732 A | | 4/2021 | |
| JP | 2010222268 A | | 10/2010 | |
| JP | 2018065806 A | * | 4/2018 | .......... C07C 211/54 |
| KR | 10-2011-0034981 A | | 4/2011 | |
| KR | 10-2016-0006007 A | | 1/2016 | |
| KR | 10-2018-0053121 A | | 5/2018 | |
| KR | 10-2018-0059043 A | | 6/2018 | |
| KR | 10-2018-0102362 A | | 9/2018 | |
| KR | 10-2019-0011090 A | | 2/2019 | |
| KR | 10-2019-0035567 A | | 4/2019 | |
| KR | 2041137 B1 | * | 11/2019 | .......... C07C 211/61 |
| WO | 2014/027676 A1 | | 2/2014 | |
| WO | WO-2019185061 A1 | * | 10/2019 | .......... C07C 211/61 |

OTHER PUBLICATIONS

Office Action issued in corresponding Chinese Patent Application No. 202010305081.1 dated Sep. 30, 2022, with English translation.
Second Office Action issued in corresponding Chinese Patent Application No. 202010305081.1 dated Apr. 7, 2023, with English translation.

* cited by examiner

[FIG. 1]
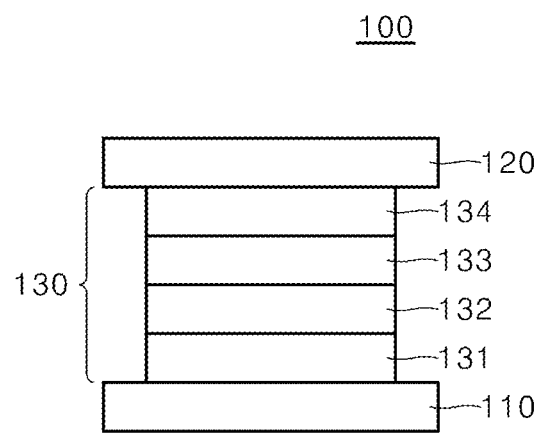
[FIG. 2]
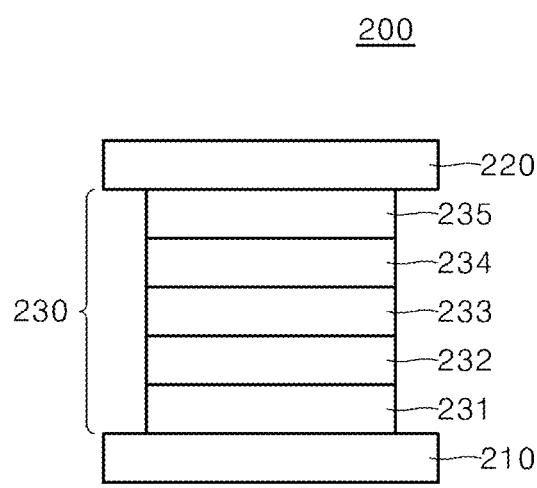

[FIG. 3]
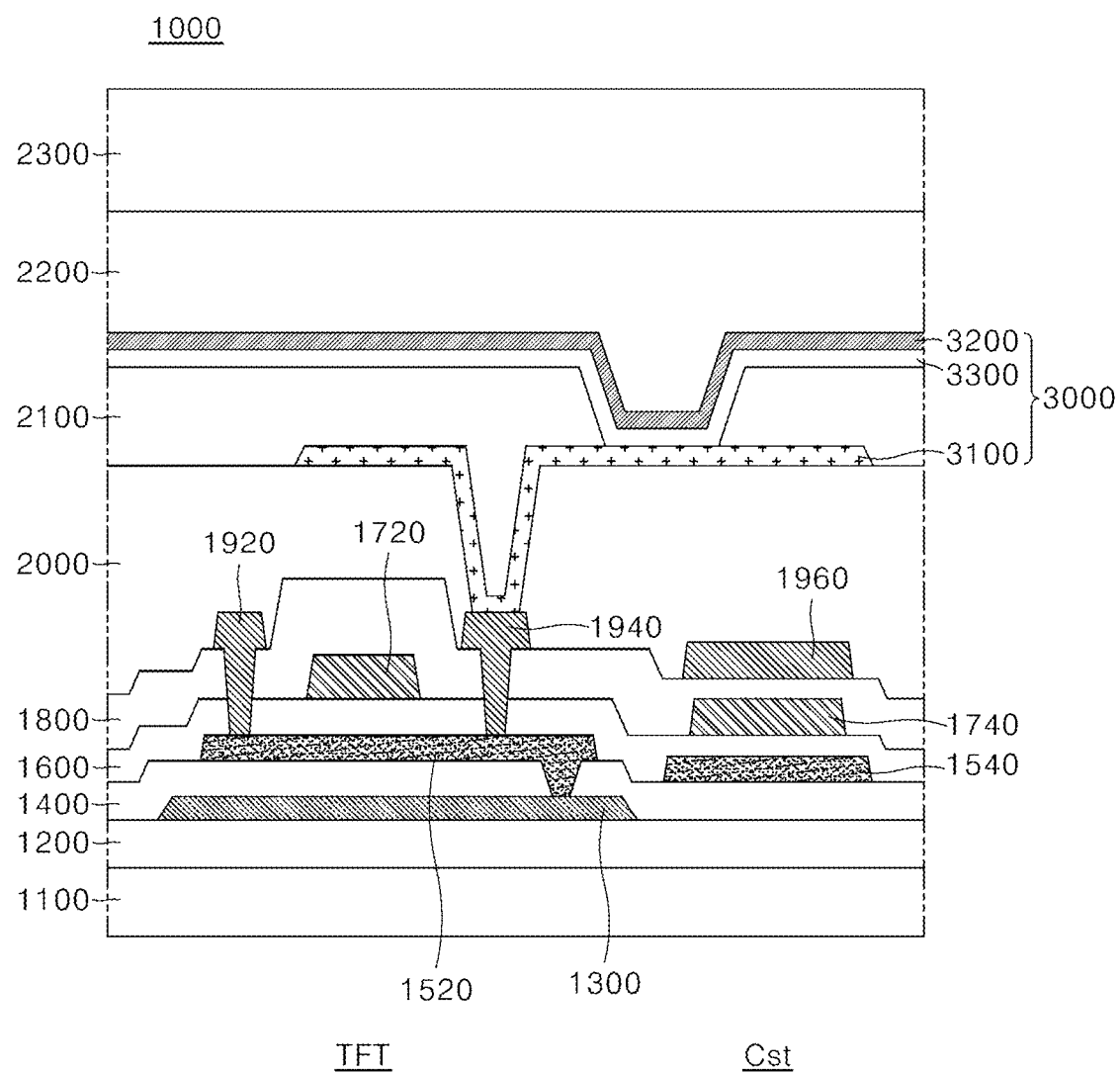

COMPOUND AND ORGANIC LIGHT EMITTING DEVICE INCLUDING THE SAME

CROSS-REFERENCE TO RELATED APPLICATION

This application claims the priority of Korean Patent Application No. 10-2019-0044979, filed on Apr. 17, 2019, in the Korean Intellectual Property Office, the disclosure of which is hereby incorporated by reference in its entirety.

BACKGROUND

Technical Field

The present disclosure relates to a novel compound and an organic light-emitting device comprising the same.

Description of the Related Art

As a display device becomes larger recently, a flat display device with good space utilization is getting more attention. One of such flat display devices may include an organic light-emitting display device including an organic light-emitting diode (OLED). The organic light-emitting display device is rapidly developing.

In the organic light-emitting diode (OLED), when charges are injected into a light-emitting layer formed between a first electrode and a second electrode to form paired electrons and holes to form excitons, exciton energy is converted to light for emission. The organic light emitting diode may be driven at a lower voltage and has a relatively low power consumption than a conventional display device. The organic light emitting diode may have advantages of having excellent color rendering and being able to be applied to a flexible substrate for various applications.

SUMMARY

Accordingly, embodiments of the present disclosure are directed to a novel compound and an organic light-emitting device that substantially obviate one or more of the problems due to limitations and disadvantages of the related art.

One aspect of the present disclosure is to provide a novel compound of a novel structure that is stable materially and has high hole mobility.

Another aspect of the present disclosure is to develop an organic light-emitting device with low driving voltage, high efficiency, and long lifespan by applying the novel compound to a hole transport layer or an auxiliary hole transport layer of the organic light-emitting device.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described, a compound is represented by a following Chemical Formula 1:

[Chemical Formula 1]

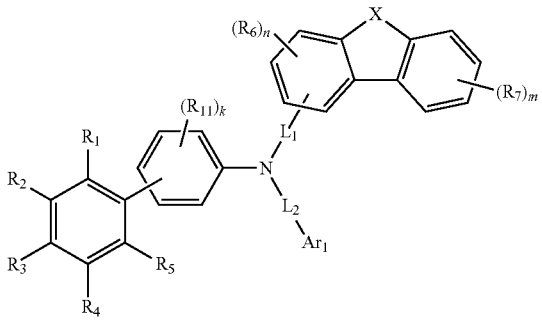

where in the Chemical Formula 1,

X is selected from a group consisting of $CR_9R_{10}$, each of $L_1$ and $L_2$ independently represents one selected from a group consisting of a single bond, a substituted or unsubstituted C6 to C30 arylene group, a substituted or unsubstituted C3 to C30 heteroarylene group, a substituted or unsubstituted C1 to C20 alkylene group, a substituted or unsubstituted C2 to C20 alkenylene group, a substituted or unsubstituted C1 to C20 heteroalkylene group, a substituted or unsubstituted C3 to C20 heterocycloalkylene group, a substituted or unsubstituted C1 to C20 heteroalkenylene group, and a substituted or unsubstituted C3 to C20 heterocycloalkenylene group, $Ar_1$ represents one selected from a group consisting of a substituted or unsubstituted C6 to C30 aryl group, a substituted or unsubstituted C3 to C30 heteroaryl group, a substituted or unsubstituted C1 to C20 alkyl group, a substituted or unsubstituted C2 to C20 alkenyl group, substituted or unsubstituted C2 to C20 alkynyl group, a substituted or unsubstituted C1 to C20 heteroalkyl group, a substituted or unsubstituted C3 to C20 heterocycloalkyl group, and a substituted or unsubstituted C1 to C20 heteroalkenyl group, $R_1$ to $R_7$ and $R_9$ to $R_{11}$ are the same as or different from each other, and each of $R_1$ to $R_7$ and $R_9$ to $R_{11}$ independently represents one selected from a group consisting of hydrogen, deuterium, a substituted or unsubstituted C1 to C20 alkyl group, a substituted or unsubstituted C3 to C20 cycloalkyl group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C7 to C20 aralkyl group, a substituted or unsubstituted C6 to C30 aryl group, a substituted or unsubstituted C3 to C30 heteroaryl group, and a substituted or unsubstituted C3 to C20 heteroaralkyl group, adjacent two of $R_1$ to $R_7$ and $R_9$ to $R_{11}$ may be connected to each other to form a saturated or unsaturated alicyclic or aromatic monocyclic or polycyclic ring, the formed alicyclic or aromatic monocyclic or polycyclic ring may contain or may not contain at least one heteroatom selected from a group consisting of N, O, S and Si in addition to a carbon atom, a case where all of $R_1$ to $R_5$ are hydrogen is excluded, k is an integer from 1 to 4, m is an integer from 0 to 4, n is an integer from 0 to 3.

In another aspect of the present disclosure, there is provided an organic light-emitting device that includes a first electrode, a second electrode, and at least one organic material layer between the first and second electrodes, wherein the organic material layer contains the compound represented by the Chemical Formula 1.

The organic light-emitting device according to the present disclosure may have lowered drive voltage, improved efficiency, and long lifespan.

It is to be understood that both the foregoing general description and the following detailed description are exemplary and explanatory and are intended to provide further explanation of the inventive concepts as claimed.

BRIEF DESCRIPTION OF DRAWINGS

The accompanying drawings, which are included to provide a further understanding of the disclosure and are incorporated in and constitute a part of this application, illustrate embodiments of the disclosure and together with the description serve to explain various principles. In the drawings:

FIG. 1 is a schematic cross-sectional view of an organic light-emitting device incorporating the compound represented by the Chemical Formula 1 according to one embodiment of the present disclosure.

FIG. 2 is a schematic cross-sectional view of an organic light-emitting device incorporating the compound represented by the Chemical Formula 1 according to one implementation of the present disclosure.

FIG. 3 is a schematic cross-sectional view of an organic light-emitting display device employing the organic light-emitting device according to another implementation of the present disclosure.

DETAILED DESCRIPTION

For simplicity and clarity of illustration, elements in the figures are not necessarily drawn to scale. The same reference numbers in different figures denote the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, a term "unsubstituted" means that a hydrogen atom has not been substituted. In some cases, the hydrogen atom includes protium, deuterium and tritium. In some cases, the hydrogen atom refers to protium.

As used herein, a substituent in the term "substituted" may include one selected from a group consisting of, for example, deuterium, an alkyl group of 1 to 20 carbon atoms unsubstituted or substituted with halogen, an alkoxy group having 1 to 20 carbon atoms unsubstituted or substituted with halogen, halogen, a cyano group, a carboxy group, a carbonyl group, an amine group, an alkylamine group having 1 to 20 carbon atoms, a nitro group, an alkylsilyl group having 1 to 20 carbon atoms, an alkoxysilyl group having 1 to 20 carbon atoms, a cycloalkylsilyl group having 3 to 30 carbon atoms, an arylsilyl group having 6 to 30 carbon atoms, an aryl group having 6 to 30 carbon atoms, an arylamine group having 6 to 20 carbon atoms, a heteroaryl group having 4 to 30 carbon atoms, and a combination thereof. However, the present disclosure is not limited thereto.

As used herein, the term "alkyl" includes "cycloalkyl", and refer to a monovalent substituent derived from a straight chain or side chain saturated hydrocarbon having 1 to 40 carbon atoms and a monocyclic or polycyclic non-aromatic hydrocarbon having 3 to 40 carbon atoms. Examples thereof include methyl, ethyl, propyl, isobutyl, sec-butyl, pentyl, iso-amyl, hexyl, cyclopropyl, cyclobutyl, cyclopentyl, cyclohexyl, norbornyl, adamantyl, etc. However, the present disclosure is not limited thereto.

As used herein, the term "alkenyl" includes "cycloalkenyl" and refers to a monovalent substituent derived from a straight chain or side chain or cyclic unsaturated hydrocarbon having 2 to 40 carbon atoms and having one or more carbon-carbon double bonds. Examples thereof include, but are not limited to, vinyl, allyl, isopropenyl, 2-butenyl, cyclopropenyl, cyclobutenyl, cyclopentenyl, cyclohexenyl, and the like.

As used herein, the term "alkylene" includes "cycloalkylene", and refers to a divalent atomic group formed by excluding two hydrogen atoms from carbon atoms of aliphatic saturated hydrocarbon. Examples thereof include, but are not limited to, ethylene, propylene, butylene, amylene, hexylene, cyclopropylene, cyclobutylene, cyclopentylene, cyclohexylene, and adamantylene.

As used herein, a term "heterocyclic ring" includes a hetero aromatic ring and a hetero alicyclic ring. Each of the "hetero aromatic ring" and the "hetero alicyclic ring" may contain a single ring or a polycyclic ring. Further, each of the terms "hetero aromatic ring" and "hetero alicyclic ring" may contain at least two single rings as in biphenyl.

As used herein, the term "hetero" as used in the term 'hetero ring', 'hetero aromatic ring', or 'hetero alicyclic ring' means that one or more carbon atoms, for example, 1 to 5 carbon atoms among carbon atoms constituting the aromatic or alicyclic ring are substituted with at least one hetero atom selected from a group consisting of N, O, S and combinations thereof.

As used herein, the phase "combination thereof" as used in the definition of the substituent means that two or more substituents are bonded to each other via a linking group or two or more substituents are bonded to each other via condensation, unless otherwise defined.

Hereinafter, the present disclosure describes a novel compound according to some embodiments of the present disclosure, and an organic electro-luminescent device including the compound.

According to one implementation of the present disclosure, there is provided a compound represented by a following Chemical Formula 1:

[Chemical Formula 1]

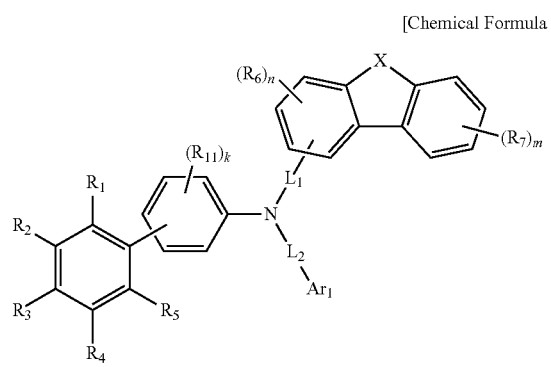

where in the Chemical Formula 1,

X is selected from a group consisting of $CR_9R_{10}$, each of $L_1$ and $L_2$ independently represents one selected from a group consisting of a single bond, a substituted or unsubstituted C6 to C30 arylene group, a substituted or unsubstituted C3 to C30 heteroarylene group, a substituted or unsubstituted C1 to C20 alkylene group, a substituted or unsubstituted C2 to C20 alkenylene group, a substituted or unsubstituted C1 to C20 heteroalkylene group, a substituted or unsubstituted C3 to C20 heterocycloalkylene group, a substituted or unsubstituted C1 to C20 heteroalkenylene group, and a substituted or unsubstituted C3 to C20 heterocycloalkenylene group, $Ar_1$ represents one selected from a group consisting of a substituted or unsubstituted C6 to C30 aryl group, a substituted or unsubstituted C3 to C30 heteroaryl group, a substituted or unsubstituted C1 to C20 alkyl group, a substituted or unsubstituted C2 to C20 alkenyl group, substituted or unsubstituted C2 to C20 alkynyl group, a substituted or unsubstituted C1 to C20 heteroalkyl group, a substituted or unsubstituted C3 to C20 heterocycloalkyl group, and a substituted or unsubstituted C1 to C20 heteroalkenyl group, $R_1$ to $R_7$ and $R_9$ to $R_{11}$ are the same as or different from each other, and each of $R_1$ to $R_7$ and $R_9$ to $R_{11}$ independently represents one selected from a group consisting of hydrogen, deuterium, a substituted or unsubstituted C1 to C20 alkyl group, a substituted or unsubstituted C3 to C20 cycloalkyl group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C7 to C20 aralkyl group, a substituted or unsubstituted C6 to C30 aryl group, a substituted or unsubstituted C3 to C30 heteroaryl group, and a substituted or unsubstituted C3 to C20 heteroaralkyl group, adjacent two of $R_1$ to $R_7$ and $R_9$ to $R_{11}$ optionally are connected to each other to form a saturated or unsaturated alicyclic or aromatic monocyclic or polycyclic ring, the formed alicyclic or aromatic monocyclic or polycyclic ring may contain or may not contain at least one heteroatom selected from a group consisting of N, O, S and Si in addition to a carbon atom, a case where all of $R_1$ to $R_5$ are hydrogen is excluded, k is an integer from 1 to 4, m is an integer from 0 to 4, n is an integer from 0 to 3.

In one implementation, at least one of $R_{11}$ may include a substituted or unsubstituted C1 to C10 alkyl group or a substituted or unsubstituted C6 to C20 aryl group.

The compound may be contained in a hole transport layer and/or an auxiliary hole transport layer of an organic light-emitting device.

In one implementation, the compound represented by the Chemical Formula 1 may include a compound represented by a following Chemical Formula 2:

[Chemical Formula 2]

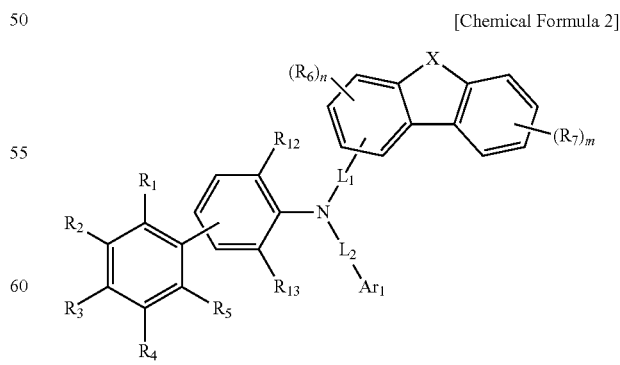

where in the Chemical Formula 2, each of X, $L_1$, $L_2$, $Ar_1$, $R_1$ to $R_7$, $R_9$, $R_{10}$, m, and n is the same as defined in the Chemical Formula 1, each of $R_{12}$ and $R_{13}$ independently represents one selected from a group consisting of hydrogen, deuterium, a substituted or unsubstituted C1 to C20 alkyl group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C7 to C20 aralkyl group, a substituted or unsubstituted C6 to C30 aryl group, a substituted or unsubstituted C3 to C30 heteroaryl group, and a substituted or unsubstituted C3 to C20 heteroaralkyl group.

In one implementation, at least one of $R_{12}$ and $R_{13}$ may include a substituted or unsubstituted C1 to C10 alkyl group or a substituted or unsubstituted C6 to C20 aryl group.

Specifically, the compound represented by the Chemical Formula 1 may be represented by one of following Chemical Formulas:

1

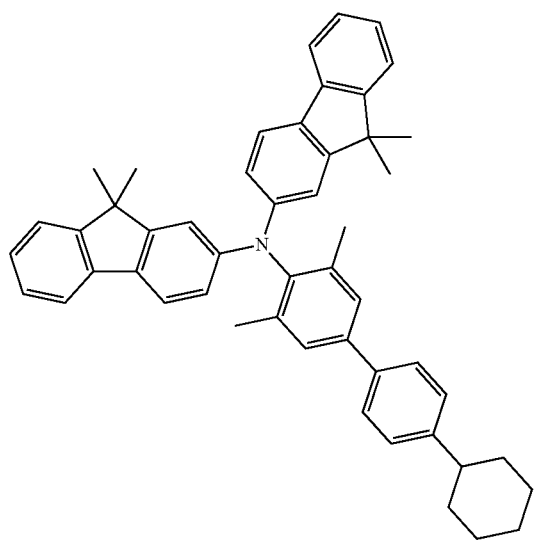

2

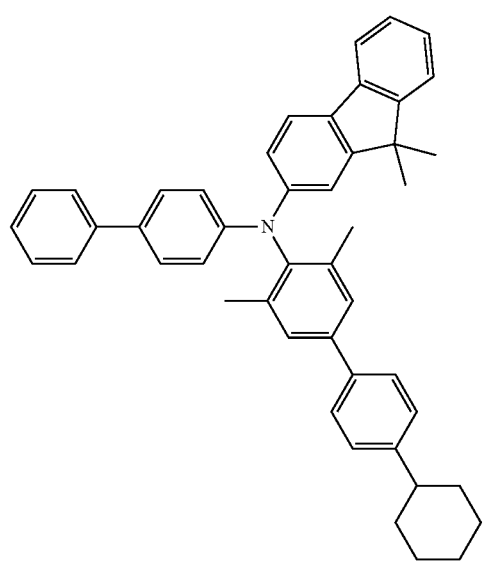

3

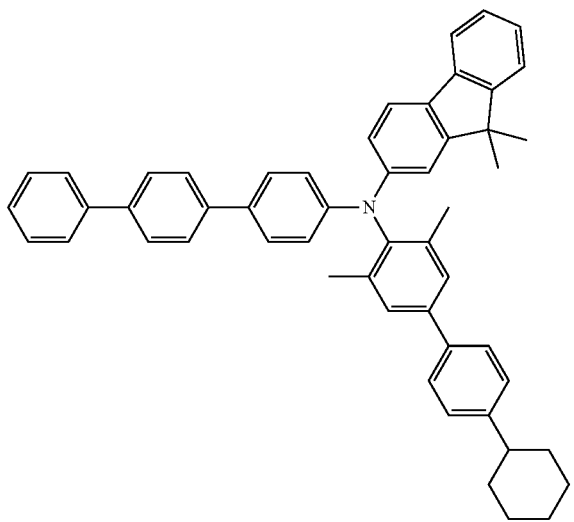

4

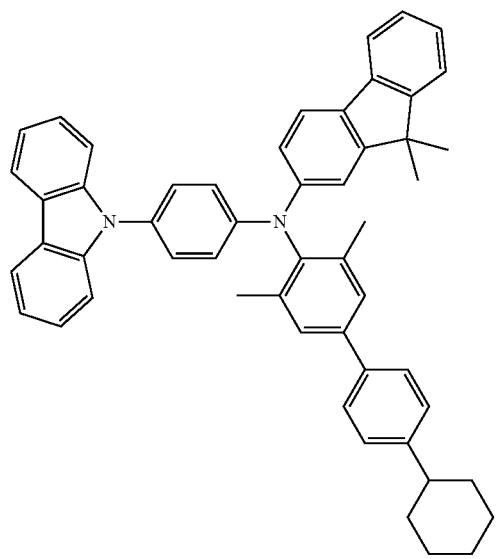

5

6
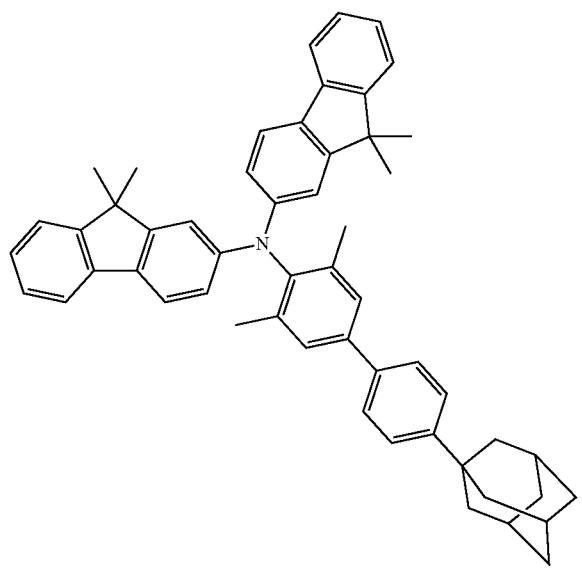
5
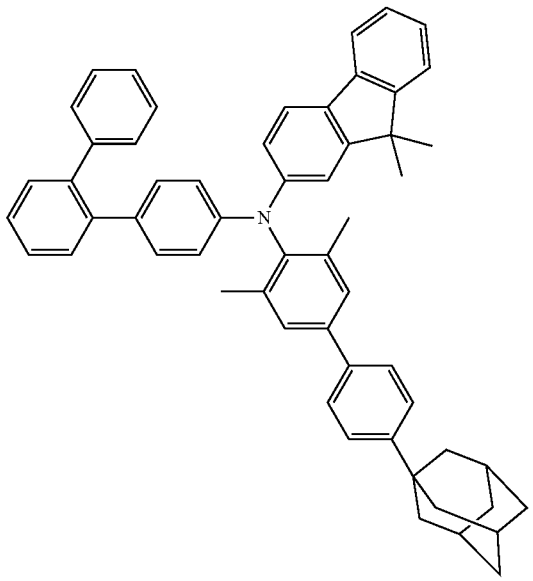
7
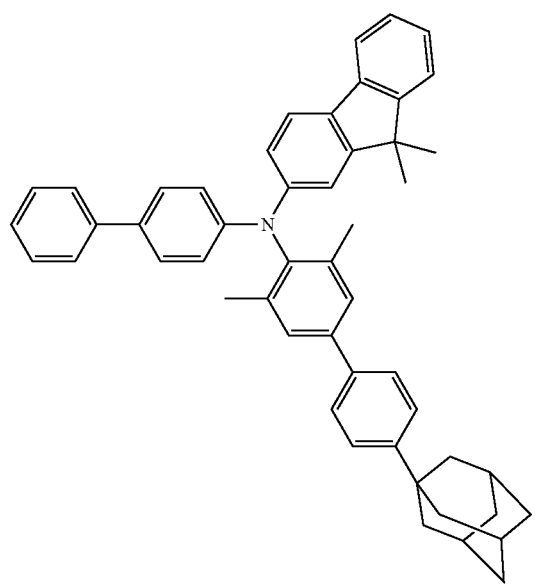
8
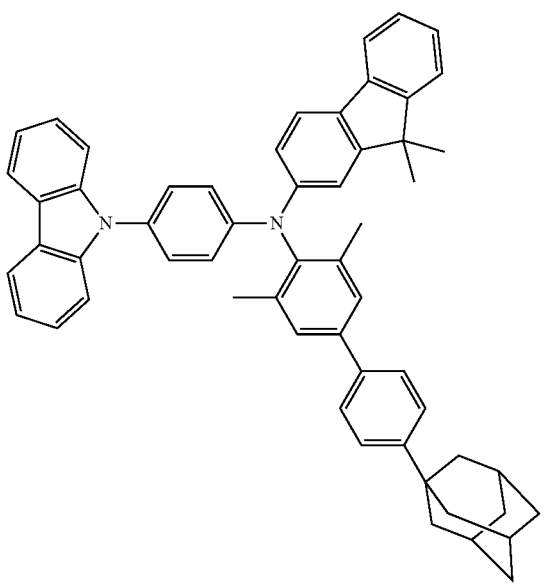

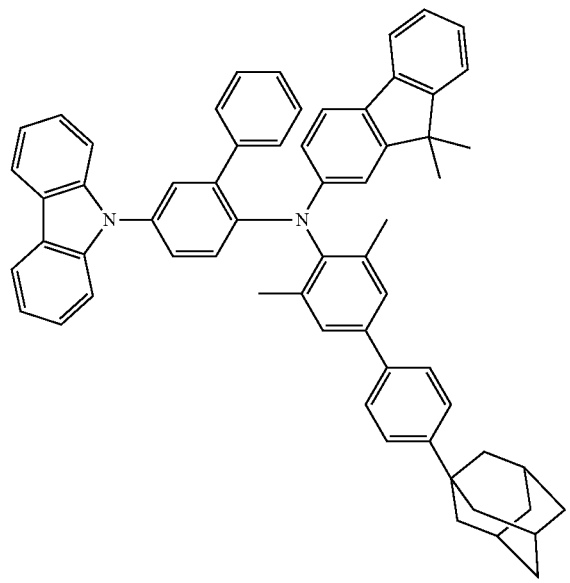
10
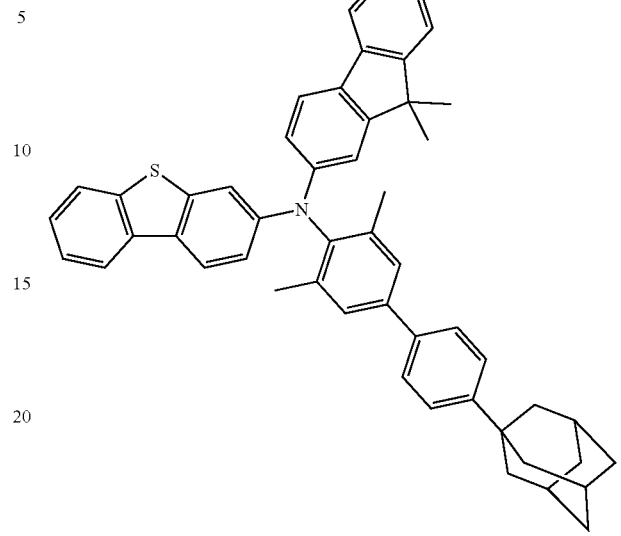
12
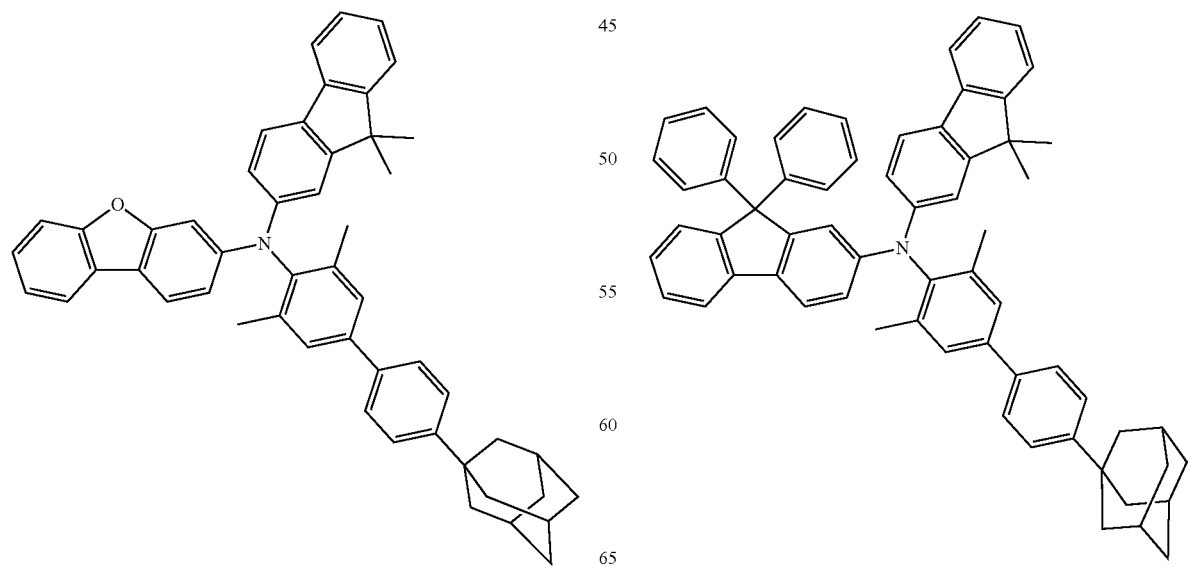

14
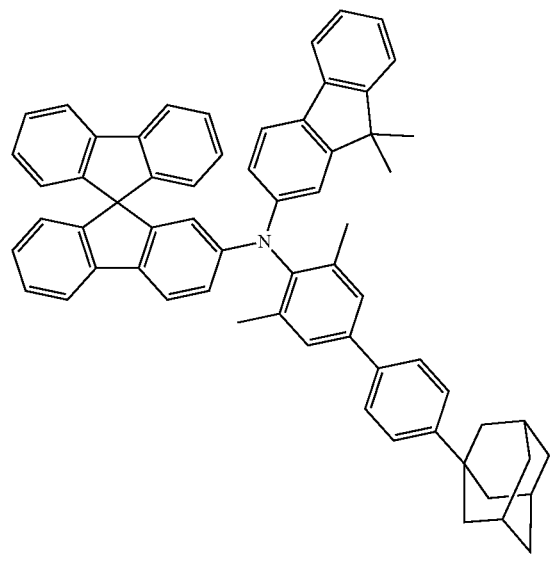
15
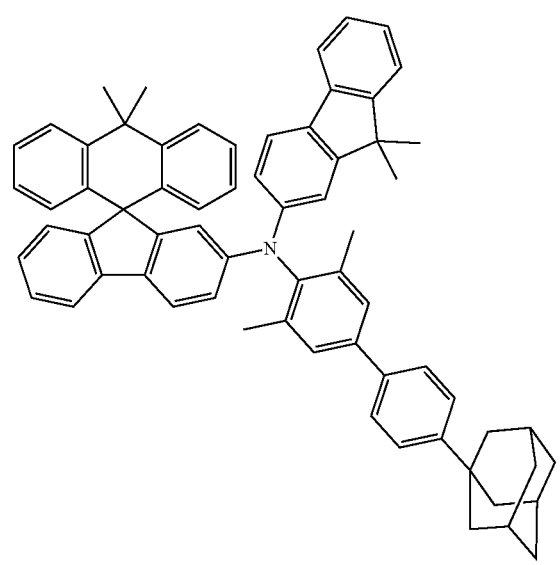
16
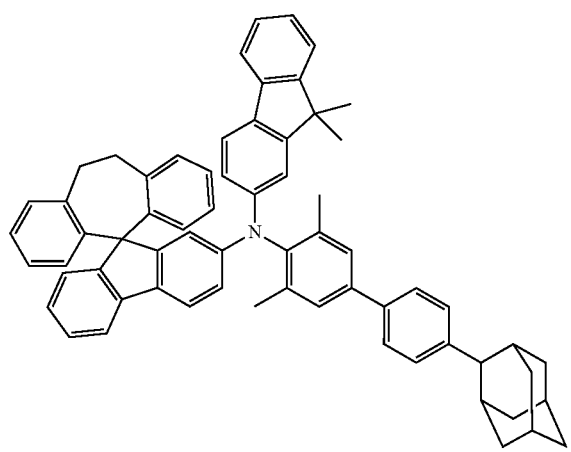
17
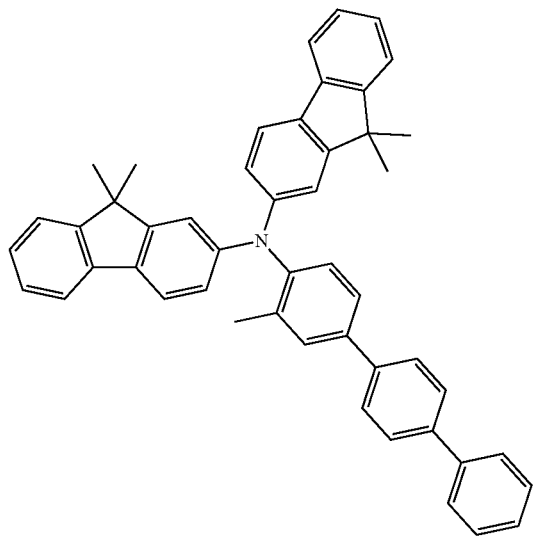
18
19
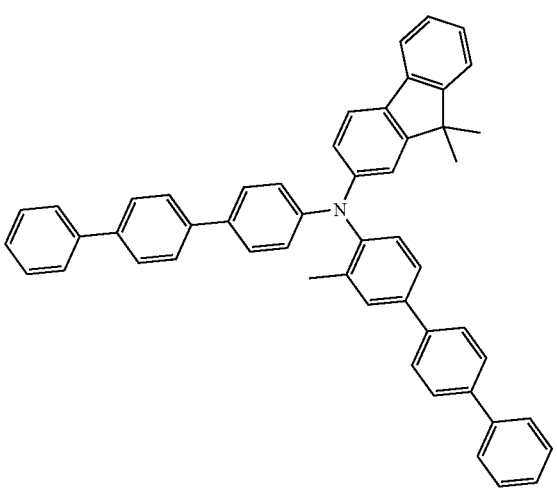

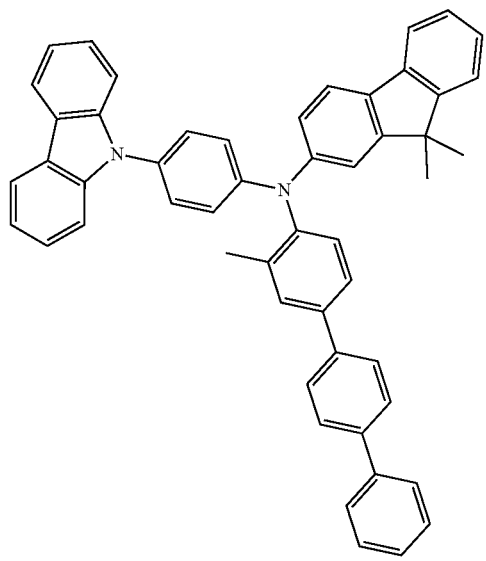
20
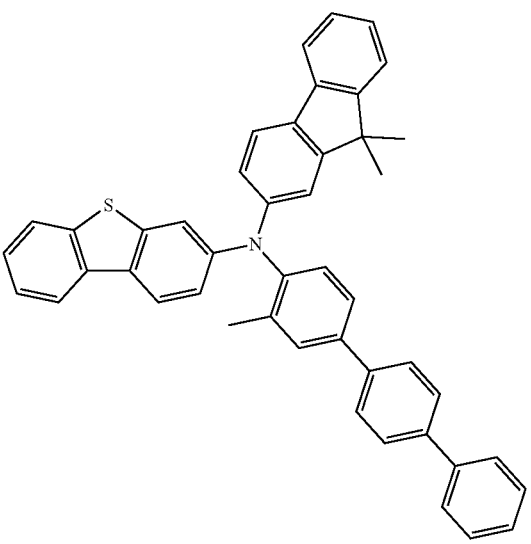
23
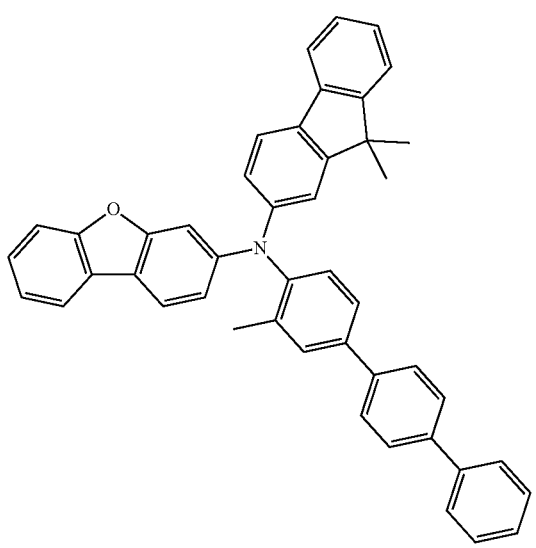
22
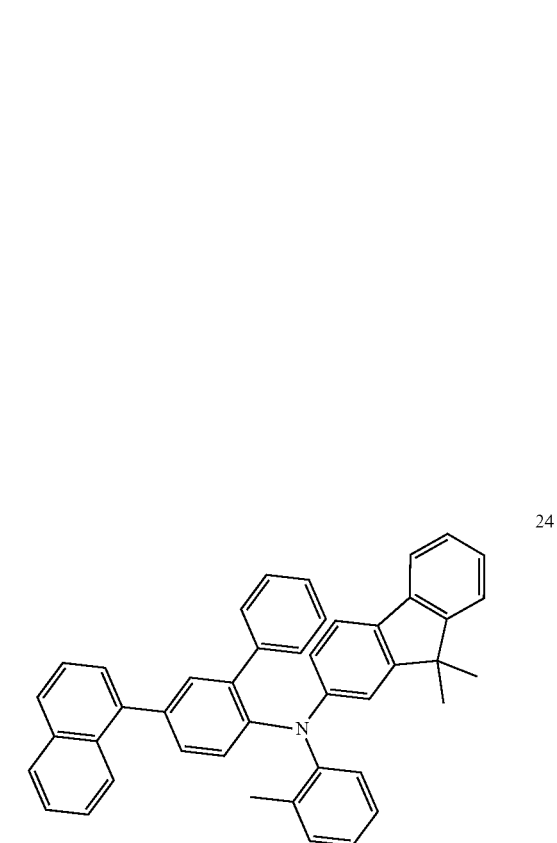
24

25
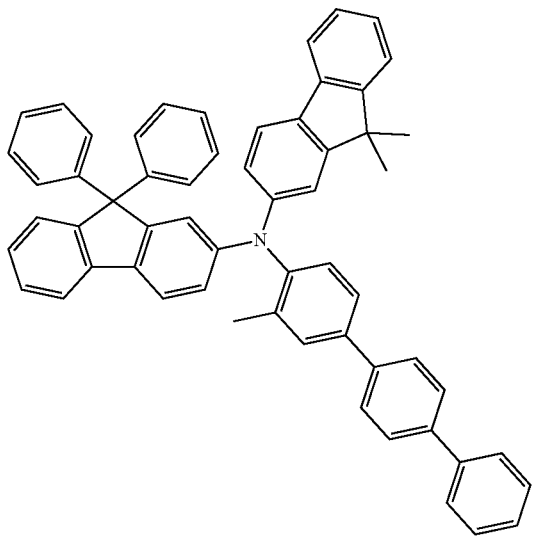
26
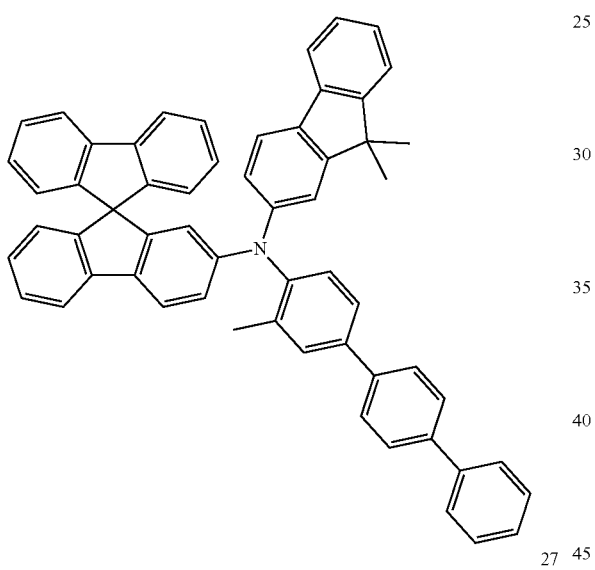
27
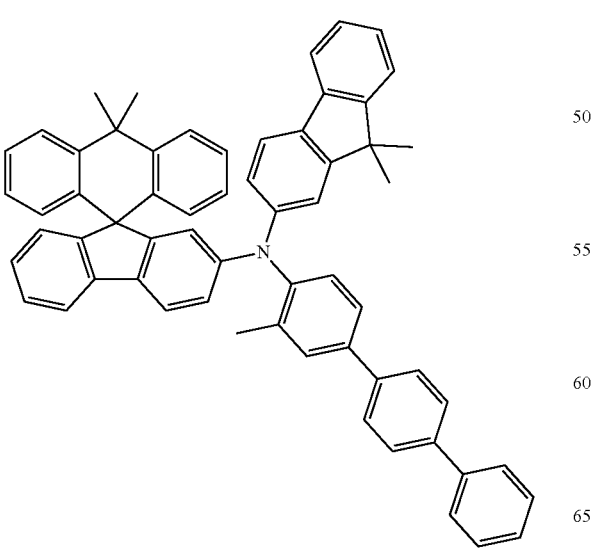
28
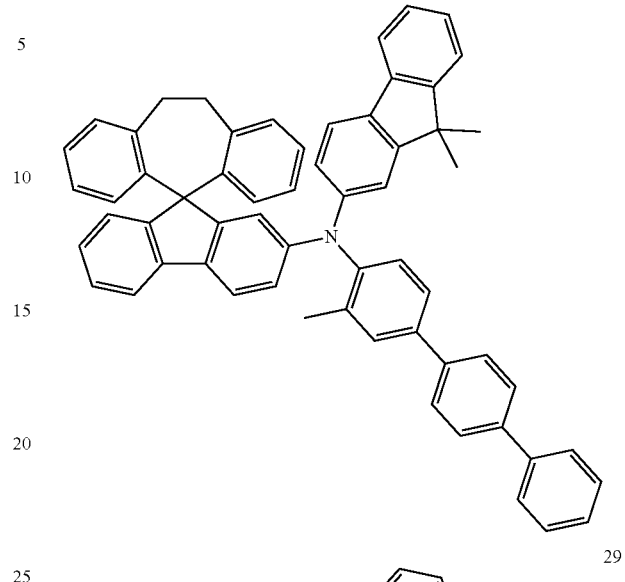
29
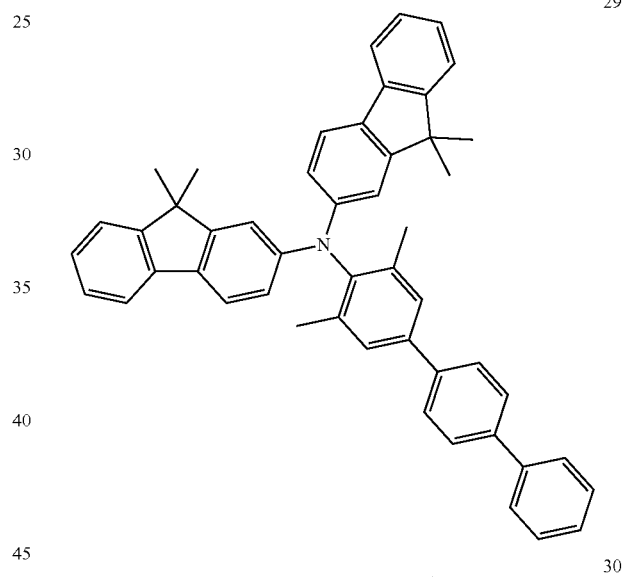
30
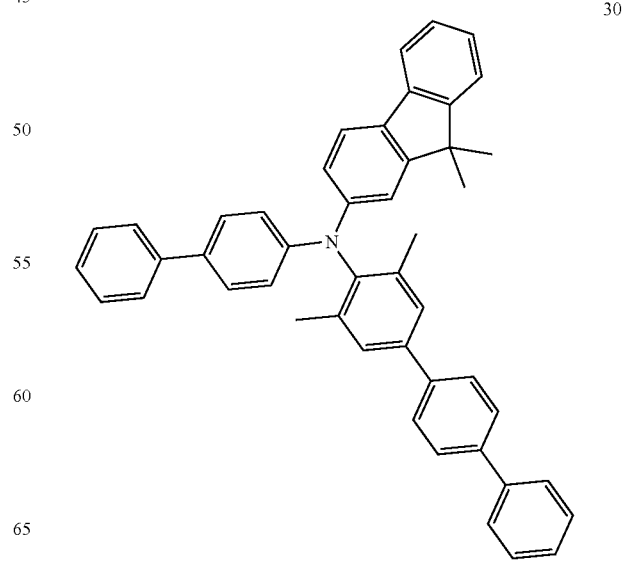

31
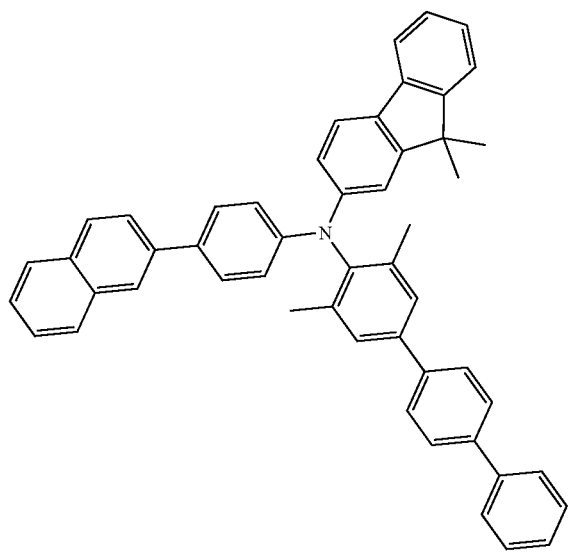
32
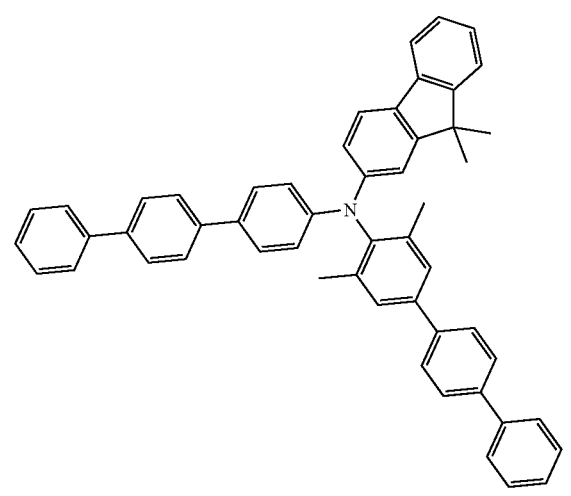
33
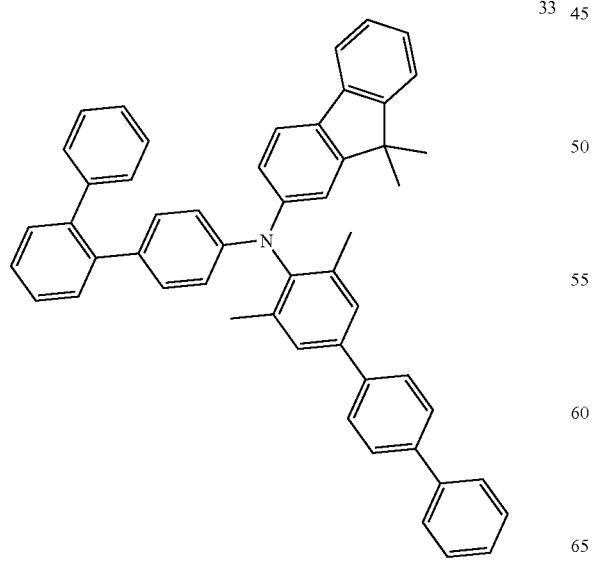
34
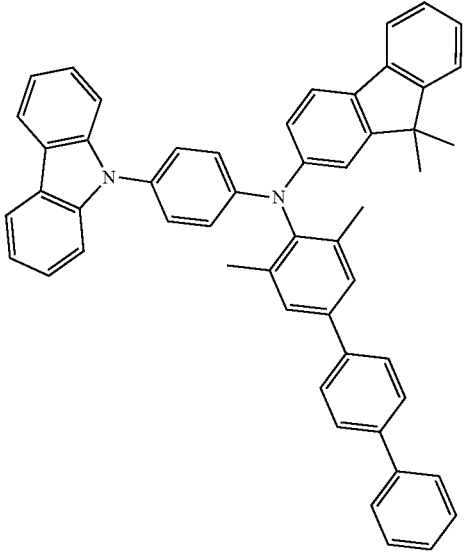
35
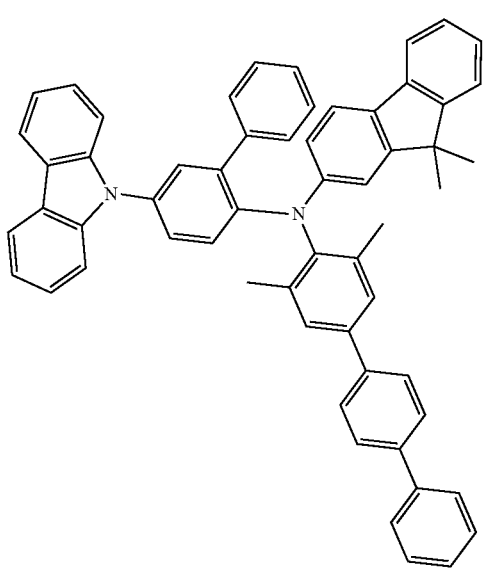

36
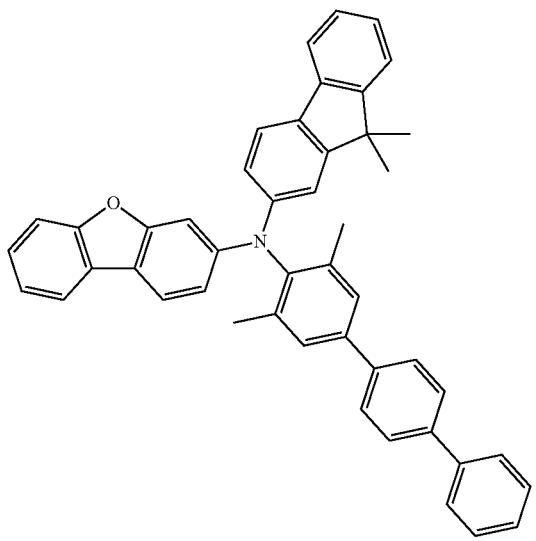
37
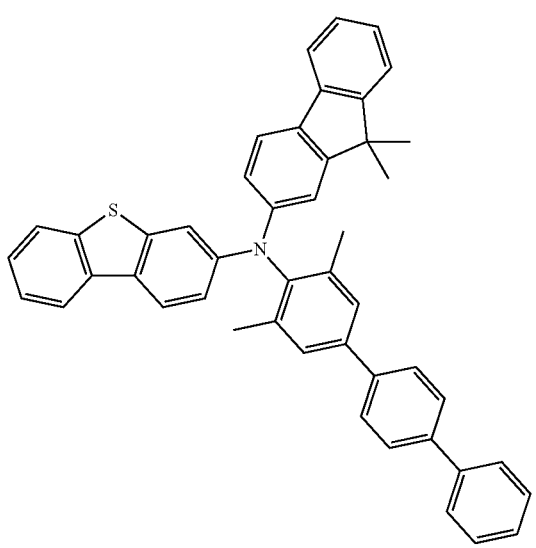
38
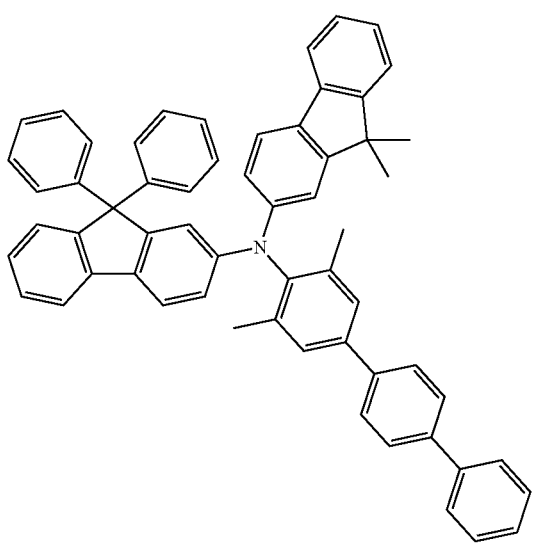
39
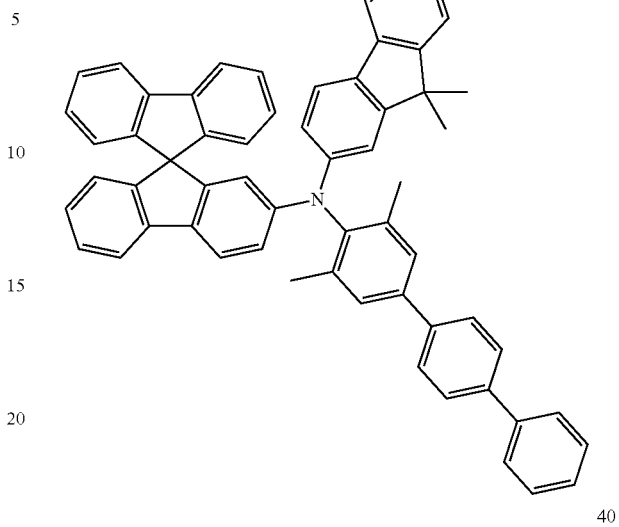
40
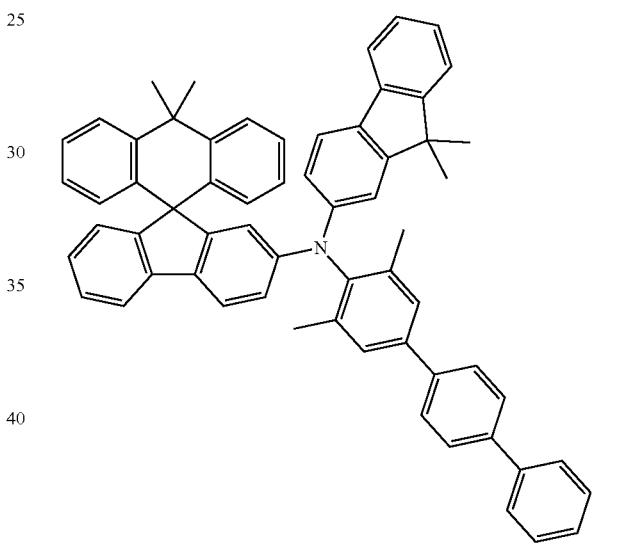
41
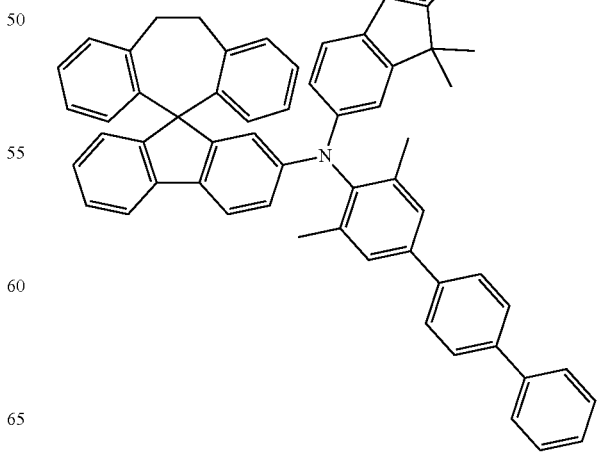

42
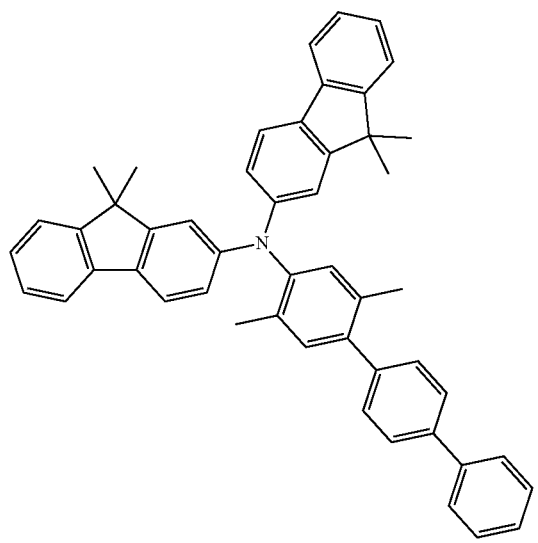
45
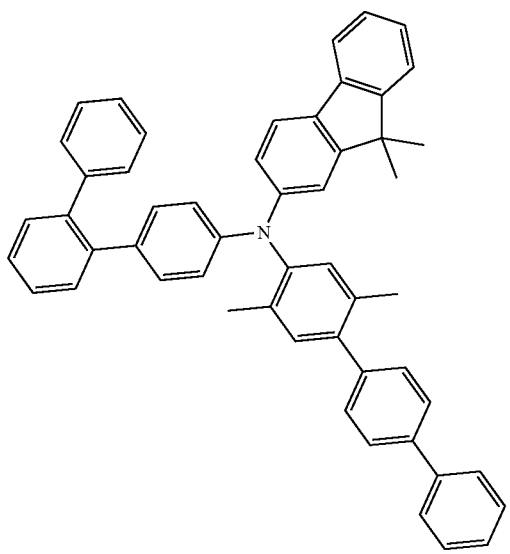
43
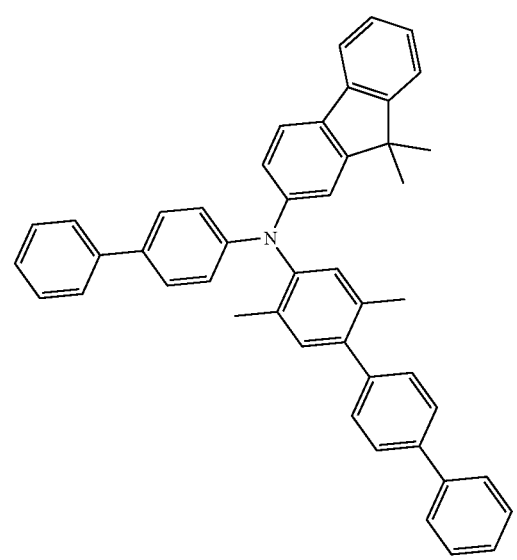
46
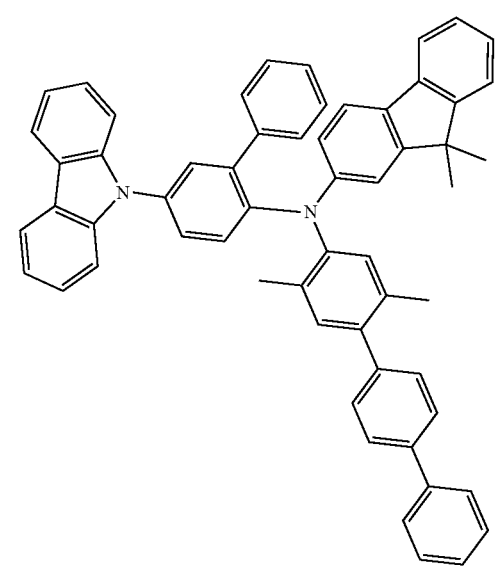
44
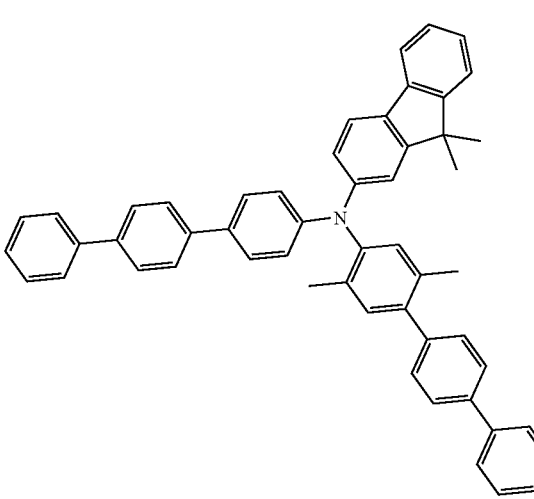
47
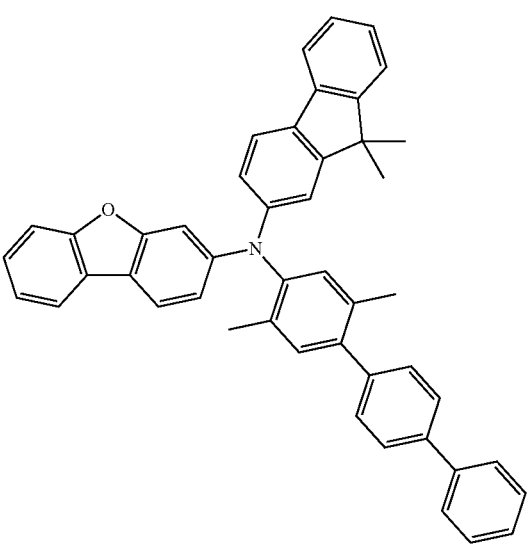

48
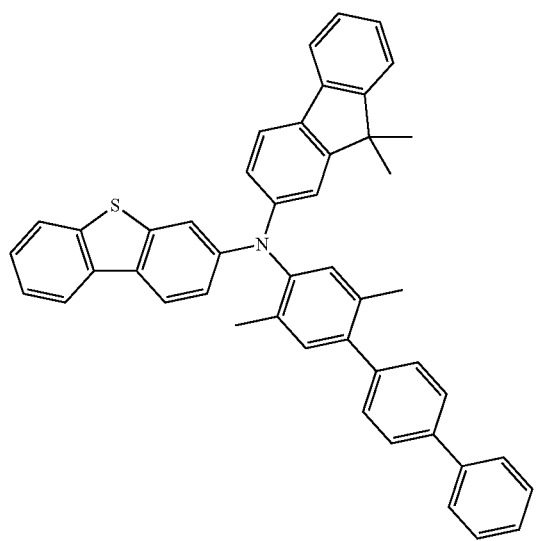
49
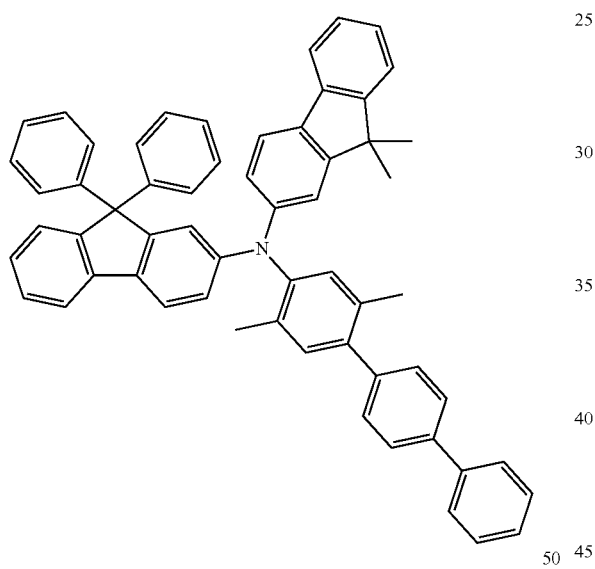
50
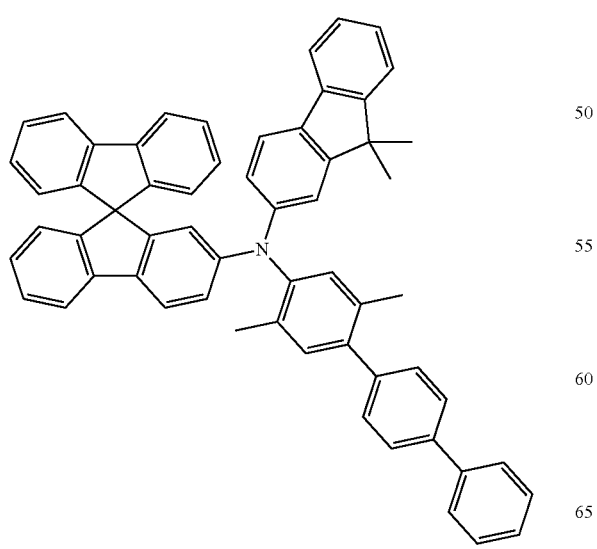
51
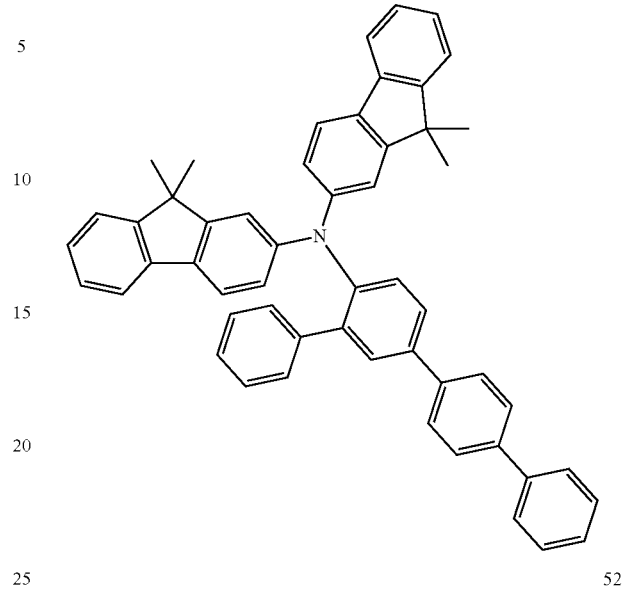
52
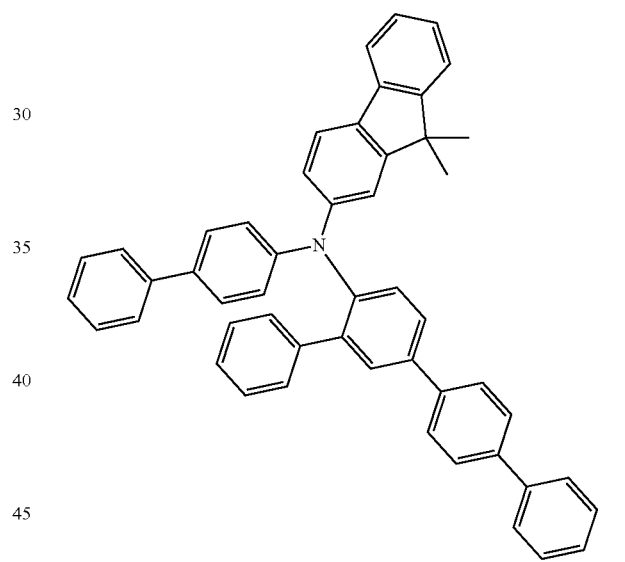
53
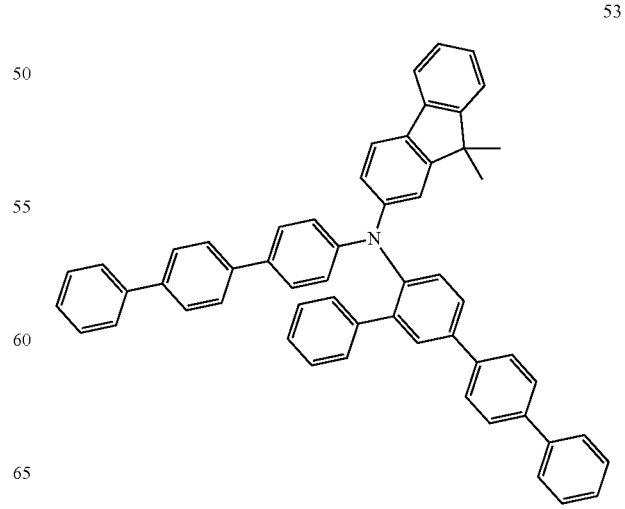

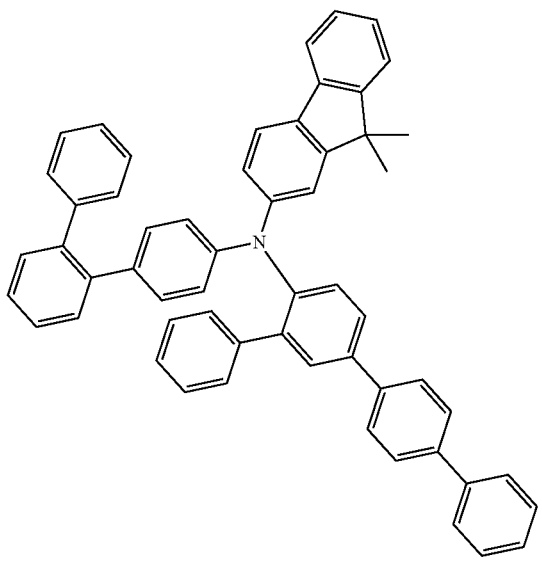
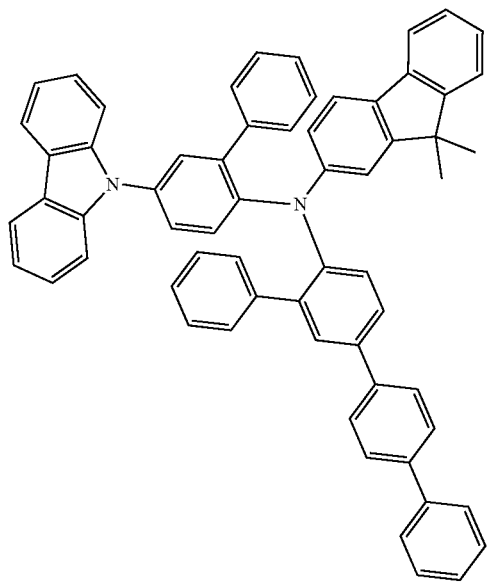
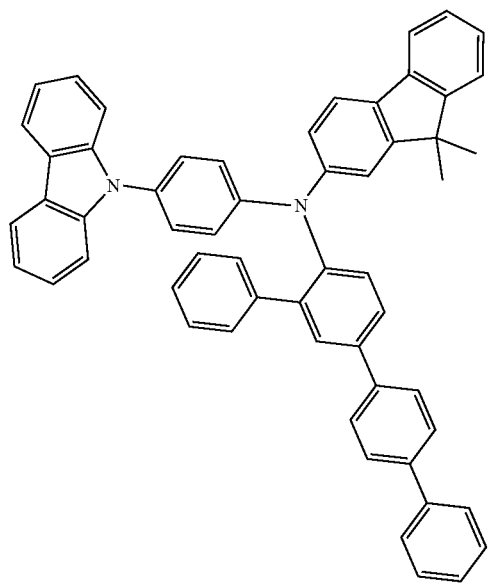
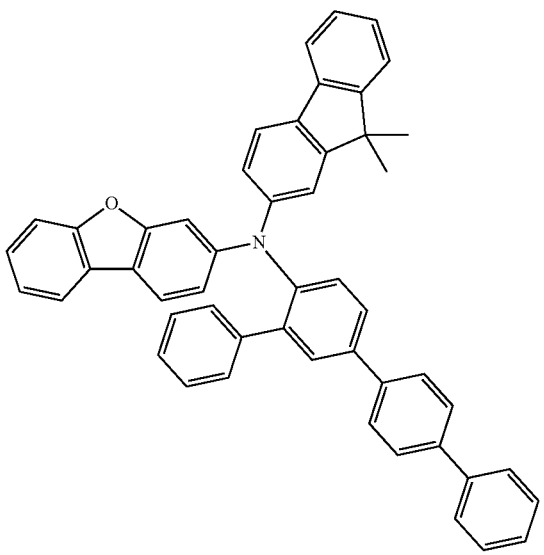

58
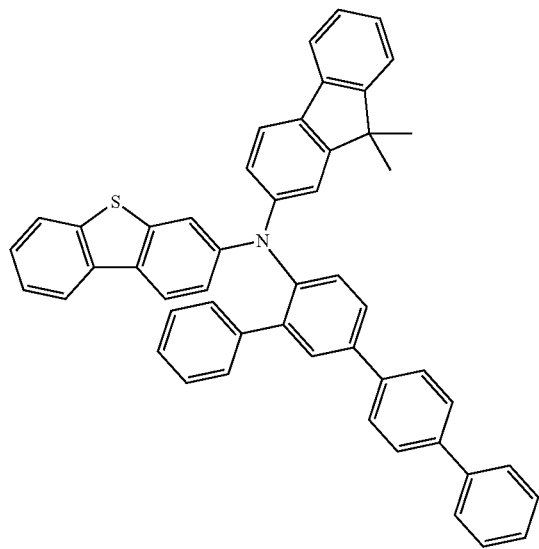
59
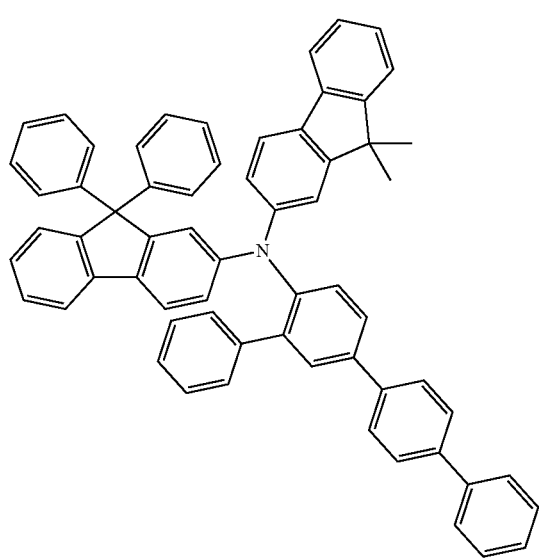
60
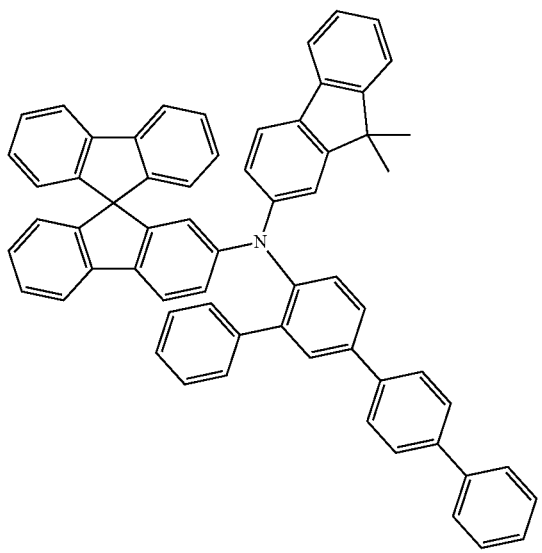
61
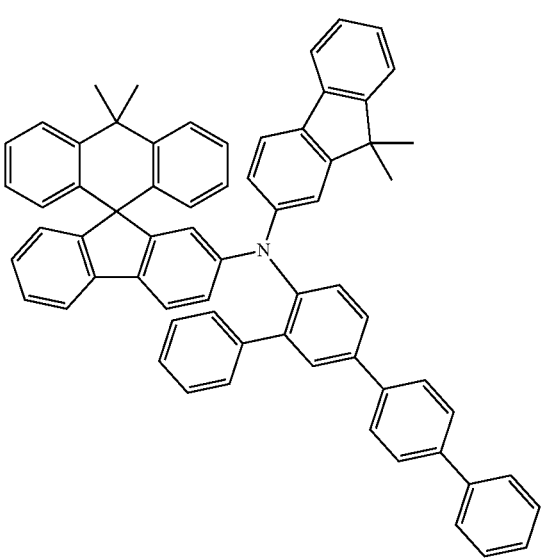

62
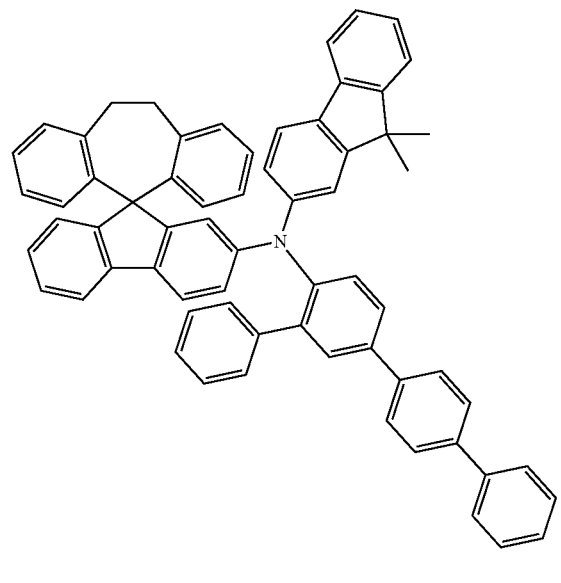
63
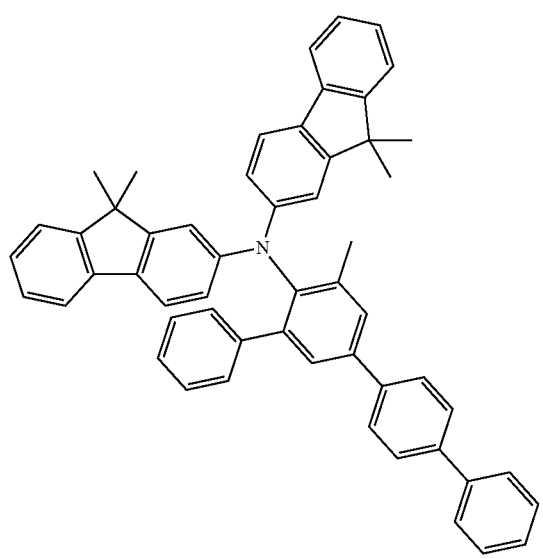
64
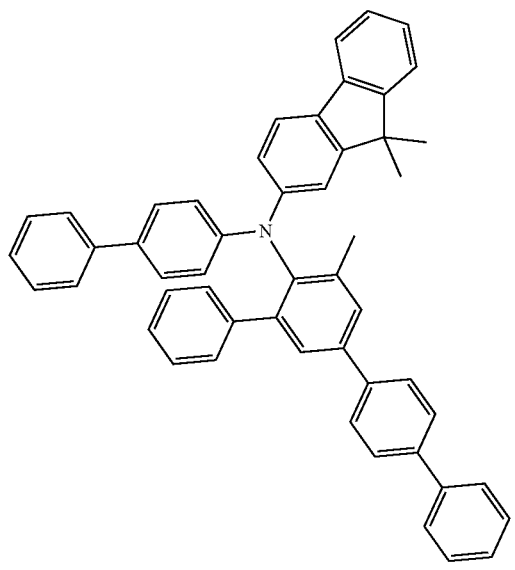
65
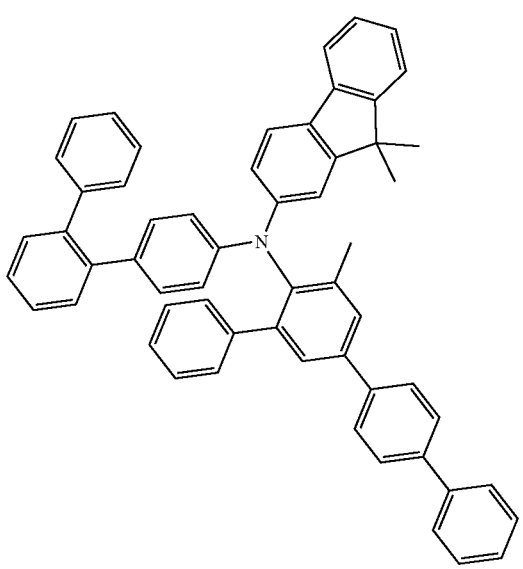
66

67
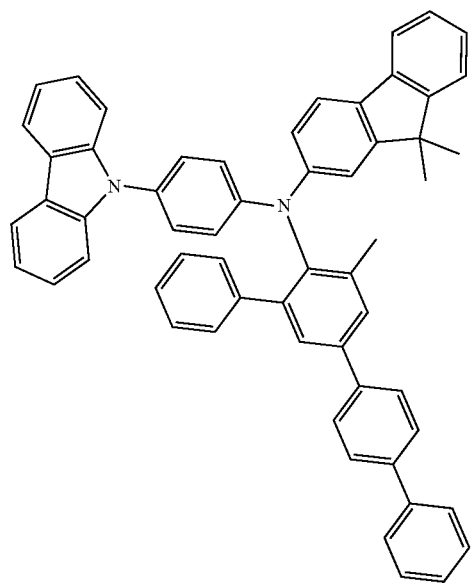
68
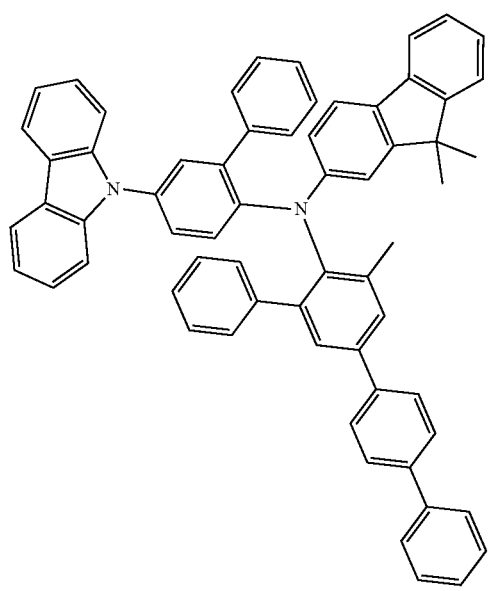
69
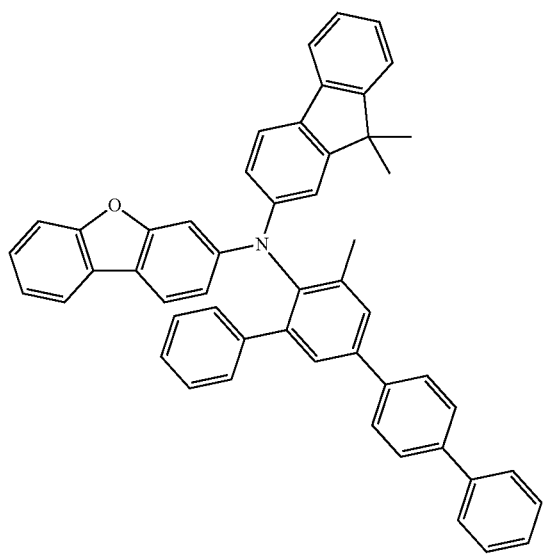
70
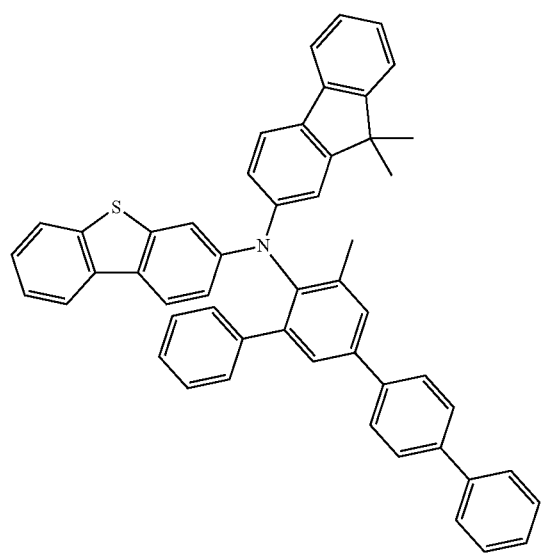

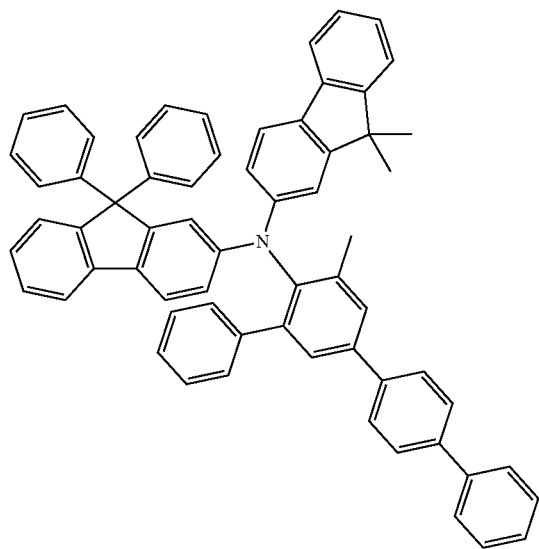
71
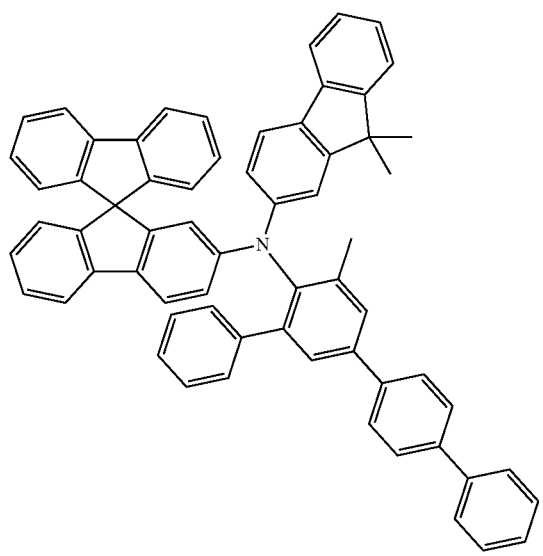
72
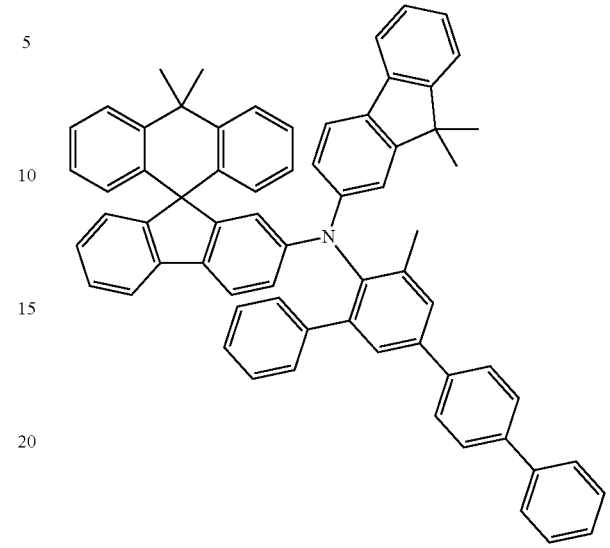
73
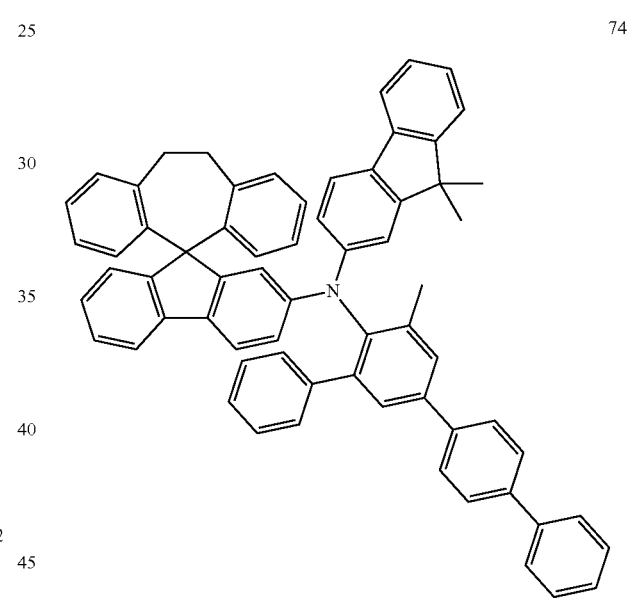
74
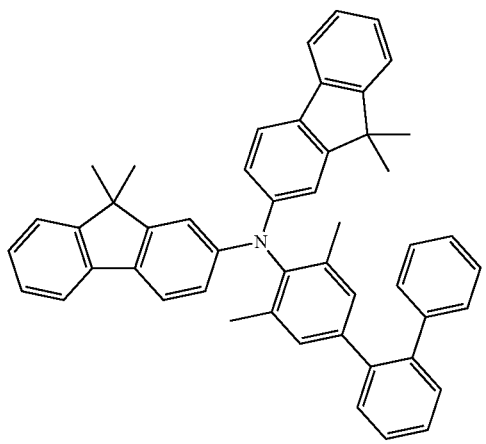
75

76
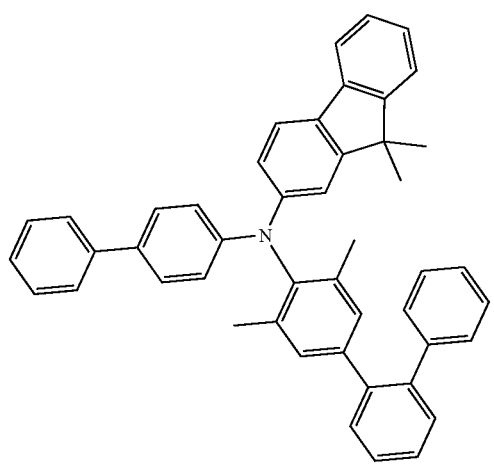
77
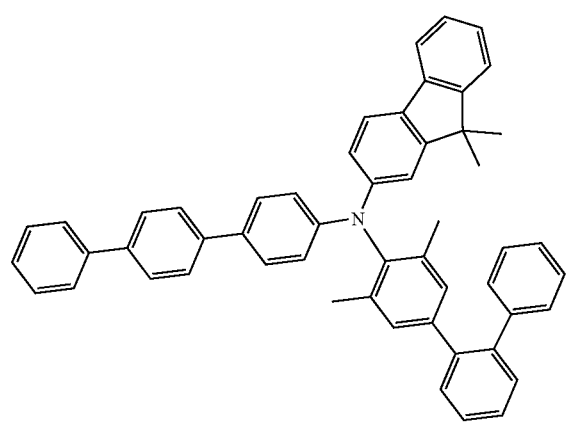
78
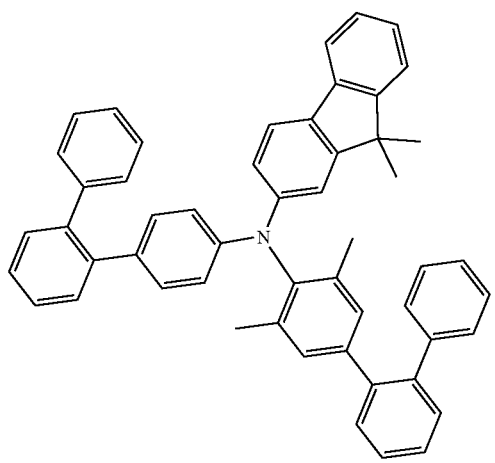
79
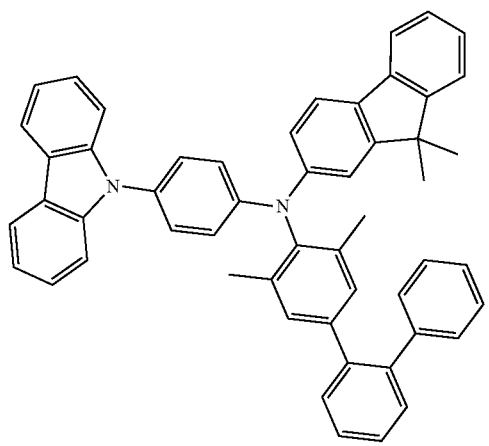
80
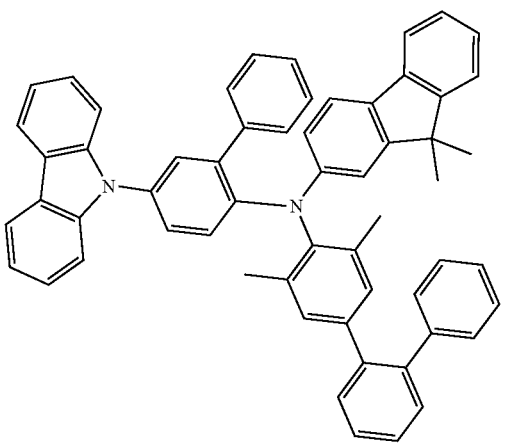
81
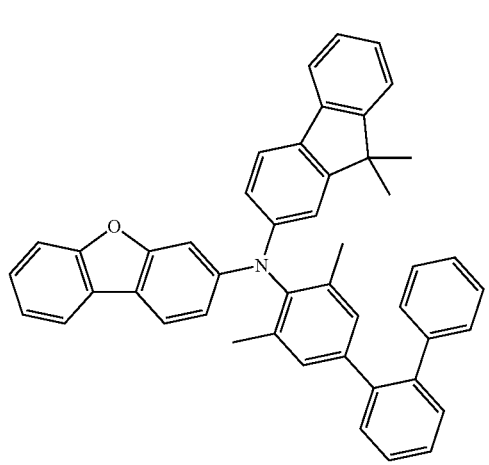

82
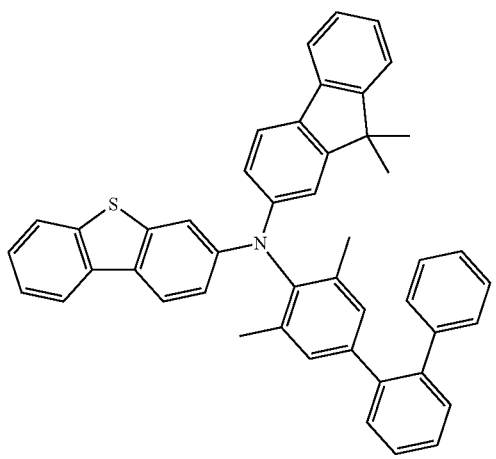
83
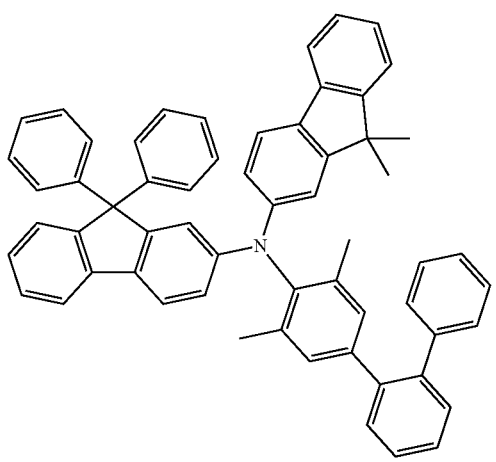
84
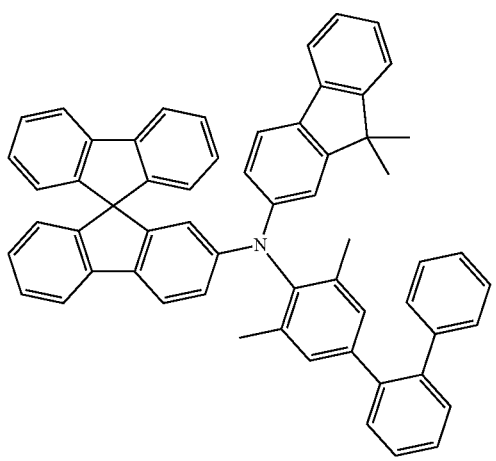
85
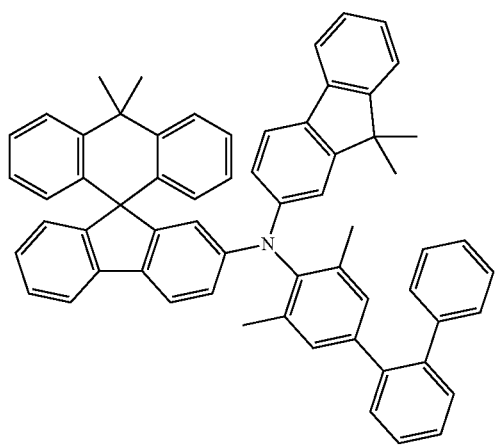
86
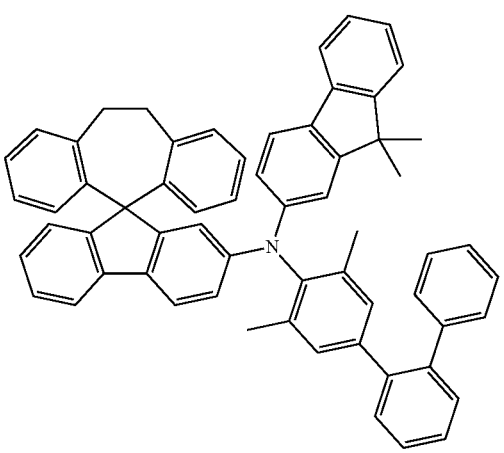
87
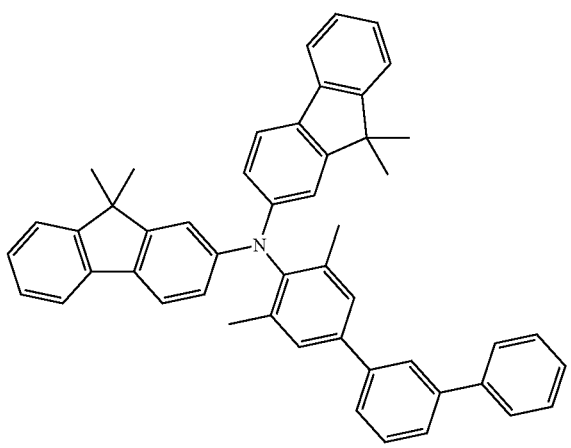

88
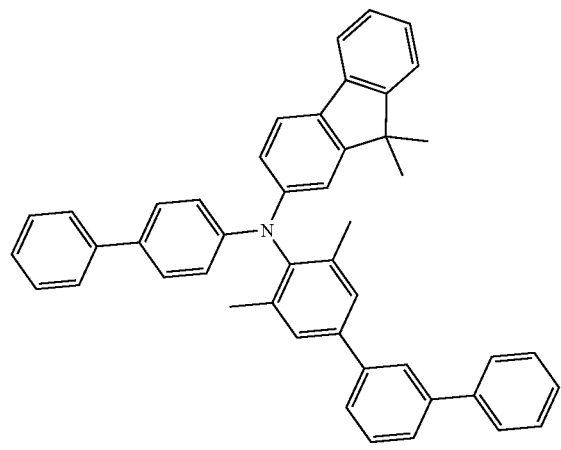
89
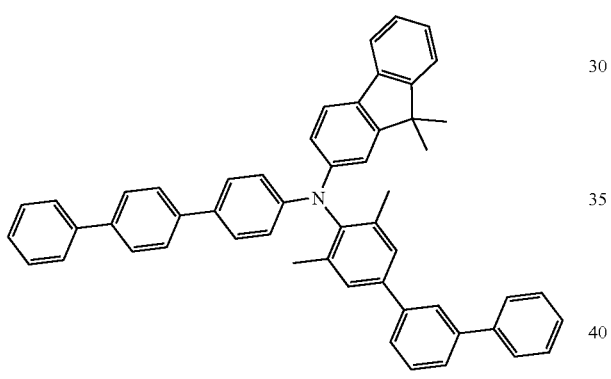
90
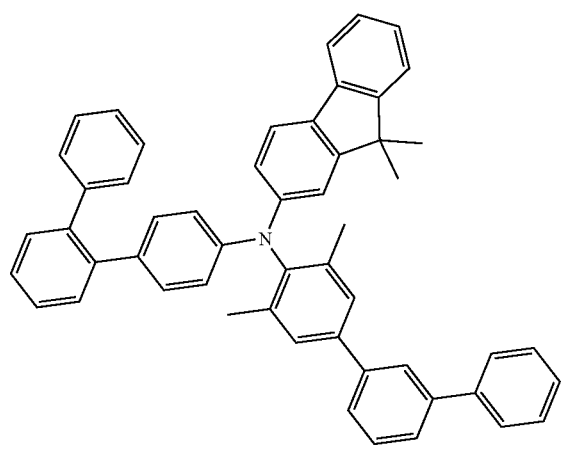
91
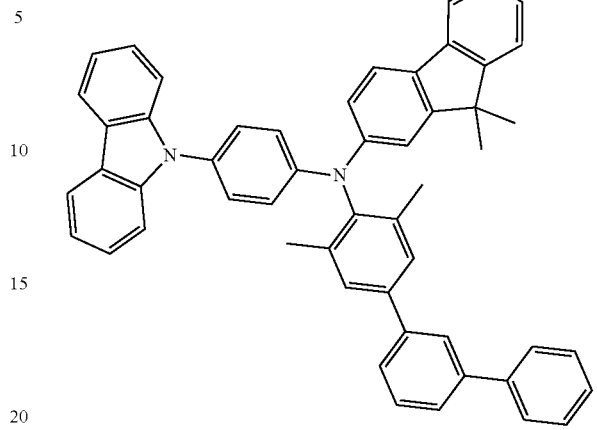
92
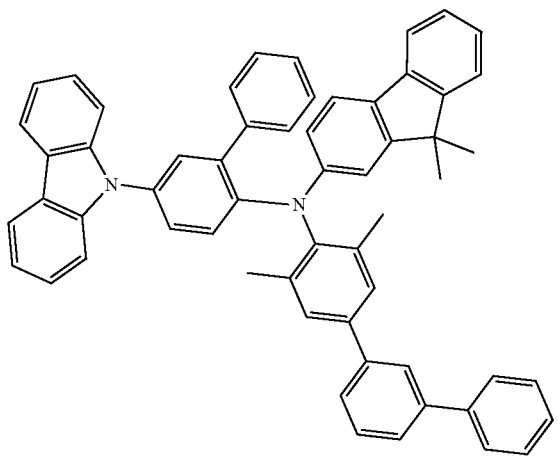
93
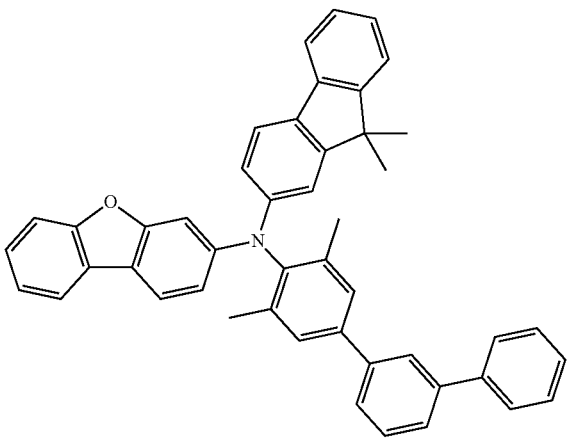

94
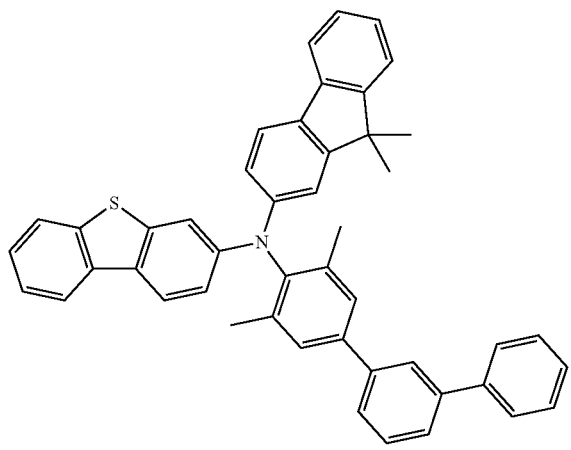
97
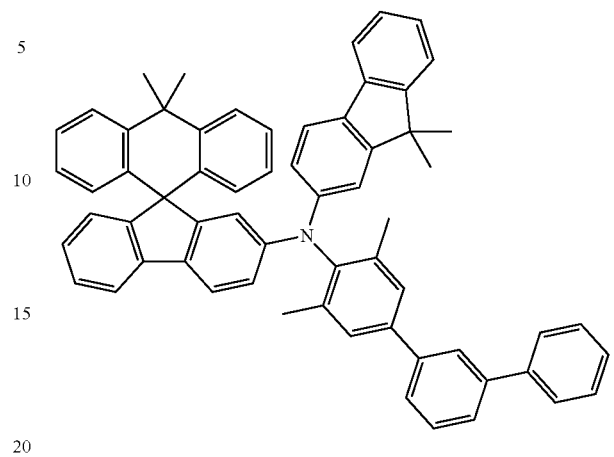
95
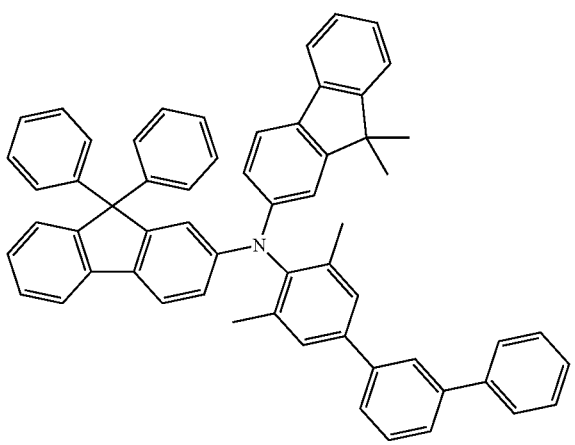
98
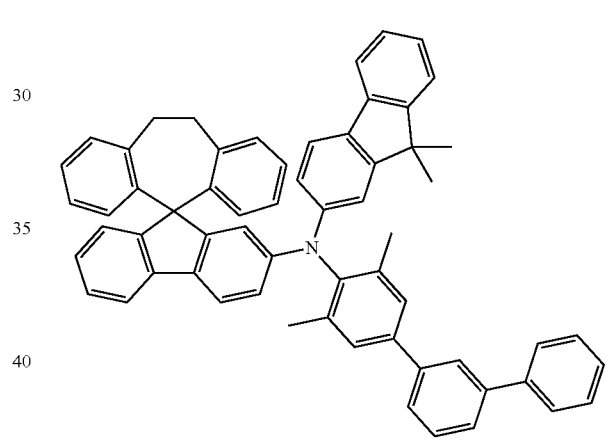
96
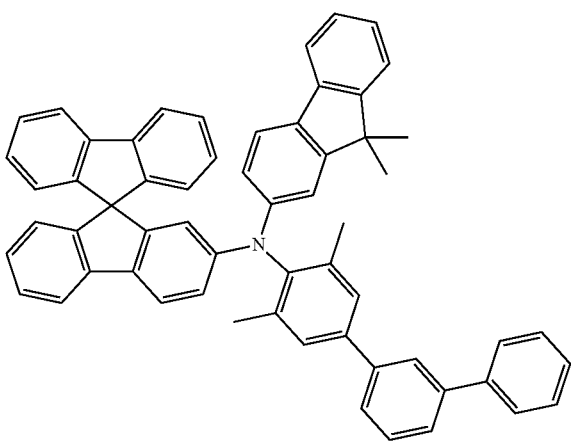
99
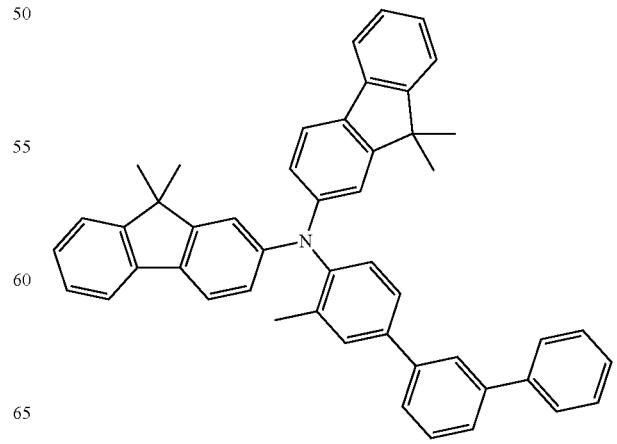

100
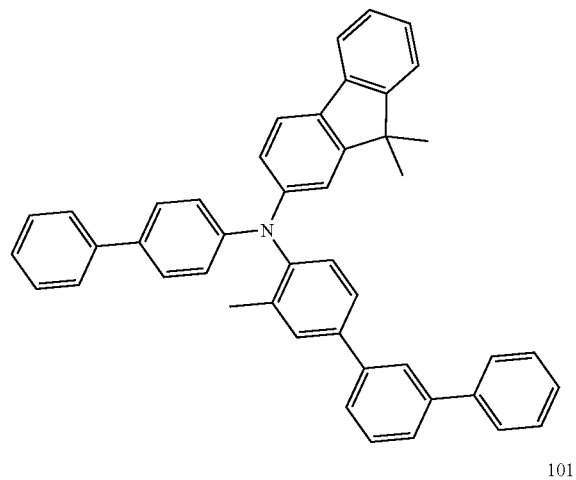
101
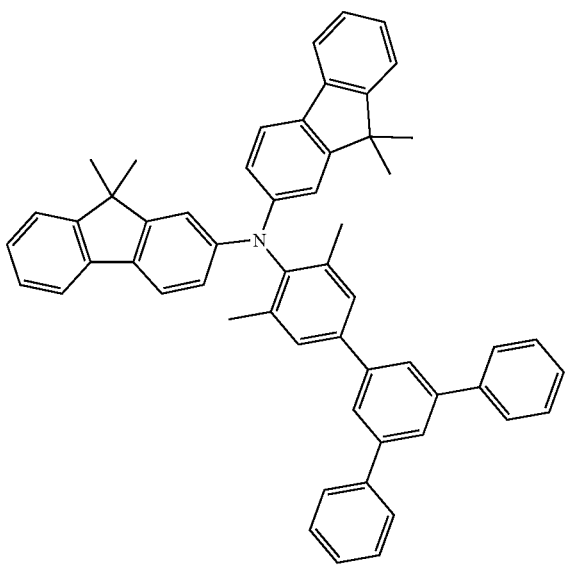
102
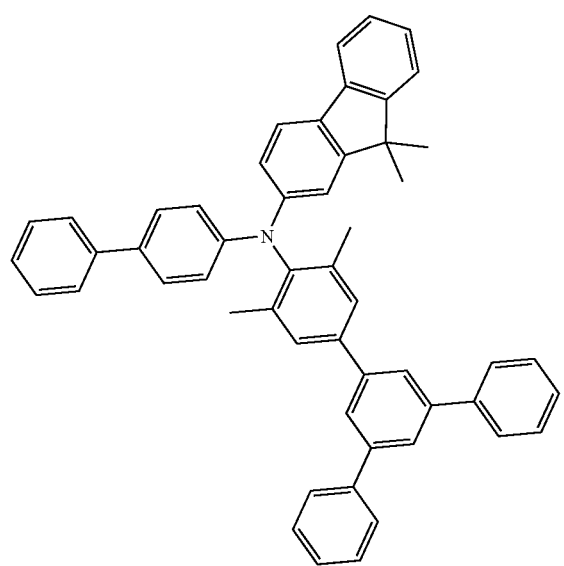
103
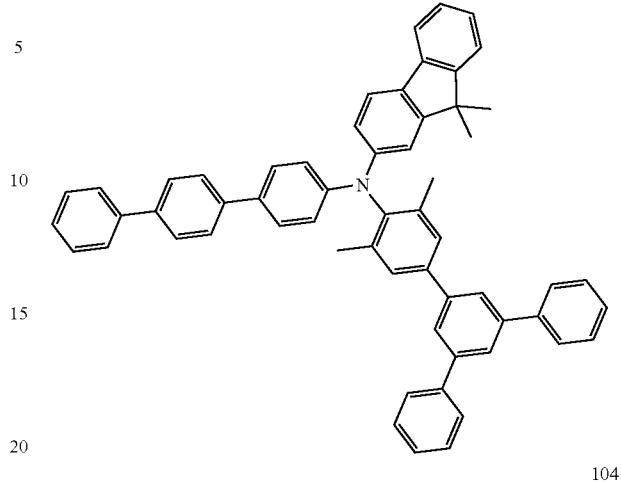
104
105
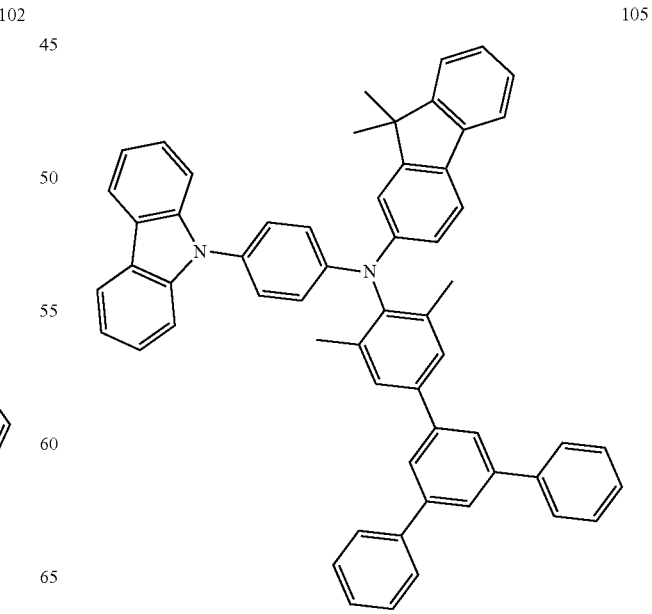

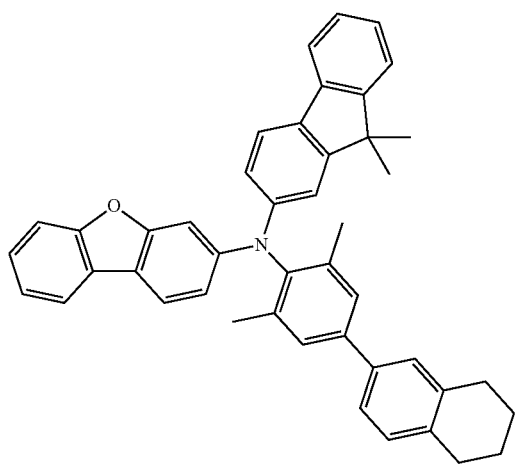
106
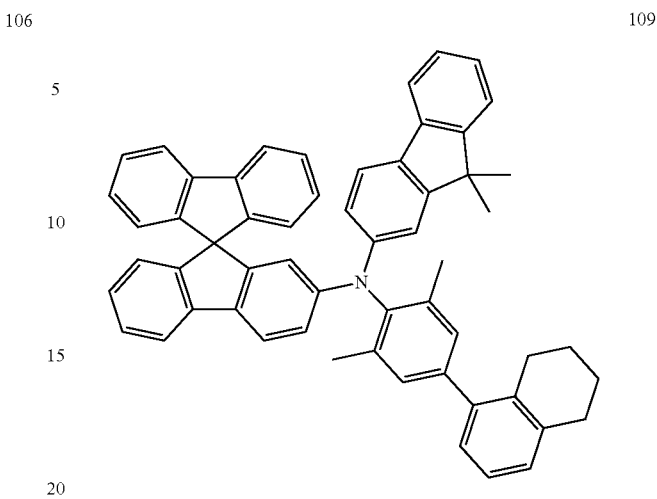
109
107
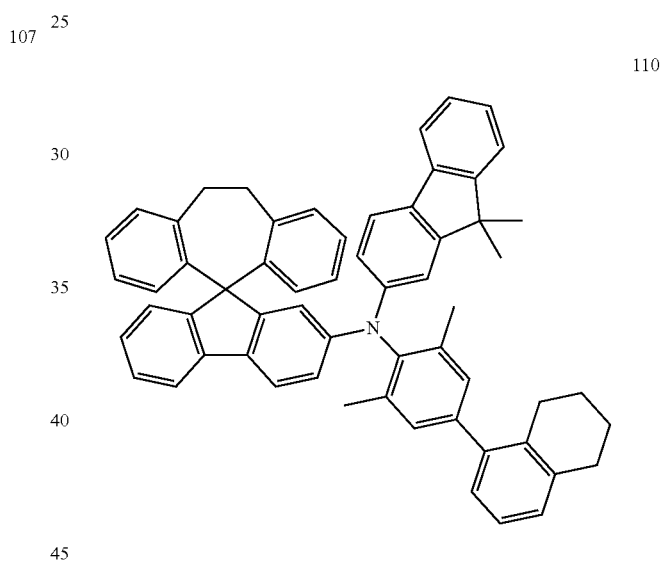
110
108
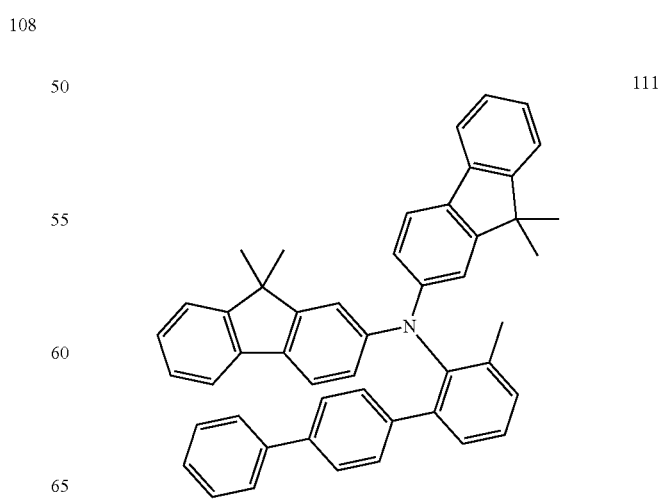
111

112
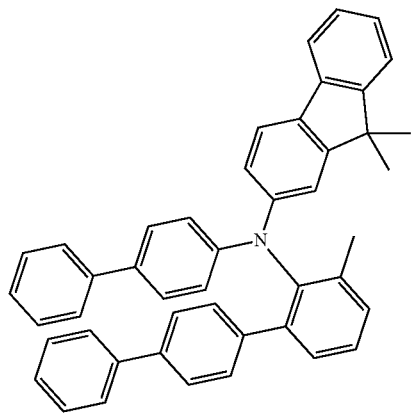
113
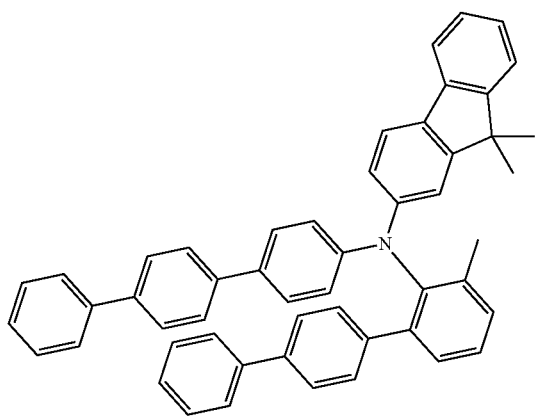
114
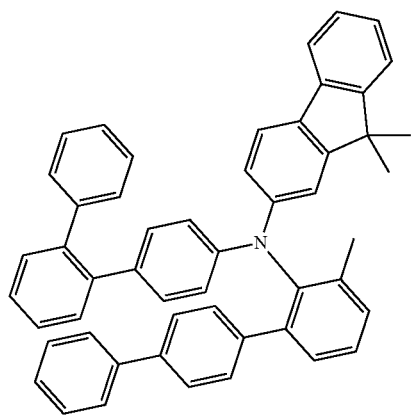
115
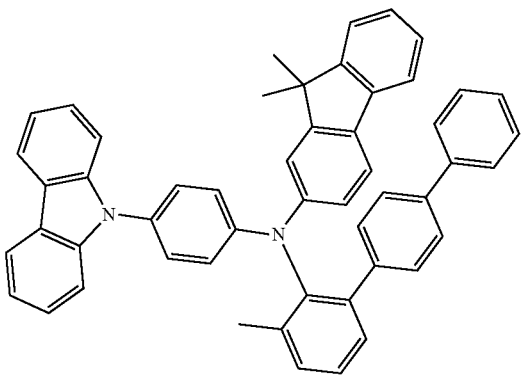
116
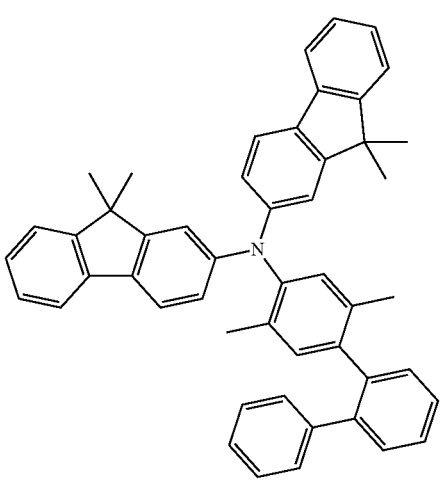
117
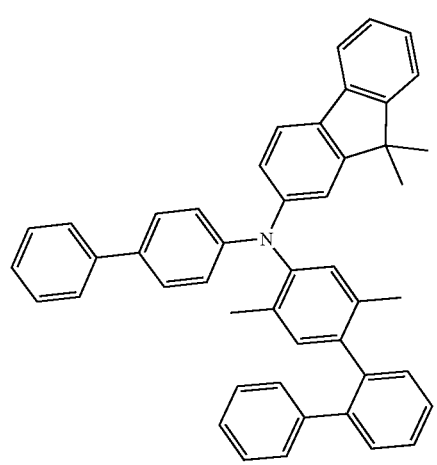

-continued
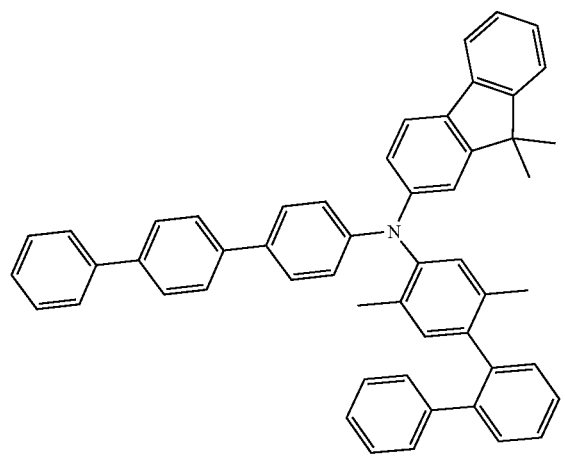
118
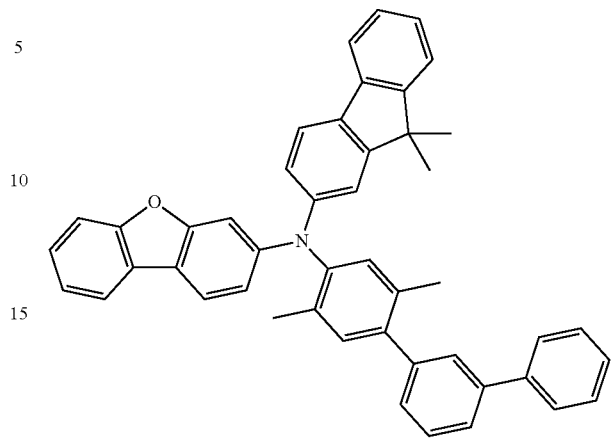
121
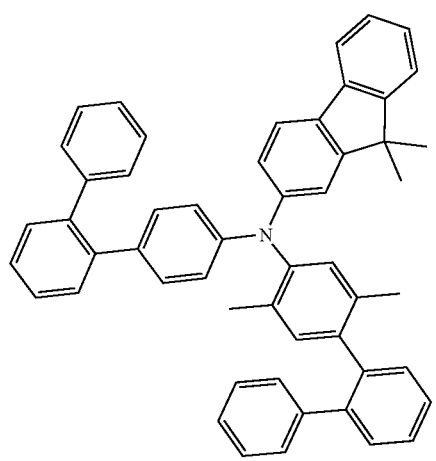
119
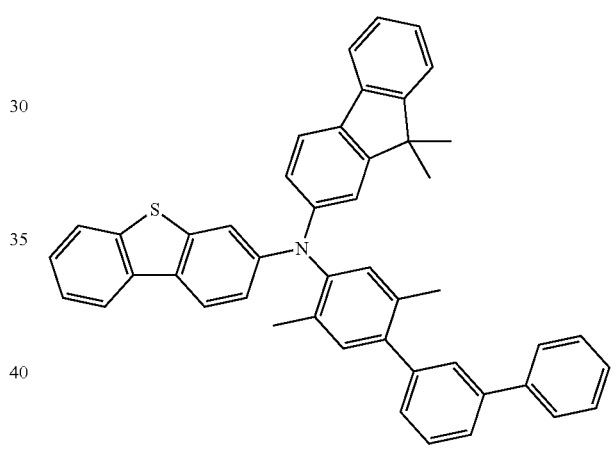
122
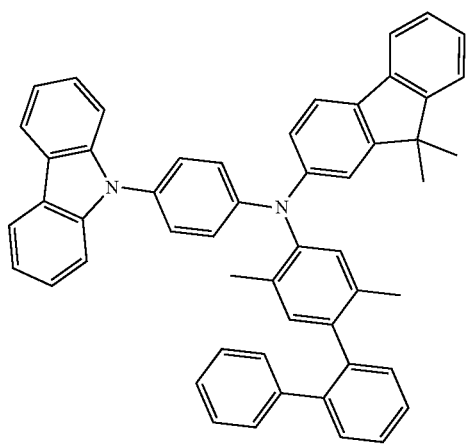
120
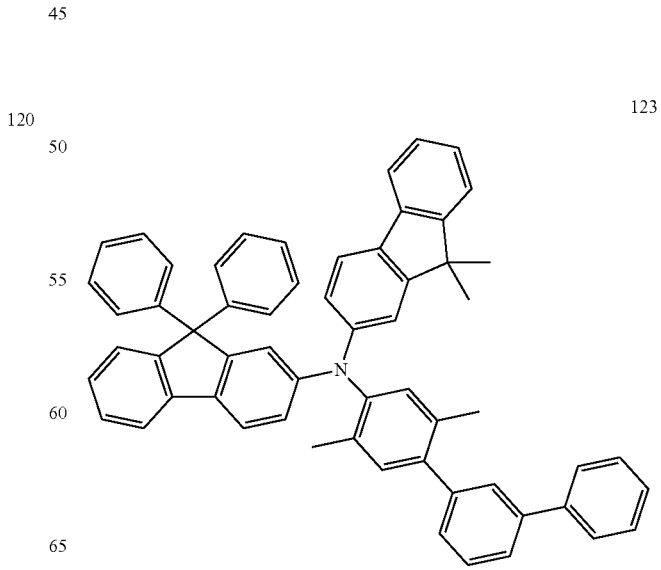
123

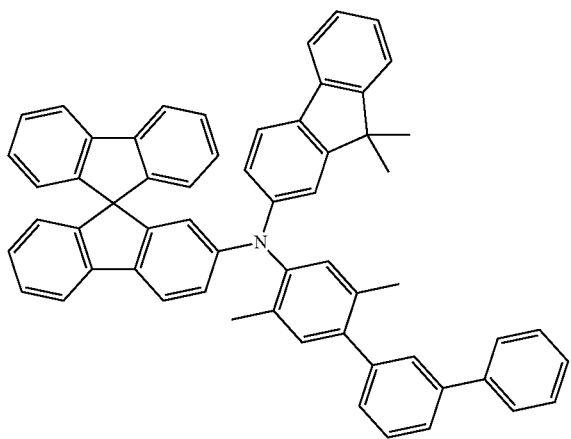
124
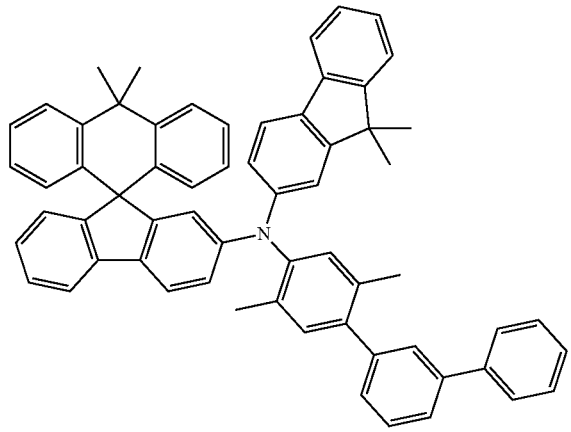
125
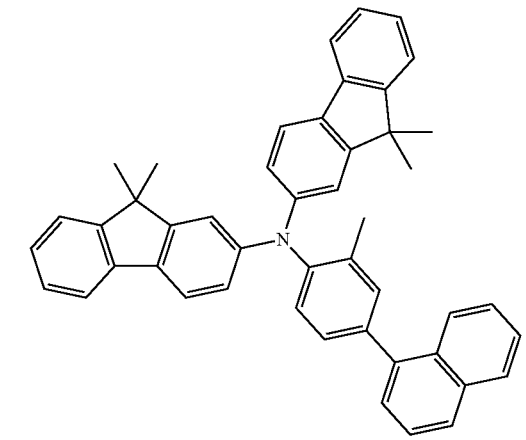
126
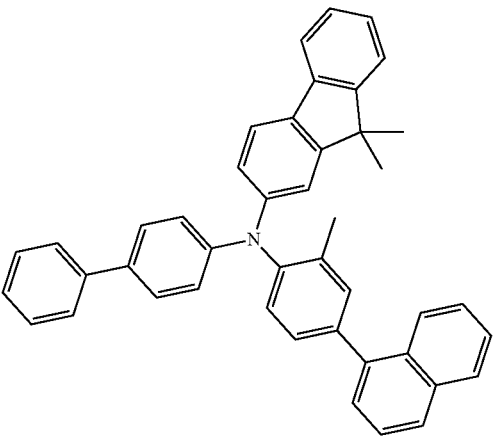
127
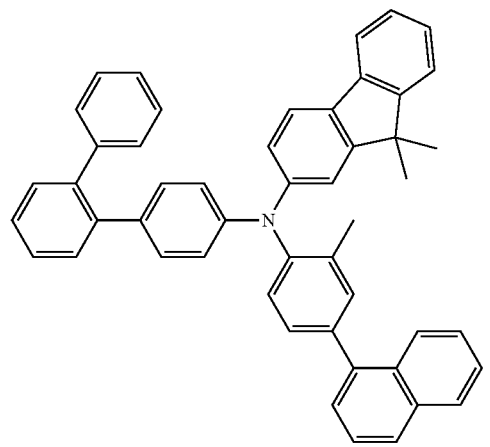
128
129

130
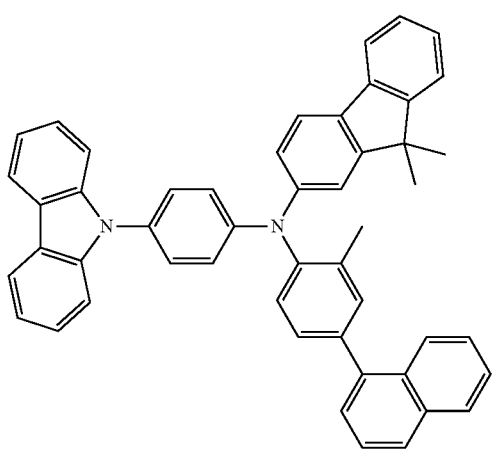
131
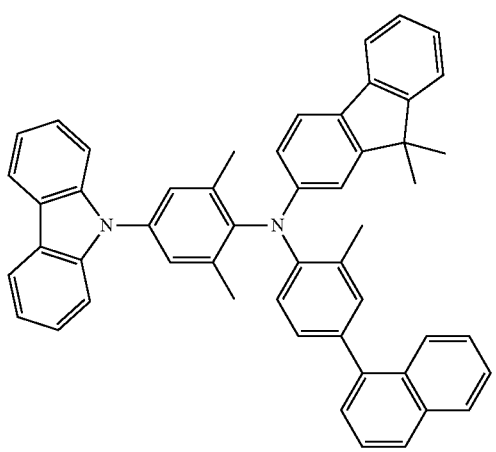
132
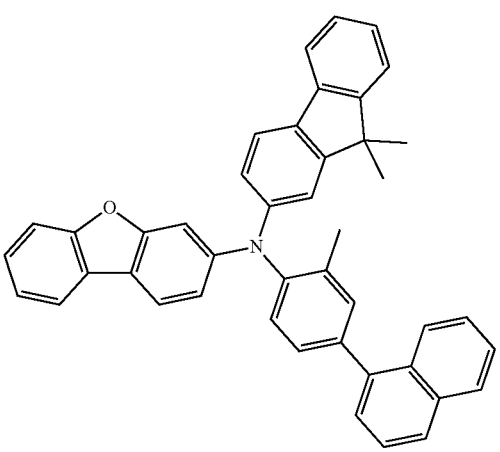
133
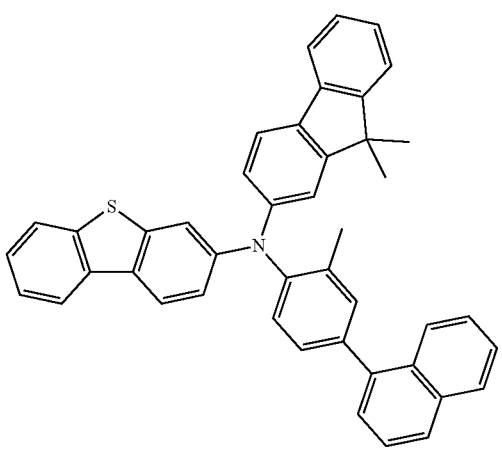
134
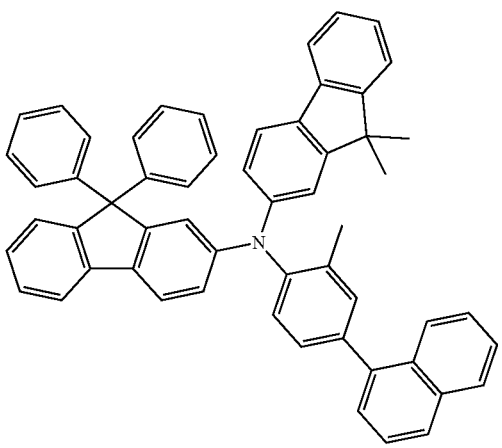
135
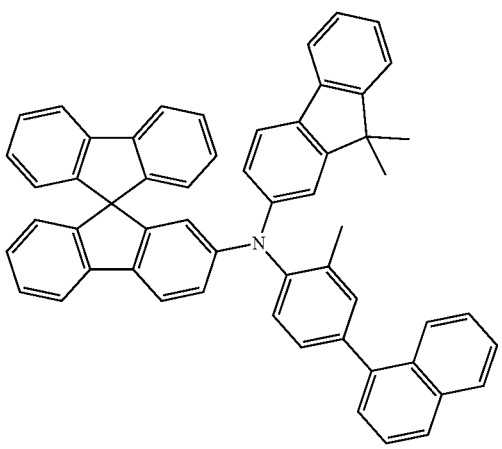

136
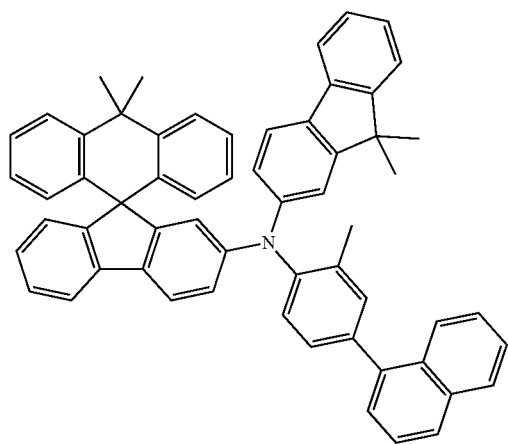
137
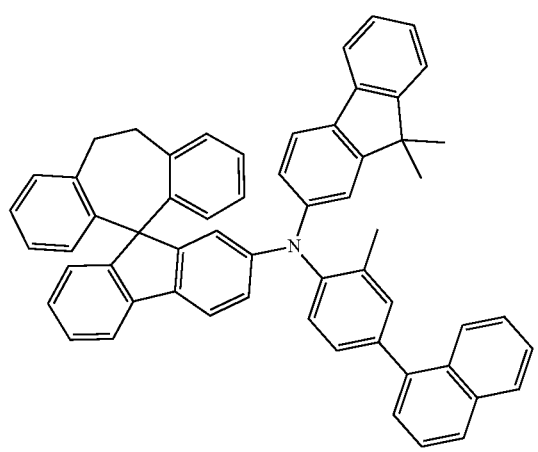
138
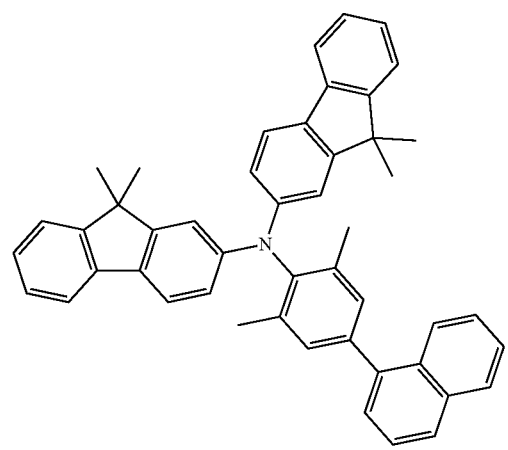
139
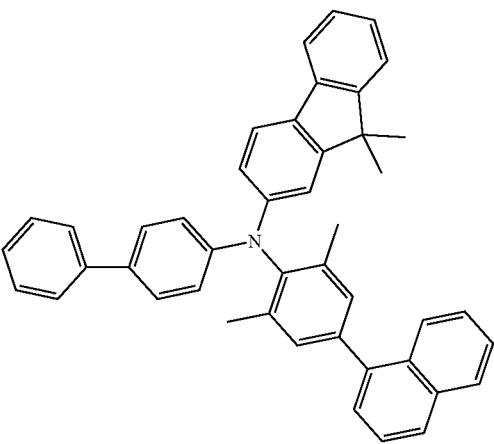
140
141
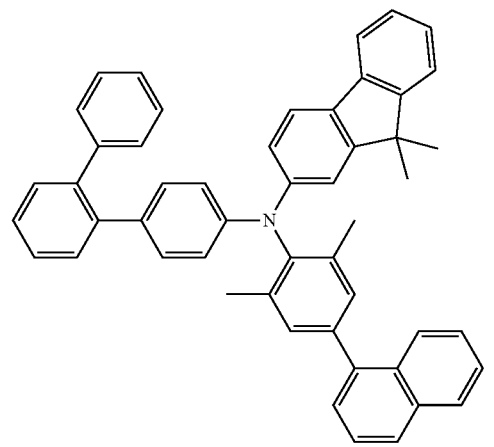

142
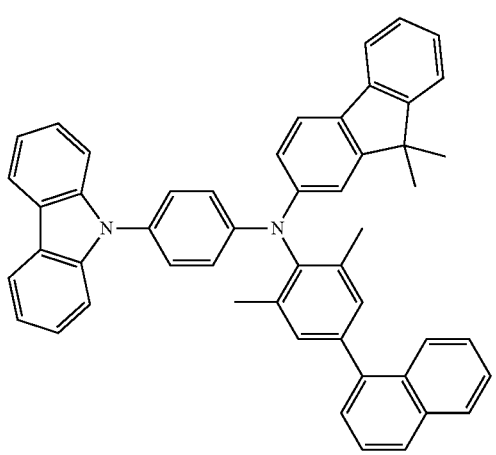
143
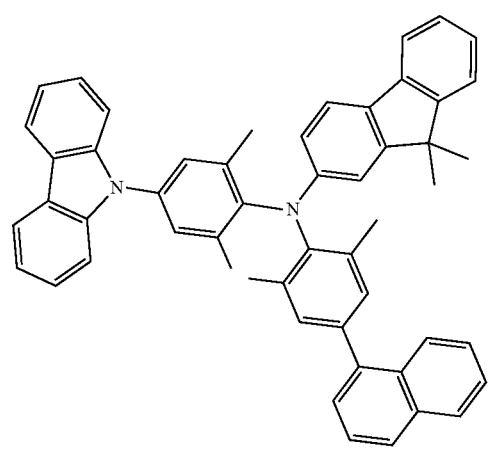
144
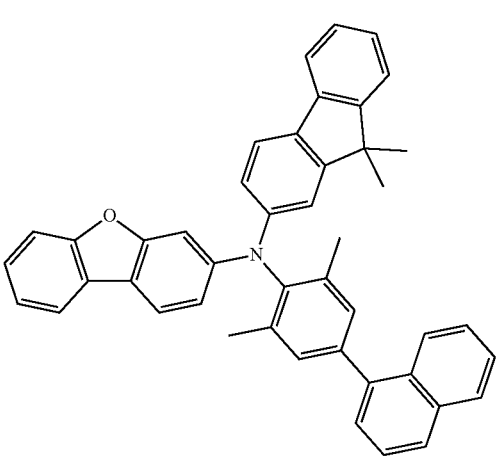
145
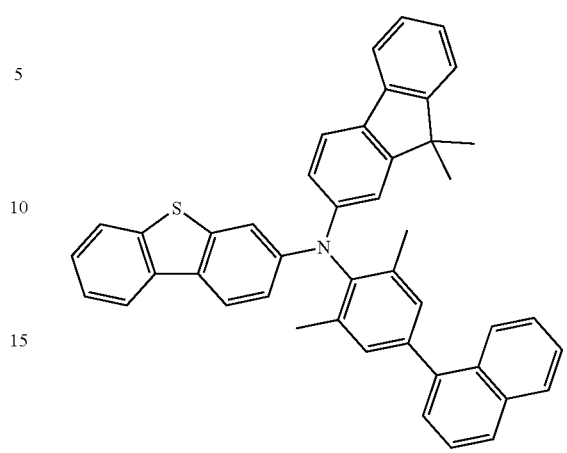
146
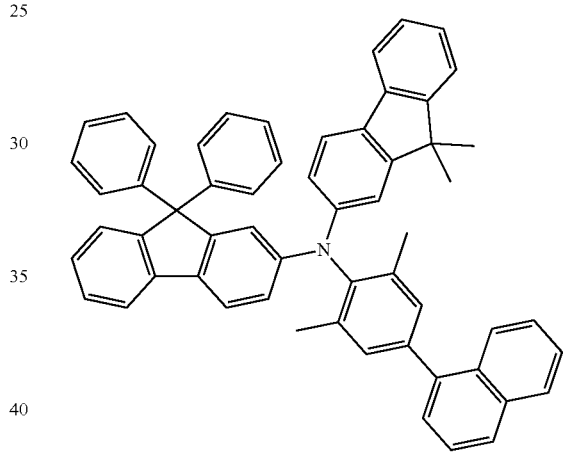
147
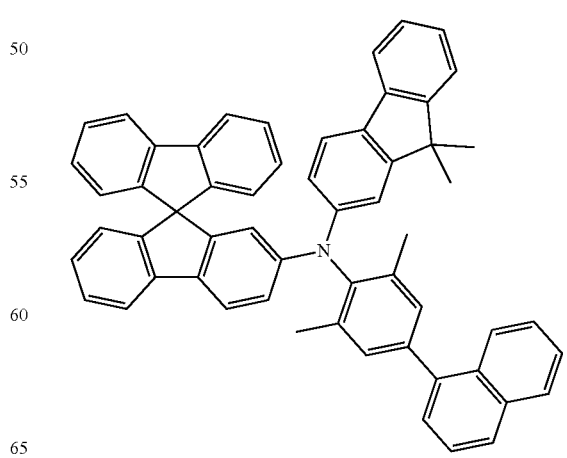

148
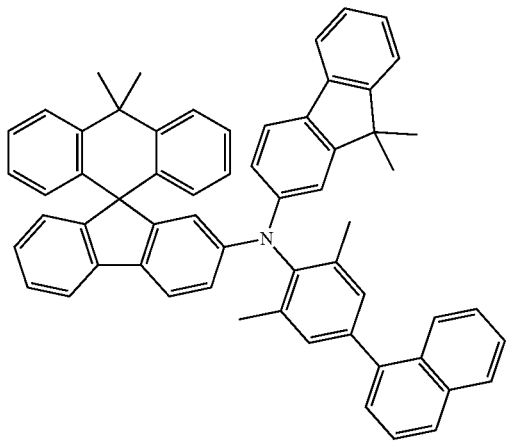
149
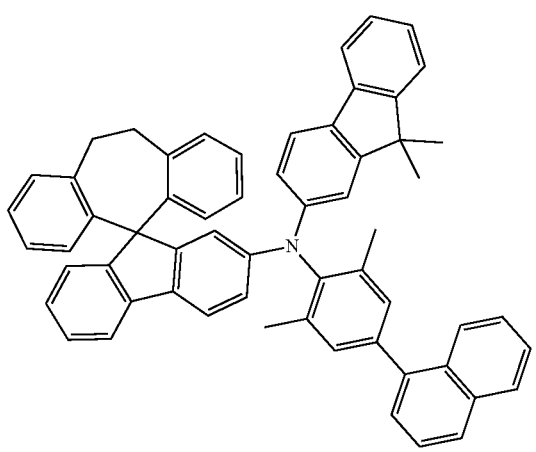
150
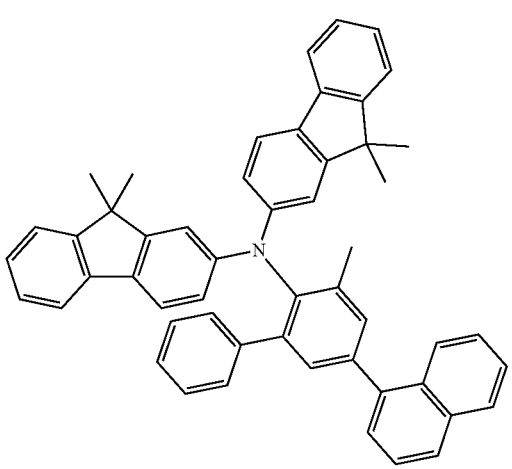
151
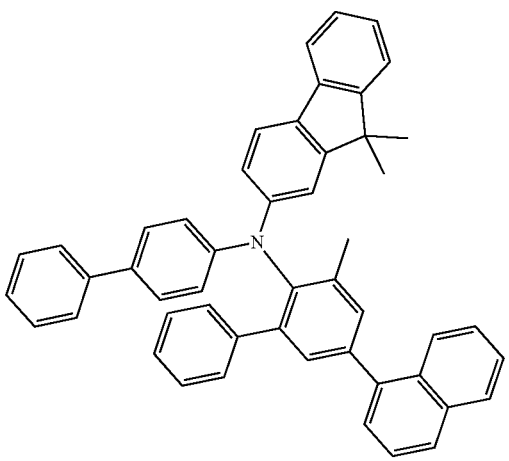
152
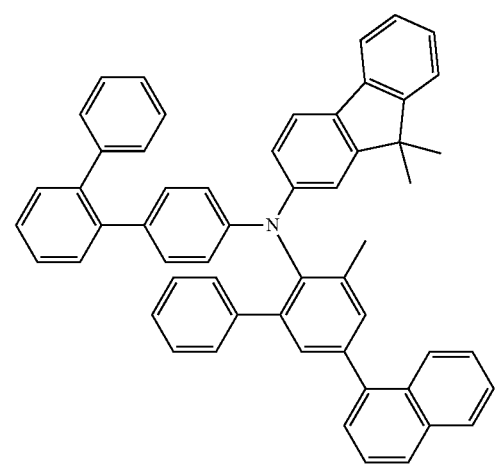
153

154
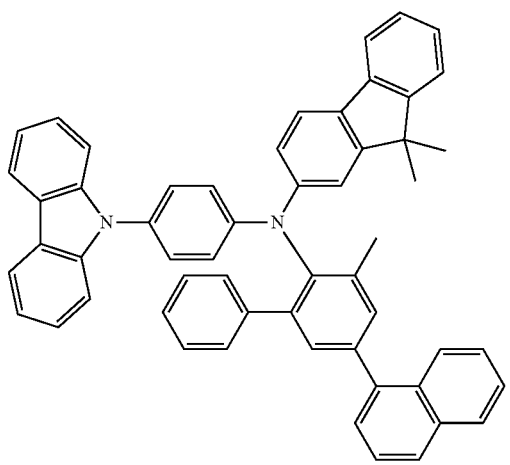
155
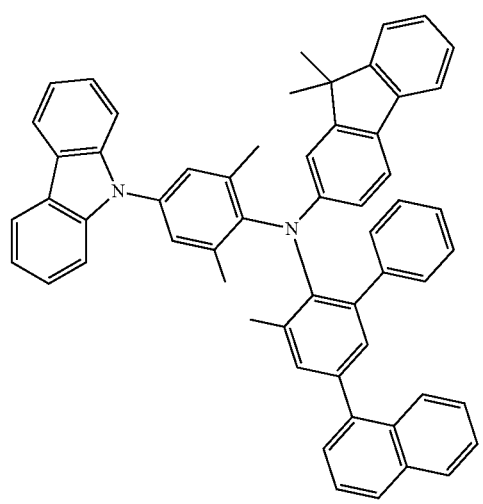
156
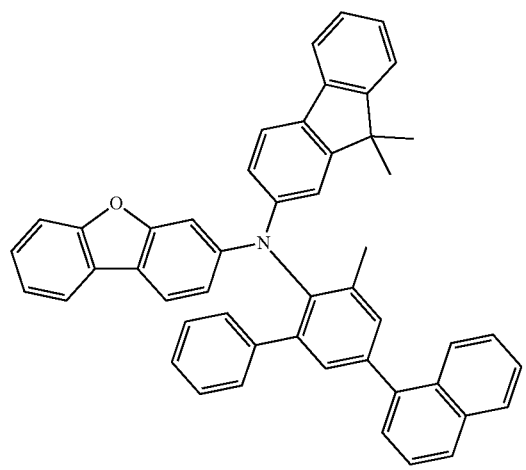
157
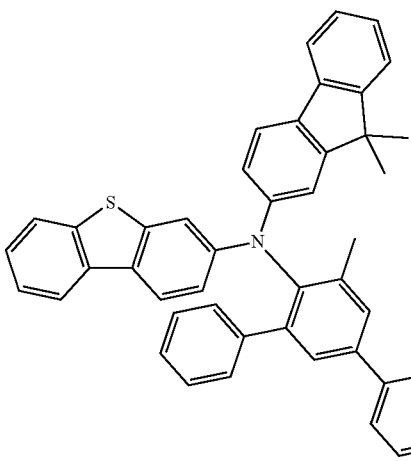
158
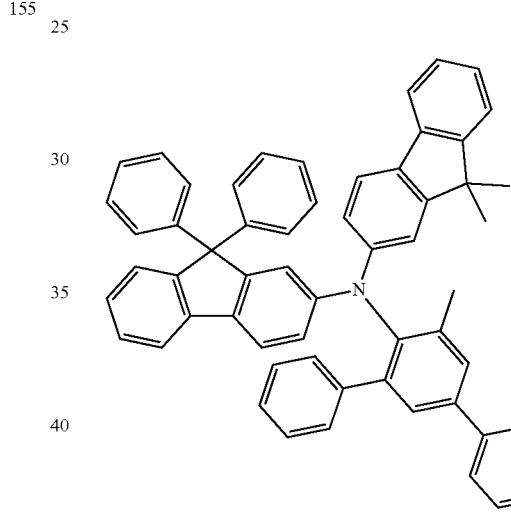
159
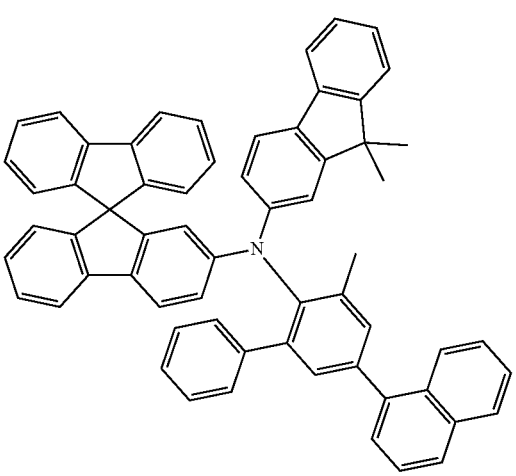

160
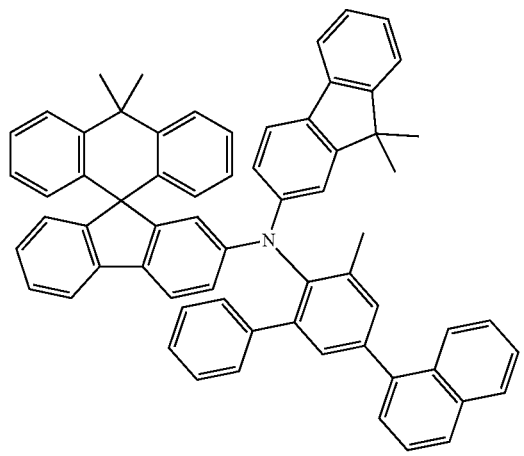
161
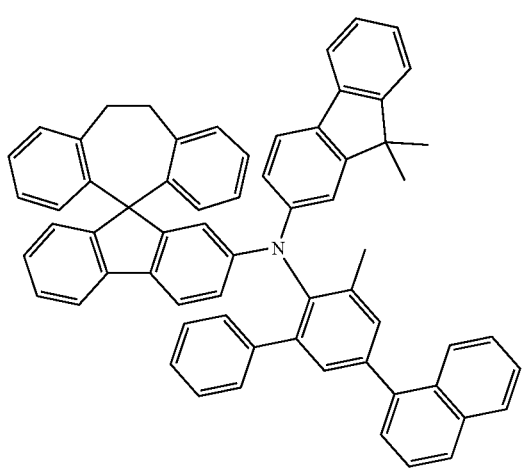
162
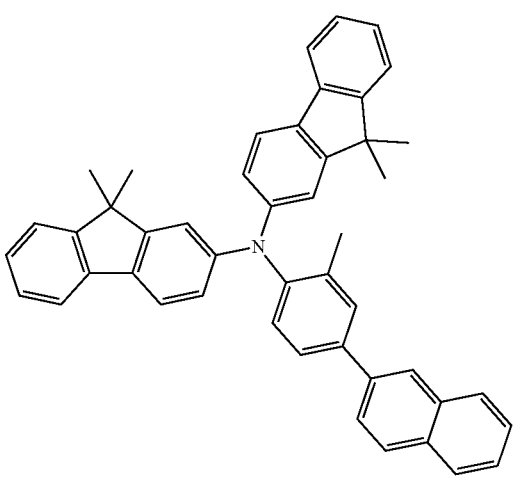
163
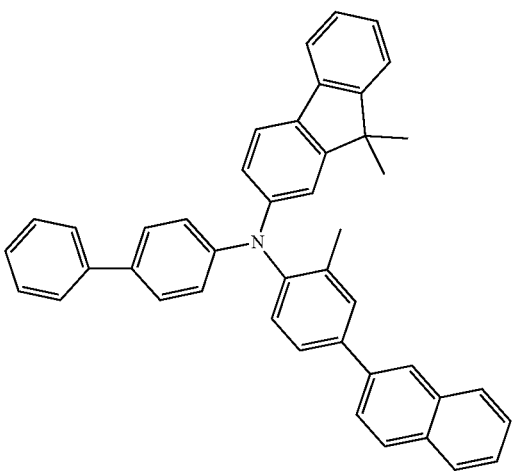
164
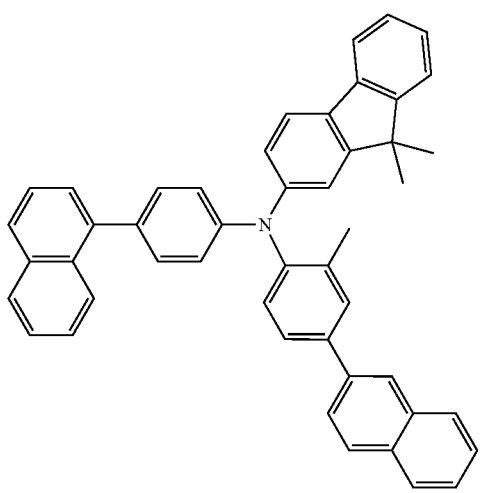
165
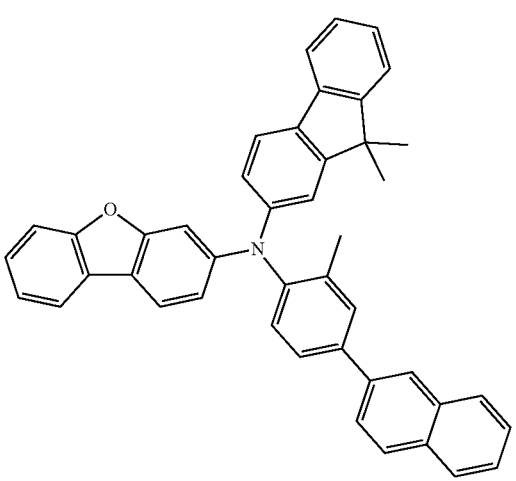

166
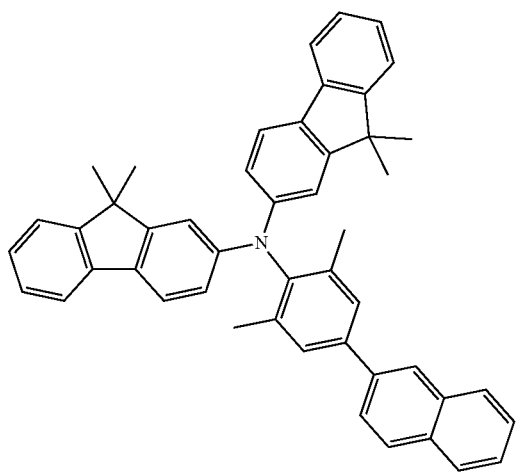
167
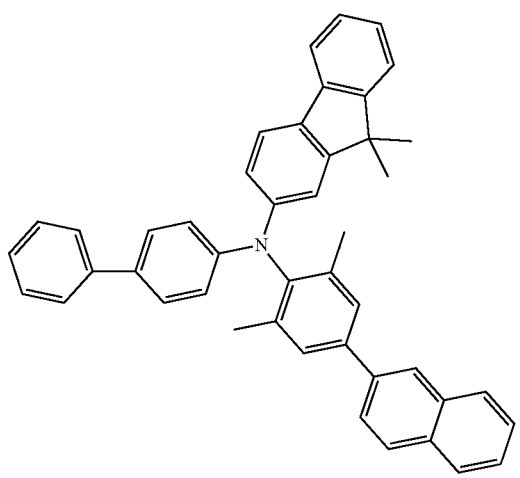
168
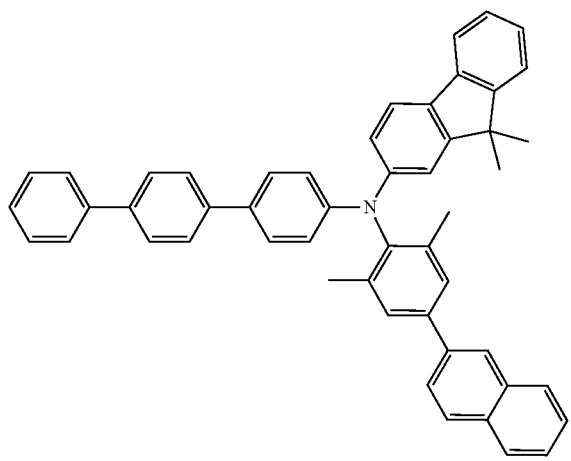
169
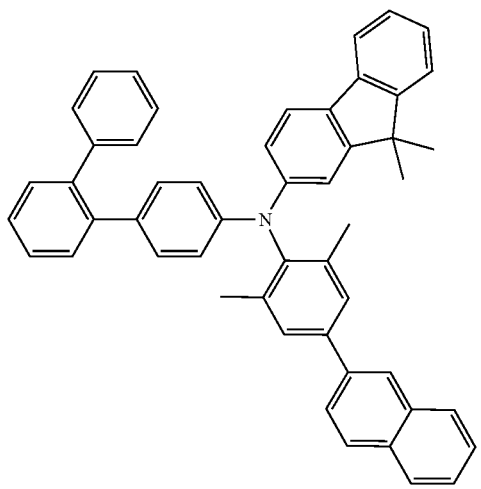
170
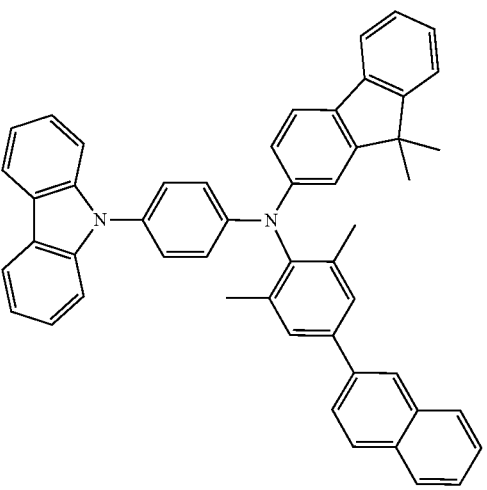
171
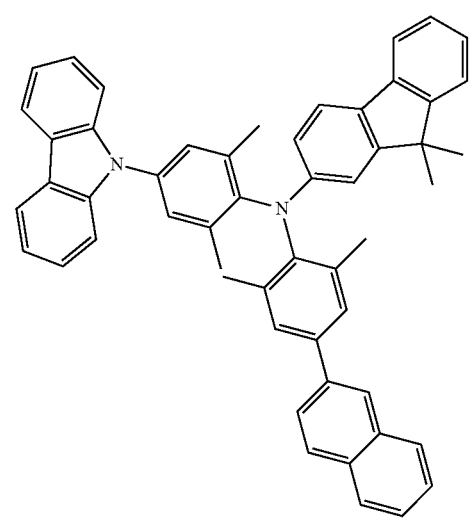

172
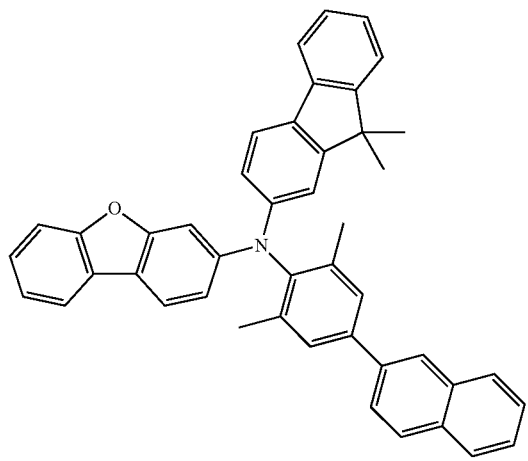
175
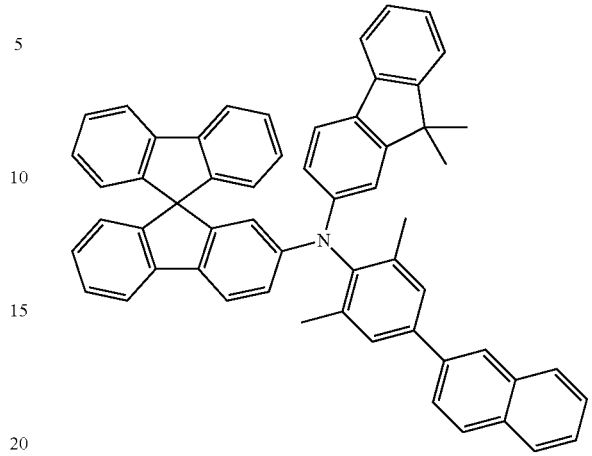
173
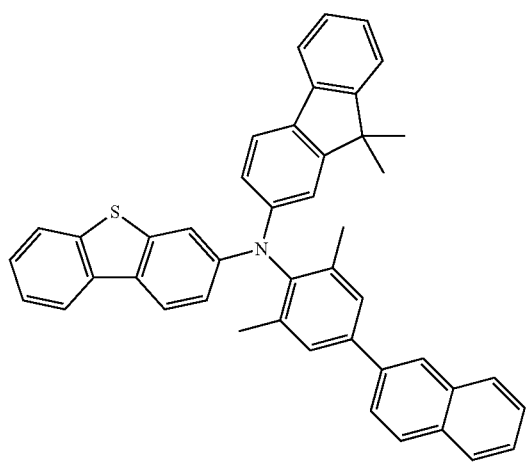
176
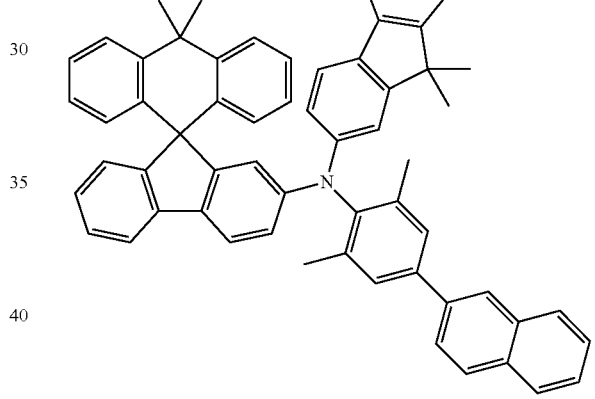
174
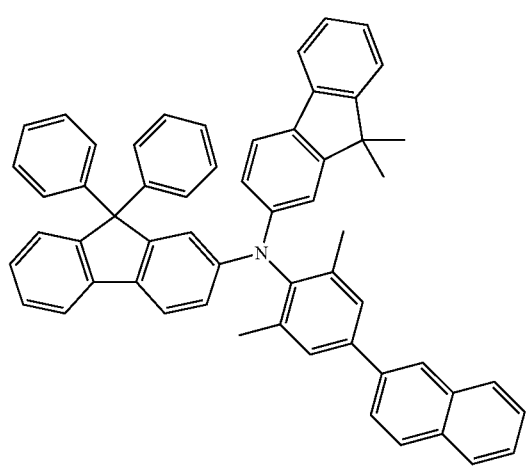
177
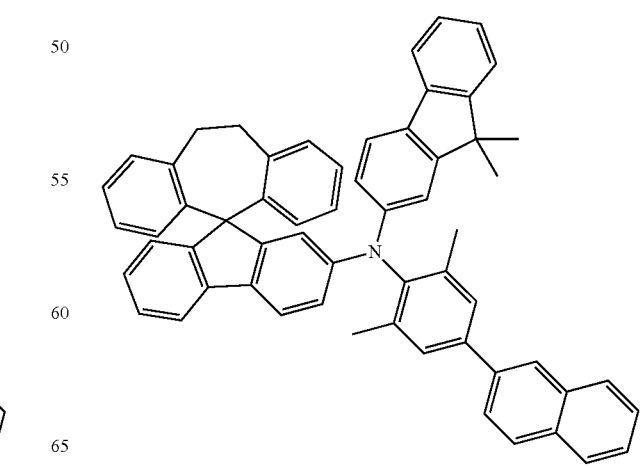

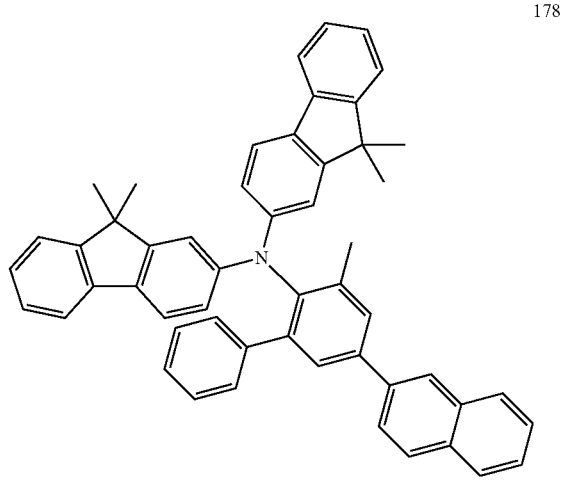
178
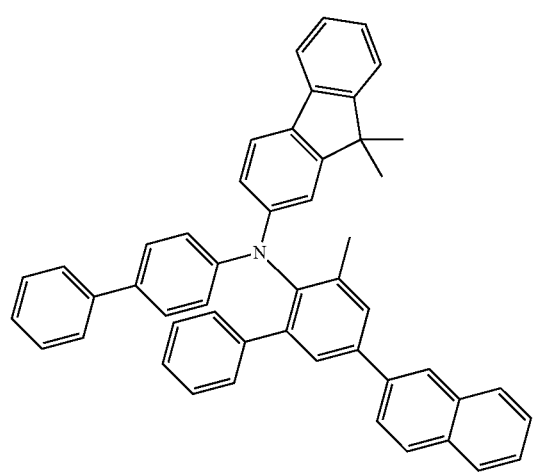
179
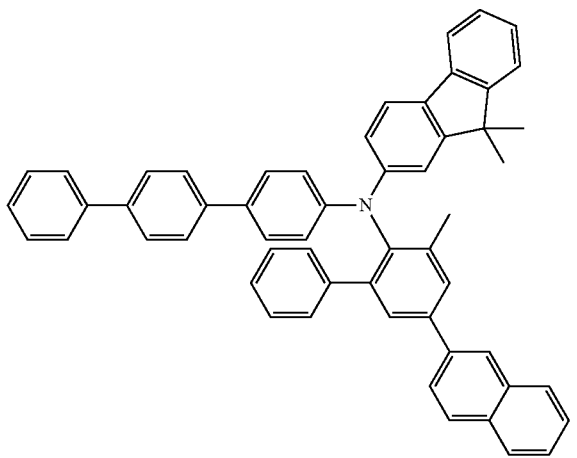
180
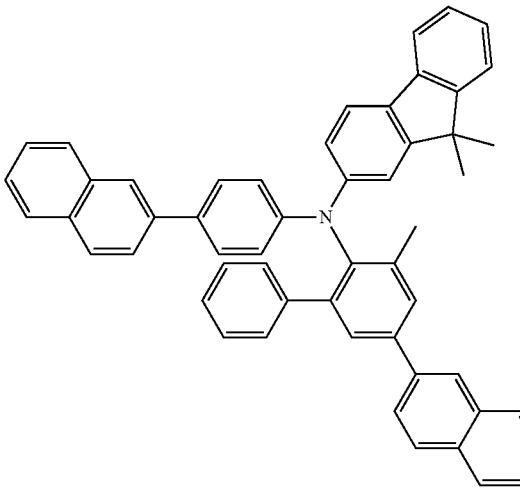
181
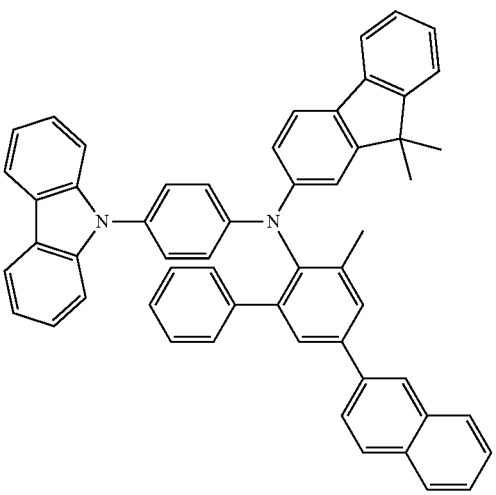
182
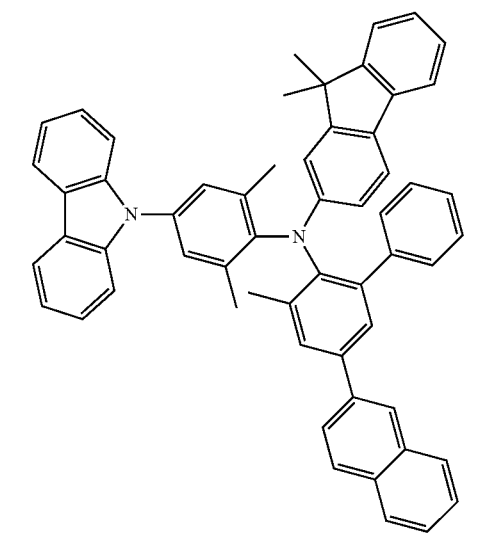
183

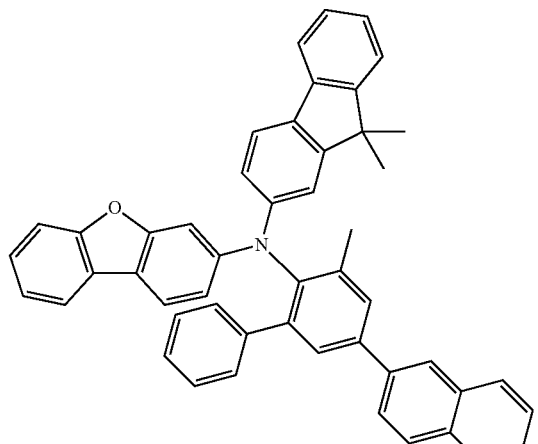
184
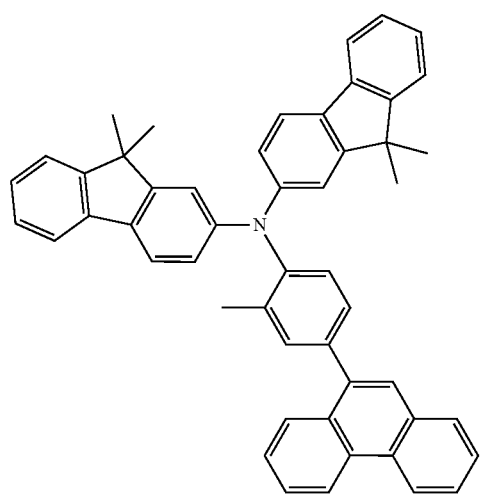
185
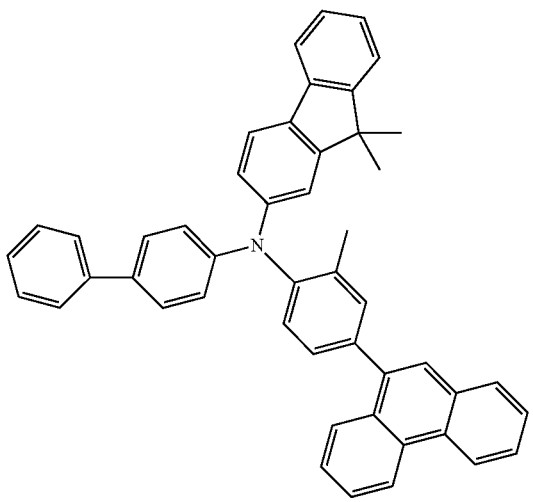
186
187
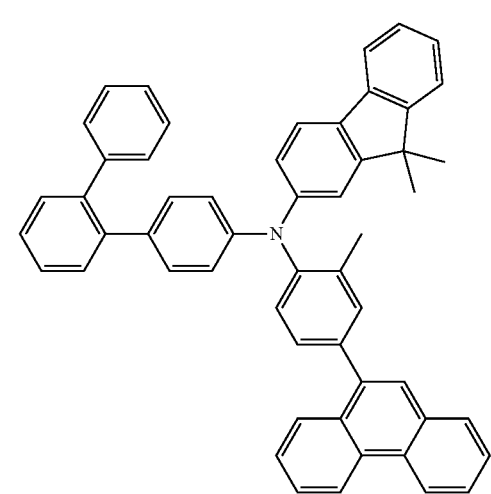
188
189

190
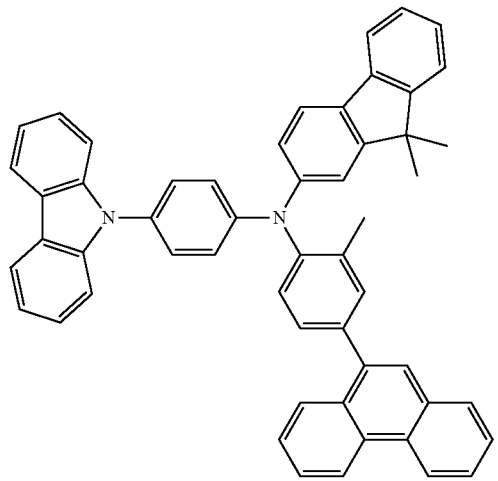
191
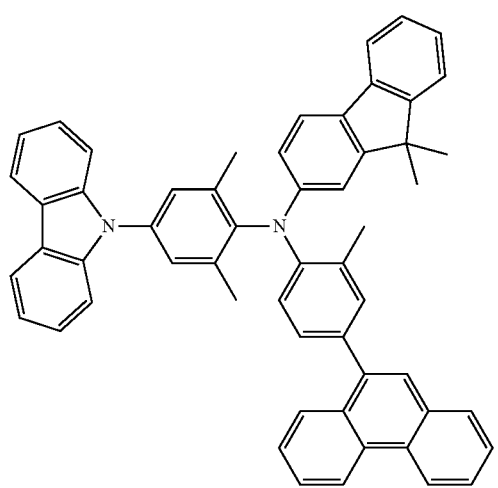
192
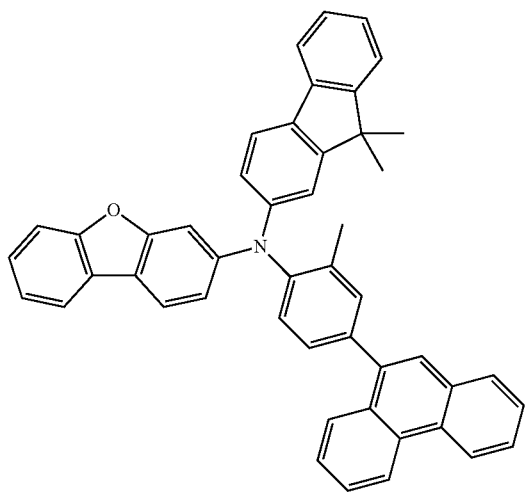
193
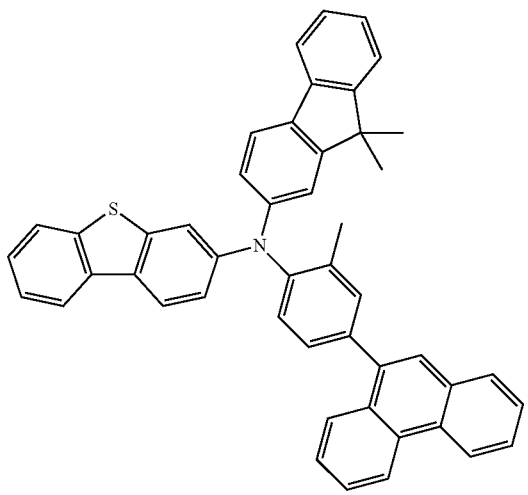
194
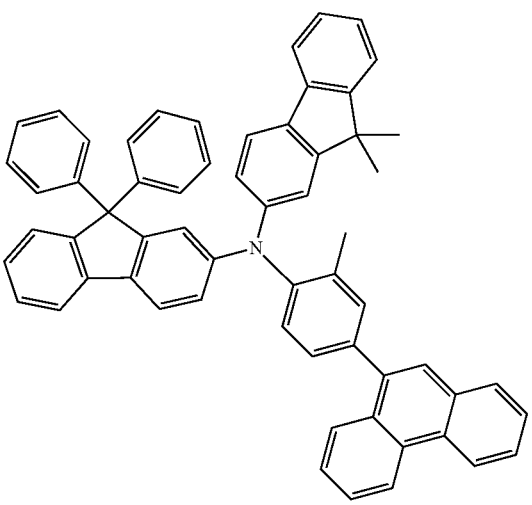
195
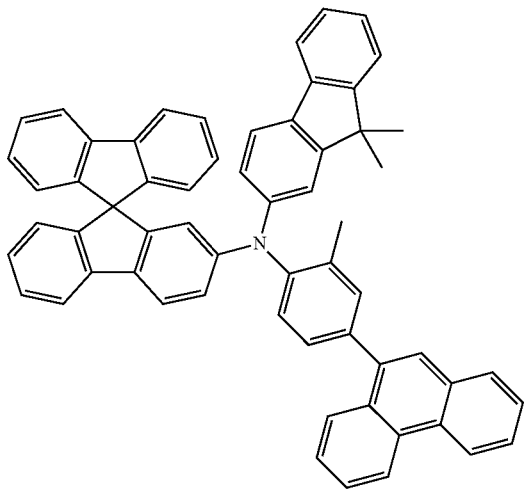

196
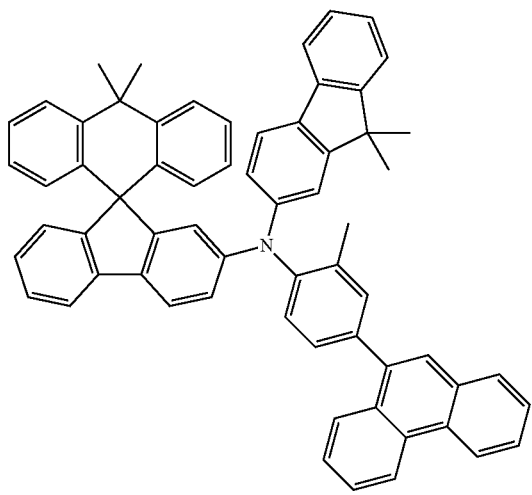
197
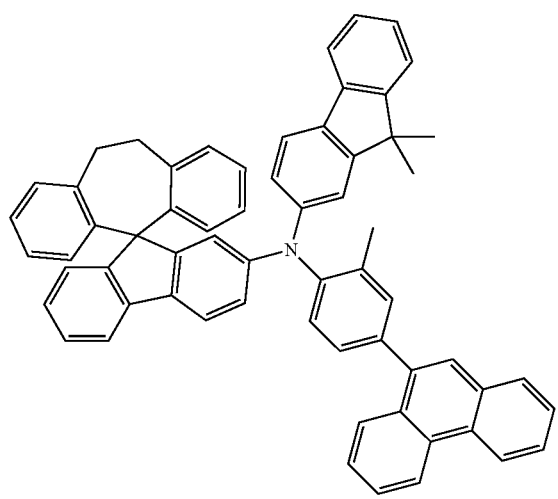
198
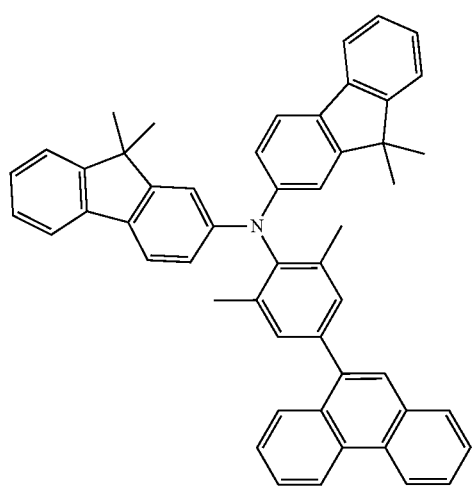
199
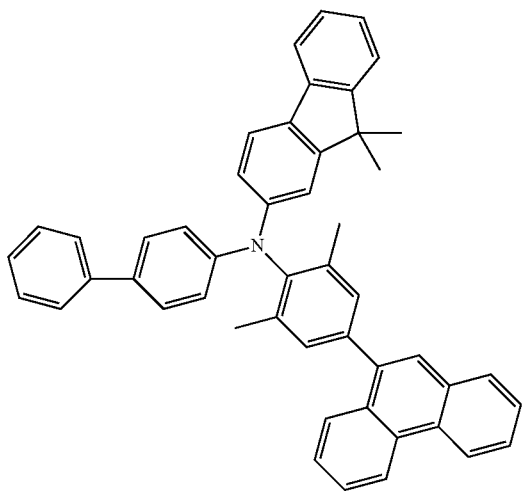
200
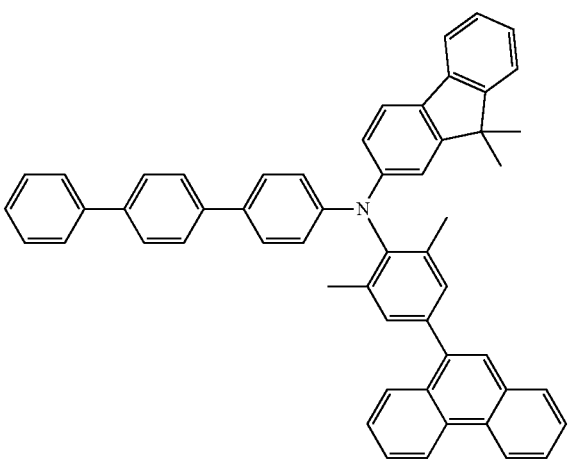
201
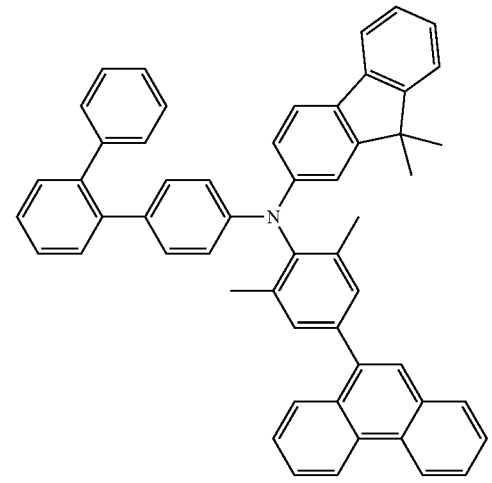

-continued
202
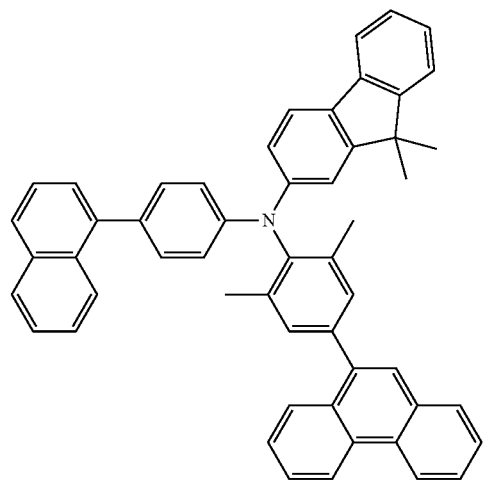
203
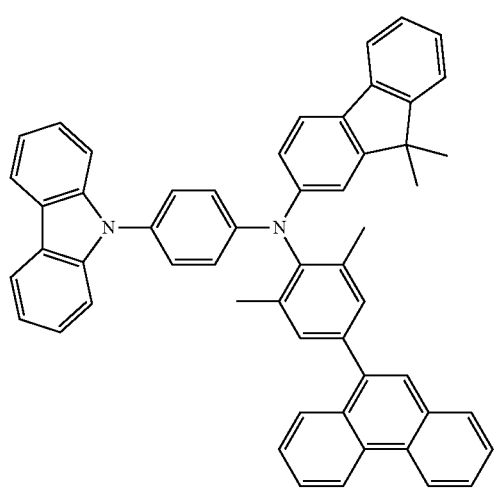
204
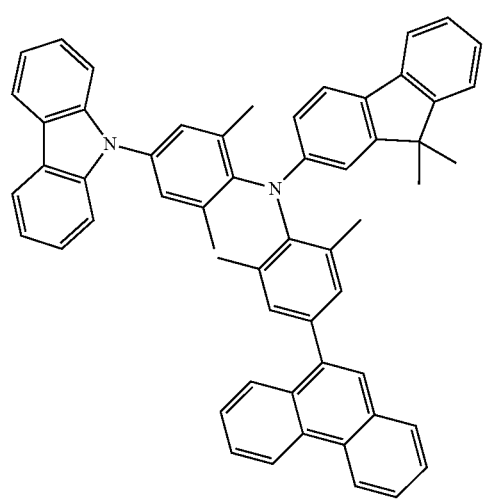
-continued
205
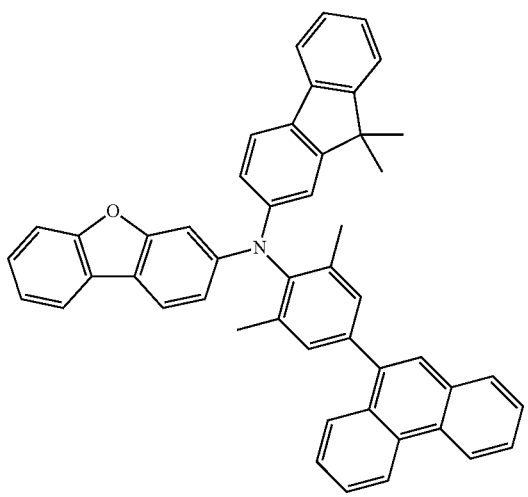
206
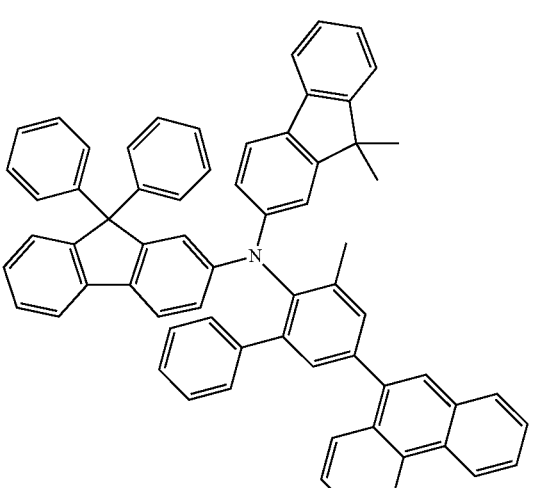
207

81
-continued
208
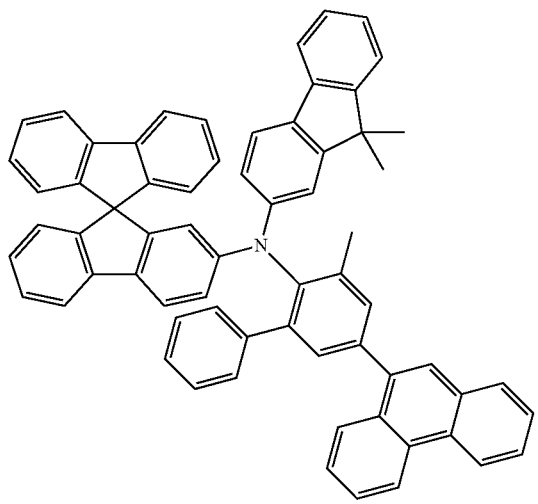
209
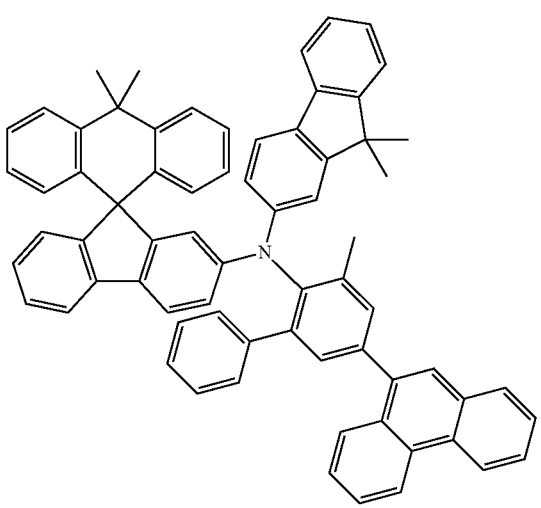
210
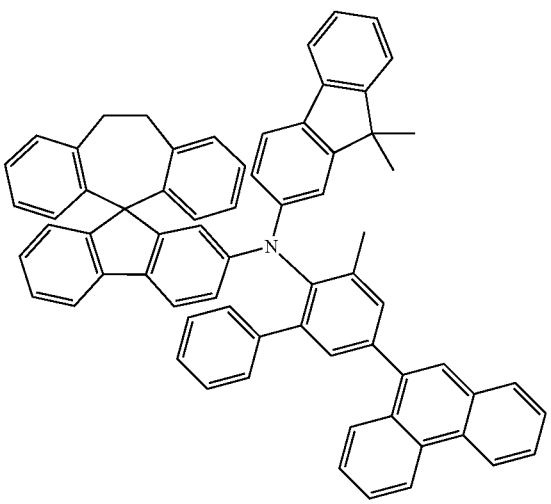
82
-continued
211
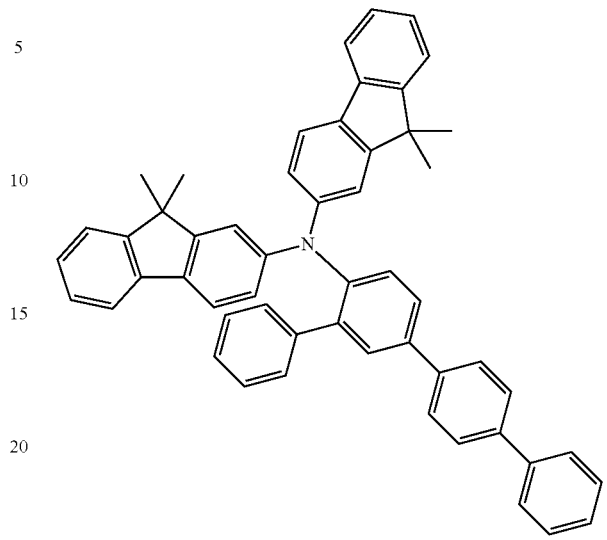
212
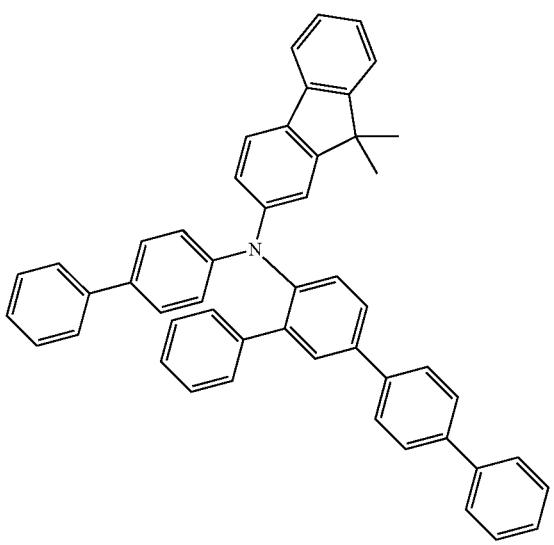
213
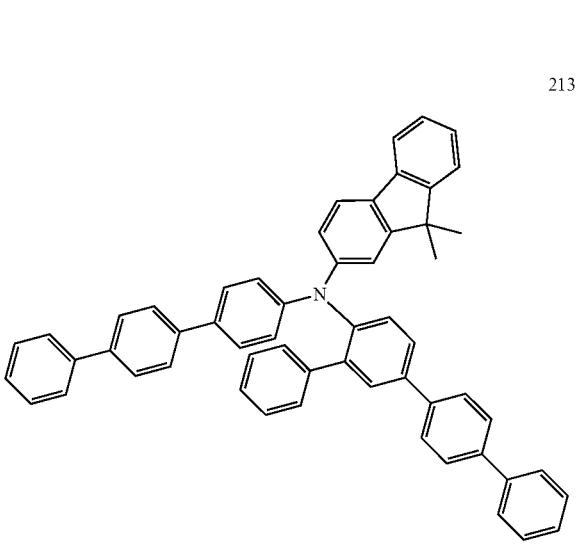

214
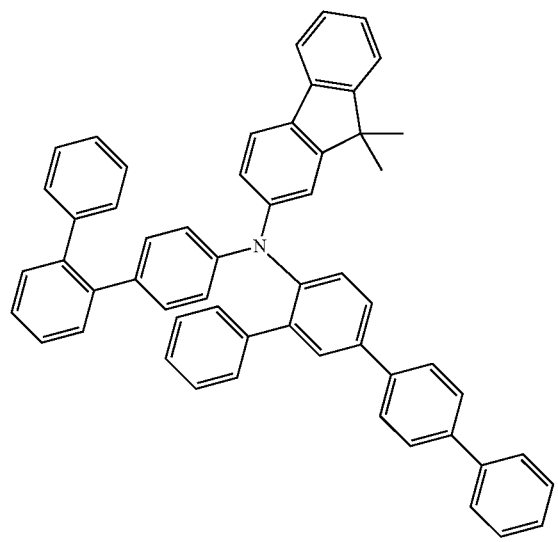
216
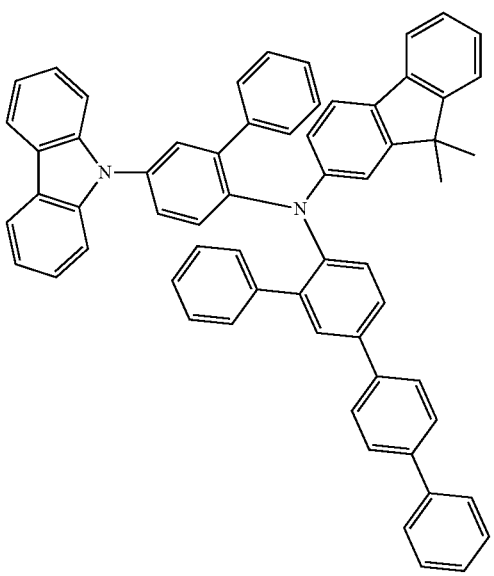
215
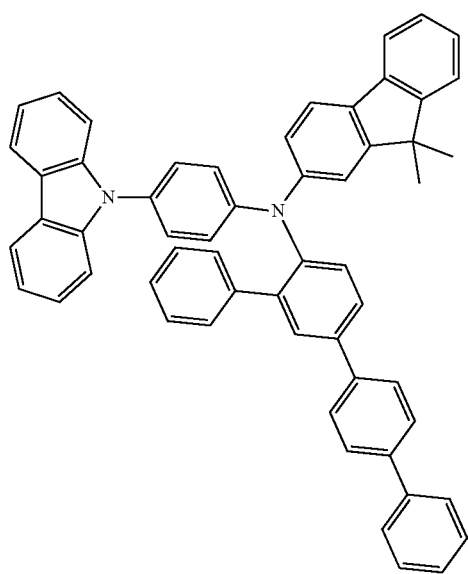
217
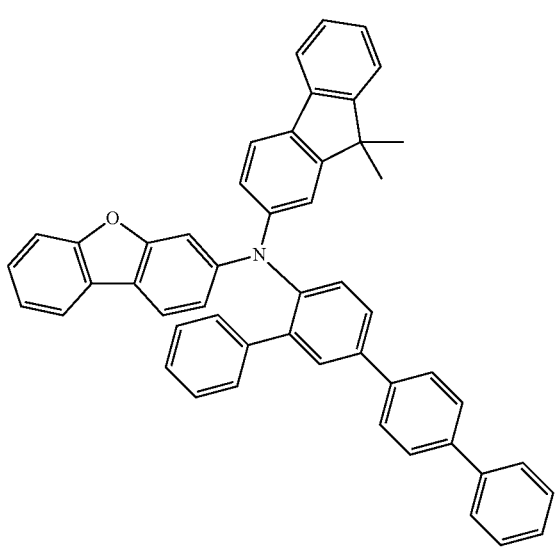

218
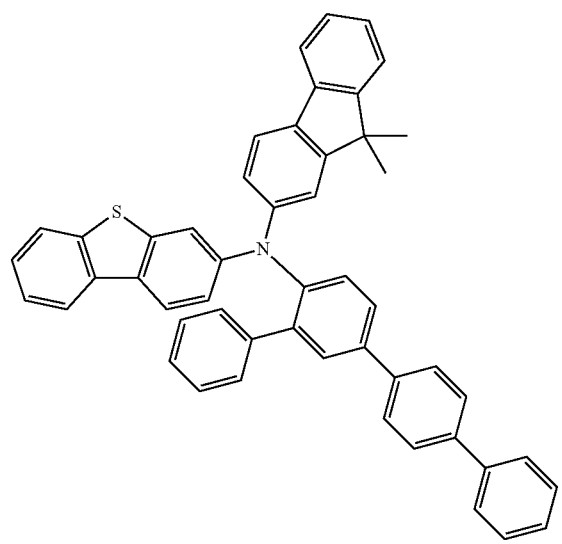
219
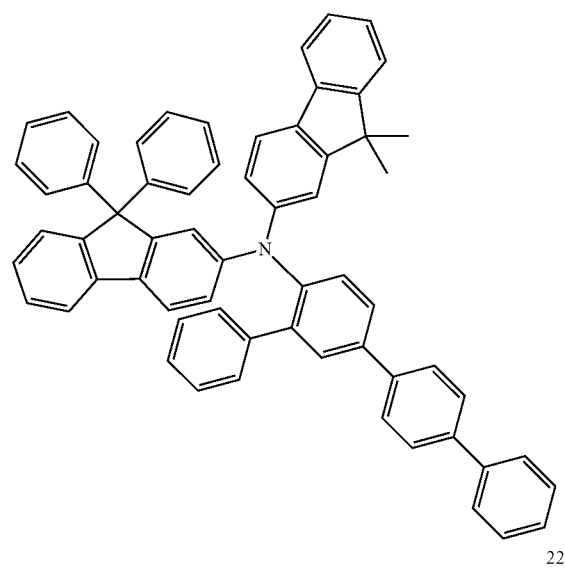
220
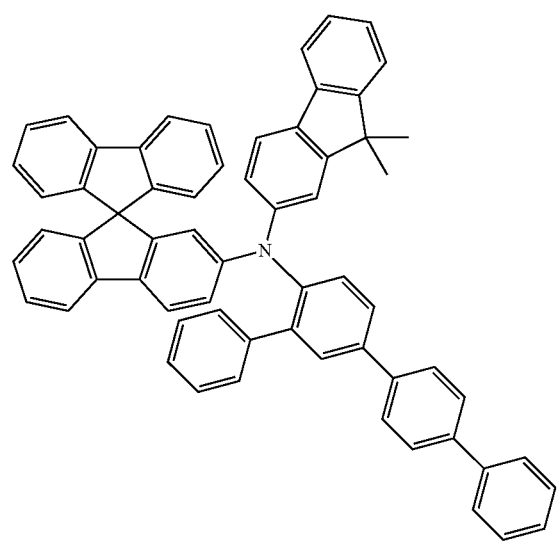
221
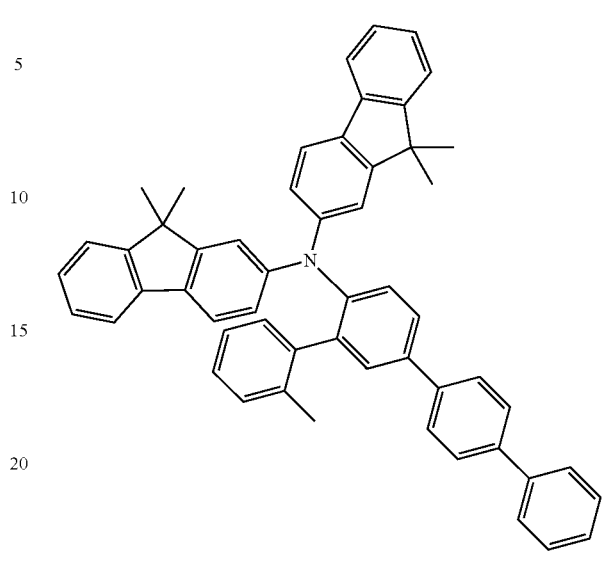
222
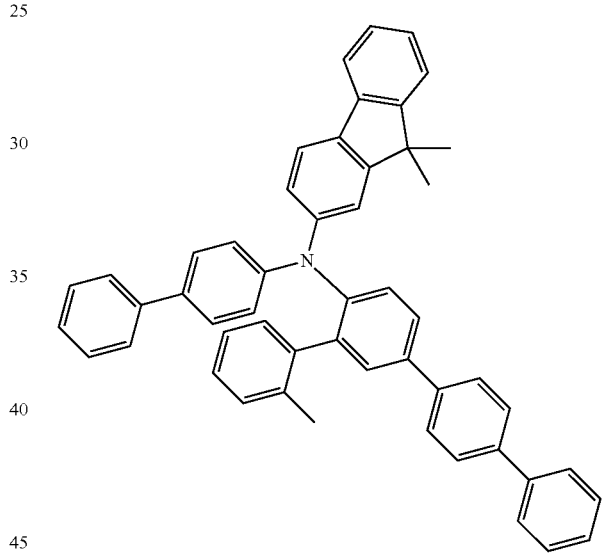
223
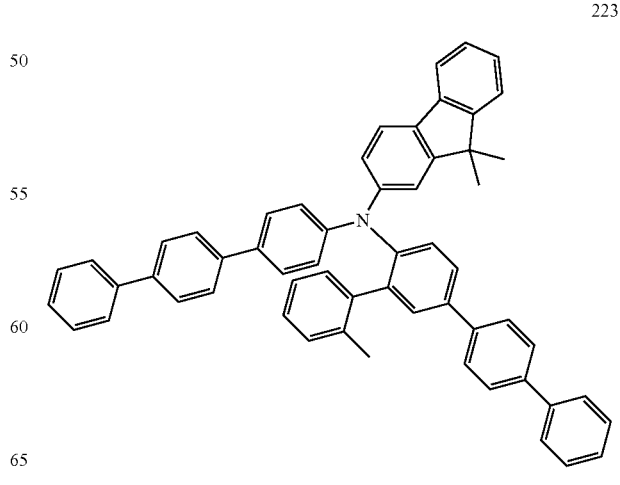

224
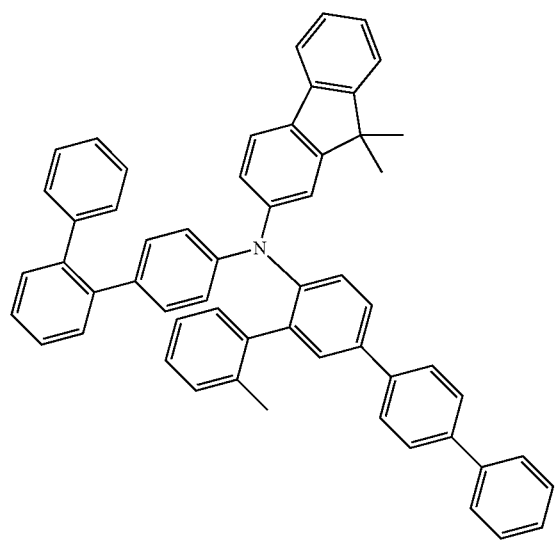
225
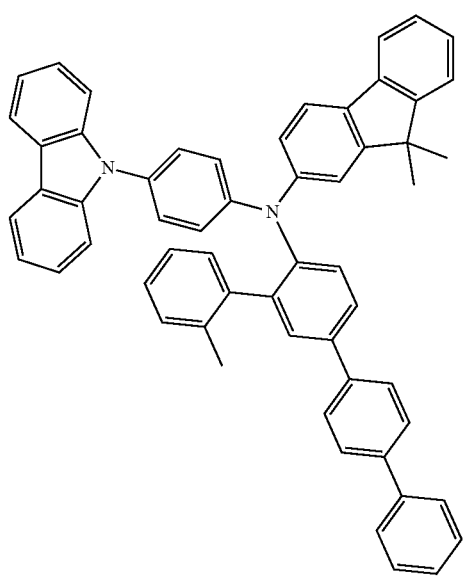
226
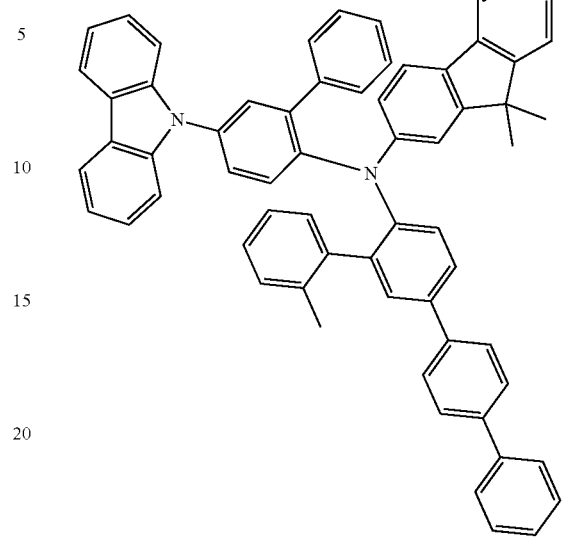
227
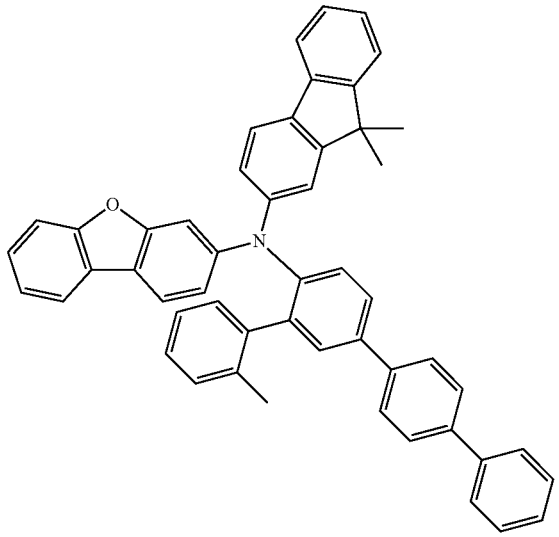

228
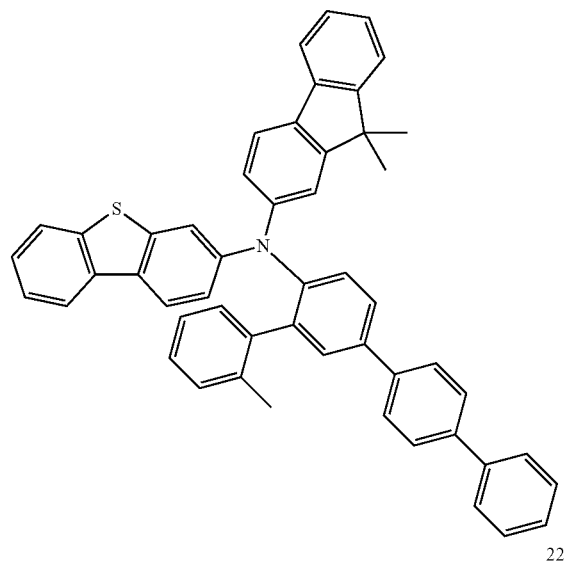
229
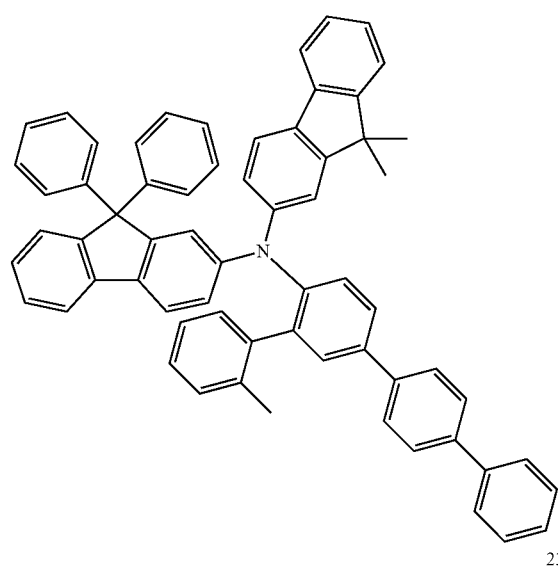
230
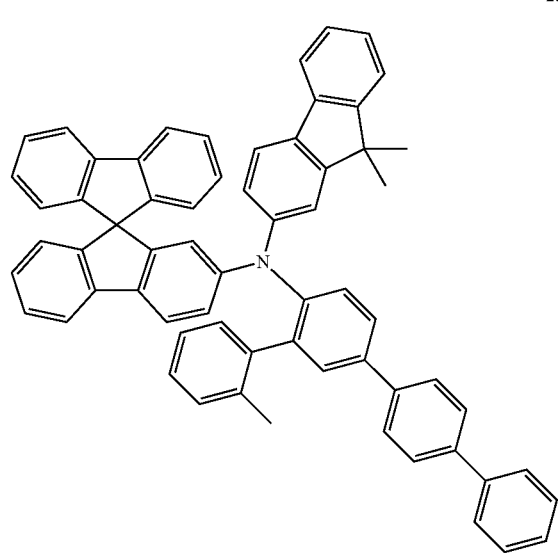
231
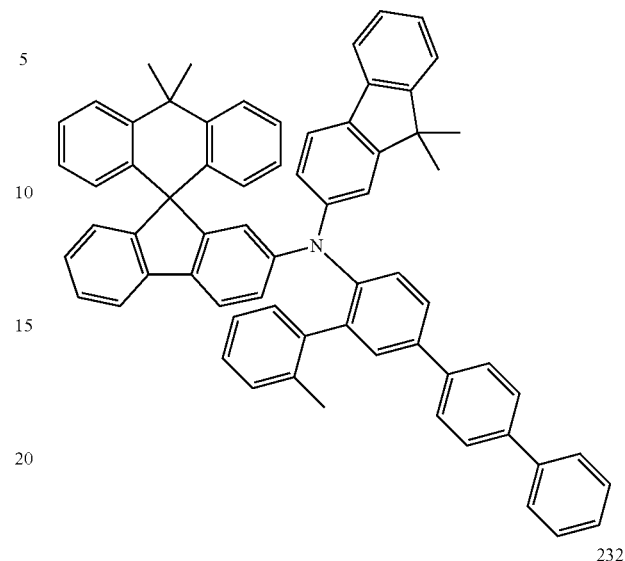
232
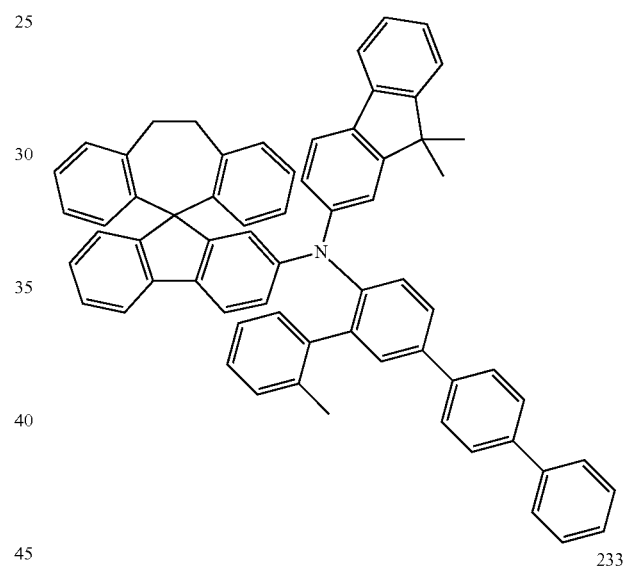
233
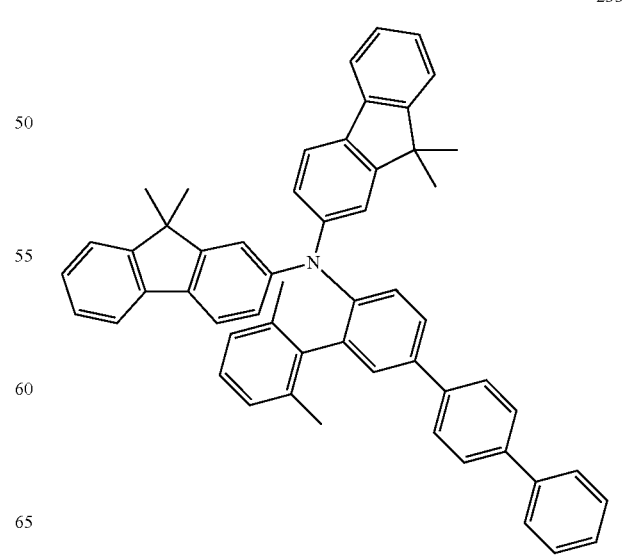

234
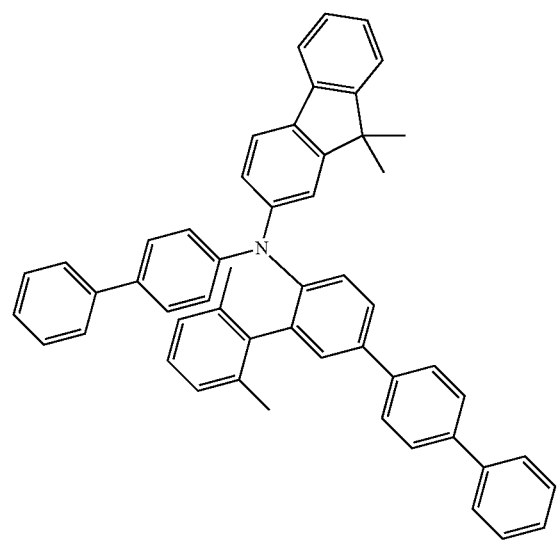
235
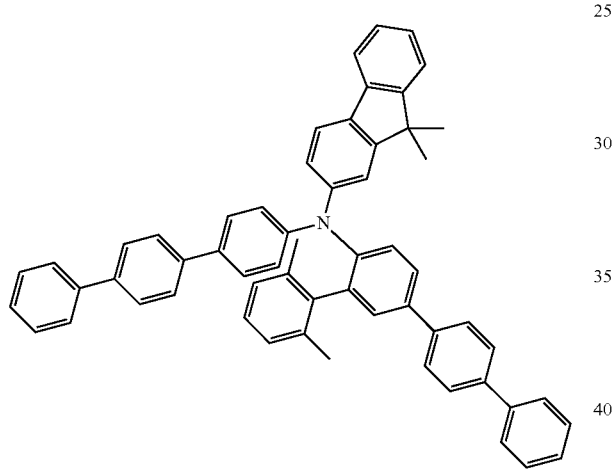
236
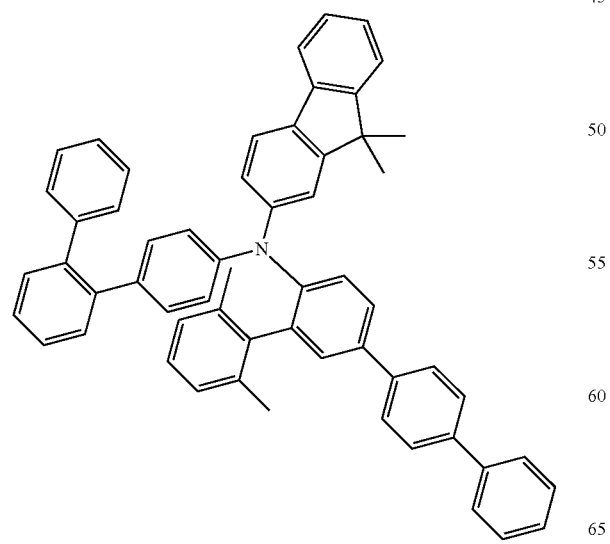
237
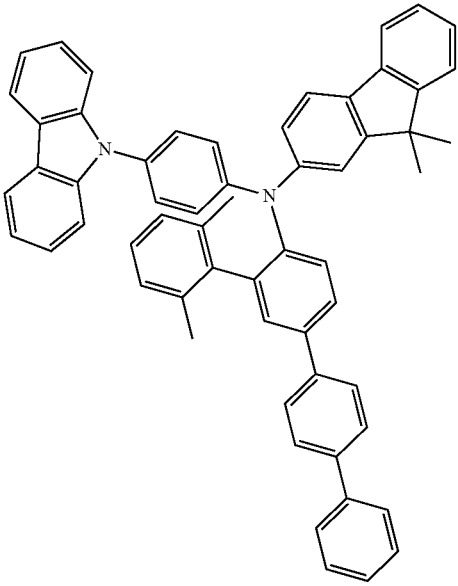
238
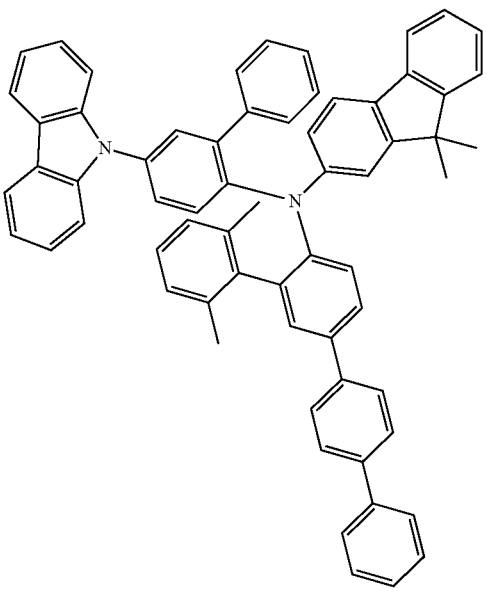

239
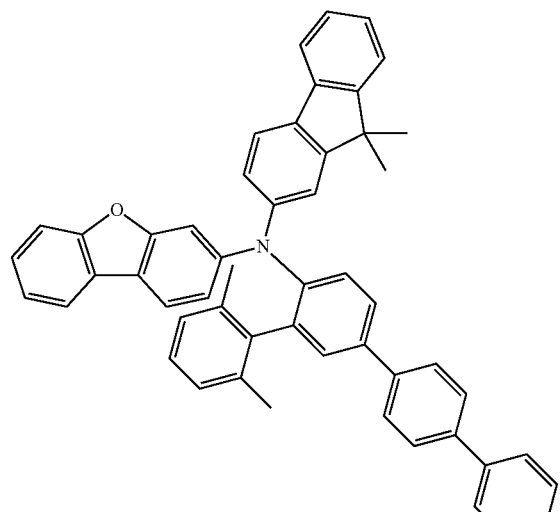
240
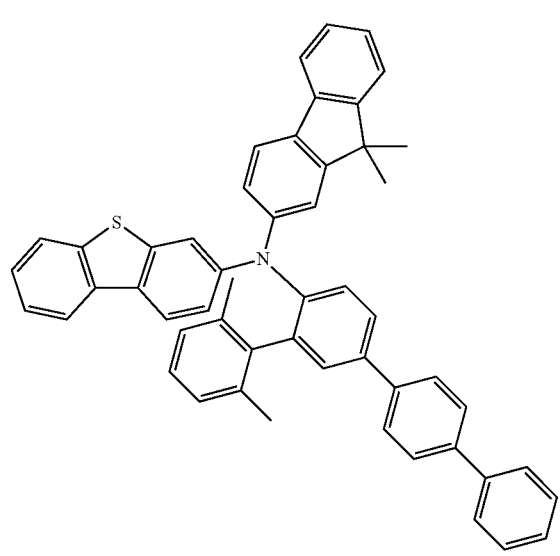
241
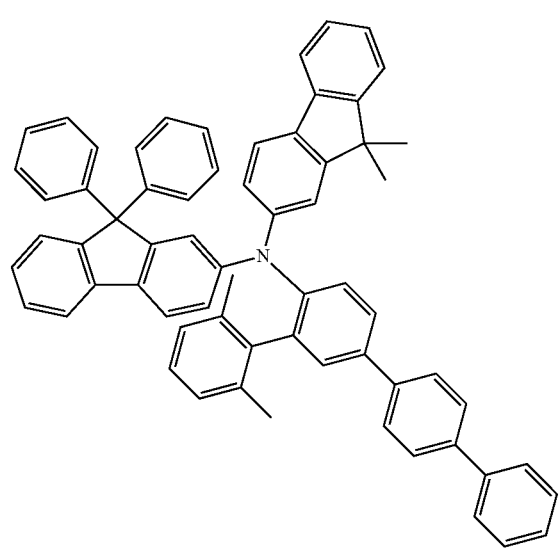
242
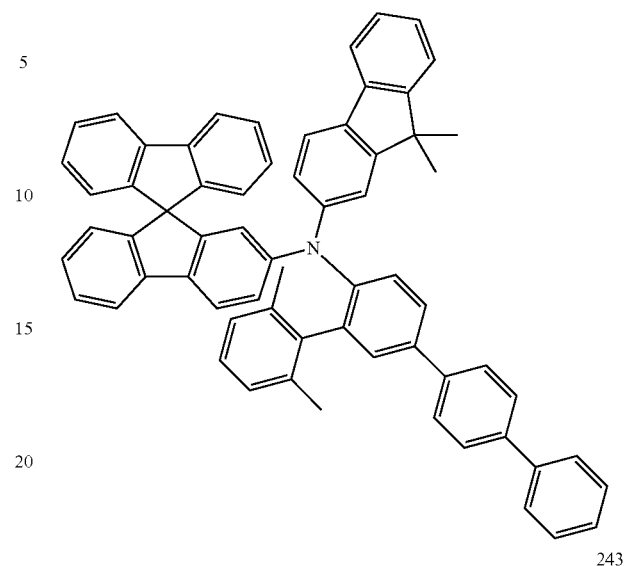
243
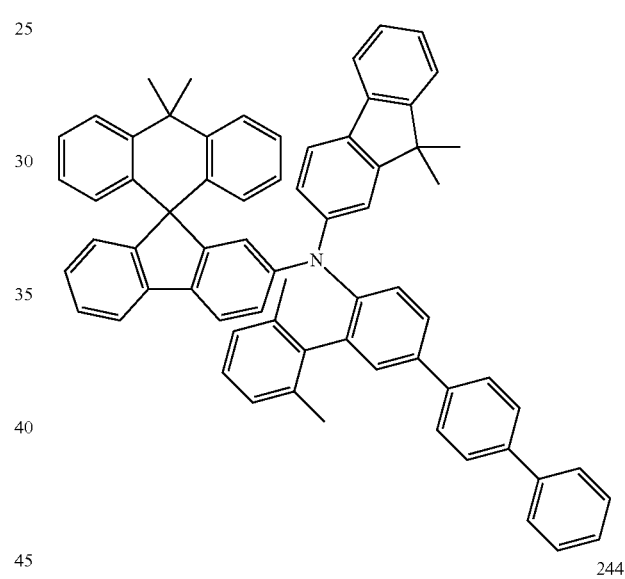
244
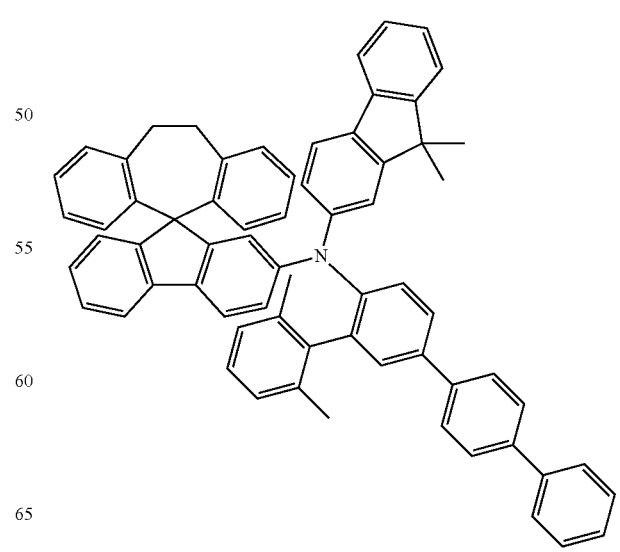

95
-continued
245
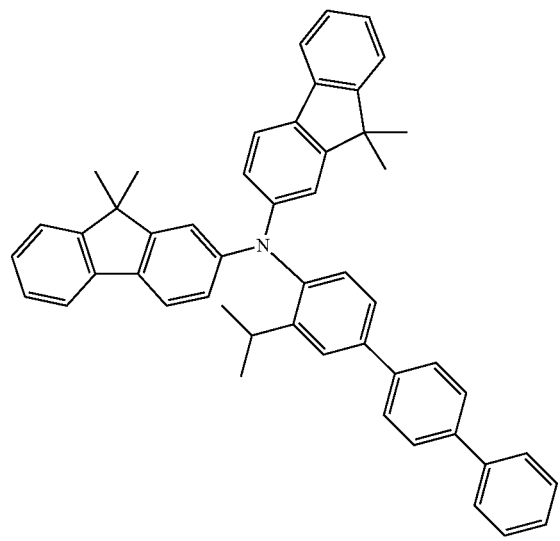
246
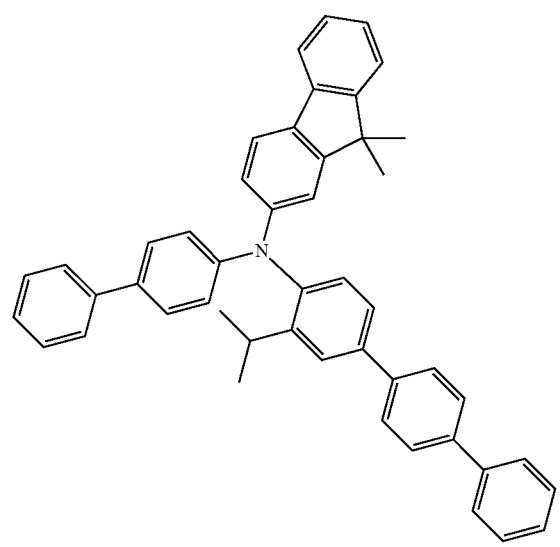
247
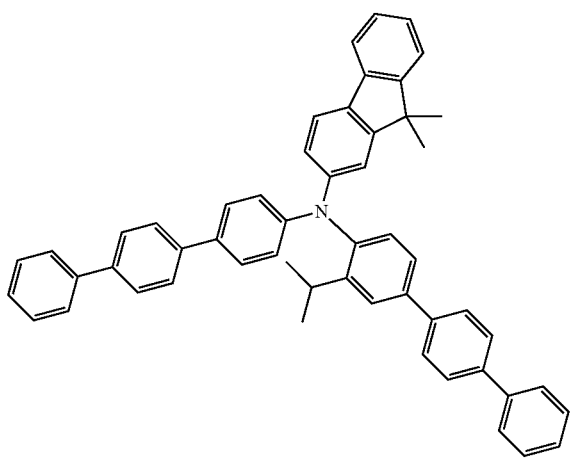
96
-continued
248
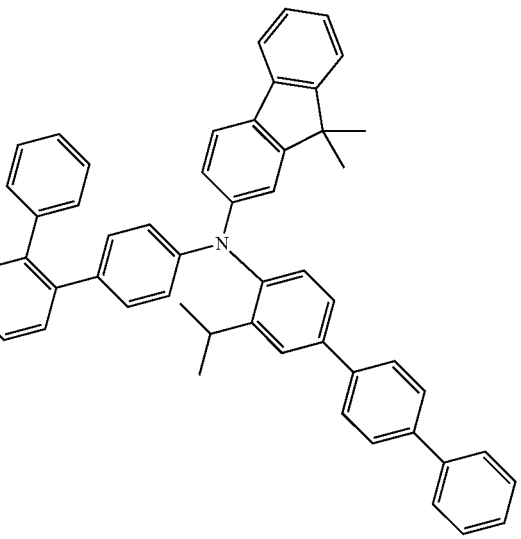
249
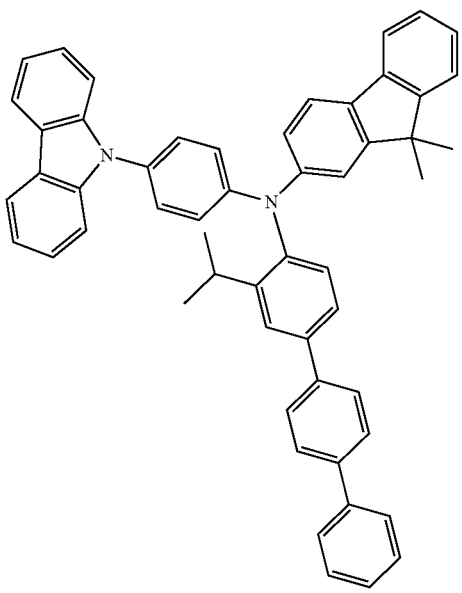

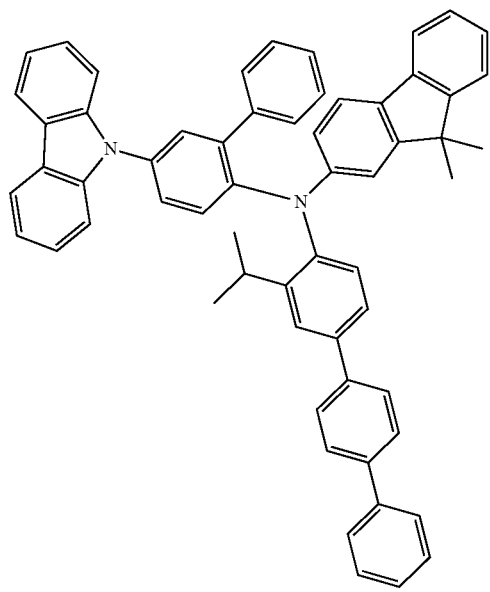
250
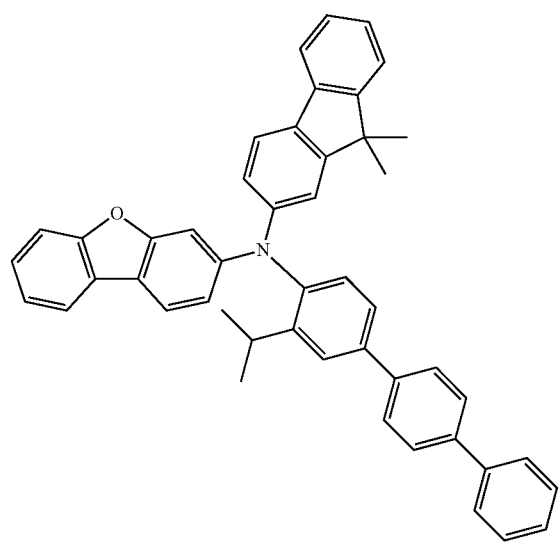
251
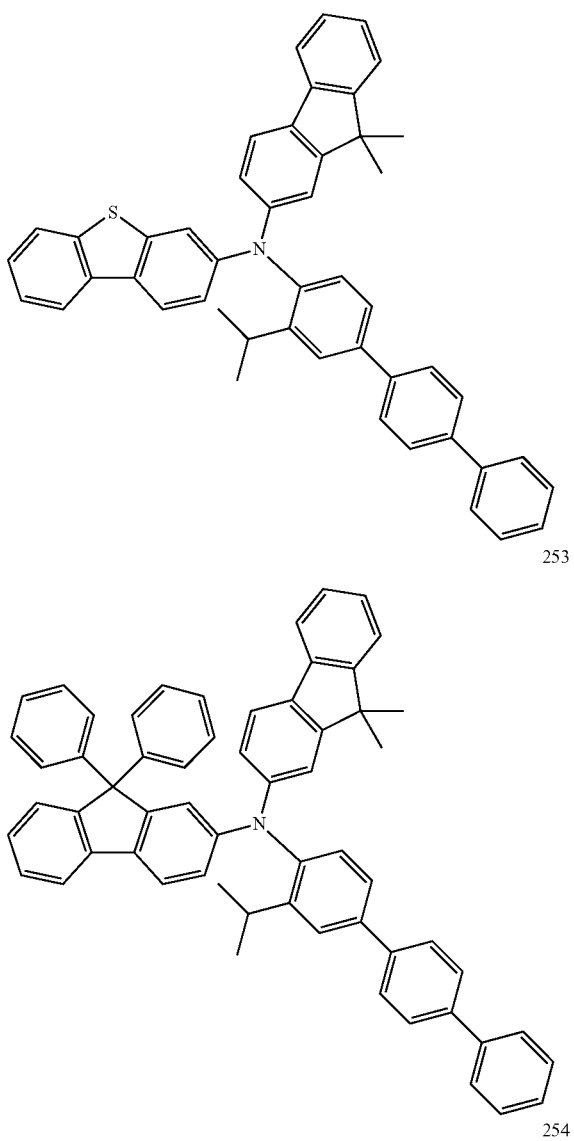
252
253
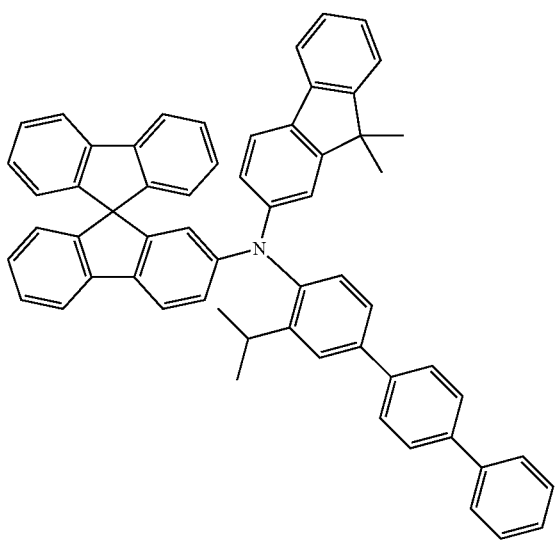
254

255
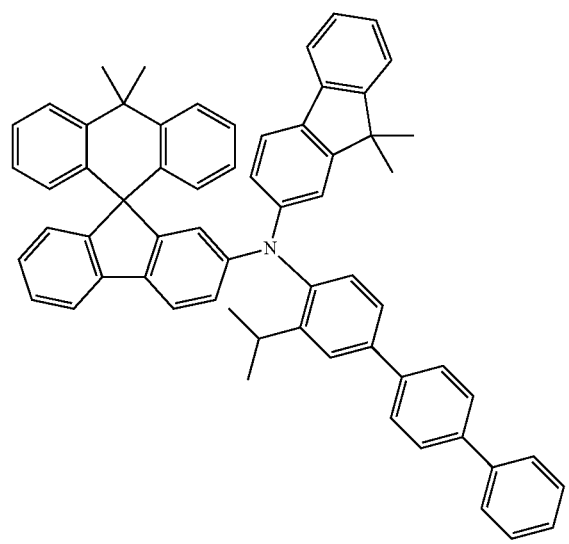
256
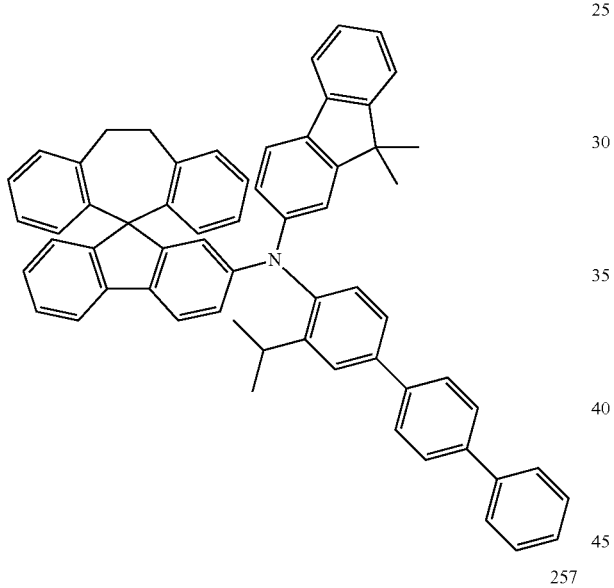
257
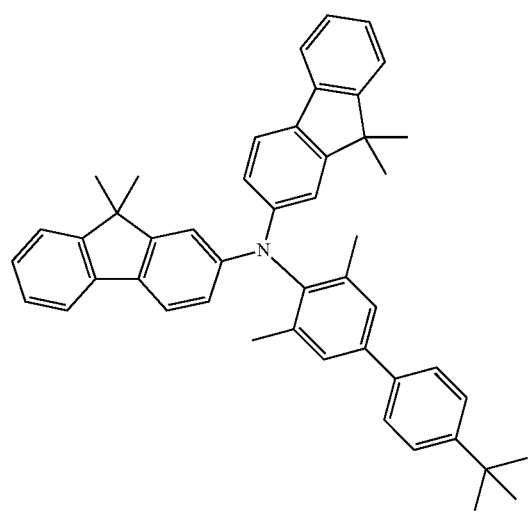
258
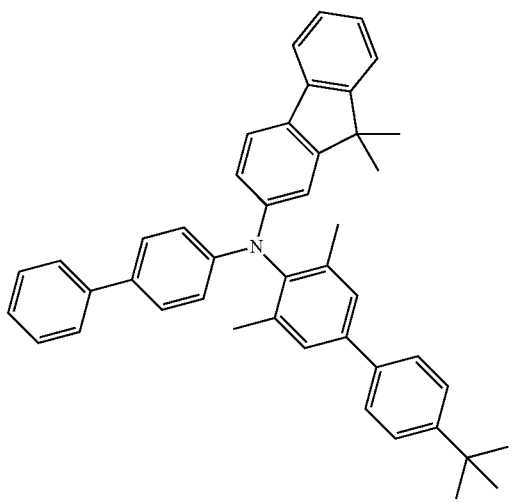
259
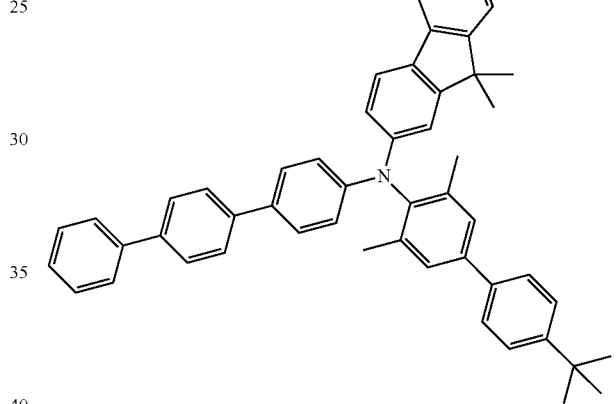
260
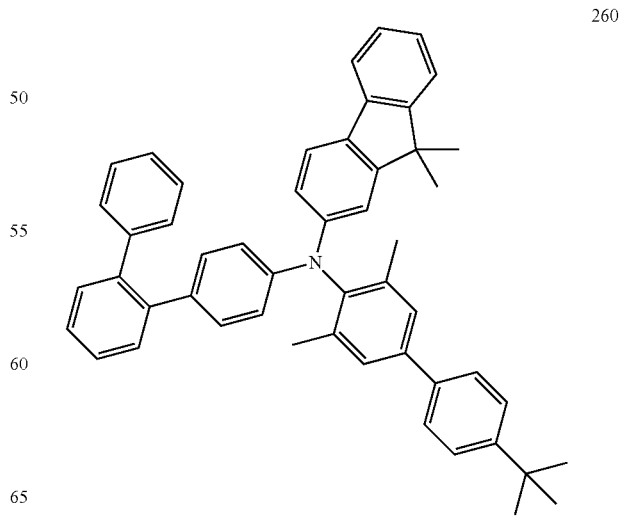

261
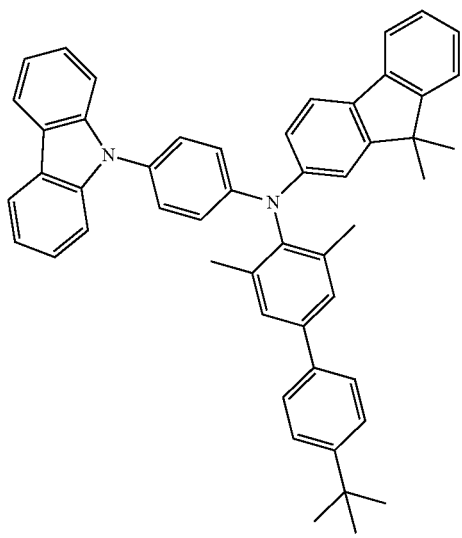
262
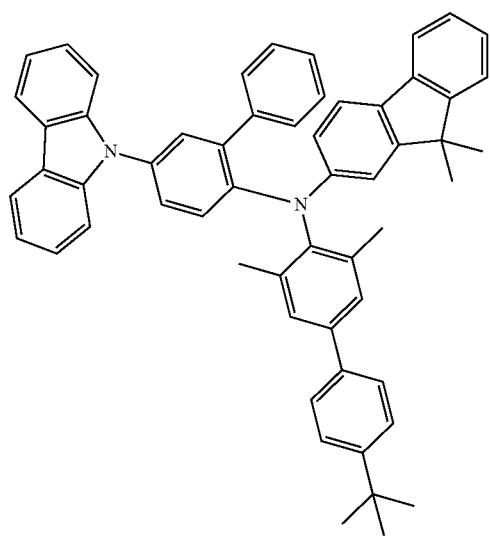
263
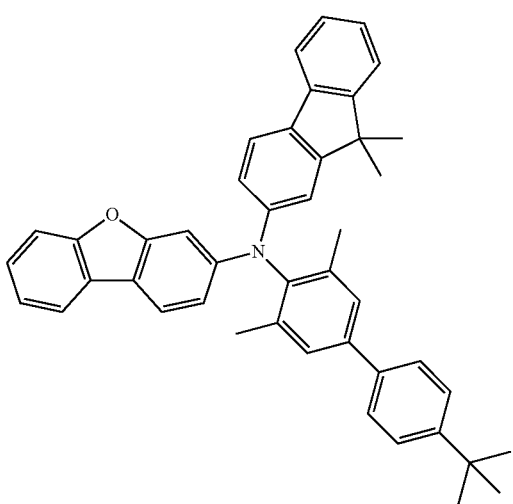
264
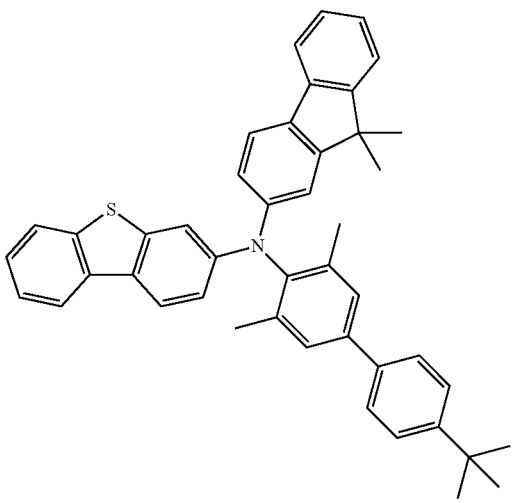
265
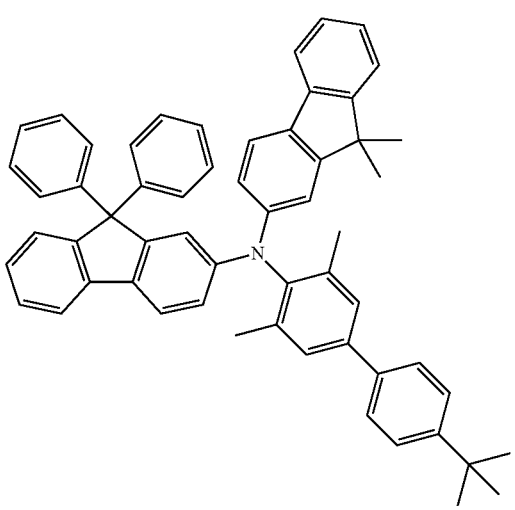
266
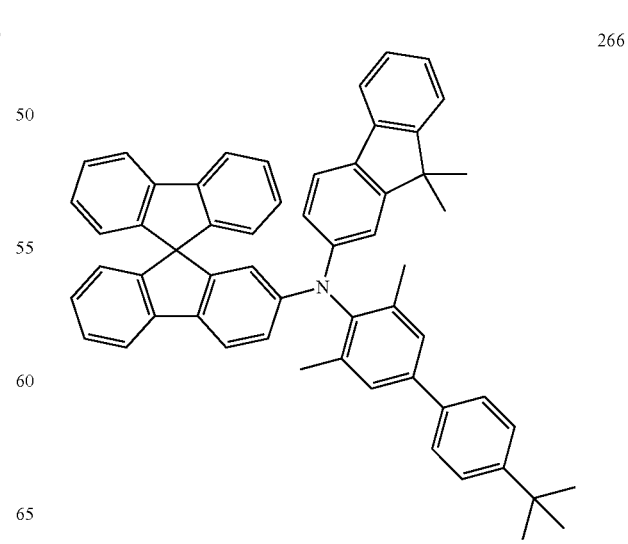

267
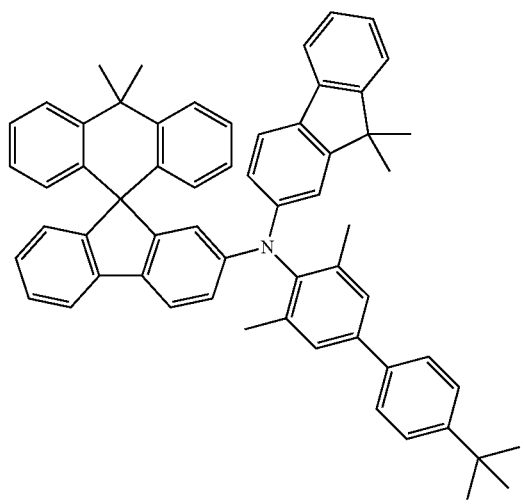
268
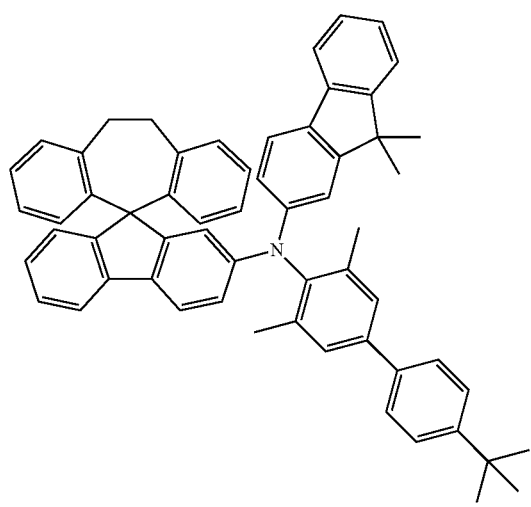
269
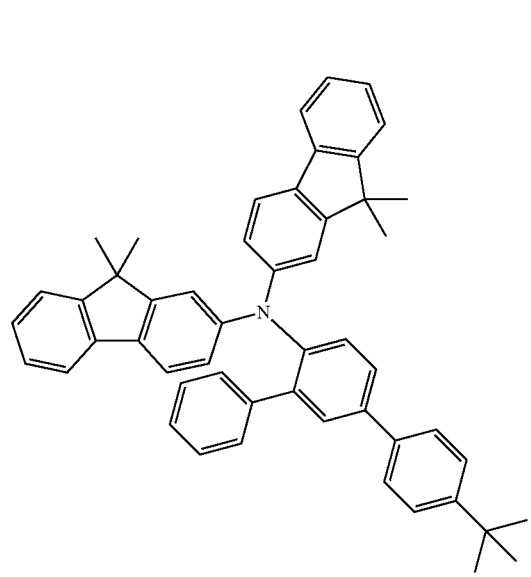
270
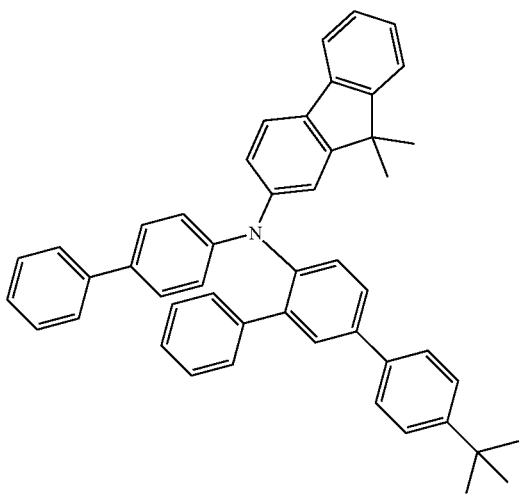
271
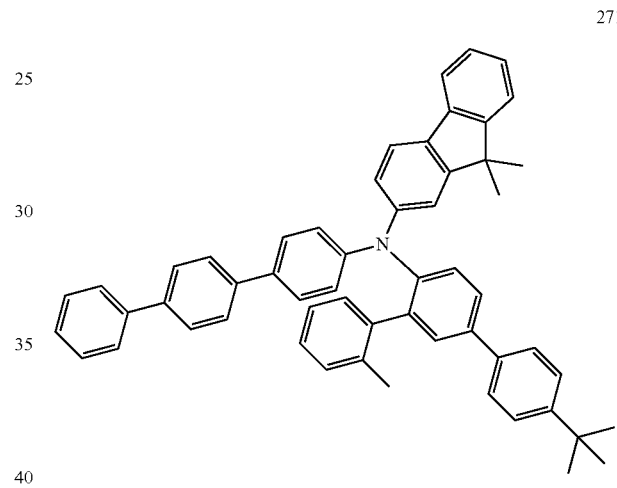
272
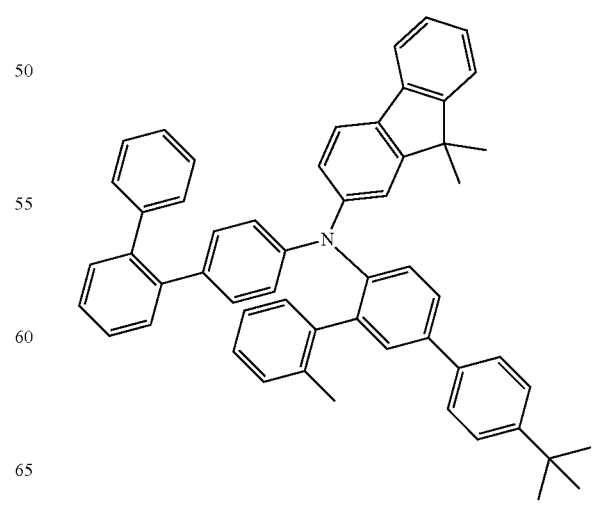

273 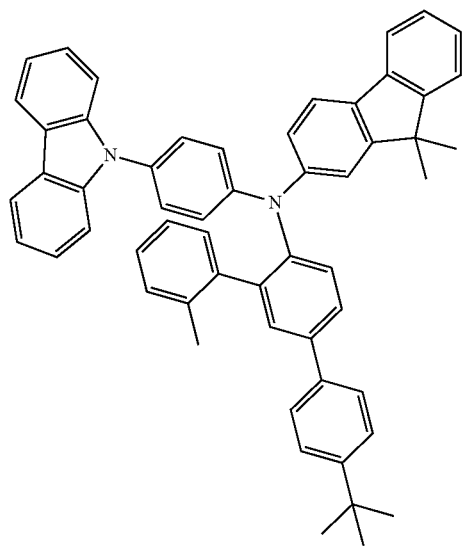
274 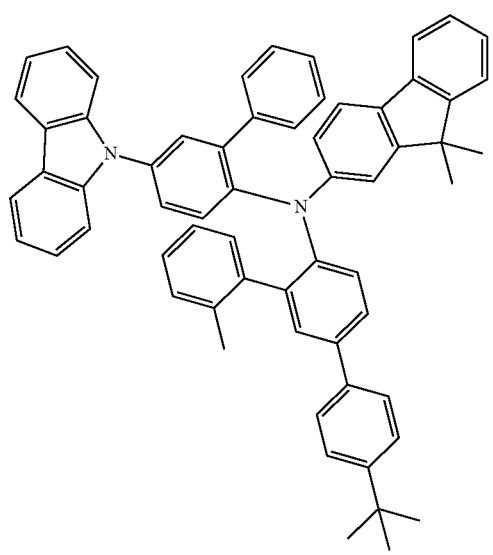
275 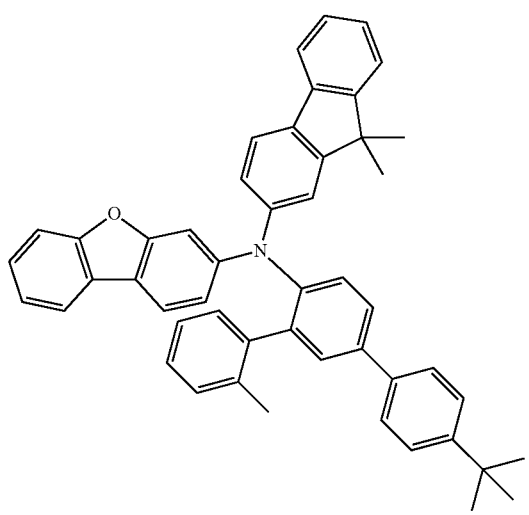
276 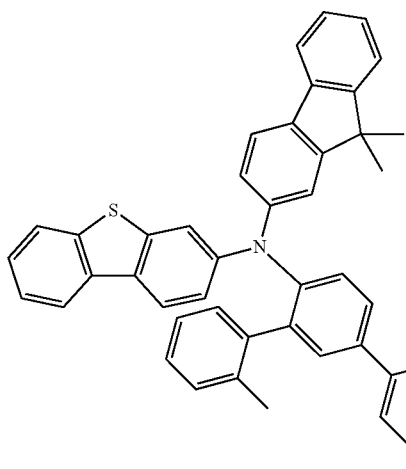
277 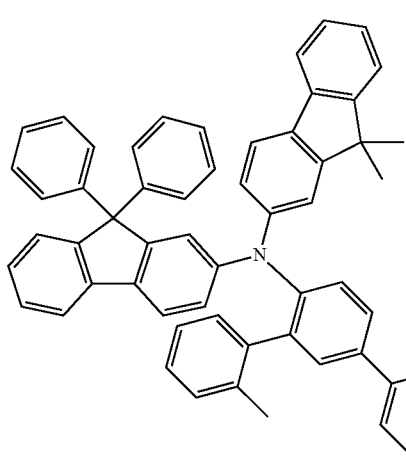
278 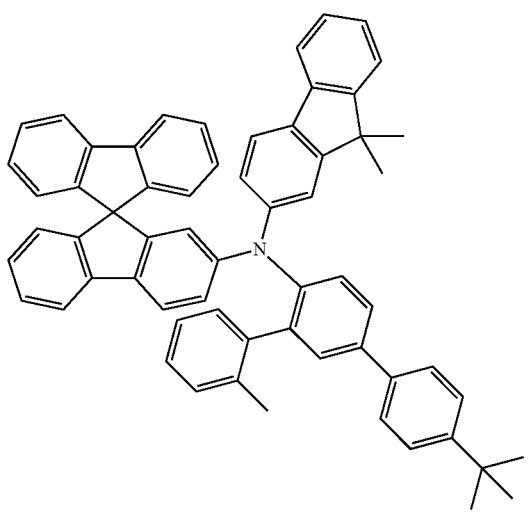

279
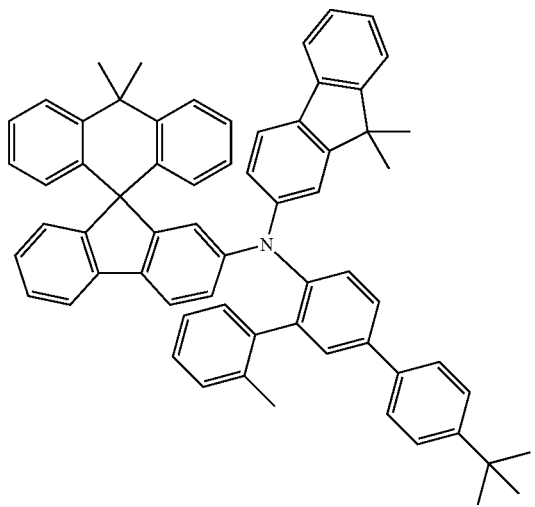
280
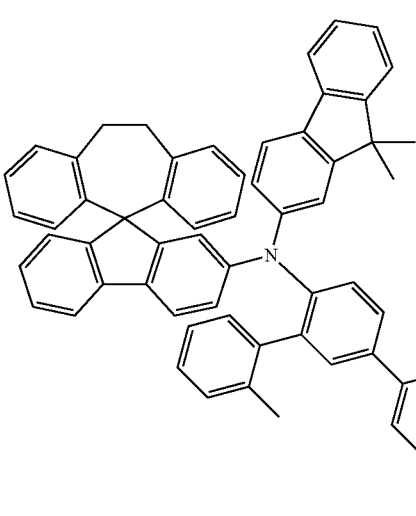
281
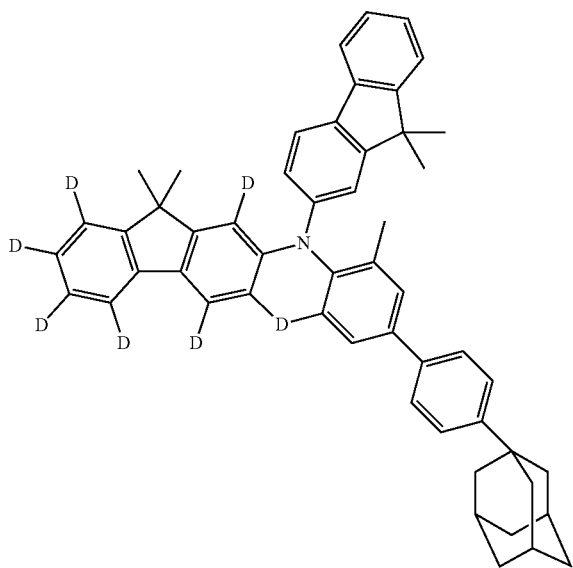
282
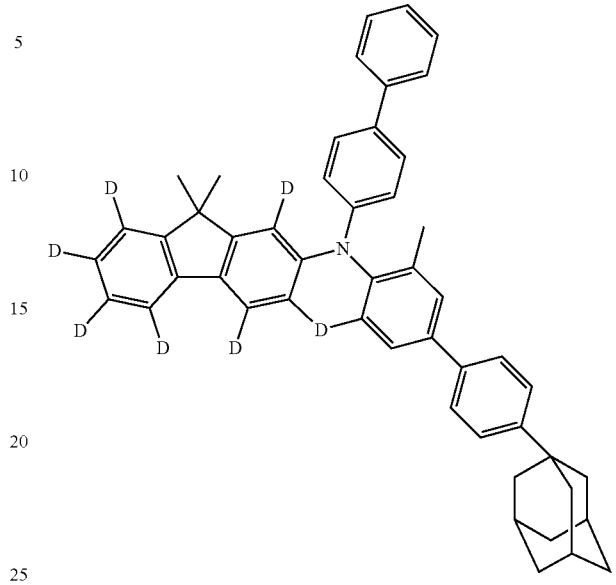
283
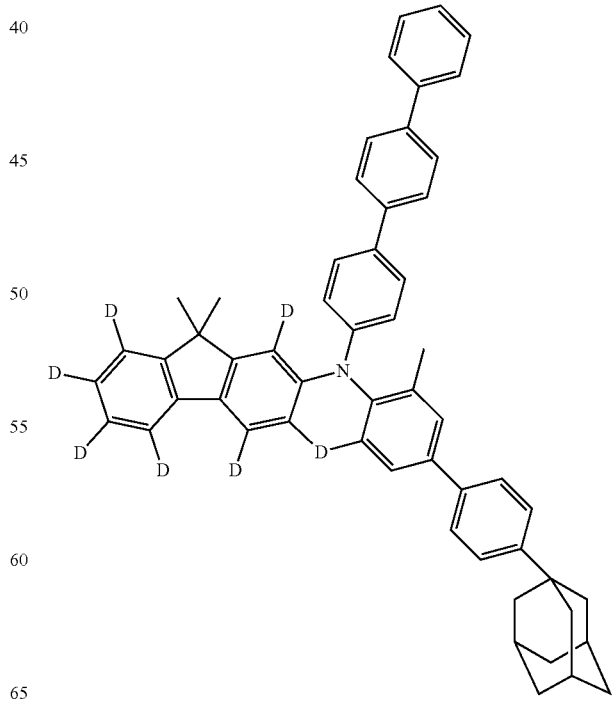

284
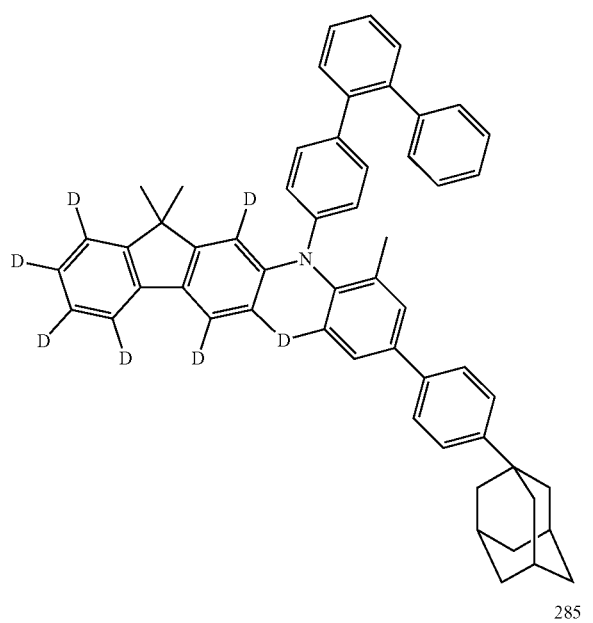
285
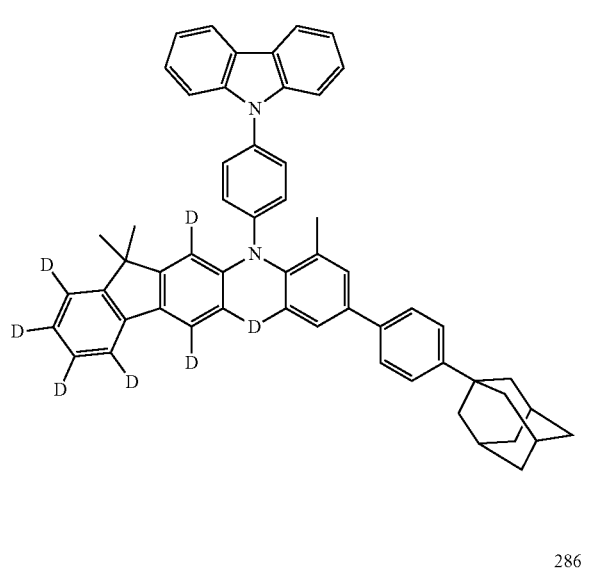
286
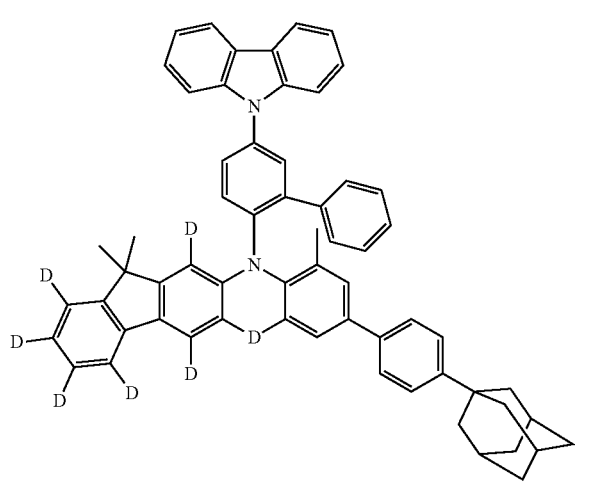
287
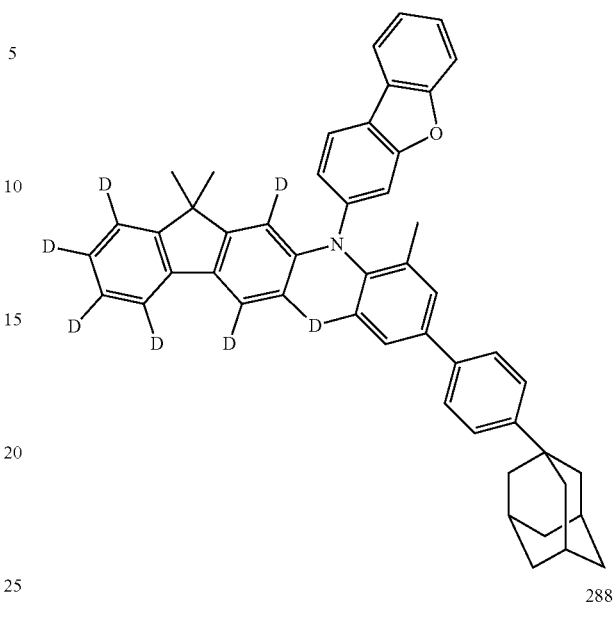
288
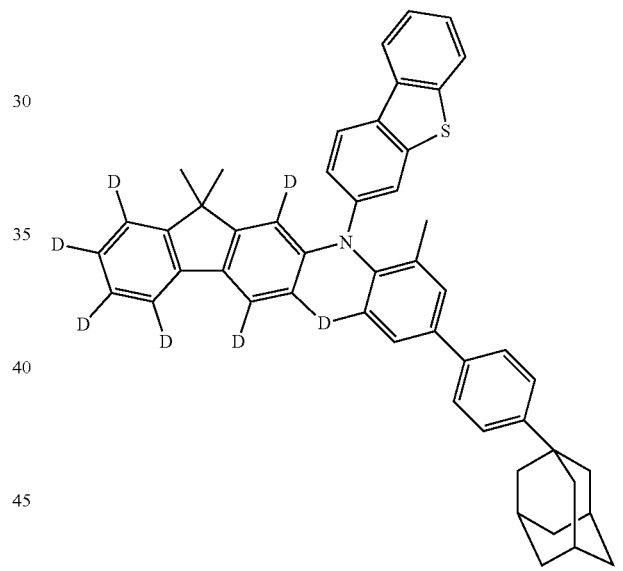
289
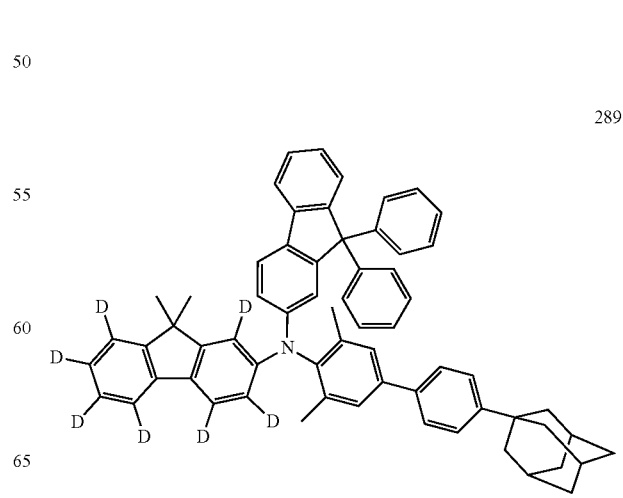

290
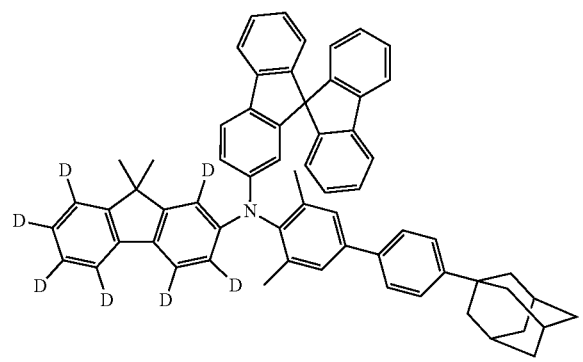
291
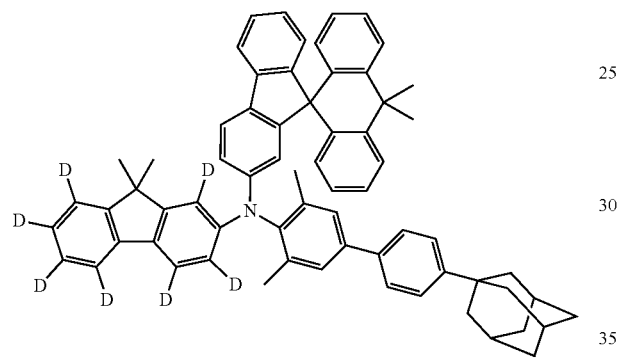
292
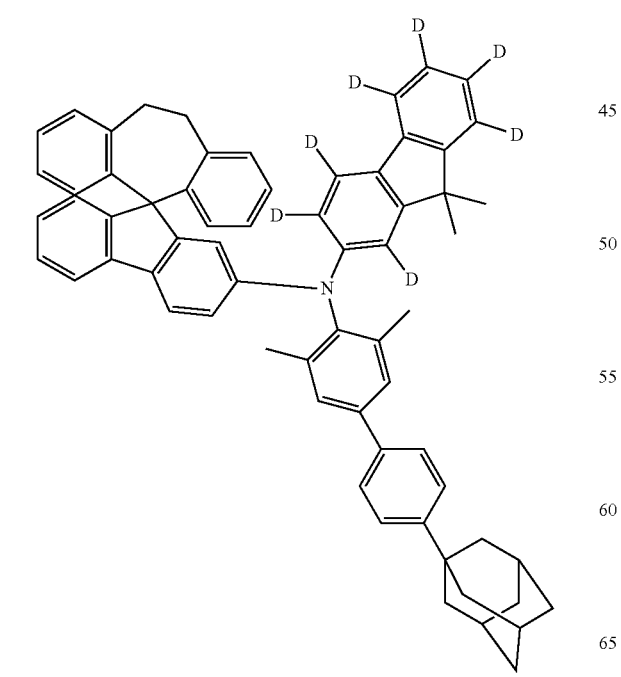
293
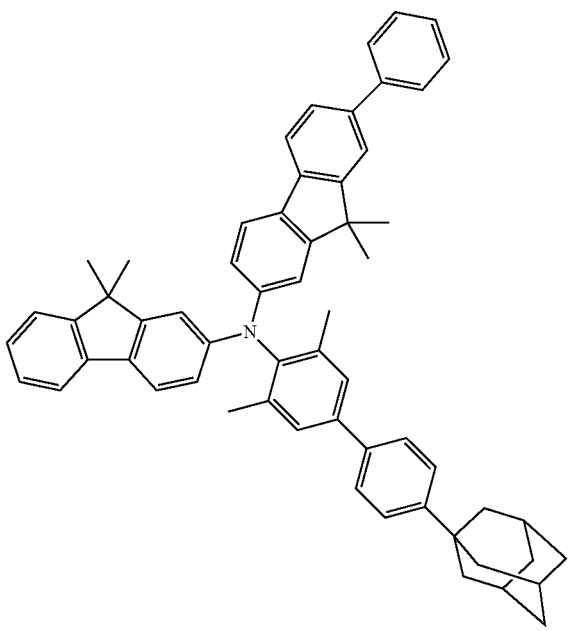
294

295
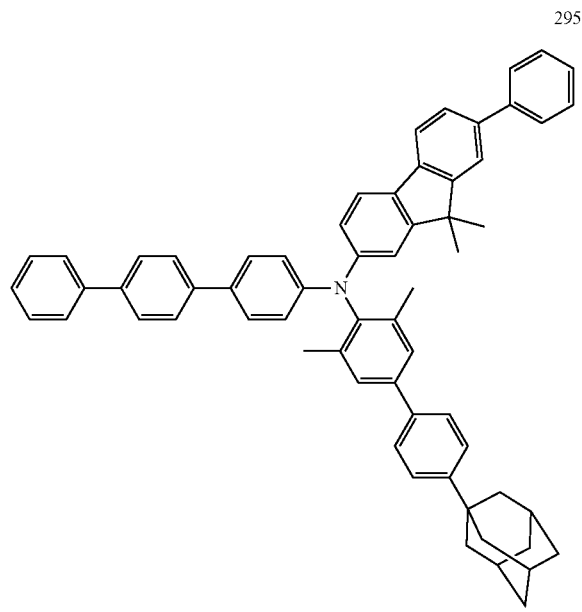
297
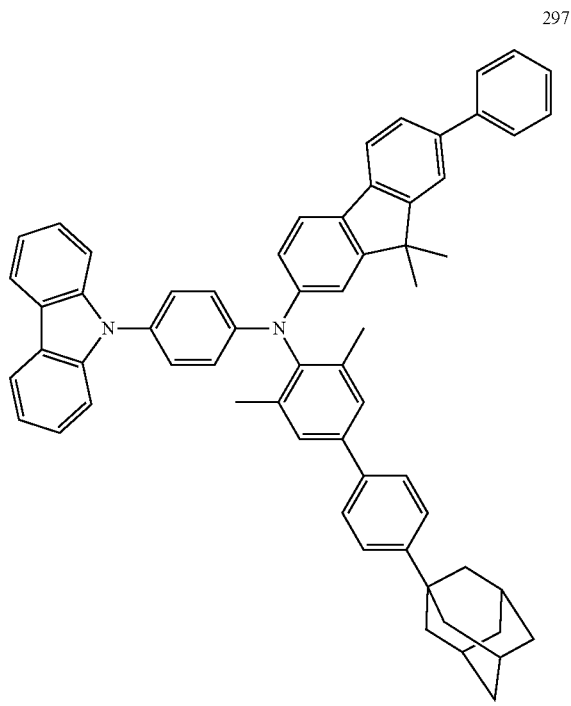
296
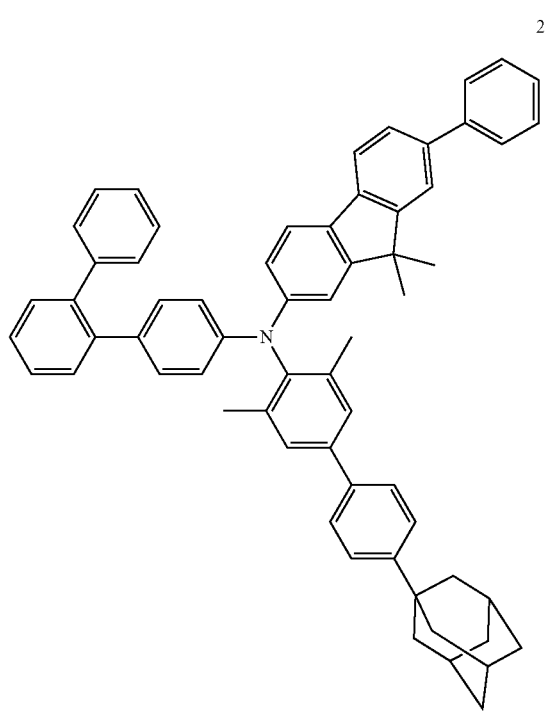
298
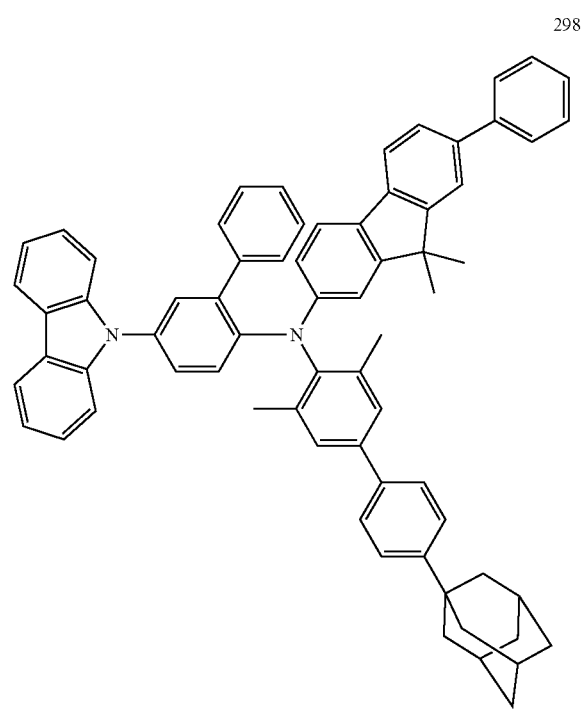

299
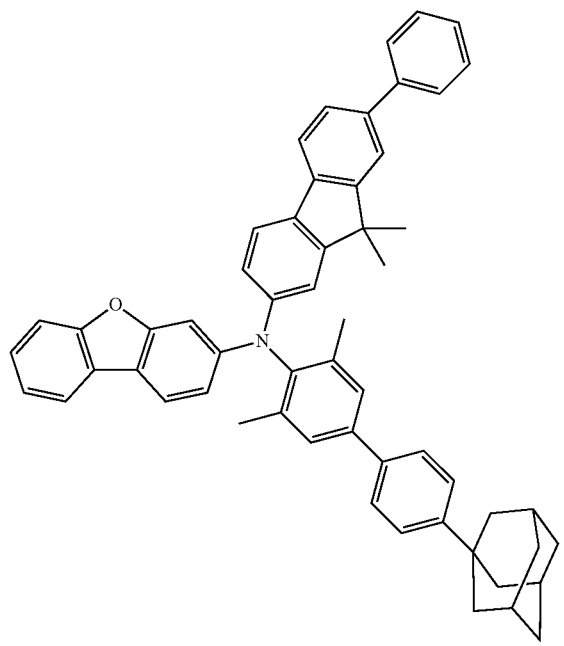
301
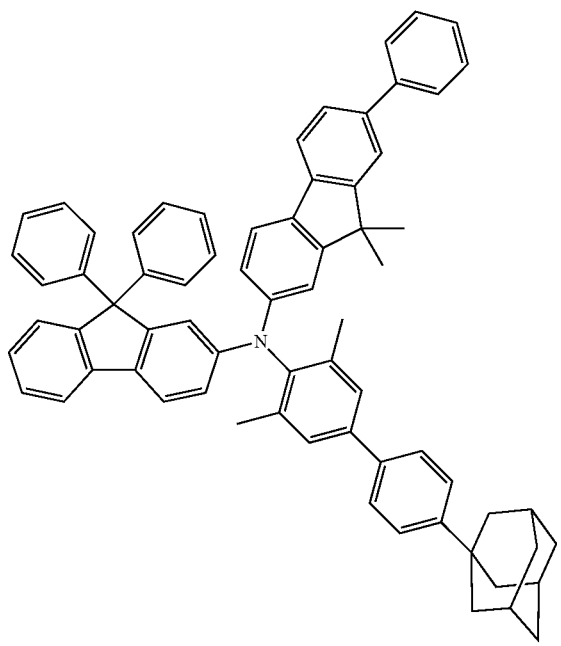
300
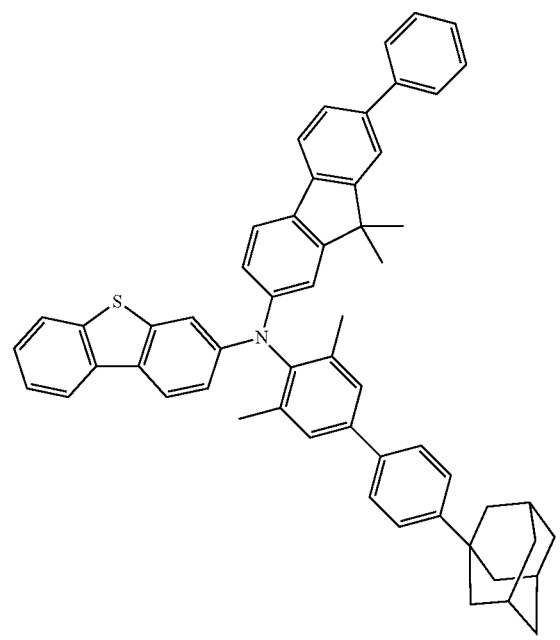
302
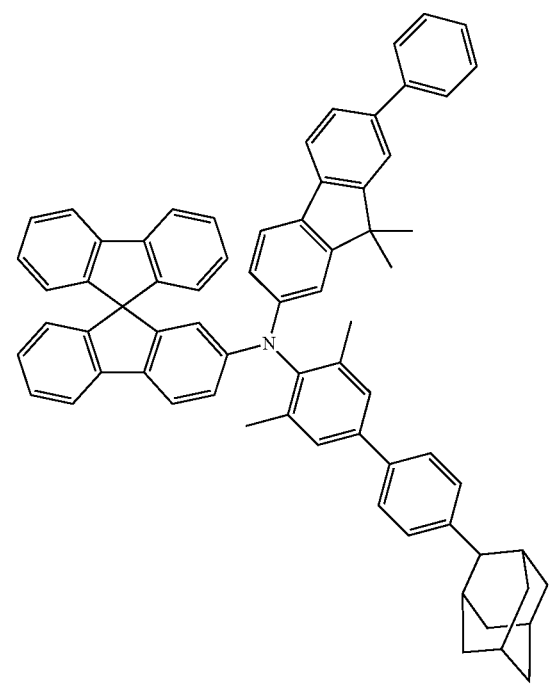

-continued

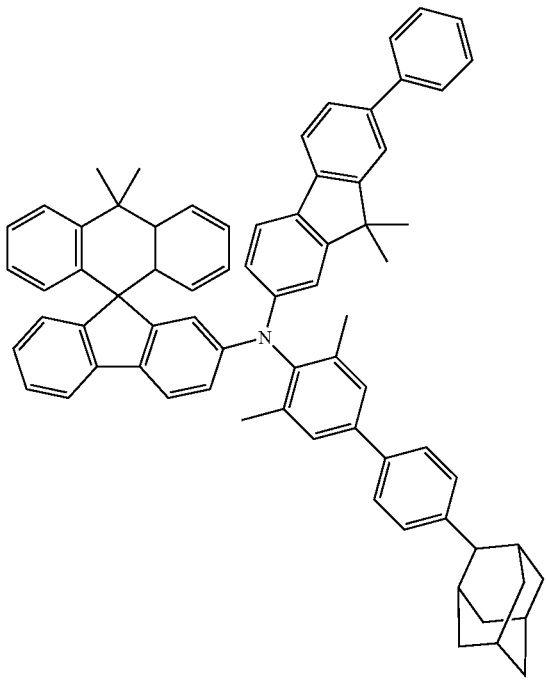

303

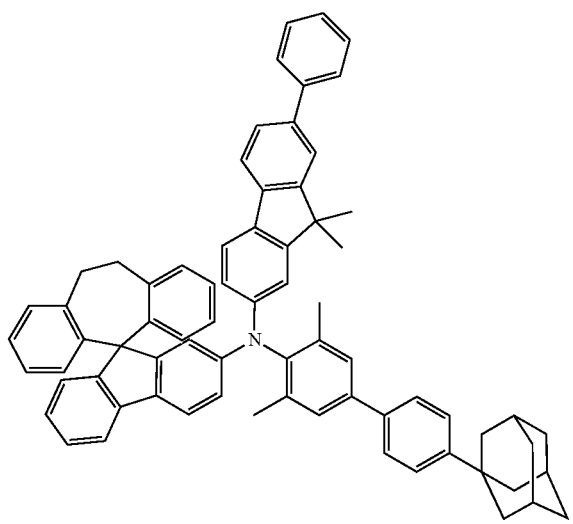

304

In another implementation of the present disclosure, there is provided an organic light-emitting device that includes a first electrode, a second electrode, and at least one organic material layer between the first and second electrodes, wherein the organic material layer contains the compound represented by the Chemical Formula 1:

[Chemical Formula 1]

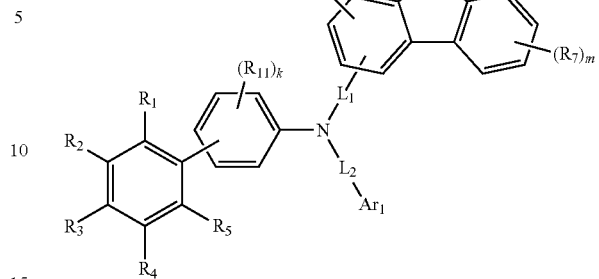

where in the Chemical Formula 1,

X is selected from a group consisting of $CR_9R_{10}$, each of $L_1$ and $L_2$ independently represents one selected from a group consisting of a single bond, a substituted or unsubstituted C6 to C30 arylene group, a substituted or unsubstituted C3 to C30 heteroarylene group, a substituted or unsubstituted C1 to C20 alkylene group, a substituted or unsubstituted C2 to C20 alkenylene group, a substituted or unsubstituted C1 to C20 heteroalkylene group, a substituted or unsubstituted C3 to C20 heterocycloalkylene group, a substituted or unsubstituted C1 to C20 heteroalkenylene group, and a substituted or unsubstituted C3 to C20 heterocycloalkenylene group, $Ar_1$ represents one selected from a group consisting of a substituted or unsubstituted C6 to C30 aryl group, a substituted or unsubstituted C3 to C30 heteroaryl group, a substituted or unsubstituted C1 to C20 alkyl group, a substituted or unsubstituted C2 to C20 alkenyl group, substituted or unsubstituted C2 to C20 alkynyl group, a substituted or unsubstituted C1 to C20 heteroalkyl group, a substituted or unsubstituted C3 to C20 heterocycloalkyl group, and a substituted or unsubstituted C1 to C20 heteroalkenyl group, $R_1$ to $R_7$ and $R_9$ to $R_{11}$ are the same as or different from each other, and each of $R_1$ to $R_7$ and $R_9$ to $R_{11}$ independently represents one selected from a group consisting of hydrogen, deuterium, a substituted or unsubstituted C1 to C20 alkyl group, a substituted or unsubstituted C3 to C20 cycloalkyl group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C7 to C20 aralkyl group, a substituted or unsubstituted C6 to C30 aryl group, a substituted or unsubstituted C3 to C30 heteroaryl group, and a substituted or unsubstituted C3 to C20 heteroaralkyl group, adjacent two of $R_1$ to $R_7$ and $R_9$ to $R_{11}$ may be connected to each other to form a saturated or unsaturated alicyclic or aromatic monocyclic or polycyclic ring, the formed alicyclic or aromatic monocyclic or polycyclic ring may contain or may not contain at least one heteroatom selected from a group consisting of N, O, S and Si in addition to a carbon atom, a case where all of $R_1$ to $R_5$ are hydrogen is excluded, k is an integer from 1 to 4, m is an integer from 0 to 4, n is an integer from 0 to 3.

A detailed description of the compound represented by the Chemical Formula 1 is as described above.

The organic light-emitting device may include an organic material layer containing the compound represented by the Chemical Formula 1 as described above.

Specifically, the organic material layer containing the compound represented by the Chemical Formula 1 may include a hole transport layer and/or an auxiliary hole transport layer. In one implementation, the organic material layer includes a hole transport layer or an auxiliary hole transport layer, and contains the compound represented by the Chemical Formula 1.

In one implementation, the organic material layer may include at least two or more compounds represented by the Chemical Formula 1.

The organic material layer may include, in addition to the organic material layer containing the compound represented by Chemical Formula 1, at least one organic material layer selected from a group consisting of a hole injection layer, a hole transport layer, an auxiliary hole transport layer, a light-emitting layer, an auxiliary electron transport layer, an electron transport layer and an electron injection layer.

According to the present disclosure, the hole transport layer may be embodied as a single layer or a stack of a plurality of layers.

According to the present disclosure, the auxiliary hole transport layer may be embodied as a single layer or a stack of a plurality of layers.

FIG. 1 shows an organic light-emitting device according to one implementation of the present disclosure. In FIG. 1, the organic light-emitting device 100 includes an organic material layer 130, and in particular, includes an anode 110, a hole injection layer 131, a hole transport layer 132, a light emitting layer 133, an electron transport layer 134, and a cathode 120 in this order.

FIG. 2 shows an organic light-emitting device according to one implementation of the present disclosure. In FIG. 2, the organic light-emitting device 200 includes an organic material layer 230, and in particular, includes an anode 210, a hole injection layer 231, a hole transport layer 232, an auxiliary hole transport layer 233, a light-emitting layer 234, an electron transport layer 235, and a cathode 220 in this order.

The anode 110 or 210 feeds a hole into the light-emitting layer 133 or 234. The anode may contain a conductive material with a high work function to facilitate the feeding of the hole. When the organic light-emitting device is applied to a bottom emission organic light-emitting display device, the anode may be a transparent electrode made of a transparent conductive material. When the organic light-emitting device is applied to a top emission organic light-emitting display device, the anode may be a multilayer structure with a transparent electrode layer and a reflective layer made of a transparent conductive material.

The cathode 120 or 220 feeds electrons to the light-emitting layer 133 or 234. The cathode may contain a conductive material having a low work function to facilitate feeding of electrons. When the organic light-emitting device is applied to a bottom emission organic light-emitting display device, the cathode may be a reflective electrode made of metal. When the organic light-emitting device is applied to a top emission organic light-emitting display device, the cathode may be embodied as a transparent electrode made of a metal and having a small thickness.

Each of the light-emitting layers 133 and 234 may emit red R, green G and blue B light beams, and may be made of a phosphorescent material or a fluorescent material.

When each of the light-emitting layers 133 and 234 emits red light, and when each of the light-emitting layers 133 and 234 is made of a phosphorescent material, each of the light-emitting layers 133 and 234 may contain: a host material including CBP (carbazole biphenyl) or mCP(1,3-bis (carbazol-9-yl); and dopants doped into the host including at least one selected from a group consisting of PIQIr (acac)(bis(1-phenylisoquinoline)acetylacetonate iridium), PQIr(acac)(bis(1-phenylquinoline)acetylacetonate iridium), PQIr(tris(1-phenylquinoline)iridium), PtOEP(octaethylporphyrin platinum), and combinations thereof. Alternatively, when each of the light-emitting layers 133 and 234 emits red light, and when each of the light-emitting layers 133 and 234 is made of a fluorescent material, each of the light-emitting layers 133 and 234 may contain PBD:Eu (DBM)3(Phen) or perylene. However, the present disclosure is not limited thereto.

When each of the light-emitting layers 133 and 234 emits green light, and when each of the light-emitting layers 133 and 234 is made of a phosphorescent material, each of the light-emitting layers 133 and 234 may contain: a host material that includes CBP or mCP; and dopants doped into the host including Ir(ppy)3(fac tris(2-phenylpyridine) iridium). Alternatively, when each of the light-emitting layers 133 and 234 emits green light, and when each of the light-emitting layers 133 and 234 is made of a fluorescent material, each of the light-emitting layers 133 and 234 may contain Alq3(tris(8-hydroxyquinolino)aluminum). However, the present disclosure is not limited thereto.

When each of the light-emitting layers 133 and 234 emits blue light, and when each of the light-emitting layers 133 and 234 is made of a phosphorescent material, each of the light-emitting layers 133 and 234 may contain: a host material that includes CBP or mCP; and dopants doped into the host including (4,6-F2ppy)2Irpic. Alternatively, when each of the light-emitting layers 133 and 234 emits blue light, and when each of the light-emitting layers 133 and 234 is made of a fluorescent material, each of the light-emitting layers 133 and 234 may contain at least one selected from a group consisting of spiro-DPVBi, spiro-6P, distyrylbenzene (DSB), distyrylarylene (DSA), PFO-based polymer and PPV-based polymer and combinations thereof. However, the present disclosure is not limited thereto.

Each of the hole injection layers 131 and 231 may facilitate the injection of holes.

Each of the hole injection layers 131 and 231 may be made of at least one selected to from a group of consisting of, for example, CuPc(cupper phthalocyanine), PEDOT (poly(3,4)-ethylenedioxythiophene), PANI(polyaniline), NPD(N,N-dinaphthyl-N,N'-diphenyl benzidine) and combinations thereof. However, the present disclosure is not limited thereto.

Each of the hole transport layers 132 and 232 may contain, as a hole transport material, a material electrochemically stabilized via cationization (i.e., by losing electrons). Alternatively, Each of the hole transport layers 132 and 232 may contain a material that produces a stable radical cation as a hole transport material. Each of the hole transport layers 132 and 232 may contain a known hole transport material or the compound represented by the Chemical Formula 1. The detailed description of the compound represented by the Chemical Formula 1 is as described above.

Each of the hole transport layers 132 and 232 may further contain an additional hole transport material other than the compound represented by the Chemical Formula 1.

The known hole transport material or the additional hole transport material may contain aromatic amine to be easily cationized. In one example, the additional hole transport material may include at least one selected from a group of consisting of NPD(N,N-dinaphthyl-N,N'-diphenylbenzidine), TPD (N,N'-bis-(3-methylphenyl)-N,N-bis-(phenyl)-benzidine), spiro-TAD(2,2',7,7'-tetrakis(N,N-dimethylamino)-9,9-spirofluorene), MTDATA (4,4',4-Tris(N-3-methylphenyl-N-phenylamino)-triphenylamine) and combinations thereof. However, the present disclosure is not limited thereto.

The auxiliary hole transport layer 233 may contain the compound represented by the Chemical Formula 1, or may contain a known auxiliary hole transport material. The detailed description of the compound represented by the Chemical Formula 1 is as described above.

The auxiliary hole transport layer 233 may further contain an additional auxiliary hole transport material other than the compound represented by the Chemical Formula 1.

Each of the known auxiliary hole transport material and the additional auxiliary hole transport material may include at least one selected from a group of consisting of, for example, TCTA, tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, tri-p-tolylamine, 1,1-bis (4-(N,N'-di(p-tolyl)amino)phenyl)cyclohexane (TAPC), MTDATA, mCP, mCBP, CuPc, N,N'-bis[4-[bis(3-methylphenyl)amino]phenyl]-N,N'-diphenyl-[1,1'-biphenyl]-4, 4'-diamine (DNTPD), TDAPB, and combinations thereof. However, the present disclosure is not limited thereto.

The auxiliary electron transport layer may be positioned between each of the electron transport layers 134 and 235 and each of the light-emitting layers 133 and 234. The auxiliary electron transport layer may further contain an auxiliary electron transport material.

The auxiliary electron transport material may include at least one selected from a group of consisting of, for example, oxadiazole, triazole, phenanthroline, benzoxazole, benzothiazole, benzimidazole, triazine, and combinations thereof. However, the present disclosure is not limited thereto.

Each of the electron transport layers 134 and 235 receive electrons from the cathode. Each of the electron transport layers 134 and 235 may transfer the supplied electrons to the light-emitting layer.

Each of the electron transport layers 134 and 235 may serve to facilitate the transport of electrons. Each of the electron transport layers 134 and 235 contains an electron transport material.

The electron transport material may be electrochemically stabilized by being anionic (i.e., by obtaining electrons). Alternatively, the electron transport material may produce the stable radical anion. Alternatively, the electron transport material may contain a heterocyclic ring to be easily anionized by heteroatoms.

In one example, the electron transport material may include at least one selected from a group of consisting of, for example, PBD(2-(4-biphenylyl)-5-(4-tert-butylphenyl)-1,3,4-oxadiazole), TAZ(3-(4-biphenyl)4-phenyl-5-tert-butylphenyl-1,2,4-triazole), spiro-PBD, TPBi(2,2',2-(1,3,5-benzinetriyl)-tris(1-phenyl-1-H-benzimidazole), oxadiazole, triazole, phenanthroline, benzoxazole, benzthiazole, and combinations thereof. However, the present disclosure is not limited thereto.

In one example, the electron transport material may include an organic metal compound such as an organic aluminum compound, or an organic lithium compound including at least one selected from a group of consisting of, for example, Alq3(tris(8-hydroxyquinolino)aluminum), Liq (8-hydroxyquinolinolatolithium), BAlq(bis(2-methyl-8-quinolinolate)-4-(phenylphenolato)aluminium), and SAlq, etc. However, the present disclosure is not limited thereto.

Specifically, the organometallic compound may be an organic lithium compound.

More specifically, a ligand bound to the lithium of the organolithium compound may be a hydroxyquinoline based ligand.

The organic material layer may further include an electron injection layer.

The electron injection layer serves to facilitate the injection of electrons and contains an electron injection material. The electron injection material may include, but is not limited to, at least one selected from a group of consisting of Alq3(tris(8-hydroxyquinolino)aluminum), PBD, TAZ, Spiro-PBD, BAlq, SAlq and combinations thereof. Alternatively, the electron injection layer may be made of a metal compound. The metal compound may include, but is not limited to, at least one selected from a group of consisting of, for example, LiQ, LiF, NaF, KF, RbF, CsF, FrF, $BeF_2$, $MgF_2$, $CaF_2$, $SrF_2$, $BaF_2$ and $RaF_2$.

The organic material layer may further include at least one selected from a group of consisting of the hole injection layer, the hole transport layer, the auxiliary hole transport layer, the light-emitting layer, the auxiliary electron transport layer, the electron transport layer and the electron injection layer. Each of the hole injection layer, hole transport layer, auxiliary hole transport layer, light-emitting layer, auxiliary electron transport layer, electron transport layer and electron injection layer may be embodied as a single layer or a stack of multiple layers.

The organic light-emitting device according to the present disclosure may be applied to organic light emitting display devices such as a mobile phone and TV. For example, FIG. 3 is a schematic cross-sectional view of an organic light emitting display device applicable to a mobile phone according to an exemplary embodiment of the present disclosure.

As shown in FIG. 3, the organic light-emitting display device 1000 may include a substrate 1100, an organic light-emitting device 3000, and an encapsulating layer 2200 covering the organic light-emitting device 3000.

On the substrate 1100, a drive thin-film transistor TFT, which is a drive device, and the organic light-emitting device 3000, which is connected to the drive thin-film transistor TFT, are positioned.

Although not shown, on the substrate 1100, a gate line and a data line, which define a pixel region, a power line extending parallel to and spaced from either the gate line or the data line, and a switching thin-film transistor connected to the gate line and data line are formed.

The driving thin-film transistor TFT is connected to the switching thin-film transistor, and includes an active layer 1520, a gate electrode 1720, a source electrode 1920 and a drain electrode 1940. A gate insulating film 1600 and an inter-layer insulating film 1800 are interposed therebetween. As shown in FIG. 3, the source electrode 1920 and the drain electrode 1940 are electrically connected to the active layer 1520 via a contact hole formed in the gate insulating film 1600 and the inter-layer insulating film 1800. The drain electrode 1940 is connected to a first electrode 3100 of the organic light-emitting device 3000.

A storage capacitor Cst is connected to a power line and one electrode of the switching thin-film transistor and includes a storage first electrode 1540, a storage second electrode 1740 and a storage third electrode 1960. As shown in FIG. 3, the gate insulating film 1600 and the inter-layer insulating film 1800 are interposed between the storage first electrode 1540 and the storage second electrode 1740, and between the storage second electrode 1740 and the storage third electrode 1960, respectively.

The substrate 1100 may be made of a flexible material such as polyimide, or may be made of rigid material such as glass.

A multi-buffer layer 1200 made of an insulating material such as silicon oxide or silicon nitride is formed on the entire surface over an entire face of the substrate 1100. The multi-buffer layer 1200 is embodied as a stack of multiple layers, for example, 7 or 8 layers.

A light-blocking layer 1300 is formed on the multi-buffer layer 1200, is made of molybdenum titanium alloy (MoTi) in one example. The light-blocking layer 1300 prevents light from being incident on the active layer 1520, thereby preventing the active layer 1520 from being deteriorated by light. An insulating film 1400 made of an insulating material such as silicon oxide or silicon nitride is formed on the light-blocking layer 1300 over an entire face of the substrate 1100. Alternatively, a contact hole may be formed to connect the active layer 1520 to the light-blocking layer 1300. In order to minimize change in a threshold voltage of the thin film transistor, which may occur when the light-blocking layer 1300 is in a floating state, the light-blocking layer 1300 may be electrically connected to the active layer 1520. The insulating film 1400 may be formed of a single layer.

The active layer 1520 embodied as a semiconductor film is formed on the insulating film 1400. The semiconductor film may be made of an oxide semiconductor material, or a single crystal silicon. Alternatively, the active layer 1520 may be made of polycrystalline silicon. In this case, the active layer 1520 may be doped with impurities into both edges thereof.

The storage first electrode 1540 is formed together with the active layer 1520 on the insulating film 1400. In this connection, the storage first electrode 1540 may be made of polycrystalline silicon in the same manner as the active layer 1520. The storage first electrode 1540 made of polycrystalline silicon is doped with impurities to have conductance.

A gate insulating film 1600 is formed on the insulating film 1400 so that the active layer 1520 and the storage first electrode 1540 are covered with the gate insulating film 1600. The gate insulating film 1600 is formed over an entire face of the substrate 1100. The gate insulating film 1600, for example, may be made of silicon oxide.

A gate electrode 1720 and a storage second electrode 1740 may be formed on the gate insulating film 1600. The gate electrode 1720 and the storage second electrode 1740 overlap the active layer 1520 and the storage first electrode 1540 respectively. Each of the gate electrode 1720 and the storage second electrode 1740 may be formed of a stack of double metal layers, a first layer made of Cu and a second layer made of MoTi alloy.

An inter-layer insulating film 1800 of insulating material is formed on an entire face of the gate insulating film 1600 to cover the gate electrode 1720 and the storage second electrode 1740. The inter-layer insulating film 1800 may be made of an inorganic insulating material such as silicon oxide or silicon nitride, or made of an organic insulating material such benzocyclobutene or photo-acryl.

As shown in FIG. 3, the gate insulating film 1600 and the inter-layer insulating film 1800 have two active layer contact holes defined therein for exposing both sides of the active layer 1520. The two active layer contact holes are respectively located to be spaced from both sides of the gate electrode 1720.

On the inter-layer insulating film 1800, a source electrode 1920 and a drain electrode 1940 made of a conductive material such as a metal are formed. The source electrode 1920 and the drain electrode 1940 are disposed around the gate electrode 1720 and are spaced from each other. The source electrode 1920 and the drain electrode 1940 are electrically connected to both sides of the active layer 1520 via the two active layer contact holes as described above respectively. The source electrode 1920 is connected to the power line (not shown).

Further, on the inter-layer insulating film 1800, a storage third electrode 1960 defining the storage capacitor Cst and made of a conductive material such as a metal together is formed together with the source electrode 1920 and the drain electrode 1940.

The active layer 1520, the gate electrode 1720, the source electrode 1920, and the drain electrode 1940 constitute the drive thin-film transistor TFT. The drive thin-film transistor TFT has a coplanar structure in which the gate electrode 1720, the source electrode 1920 and the drain electrode 1940 are positioned above the active layer 1520.

Alternatively, the drive thin-film transistor TFT may have an inverted staggered structure where the gate electrode is positioned below the active layer, while the source and drain electrodes are positioned above the active layer. In this case, the active layer may be made of amorphous silicon. In one example, the switching thin-film transistor (not shown) may have substantially the same structure as the drive thin-film transistor TFT.

A planarization layer 2000 having a drain contact-hole defined therein for exposing the drain electrode 1940 of the driving thin-film transistor TFT is formed to cover the drive thin-film transistor TFT and the storage capacitor Cst. The planarization layer 2000 may be made of an inorganic insulating material or an organic insulating material.

A first electrode 3100 is formed on the planarization layer 2000 such that the first electrode 3100 is connected to the drain electrode 1940 of the drive thin-film transistor TFT via the drain contact-hole defined in the planarization layer 2000. Accordingly, the active layer 1520 of the drive thin-film transistor TFT is electrically connected to the first electrode 3100.

The first electrode 3100 may act as an anode, and may be made of a conductive material having a relatively large work function value. For example, the first electrode 3100 may be made of transparent conductive material such as ITO, IZO or ZnO.

In one example, when the organic light-emitting display device 1000 is of a top emission type, a reflective electrode or reflective layer may be further formed below the first electrode 3100. For example, the reflective electrode or reflective layer may be made of any one of aluminum (Al), silver (Ag), nickel (Ni), aluminum-palladium-copper (APC alloy).

A bank layer 2100 is formed on the planarization layer 2000 to define each pixel region. The bank layer 2100 may allow a bank hole corresponding to each pixel region to be defined to partially expose the first electrode 3100.

An organic material layer 3300 is formed on the bank layer 2100 and a portion of the first electrode 3100 exposed by the bank hole. A portion of the organic material layer 3300 that is in contact with the first electrode 3100 corresponds to each pixel region, and more specifically to a light-emission region.

A second electrode 3200 is formed on the organic material layer 3300 over an entire face of the substrate 1100. The second electrode 3200 is positioned on an entirety of the expression region and may be made of a conductive material having a relatively small work function value and thus may act as a cathode. For example, the second electrode 3200 may be made of any one of aluminum Al, magnesium Mg, and aluminum-magnesium alloy AlMg.

The first electrode 3100, organic material layer 3300 and second electrode 3200 constitute the organic light-emitting device 3000.

The encapsulating layer 2200 is formed on the organic light-emitting device 3000 to prevent external moisture from penetrating the organic light-emitting device 3000.

The encapsulating layer 2200 may have, but is not limited to, a triple layer structure (not shown) sequentially composed of a first inorganic layer, and an organic layer, and a second inorganic layer.

On top of the encapsulating layer 2200, a barrier layer 2300 may be formed to more effectively prevent external moisture or oxygen from invading the organic light-emitting device 3000.

The barrier layer 2300 may be manufactured in a form of a film and adhered to the encapsulating layer 2200 via an adhesive.

Hereinafter, Present Examples and Comparative examples will be set forth. The Present Examples may be only an example of the present disclosure. Thus, the present disclosure is not limited to the Present Examples.

PRESENT EXAMPLES

Hereinafter, compounds used in Present Examples and Comparative Examples were synthesized as follows.

Synthesis Example 1—Production of Compound 6

1-A) Production of Intermediate 1-A

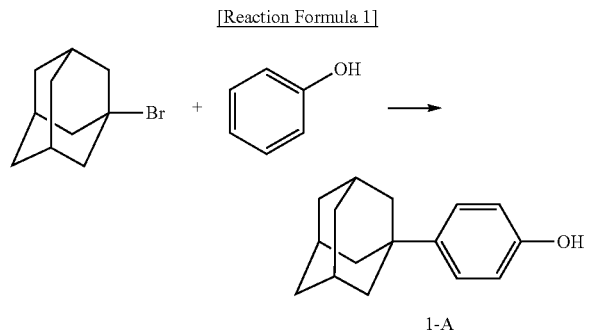

1-A 1-bromoadamantane (11.5 g, 53.45 mmol), and phenol (14.1 mL, 160.35 mmol) were added into a 250 mL flask and were stirred at 120° C. or higher. After reaction for 12 hours, the reactant was cooled to 60° C., and then 20 mL of methanol was added thereto and then the temperature was maintained. The reactant having the methanol added thereto was added to 80 mL of 80° C. water, and the temperature was maintained, followed by stirring thereof for 1 hour. Then, the solution was filtered while maintaining the solution at 70° C. or higher. After the filtration, the filtrate was washed 3 times with hot water and dried sufficiently under vacuum, thereby to obtain 9.7 g of a compound 1-A in 79.5% yield.

1-B) Production of Intermediate 1-B

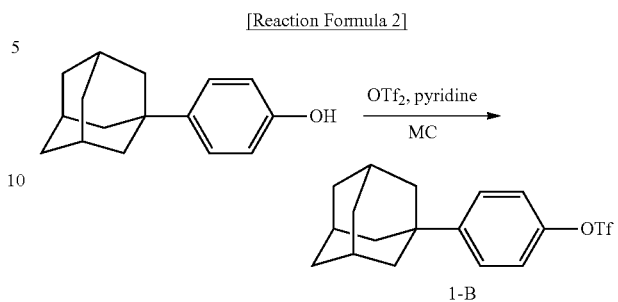

1-B

Under a stream of nitrogen, 4-(1-adamantyl)phenol (9.7 g, 4.25 mmol), pyridine (6.7 mL, 8.50 mmol), and dichloromethane 80 mL were added into a 250 mL flask and were stirred at 0° C. or lower. Then, trifluoromethanesulfone anhydride (OTf$_2$, 13.2 g, 4.67 mmol) was slowly added to the mixture in a dropwise manner. After the dropwise addition, a temperature was raised to room temperature. Then, as 4 hours has lapsed, reaction was terminated. Then, 2M hydrochloric acid was added thereto. Then, a dichloromethane layer was extracted therefrom using dichloromethane and water. The extracted solution was treated with MgSO$_4$ to remove residual moisture, followed by concentration under reduced pressure, thereby to obtain 12.0 g of a compound 1-B in 78.4% yield.

1-C) Production of Intermediate 1-C

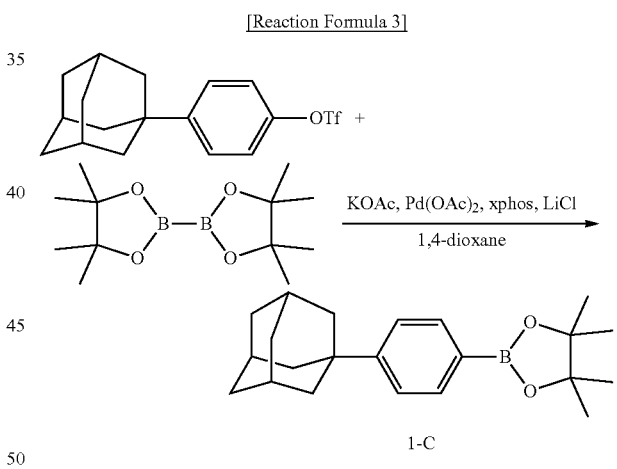

1-C 4-(adamantan-1-yl)phenyl trifluoromethanesulfonate (12.0 g, 33.30 mmol), bis(pinacolato)diboron (10.1 g, 39.96 mmol), potassium acetate (7.19 g, 73.26 mmol), 2-dicyclohexylphosphino-2',4',6'-triisopropylbiphenyl (xphos, 0.317 g, 0.665 mmol), palladium (II) acetate (0.075 g, 0.334 mmol), lithium chloride (0.28 g, 6.61 mmol), and 1,4-dioxane (100 mL) were added into a 250 mL flask under nitrogen stream and then were refluxed with stirring. After completion of reaction, 1,4-dioxane was removed therefrom via distillation under reduced pressure, and then, a dichloromethane layer was extracted therefrom using dichloromethane and water. The extracted solution was treated with MgSO$_4$ to remove residual moisture, and then was concentrated under reduced pressure, and then washed with methanol (60 mL) and then filtered to obtain 10.5 g of a compound 1-C in 93.7% yield.

1-D) Production of Intermediate 1-D

[Reaction Formula 4]

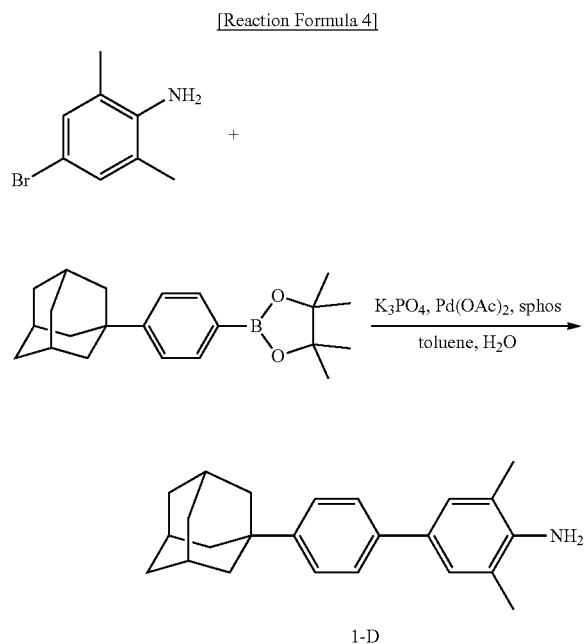

1-D 4-bromo-2,6-dimethylaniline (5.2 g, 25.99 mmol), 2-(4-((3r, 5r, 7r)-adamantan-1-yl)phenyl)-4,4,5,5-tetramethyl-1,3,2-dioxane borane (10.6 g, 31.33 mmol), tripotassium phosphate (16.6 g, 78.20 mmol), palladium (II) acetate (0.117 g, 0.521 mmol), 2-dicyclohexylphosphino-2',6'-dimethoxybiphenyl (sphos, 0.427 g, 1.040 mmol), toluene (80 mL) and H₂O (10 mL) were added into a 250 mL flask under nitrogen stream and were refluxed with stirring. After completion of reaction, a toluene layer was extracted therefrom with toluene and water. The extracted solution was treated with MgSO₄ to remove residual moisture, and then concentrated under reduced pressure, and purified using column chromatography, thereby to obtain 6.0 g of a compound 1-D in 69.6% yield.

1-E) Production of Compound 6

[Reaction Formula 5]

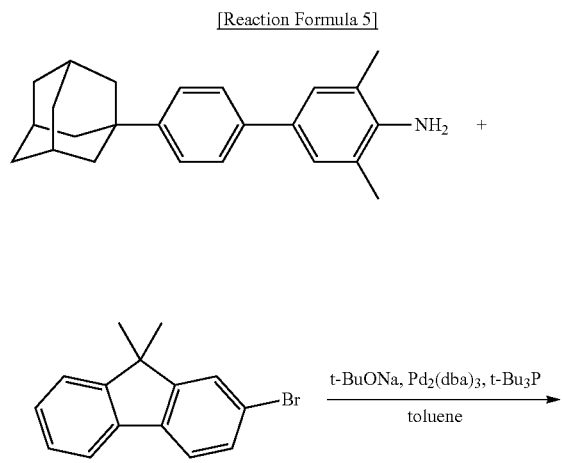

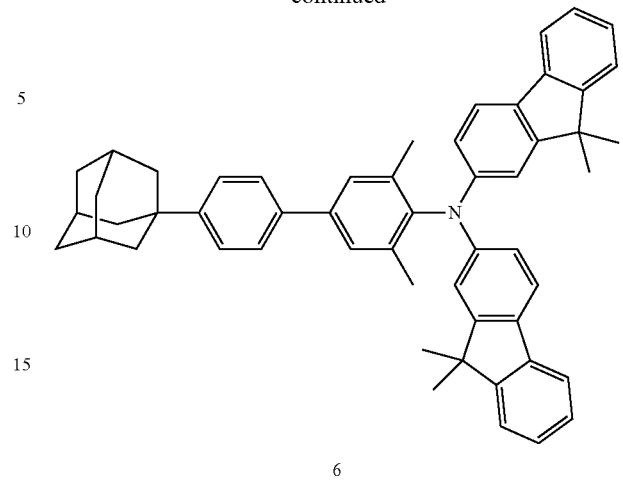

6

4'-((3r, 5r, 7r)-adamantan-1-yl)-3,5-dimethyl-[1,1'-biphenyl]-4-amine (6.0 g, 18.10 mmol), 2-bromo-9,9-dimethyl-9H-fluorene (12.0 g. 43.93 mmol), sodium tert butoxide (5.22 g, 54.32 mmol), tris(dibenzylideneacetone)dipalladium (0) (0.663 g, 0.725 mmol), tri-tert-butylphosphine (0.586 mL, 2.90 mmol), and toluene 50 mL were added into a 250 mL flask under nitrogen stream and were refluxed while stirring. After completion of reaction, a toluene layer was extracted therefrom using 50 mL of water. The extracted solution was treated with MgSO₄ to remove residual moisture, and then was concentrated under reduced pressure, and then purified using a column chromatography method, and was recrystallized with dichloromethane/heptane, thereby to obtain 6.5 g of the compound 6 in 50.2% yield.

Synthesis Example 2—Production of Compound 29

2-A) Production of Intermediate 2-A

[Reaction Formula 6]

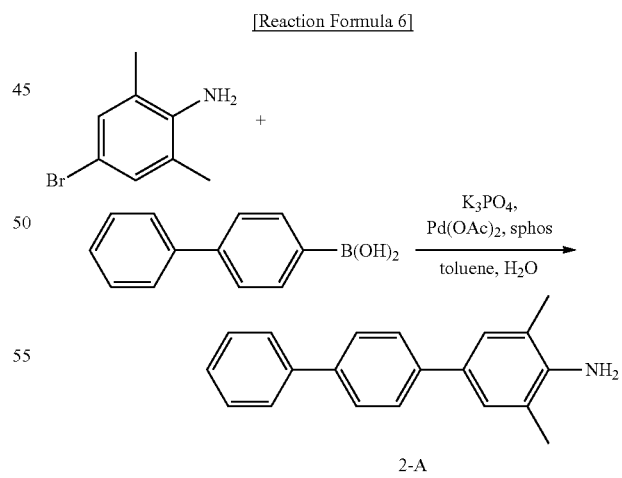

2-A 4.97 g of a compound 2-A was obtained in 70.0% yield via synthesis and purification in the same manner as in the production of the compound 1-D except that [1,1'-biphenyl]-4-yl boronic acid (6.2 g, 31.33 mmol) was used instead of 2-(4-((3r, 5r, 7r)-adamantan-1-yl)phenyl-4,4,5,5-tetramethyl-1,3,2-dioxane borane.

2-B) Production of Compound 29

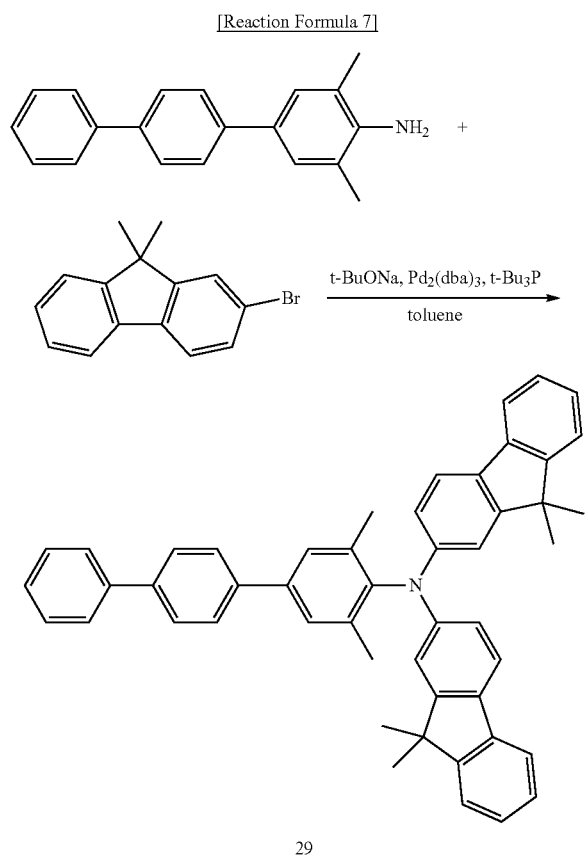

4.77 g of the compound 29 was obtained in 40.0% yield via synthesis and purification in the same manner as in the production of the compound 6 except that 3,5-dimethyl-[1,1; 4', 1''-terphenyl]-4-amine (4.94 g, 18.10 mmol) was used instead of 4'-((3r, 5r, 7r)-adamantan-1-yl)-3,5-dimethyl-[1,1'-biphenyl]-4-amine.

Synthesis Example 3—Production of Compound 138

3-A) Production of Intermediate 3-A

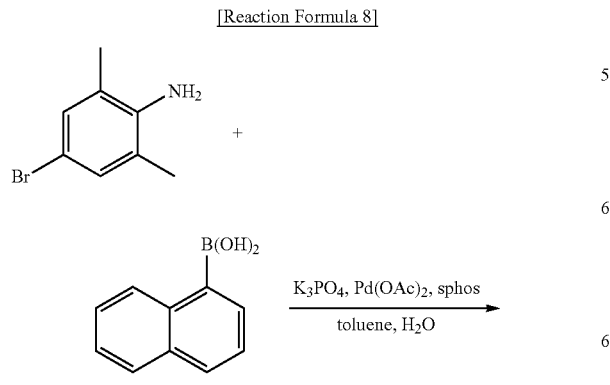

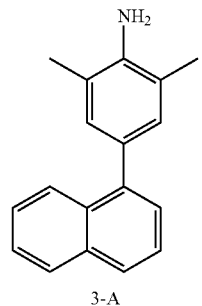

4.6 g of a compound 3-A was obtained in 71.5% yield via synthesis and purification in the same manner as in the production of the compound 1-D except that 1-naphthalene boronic acid (5.4 g, 31.33 mmol) was used instead of 2-(4-((3r, 5r, 7r)-adamantan-1-yl)phenyl)-4,4,5,5-tetramethyl-1,3,2-dioxane borane.

3-B) Production of Compound 138

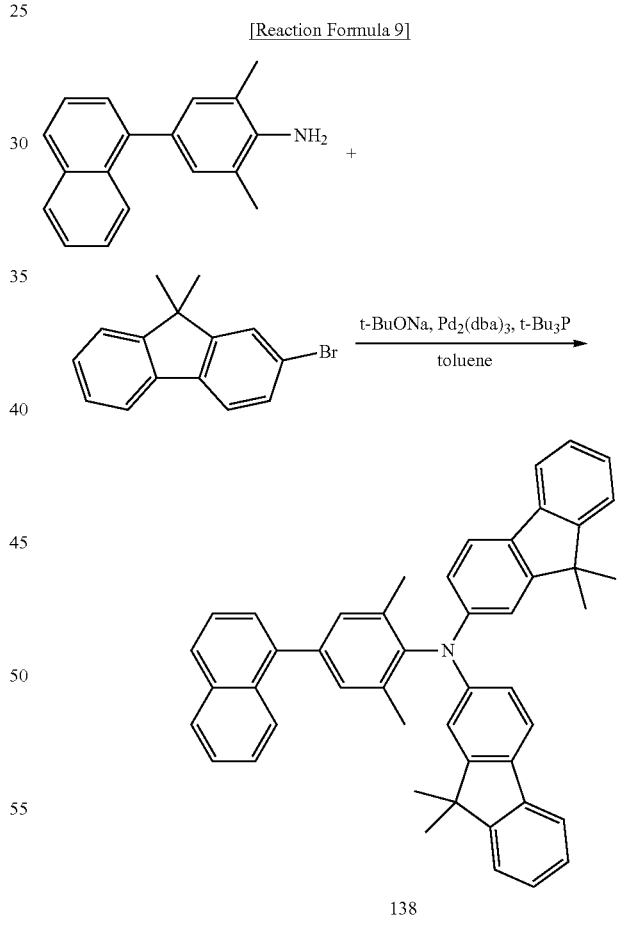

4.43 g of the compound 138 was obtained in a yield of 38.7% via synthesis and purification in the same manner as in the production of the compound 6 except that 2,6-dimethyl-4-(naphthalen-1-yl)aniline (4.48 g, 18.10 mmol) was used instead of 4'-((3r, 5r, 7r)-adamantan-1-yl)-3,5-dimethyl-[1,1'-biphenyl]-4-amine.

Synthesis Example 4—Production of Compound 101

4-A) Production of Intermediate 4-A

[Reaction Formula 10]

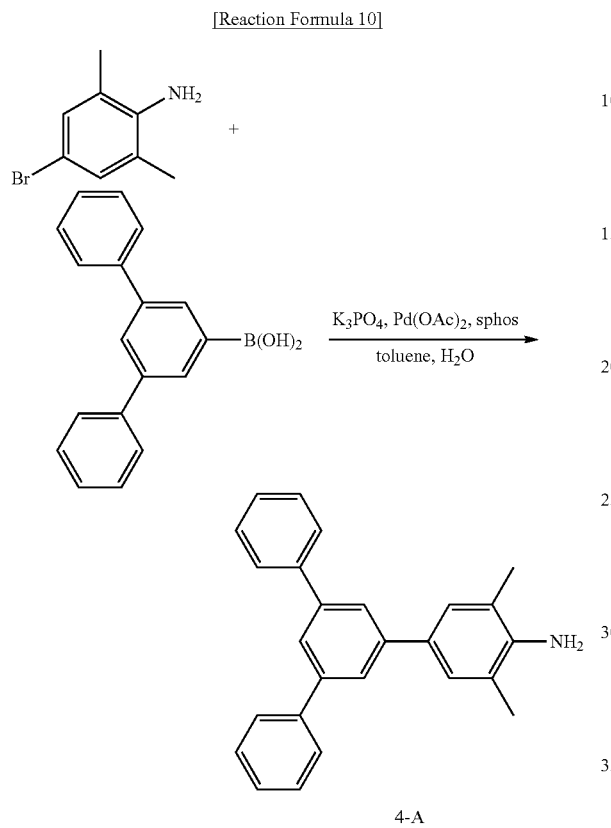

4-A 6.5 g of a compound 4-A was obtained in 71.5% yield via synthesis and purification in the same manner as in the production of the compound 1-D except that [1,1': 3', 1''-terphenyl]-5'-yl boronic acid (8.6 g, 31.33 mmol) was used instead of 2-(4-((3r, 5r, 7r)-adamantan-1-yl)phenyl)-4,4,5,5-tetramethyl-1,3,2-dioxane borane.

4-B) Production of Compound 101

[Reaction Formula 11]

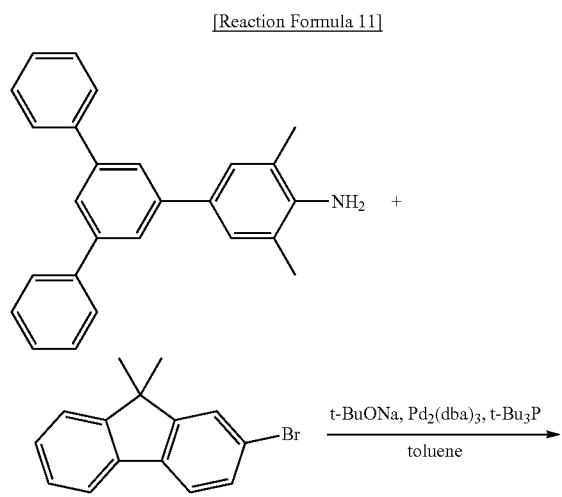

-continued

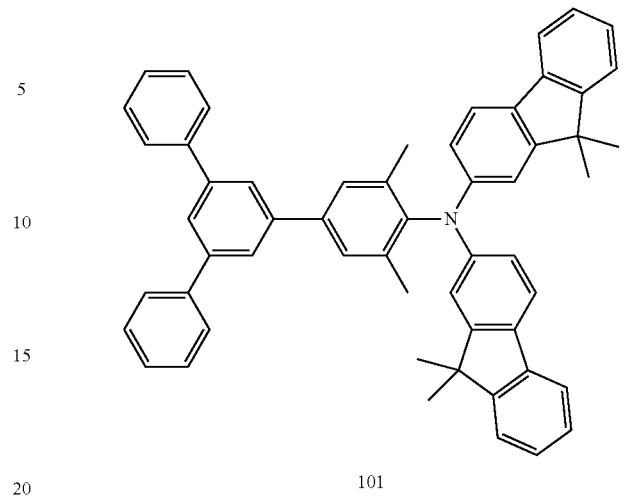

101

5.8 g of the compound 101 was obtained in 43.7% yield via synthesis and purification in the same manner as in the production of the compound 6 except that 3,5-dimethyl-5'-phenyl-[1,1': 3',1''-terphenyl]-4-amine (6.3 g, 18.10 mmol) was used instead of 4'-((3r, 5r, 7r)-adamantan-1-yl)-3,5-dimethyl-[1,1'-biphenyl]-4-amine.

Synthesis Example 5—Production of Compound 51

5-A) Production of Intermediate 5-A

[Reaction Formula 12]

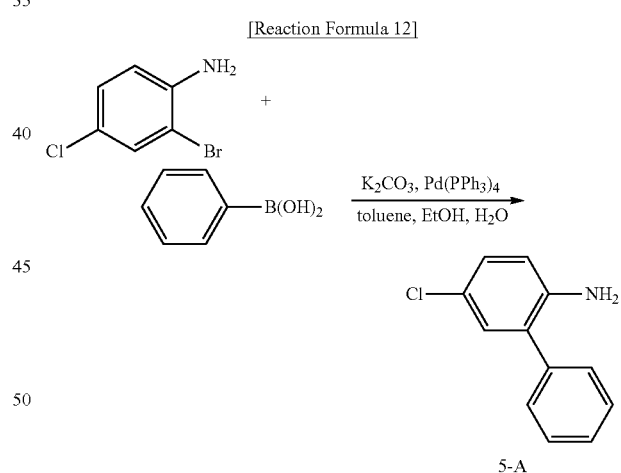

5-A 2-bromo-4-chloroaniline (18.0 g, 87.18 mmol), phenylboronic acid (12.8 g, 104.62 mmol), potassium carbonate (24.1 g, 174.36 mmol), tetrakis(triphenylphosphine)palladium (0) (3.0 g, 2.62 mmol), toluene (250 mL), EtOH (70 mL), and $H_2O$ (70 mL) were added into a 500 mL flask under a stream of nitrogen and then were refluxed while stirring. After completion of reaction, a toluene layer was extracted therefrom with toluene and water. The extracted solution was treated with $MgSO_4$ to remove residual moisture, and then was concentrated under reduced pressure, and then purified using column chromatography, thereby to obtain 12.8 g of a compound 5-A in 72.1% yield.

5-B) Production of Intermediate 5-B

[Reaction Formula 13]

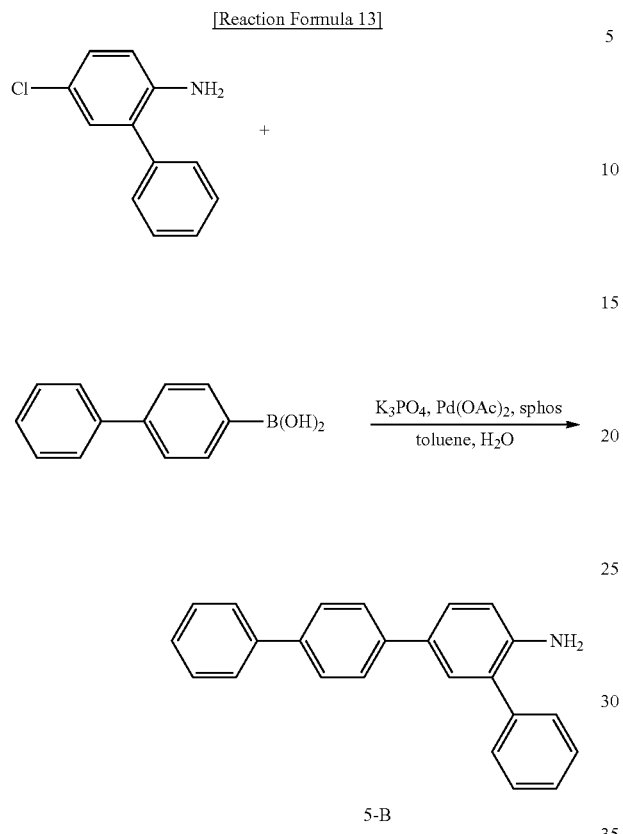

5-B 6.3 g of a compound 5-B was obtained in a yield of 66.5% via synthesis and purification in the same manner as in the production of the compound 1-D except that 5-chloro-[1,1'-biphenyl]-2-amine (6.0 g, 29.46 mmol) and [1,1'-biphenyl]-4-yl boronic acid (7.0 g, 35.35 mmol) were used.

5-C) Production of Compound 51

[Reaction Formula 14]

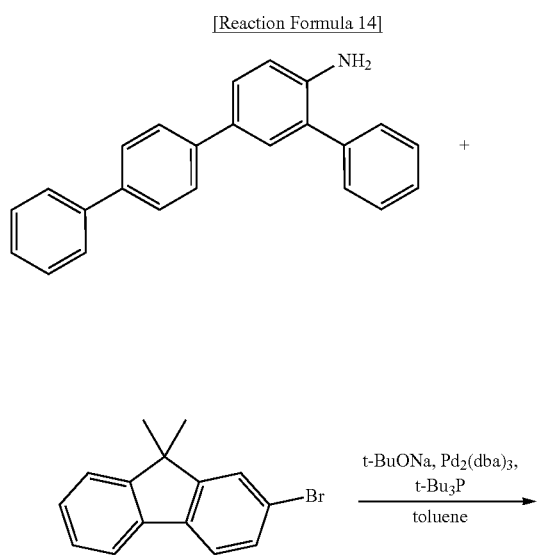

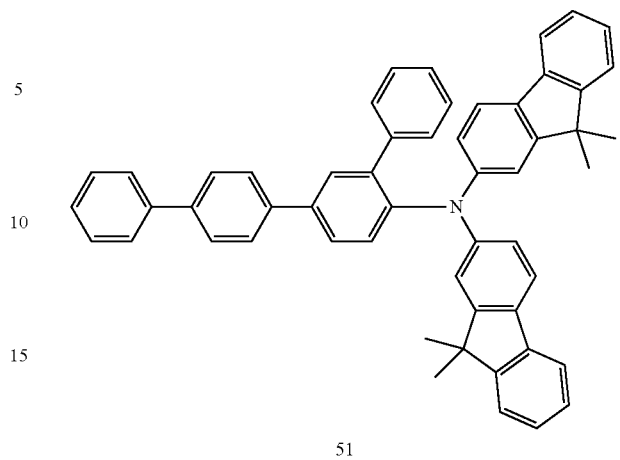

51

4.91 g of the compound 51 was obtained in 38.4% yield via synthesis and purification in the same manner as in the production of the compound 6 except that [1,1': 3',1'': 4'',1'''-quaterphenyl]-6'-amine (5.8 g, 18.10 mmol) was used instead of 4'-((3r, 5r, 7r)-adamantan-1-yl)-3,5-dimethyl-[1,1'-biphenyl]-4-amine.

Synthesis Example 6—Production of Compound 269

6-A) Production of Intermediate 6-A

[Reaction Formula 15]

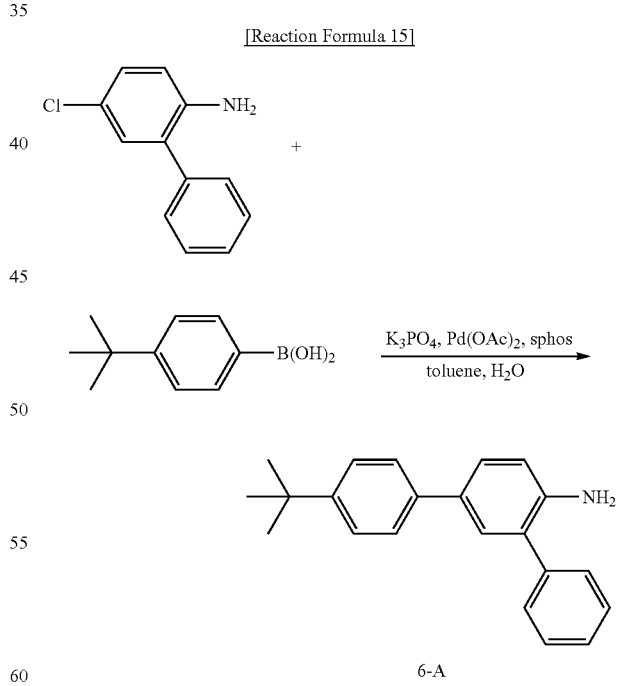

6-A 5.8 g of a compound 6-A was obtained in a yield of 66.3% via synthesis and purification in the same manner as in the production of the compound 1-D except that 5-chloro-[1,1'-biphenyl]-2-amine (6.0 g, 29.46 mmol), and (4-(tert-butyl)phenyl) boronic acid (6.3 g, 35.35 mmol) were used.

6-B) Production of Compound 269

[Reaction Formula 16]

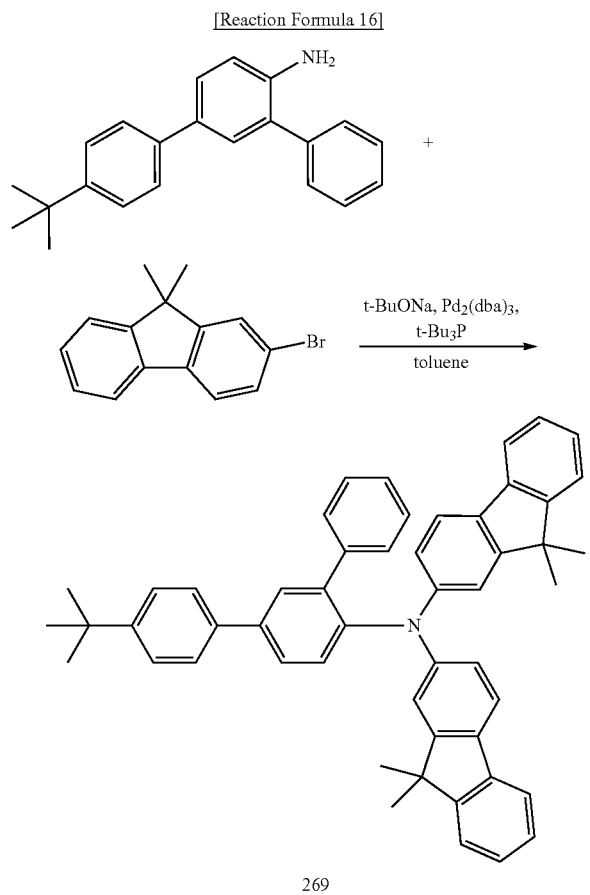

269

5.33 g of the compound 269 was obtained in 42.9% yield via synthesis and purification in the same manner as in the production of the compound 6 except that 4-(ter-butyl)-[1,1':3',1":-terphenyl]-4'-amine (5.5 g, 18.10 mmol) was used instead of 4'-((3r, 5r, 7r-adamantan-1-yl)-3,5-dimethyl-[1,1'-biphenyl]-4-amine.

Synthesis Example 7—Production of Compound 221

7-A) Production of Intermediate 7-A

[Reaction Formula 17]

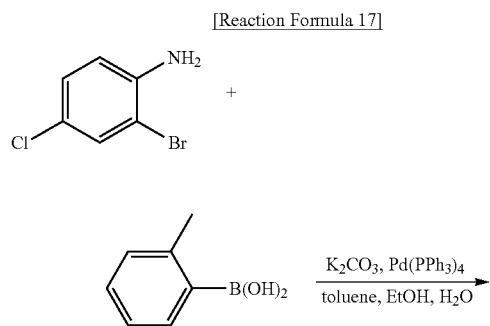

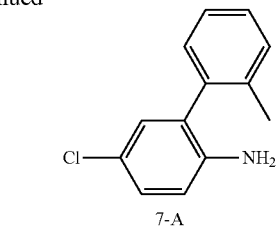

7-A 10.9 g of a compound 7-A was obtained in a yield of 57.4% via synthesis and purification in the same manner as in the production of the compound 5-A except that o-tolyl-boronic acid (14.2 g, 104.62 mmol) was used instead of phenylboronic acid.

7-B) Production of Intermediate 7-B

[Reaction Formula 18]

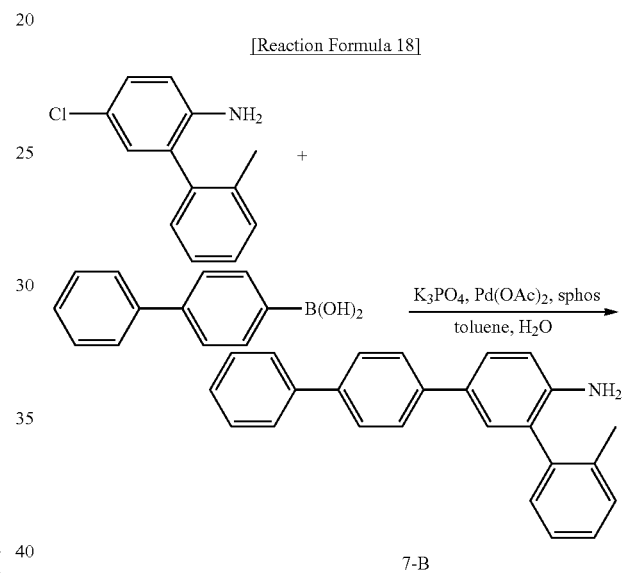

7-B 6.5 g of a compound 7-B was obtained in a yield of 60.3% via synthesis and purification in the same manner as in the production of the compound 1-D except that 5-chloro-2'-methyl-[1,1'-biphenyl]-2-amine (7.0 g, 32.15 mmol), and [1,1'-biphenyl]-4-yl boronic acid (7.6 g, 38.59 mmol) were used.

7-C) Production of Compound 221

[Reaction Formula 19]

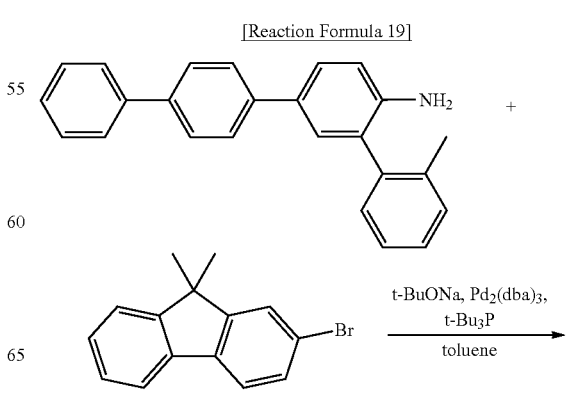

-continued

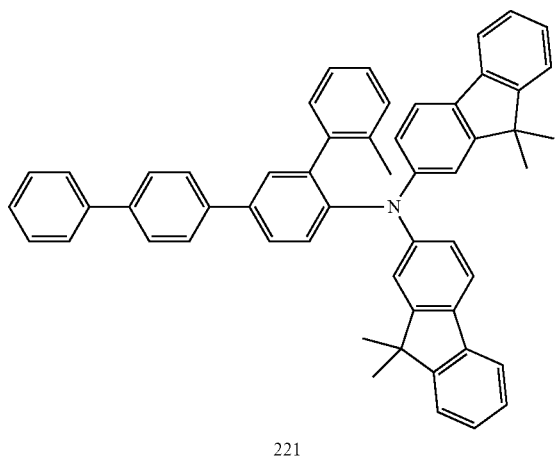

221

4.81 g of the compound 221 was obtained in 36.9% yield via synthesis and purification in the same manner as in the production of the compound 6 except that 2-methyl-[1,1': 3',1'': 4'', 1'''-quaterphenyl]-6'-amine (6.1 g, 18.10 mmol) was used instead of 4'-((3r, 5r, 7r)-adamantan-1-yl)-3,5-dimethyl-[1,1'-biphenyl]-4-amine.

Synthesis Example 8—Production of Compound 233

8-A) Production of Intermediate 8-A

[Reaction Formula 20]

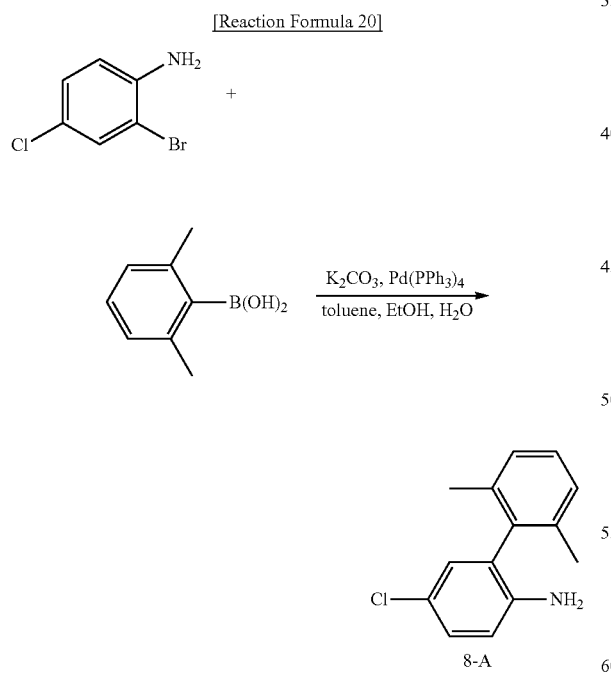

8-A 10.6 g of a compound 8-A was obtained in a yield of 52.5% via synthesis and purification in the same manner as in the production of the compound 5-A except that (2,6-dimethylphenyl)boronic acid (15.7 g, 104.62 mmol) was used instead of phenylboronic acid.

8-B) Production of Intermediate 8-B

[Reaction Formula 21]

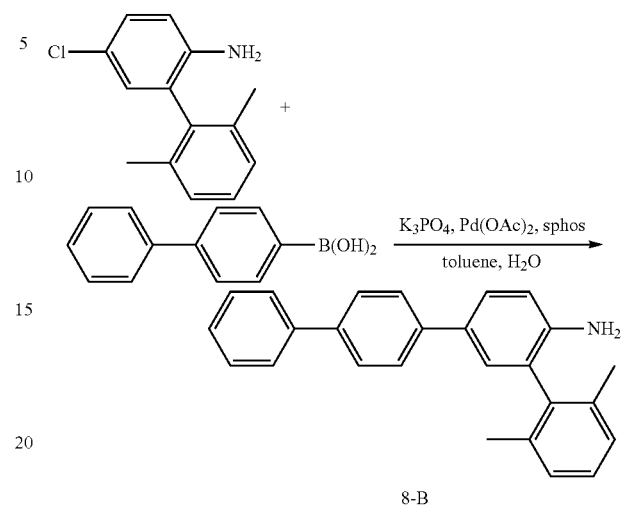

8-B 6.5 g of a compound 8-B was obtained in a yield of 59.9% via synthesis and purification in the same manner as in the production of the compound 1-D except that 5-chloro-2',6'-dimethyl-[1,1'-biphenyl]-2-amine (7.2 g, 31.07 mmol), and [1,1'-biphenyl]-4-yl boronic acid (7.4 g, 37.29 mmol) were used.

8-C) Production of Compound 233

[Reaction Formula 22]

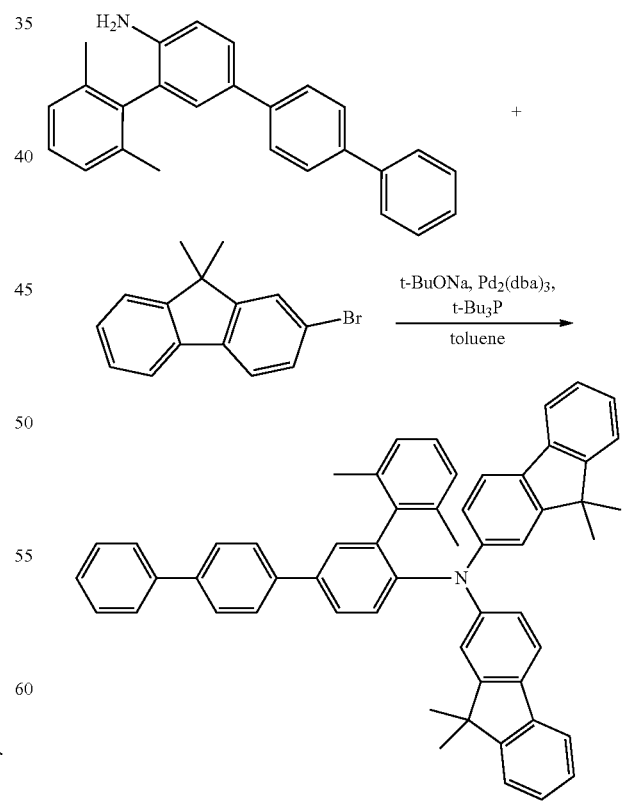

233

5.47 g of the compound 233 was obtained in 41.2% yield via synthesis and purification in the same manner as in the production of the compound 6 except that 2,6-dimethyl-[1,1': 3',1": 4",1'''-quaterphenyl]-6'-amine (6.3 g, 18.10 mmol) was used instead of 4'-((3r, 5r, 7r)-adamantan-1-yl)-3,5-dimethyl-[1,1'-biphenyl]-4-amine.

Synthesis Example 9—Production of Compound 63

9-A) Production of Intermediate 9-A

[Reaction Formula 23]

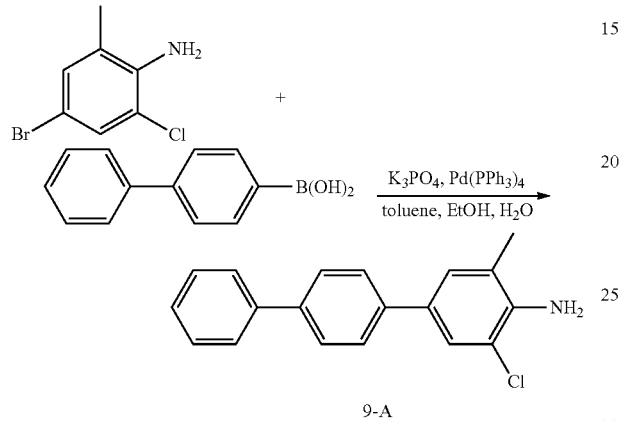

9-A 9.1 g of a compound 9-A was obtained in a yield of 68.3% via synthesis and purification in the same manner as in the production of the compound 5-A except that 4-bromo-2-chloro-6-methylaniline (10.0 g, 45.35 mmol), and [1,1'-biphenyl]-4-yl boronic acid (10.8 g, 54.42 mmol) were used.

[Reaction Formula 24]

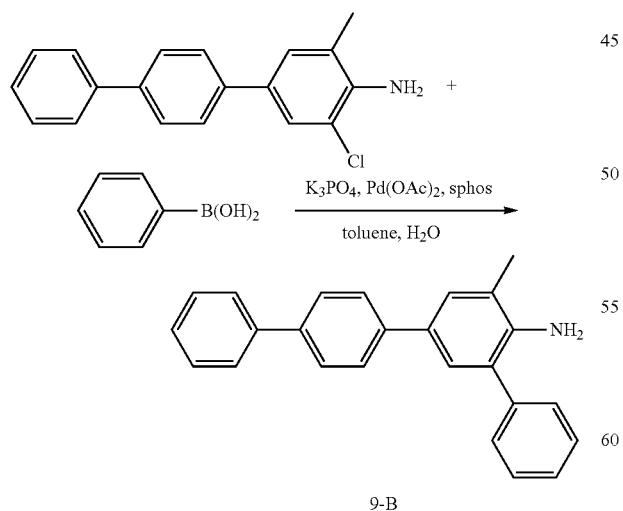

9-B 6.3 g of a compound 9-B was obtained in a yield of 61.3% via synthesis and purification in the same manner as in the production of the compound 1-D except that 3-chloro-5-methyl-[1,1':4',1"-terphenyl]-4-amine (7.0 g, 30.63 mmol), and phenylboronic acid (4.5 g, 36.76 mmol) were used.

9-C) Production of Compound 63

[Reaction Formula 25]

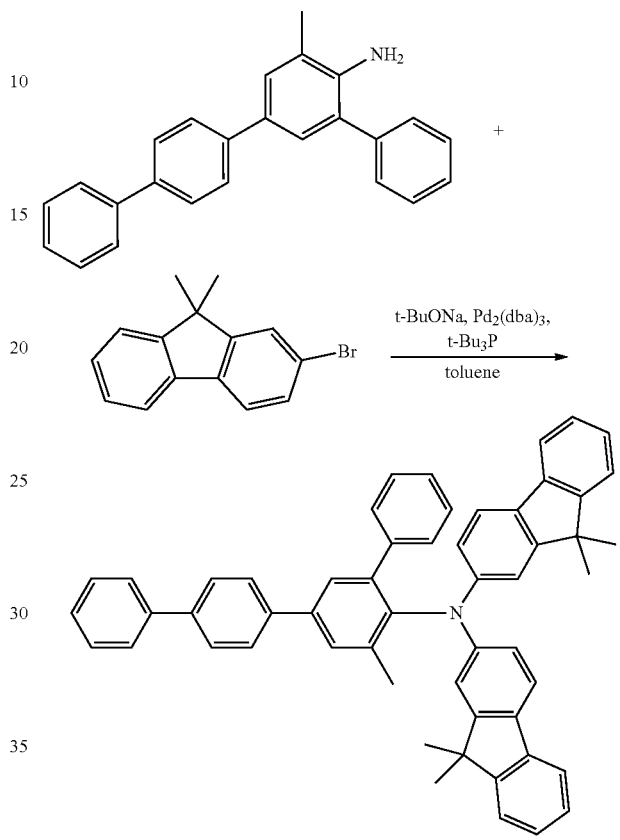

63

5.80 g of the compound 63 was obtained in 44.5% yield via synthesis and purification in the same manner as in the production of the compound 6 except that 5'-methyl-[1,1': 3',1": 4",1'''-quaterphenyl]-6'-amine (6.1 g, 18.10 mmol) was used instead of 4'-((3r, 5r, 7r)-adamantan-1-yl)-3,5-dimethyl-[1,1'-biphenyl]-4-amine.

Synthesis Example 10—Production of Compound 245

10-A) Production of Intermediate 10-A

[Reaction Formula 26]

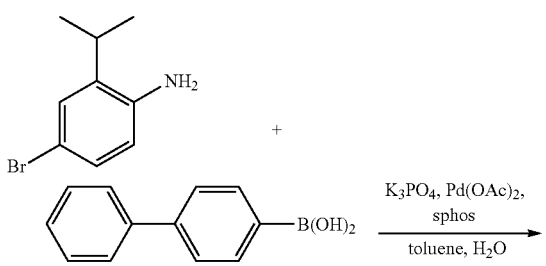

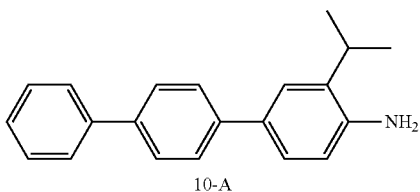

10-A 6.2 g of a compound 10-A was obtained in a yield of 66.0% via synthesis and purification in the same manner as in the production of the compound 1-D except that 4-bromo-2-isopropylaniline (7.0 g, 32.69 mmol) and [1,1'-biphenyl]-4-yl boronic acid (7.8 g, 39.23 mmol) were used.

10-B) Production of Compound 245

[Reaction Formula 27]

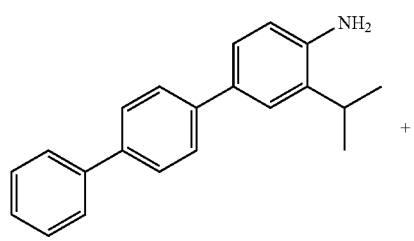

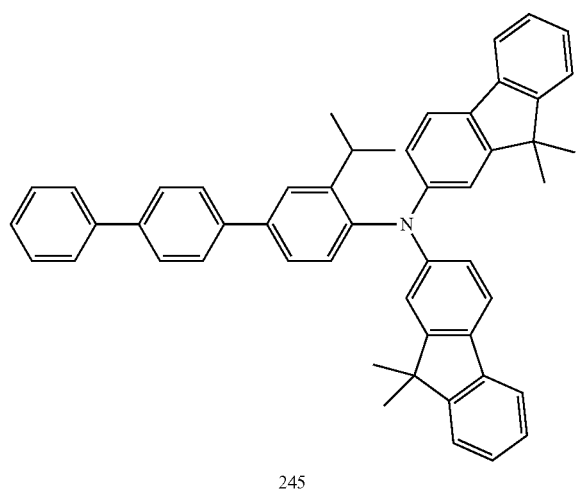

245

4.37 g of the compound 245 was obtained in 35.9% yield via synthesis and purification in the same manner as in the production of the compound 6 except that 3-isopropyl-[1,1': 4',1''-terphenyl]-4-amine (5.2 g, 18.10 mmol) was used instead of 4'-((3r, 5r, 7r)-adamantan-1-yl)-3,5-dimethyl-[1, 1'-biphenyl]-4-amine.

Synthesis Example 11—Production of Compound 30

11-A) Production of Intermediate 11-A

[Reaction Formula 28]

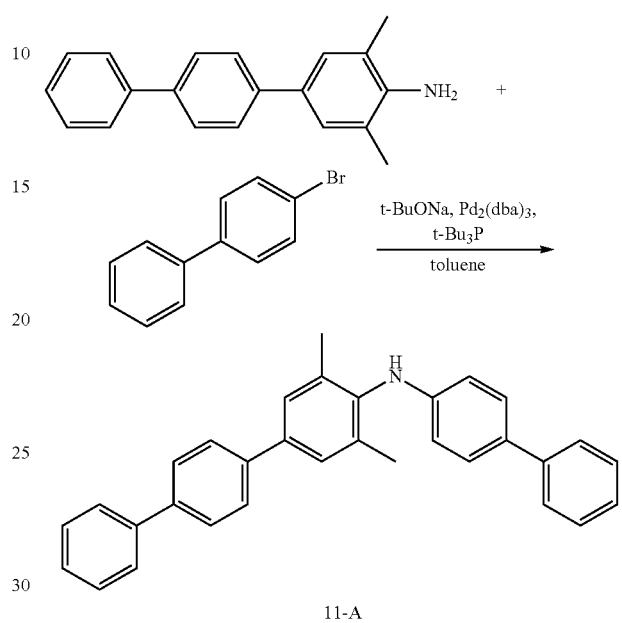

11-A 3,5-dimethyl-[1,1': 4',1''-terphenyl]-4-amine (10.0 g, 36.58 mmol), 4-bromo-1,1'-biphenyl (8.1 g, 34.75 mmol), sodium tert butoxide (5.3 g, 54.87 mmol), tris(dibenzylideneacetone) dipalladium (0) (0.67 g, 0.732 mmol), tri-tert-butylphosphine (0.59 mL, 2.93 mmol), and 150 mL of toluene were added into a 250 mL flask under nitrogen stream and were refluxed while stirring. After completion of reaction, a toluene layer was extracted therefrom using 50 mL of water. The extracted solution was treated with MgSO₄ to remove residual moisture, and then was concentrated under reduced pressure, and then purified using a column chromatography method, and was recrystallized with dichloromethane/heptane, thereby to obtain 10.15 g of a compound 11-A in 68.6% yield.

11-B) Production of Compound 30

[Reaction Formula 29]

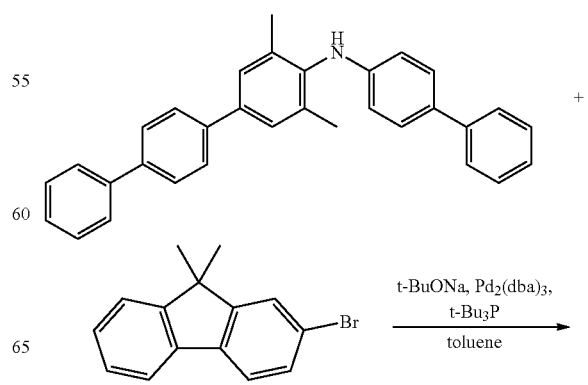

-continued

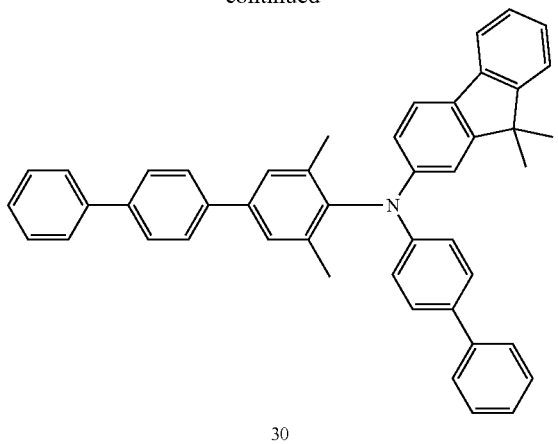

30

N-([1,1'-biphenyl]-4-yl)-3,5-dimethyl-[1,1': 4',1''-terphenyl]-4-amine (8.0 g, 18.80 mmol), 2-bromo-9,9-dimethyl-9H-fluorene (5.6 g, 20.68 mmol), sodium tert butoxide (3.6 g, 37.60 mmol), tris(dibenzylideneacetone) dipalladium (0) (0.34 g, 0.376 mmol), tri-tert-butylphosphine (0.35 mL, 1.50 mmol), and toluene 150 mL were added into a 250 mL flask under nitrogen stream and were refluxed while stirring. After completion of reaction, a toluene layer was extracted therefrom using 50 mL of water. The extracted solution was treated with $MgSO_4$ to remove residual moisture, and then was concentrated under reduced pressure, and then purified using a column chromatography method, and was recrystallized with dichloromethane/heptane, thereby to obtain 4.6 g of a compound 30 in 39.6% yield.

[Present Example 1] Production of Organic Electroluminescent Device Using Compound 6 as Hole Transport Layer Material A light-reflective layer made of Ag alloy, and an anode (ITO) (10 nm) of an organic light emitting device were sequentially stacked on a substrate. Then, the substrate is subjected to an exposure (photo-lithography) process to pattern the substrate such that a cathode region, an anode region, and an insulating layer region are defined thereon. Afterwards, a surface thereof was treated with $O_2$ plasma for increasing a work function of the anode (ITO) and for cleaning.

On the anode, a hole injection layer (HIL) made of 1,4,5,8,9,11-hexaazatriphenylene-hexacarbonitrile (HAT-CN) was formed to have a thickness of 100 Å. Subsequently, on the hole injection layer, the compound 6 was vacuum-deposited to form a hole transport layer having a thickness of 1000 Å.

On the hole transport layer (HTL), an electron blocking layer (EBL) made of N-phenyl-N-(4-(spiro[benzo[de]anthracene-7,9'-fluorene]-2'-yl)phenyl)dibenzo[b,d]furan-4-amine was formed to have a thickness of 100 Å. Then, on the electron blocking layer (EBL), a light emission layer (EML) composed of α, β-AND as a host material capable of forming a blue EML was deposited while doping N1,N1, N6,N6-tetrakis(4-(1-silyl)phenyl)pyrene-1,6-diamine as dopant into the host material. Thus, a light emitting layer with a thickness of 250 Å was formed.

Then, on the light emitting layer (EML), an electron transport layer (ETL) was formed to have a thickness of 360 Å by mixing 2-(4-(9,10-di(naphthalen-2-yl)anthracen-2-yl)phenyl)-1-phenyl-1H-benzo[d]imidazole and LiQ at a 1:1 ratio and then depositing the mixture on the light emitting layer (EML). Then, magnesium (Mg) and silver (Ag) were deposited on the ETL layer at a ratio of 9:1, thereby to form a cathode of a thickness of 160 Å.

On the cathode, N4,N4'-diphenyl-N4,N4'-bis(4-(9-phenyl-9H-carbazol-3-yl)phenyl)-[1,1'-biphenyl]-4,4'-diamine was deposited, thereby to form a capping layer of a thickness of 60 nm.

Then, a seal cap was bonded to the capping layer (CPL) using a UV curable adhesive to protect an organic electroluminescent device from $O_2$ or moisture in the atmosphere. In this way, the organic electroluminescent device was produced.

[Present Examples 2 to 11] Production of Organic Electroluminescent Devices

Organic electroluminescent devices were manufactured in the same manner as in Present Example 1 except that the compounds 29, 138, 101, 51, 269, 221, 233, 63, 245, and 30 as obtained in Synthesis Examples 2 to 11 respectively were used instead of the compound 6.

Comparative Examples 1 to 2

Organic electroluminescent devices were manufactured in the same manner as in Present Example 1 except that the compound NPB or Compound A used as a conventional hole transport layer were used instead of the compound 6.

[NPB]

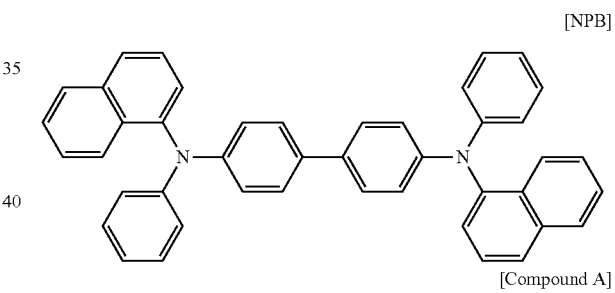

[Compound A]

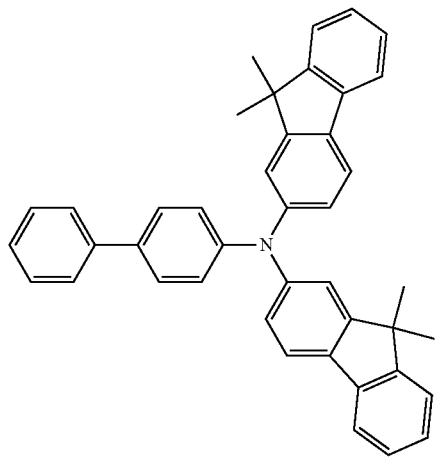

Experimental Example 1

The devices of Present Examples 1 to 11 and Comparative Examples 1 to 2 are measured in terms of a voltage and an efficiency at a current of 10 mA/cm², and a 95% life at a constant current of 20 mA/cm². The measurements are shown in Table 1.

TABLE 1

| HTL | V | Cd/A | lm/W | EQE (%) | CIEx | CIEy | T95 |
|---|---|---|---|---|---|---|---|
| Comparative Example 1 | NPB | 4.6 | 4.0 | 2.7 | 6.4 | 0.132 | 0.061 | 95 |
| Comparative Example 2 | Compound A | 4.0 | 5.7 | 4.4 | 11.5 | 0.142 | 0.05 | 158 |
| Present Example 1 | Compound 6 | 3.88 | 6.6 | 5.4 | 12.6 | 0.139 | 0.052 | 250 |
| Present Example 2 | Compound 29 | 3.74 | 5.8 | 4.9 | 11.5 | 0.141 | 0.049 | 315 |
| Present Example 3 | Compound 138 | 3.78 | 5.8 | 4.8 | 11.6 | 0.141 | 0.049 | 355 |
| Present Example 4 | Compound 101 | 3.92 | 6.4 | 5.1 | 11.9 | 0.139 | 0.052 | 410 |
| Present Example 5 | Compound 51 | 3.75 | 5.8 | 4.9 | 11.6 | 0.14 | 0.049 | 310 |
| Present Example 6 | Compound 269 | 3.92 | 7 | 5.6 | 14.4 | 0.14 | 0.046 | 320 |
| Present Example 7 | Compound 221 | 3.78 | 5.8 | 4.8 | 11.9 | 0.142 | 0.047 | 275 |
| Present Example 8 | Compound 233 | 3.85 | 5.8 | 4.8 | 11.8 | 0.14 | 0.048 | 250 |
| Present Example 9 | Compound 63 | 3.71 | 5.8 | 4.9 | 11.5 | 0.14 | 0.049 | 305 |
| Present Example 10 | Compound 245 | 3.91 | 6 | 4.8 | 12 | 0.141 | 0.048 | 215 |
| Present Example 11 | Compound 30 | 3.89 | 6.1 | 4.9 | 11.7 | 0.14 | 0.051 | 280 |

Table 1 indicates that the devices using the compounds according to Present Examples as the hole transport layer material are excellent in terms of drive voltage, current efficiency, external quantum efficiency (EQE), and the life span compared to the devices using the compounds according to the Comparative Examples as the hole transport layer material.

Table 1 indicates that the devices using the compounds according to Present Examples as the hole transport layer material exhibit the lifespan longer by up to 4 times or greater than that of the device using the compound NPB according to the Comparative Example 1 as the hole transport layer material. Further, Table 1 indicates that the devices using the compounds according to Present Examples as the hole transport layer material exhibit the lifespan longer by minimum 36% to maximum 160% than that of the device using the compound A having a structure similar to that of the compounds according to the present disclosure according to the Comparative Example 2 as the hole transport layer material.

It will be apparent to those skilled in the art that various modifications and variations can be made in the novel compound and the organic light-emitting device of the present disclosure without departing from the technical idea or scope of the disclosure. Thus, it is intended that the present disclosure cover the modifications and variations of this disclosure provided they come within the scope of the appended claims and their equivalents.

What is claimed is:

1. An organic light-emitting device comprising:
a first electrode;
a second electrode; and
at least one organic material layer between the first and second electrodes,
wherein the organic material layer includes a hole transport layer,
wherein the hole transport layer contains a compound which is represented by one of the following Chemical Formulas:

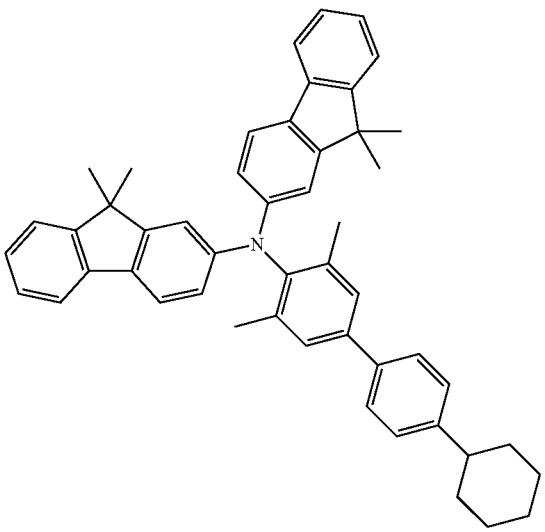

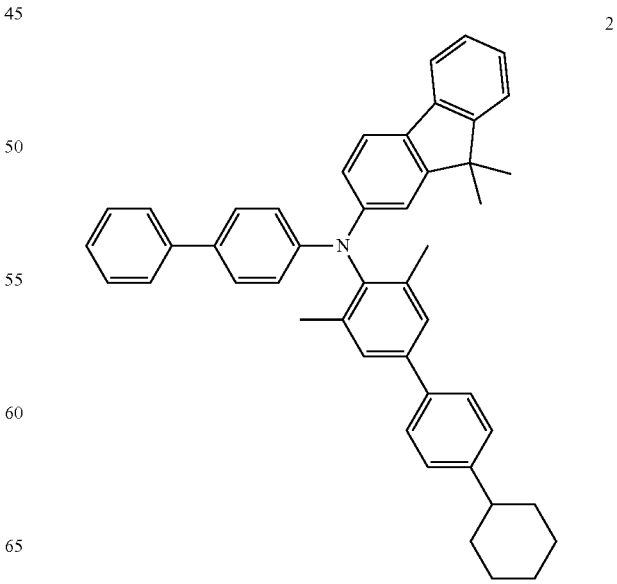

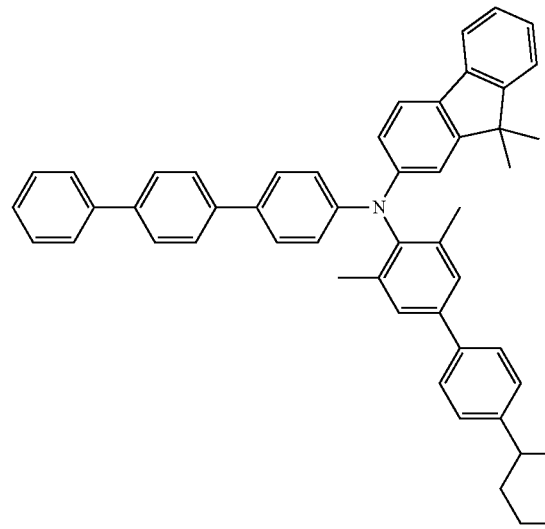
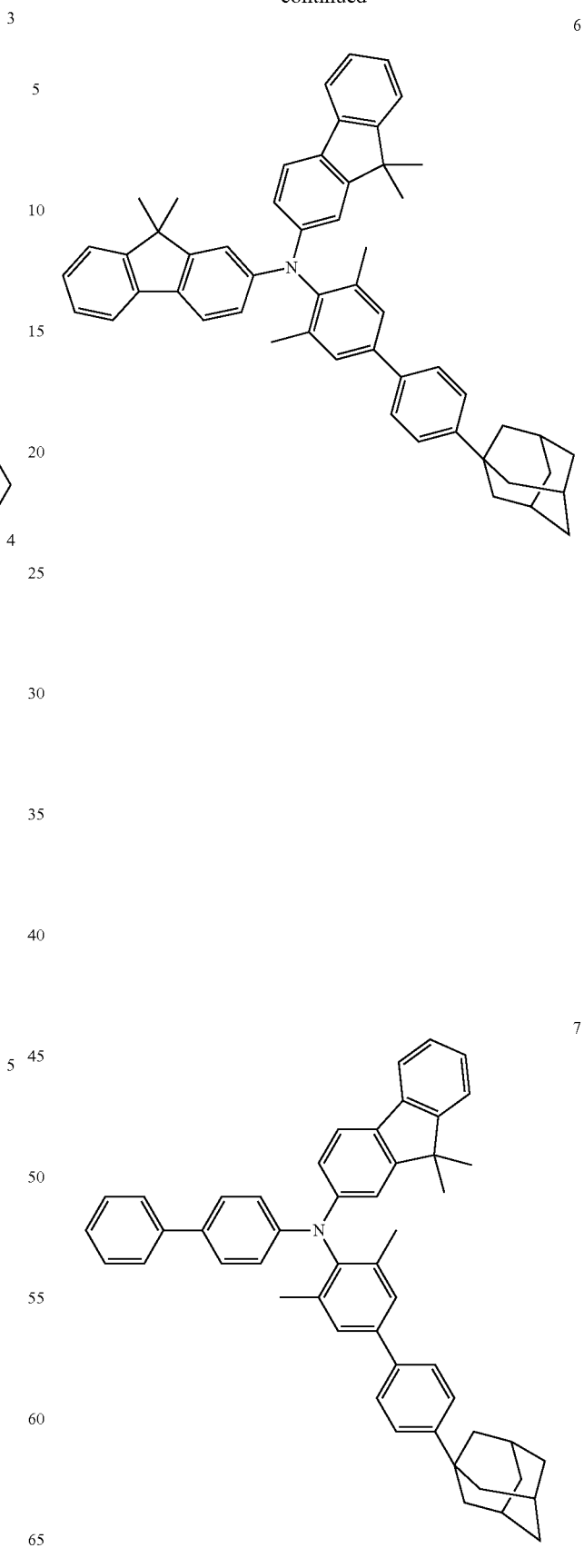

8
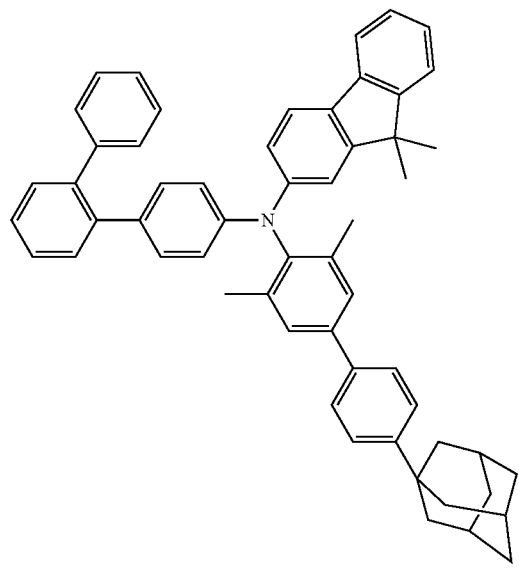
9
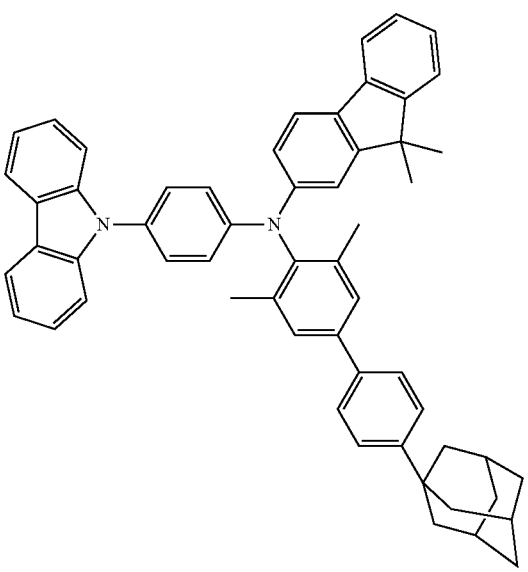
10
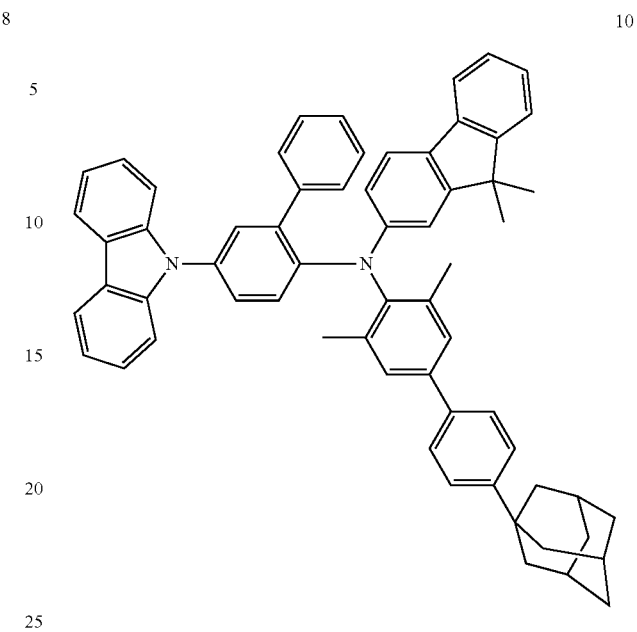
11
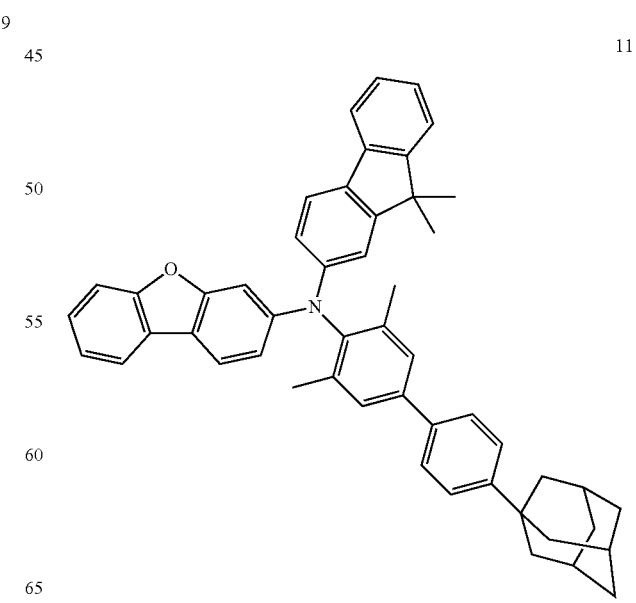

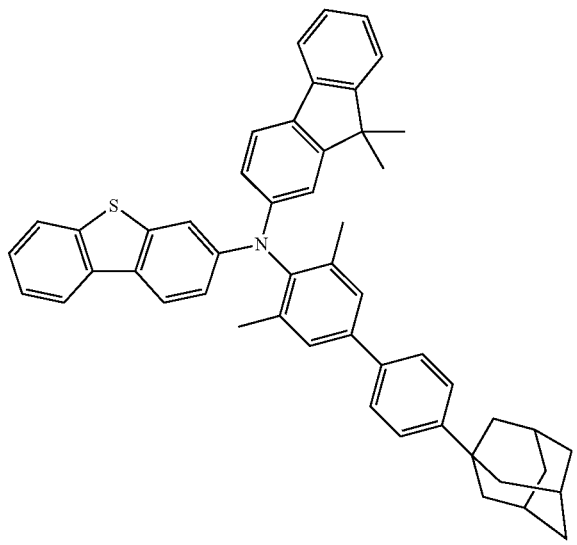
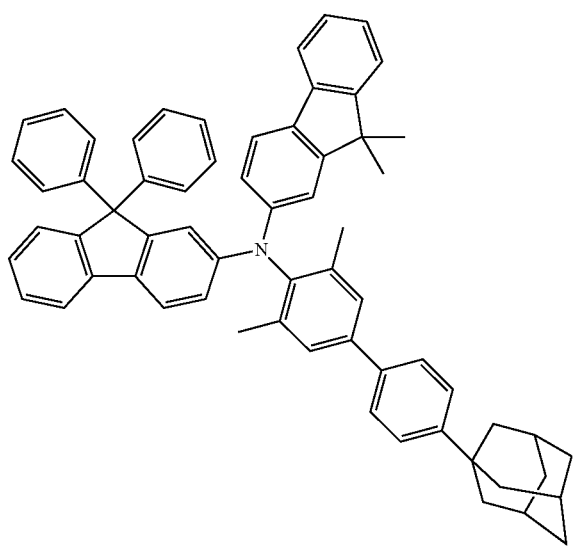
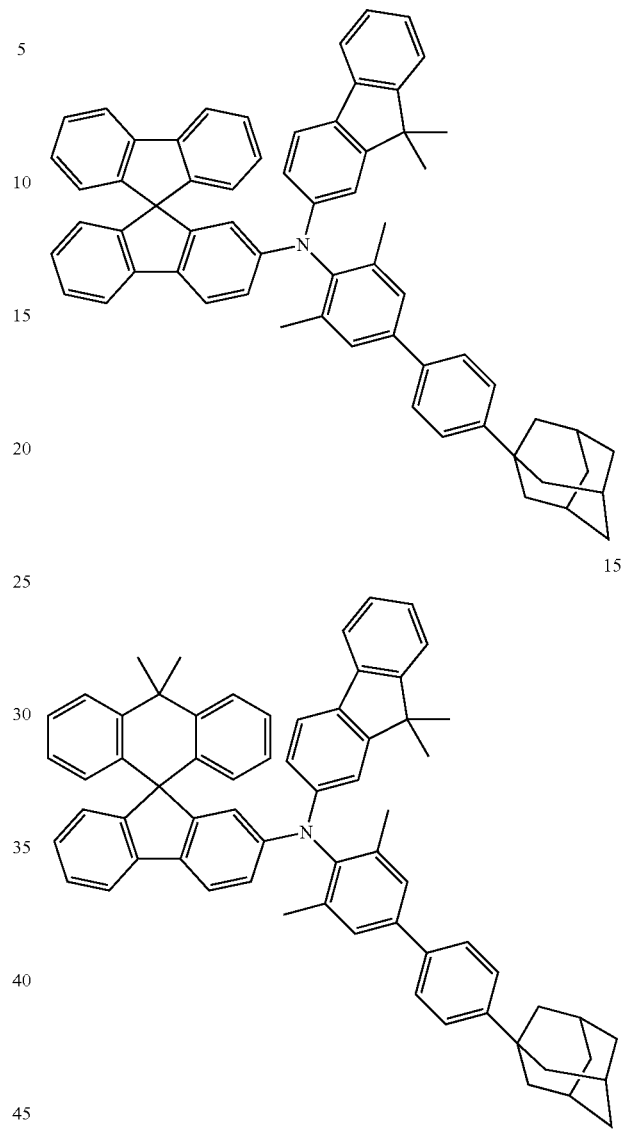
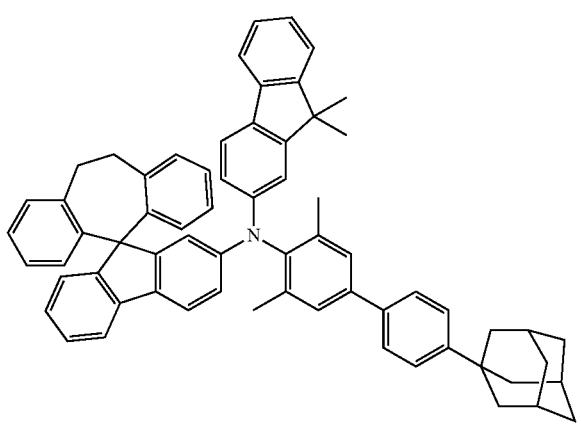

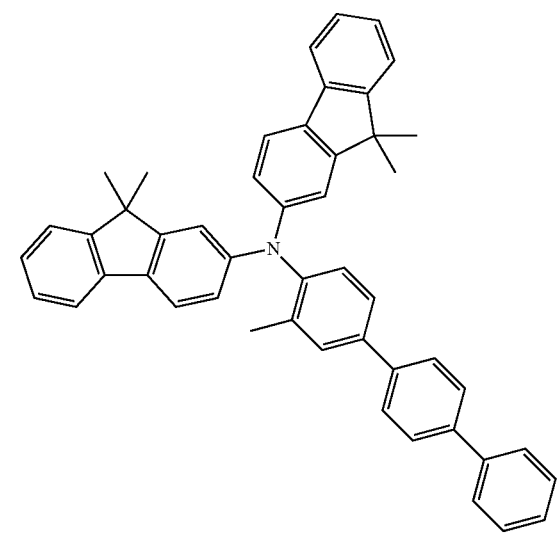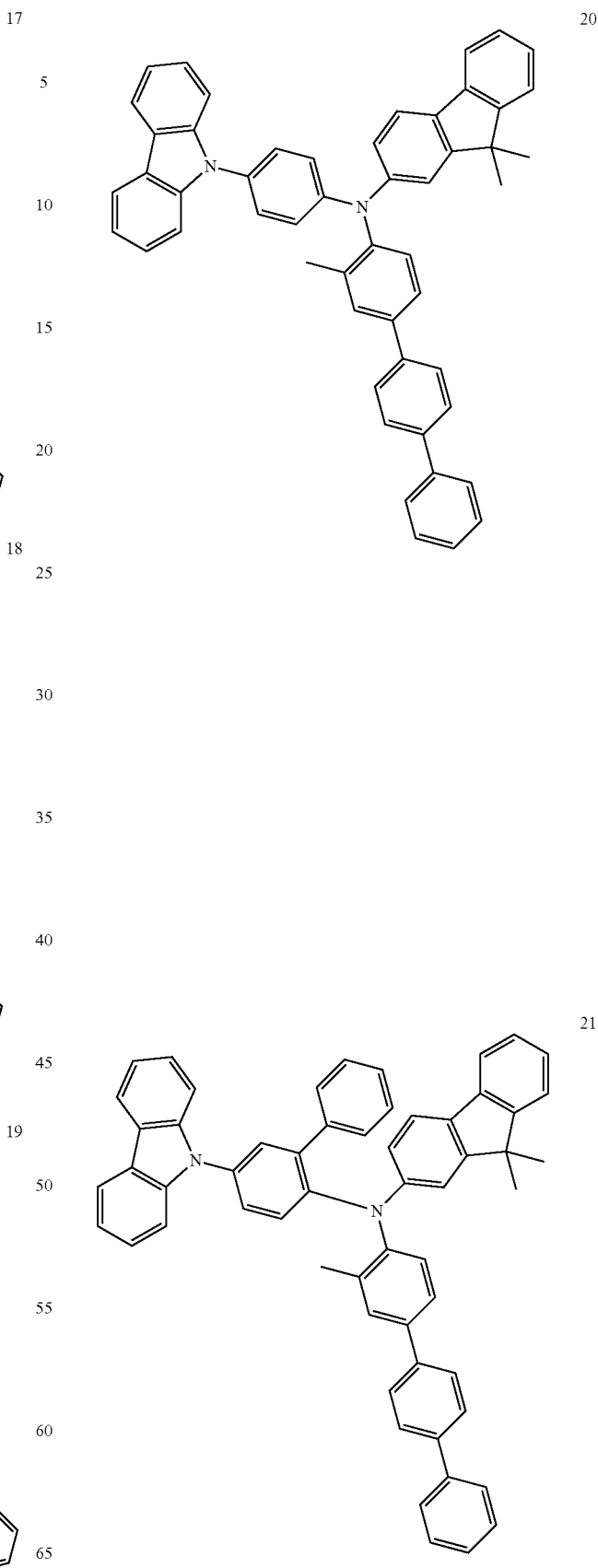

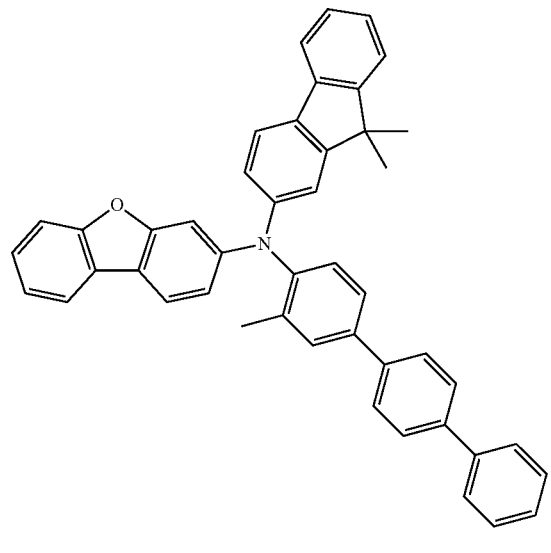
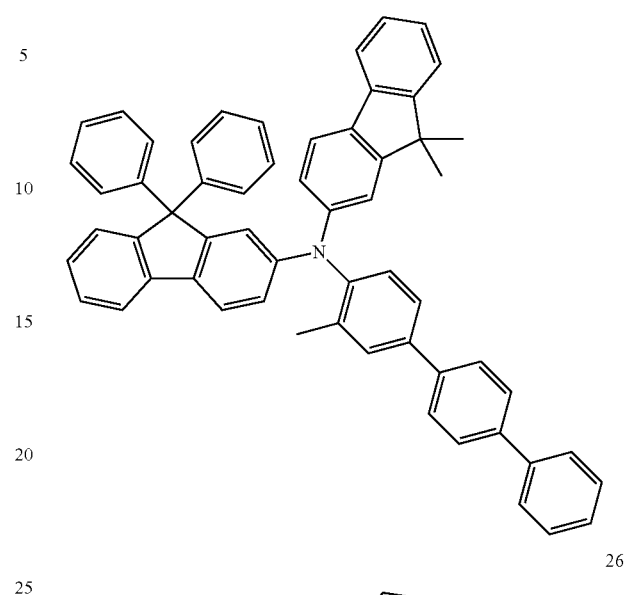
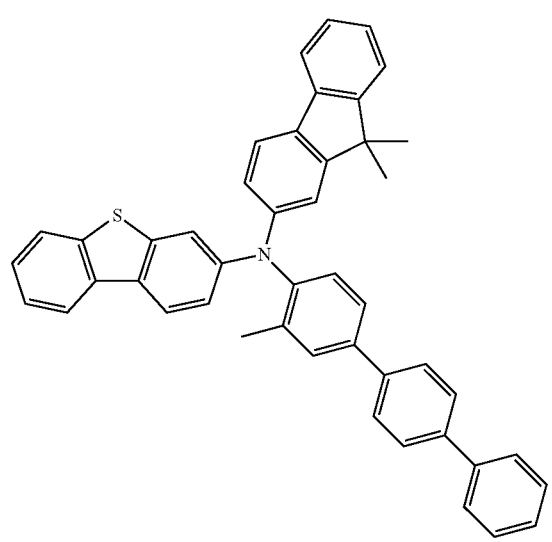
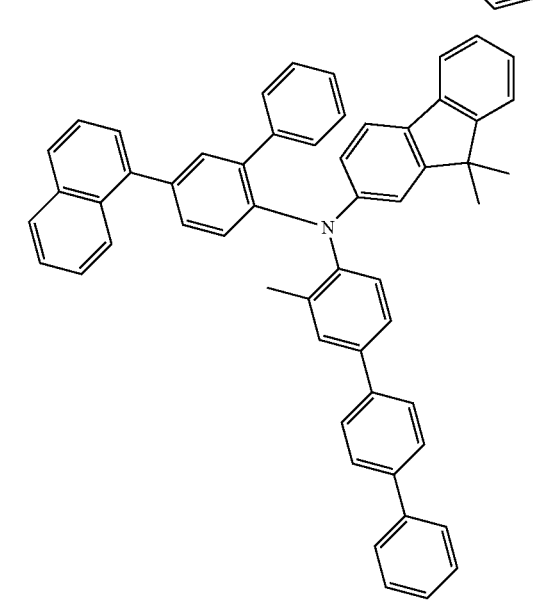
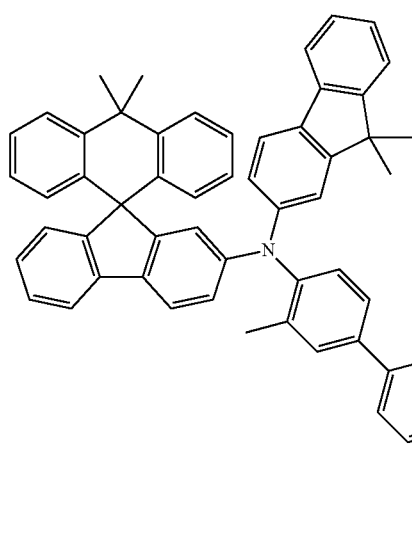

28
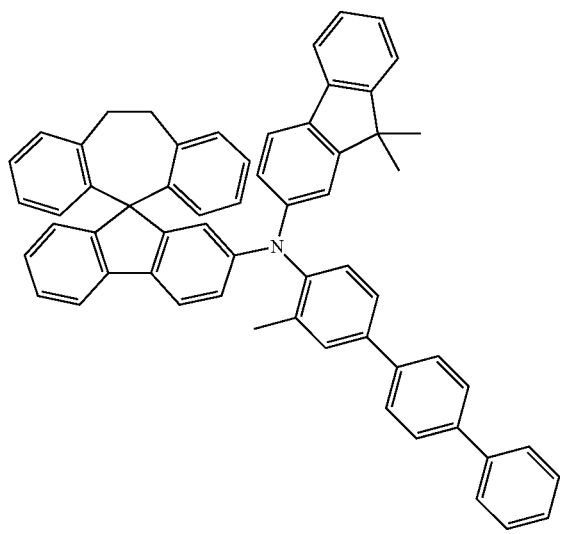
29
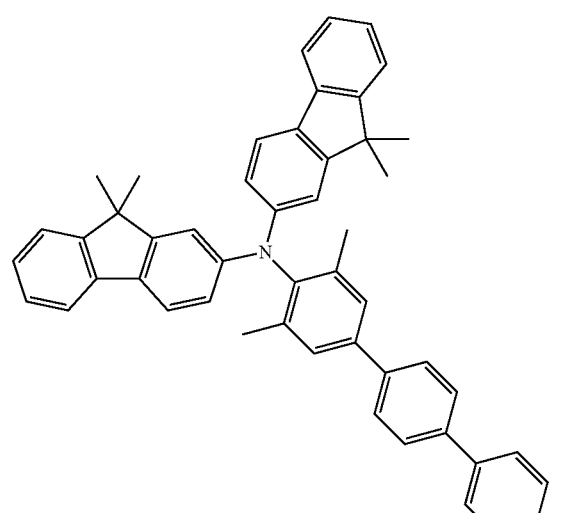
30
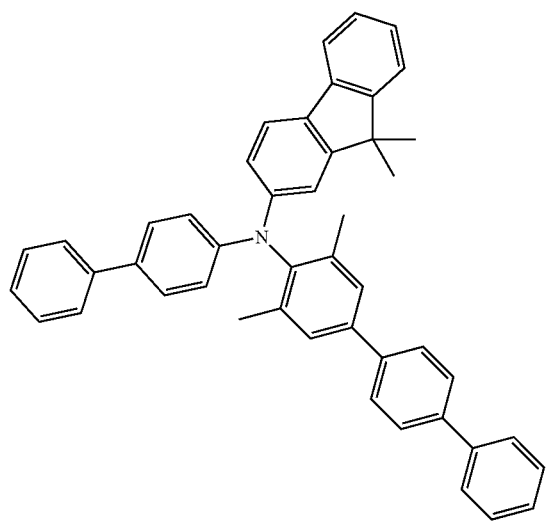
31
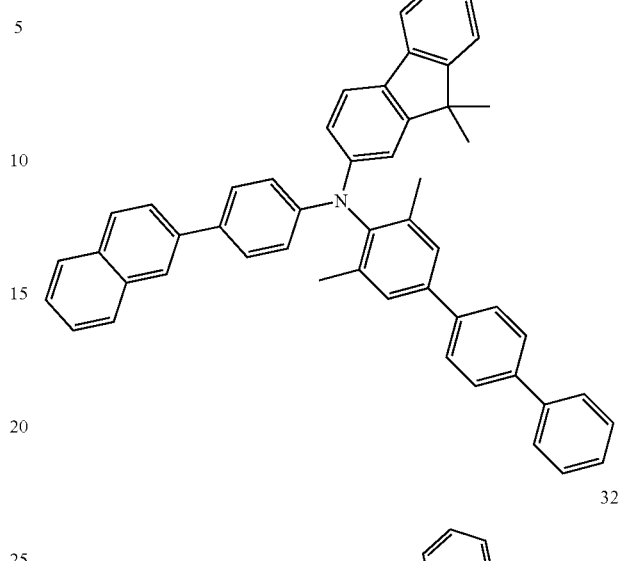
32
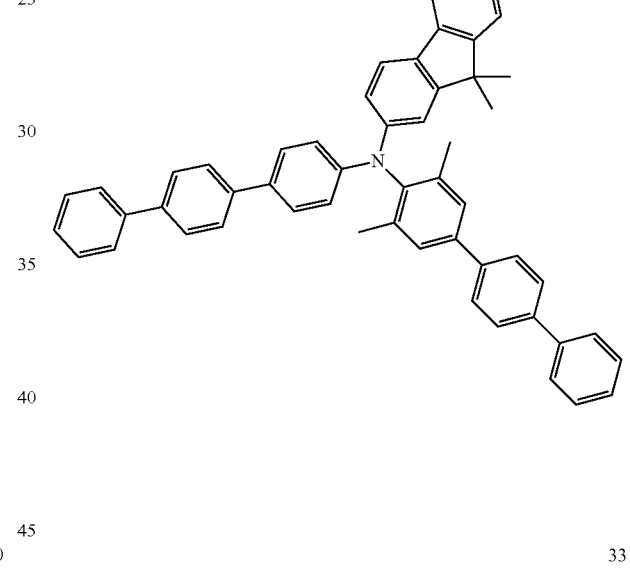
33
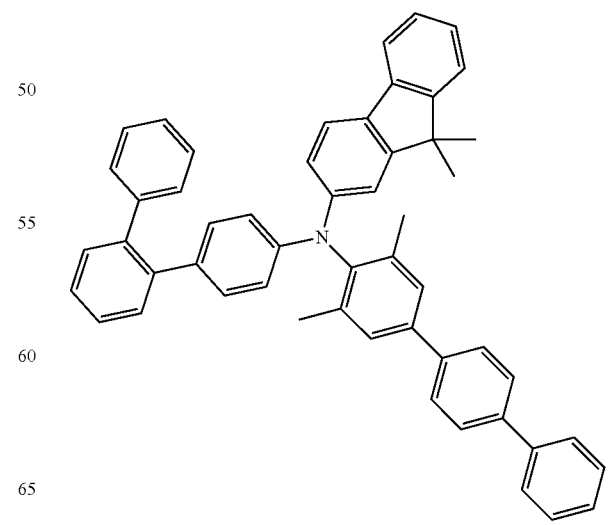

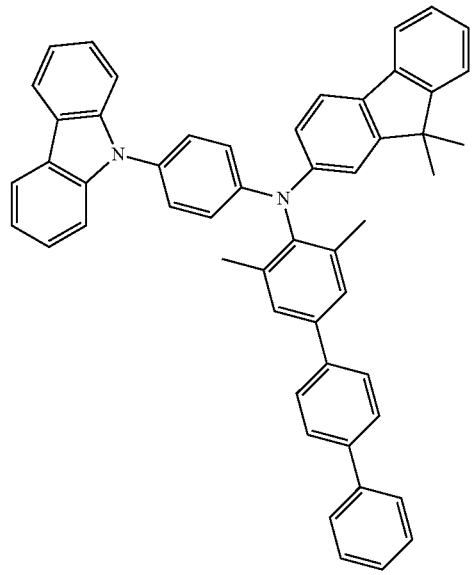
34
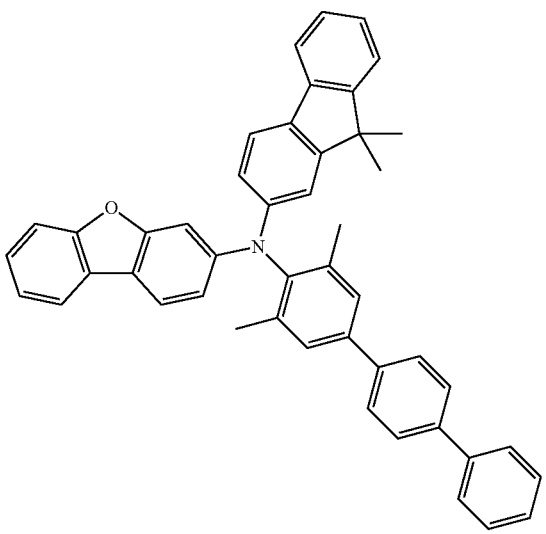
36
37
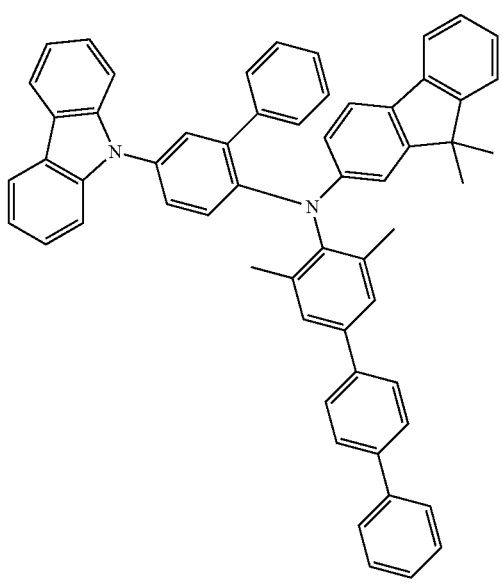
35
38

39
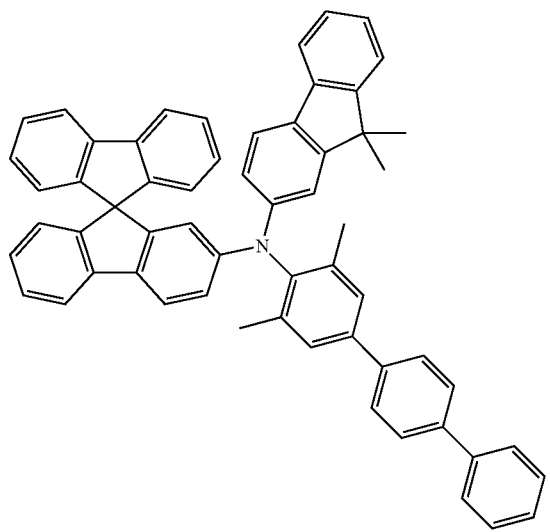
40
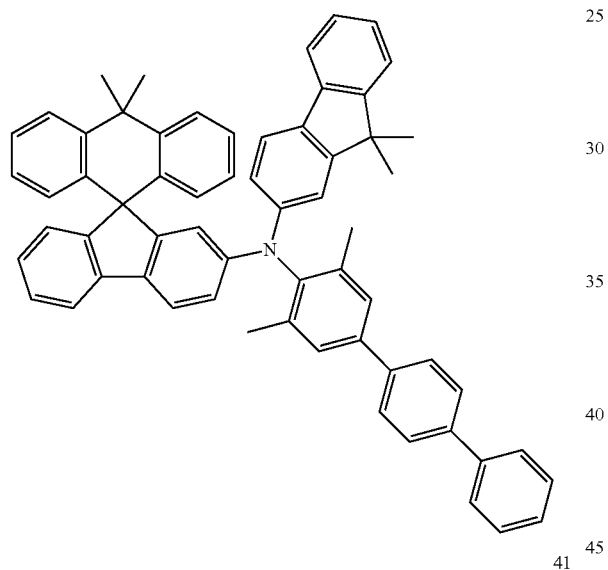
41
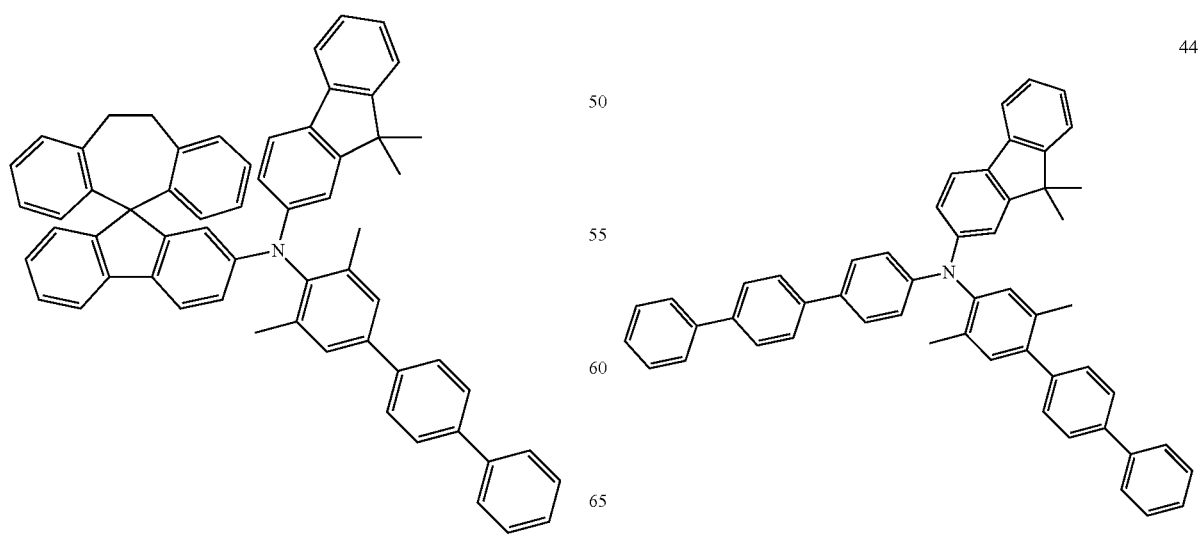
42
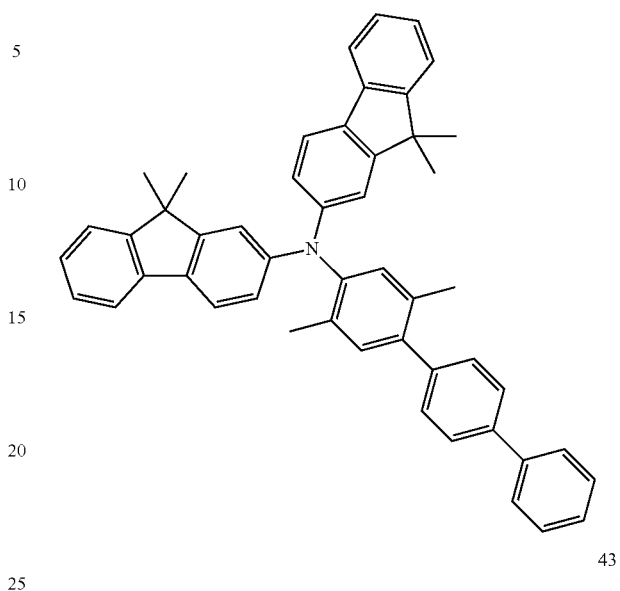
43
44

45
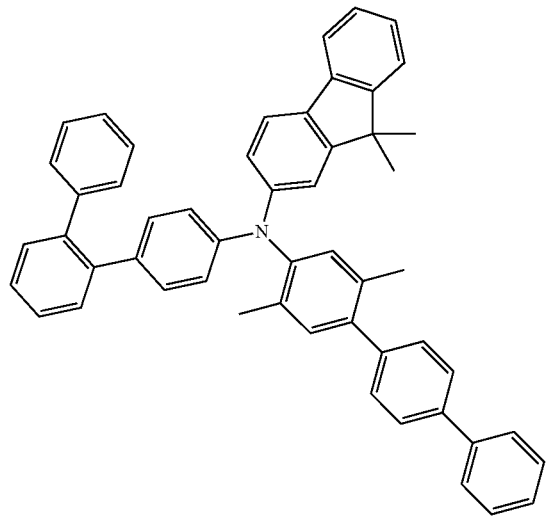
46
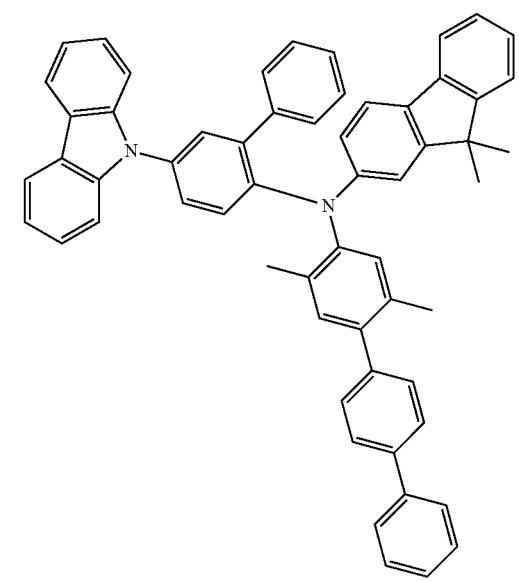
47
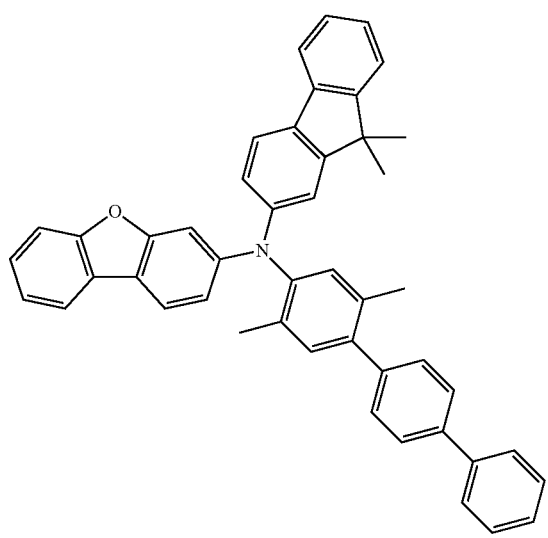
48
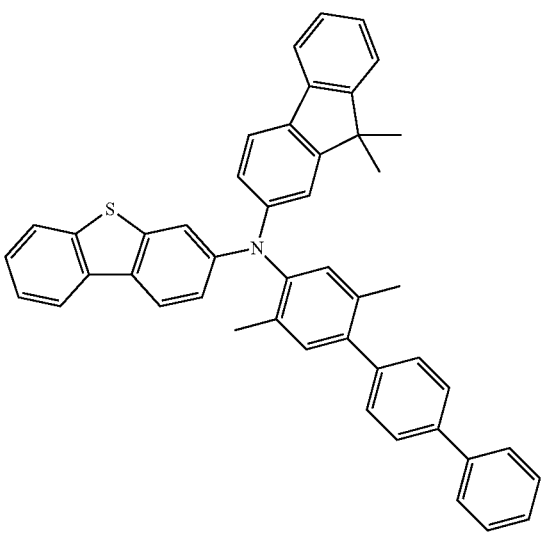
49
50
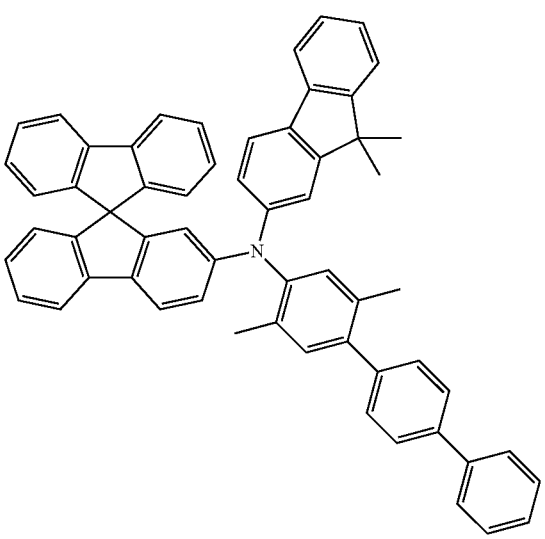

51
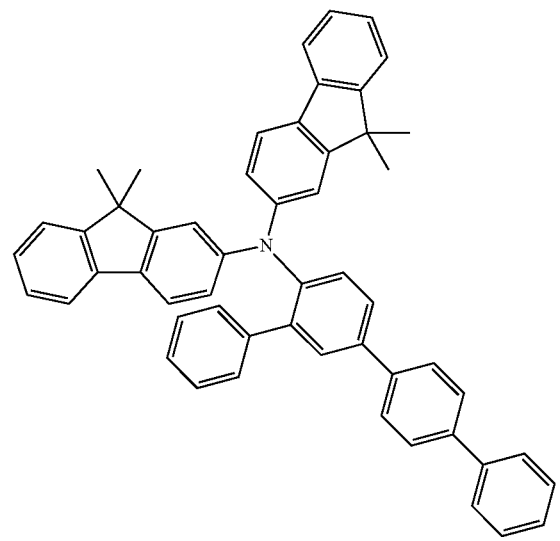
52
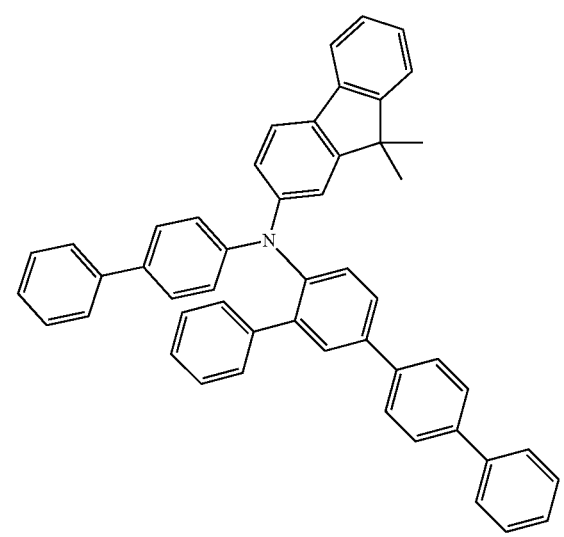
53
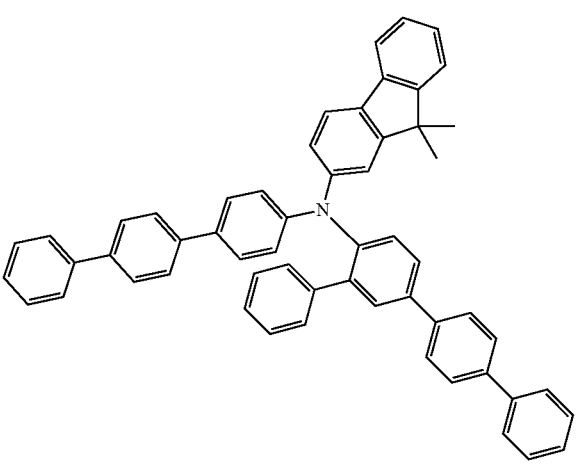
54
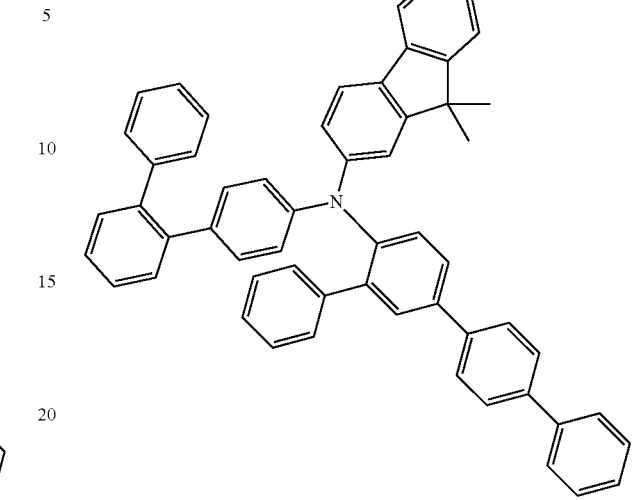
55
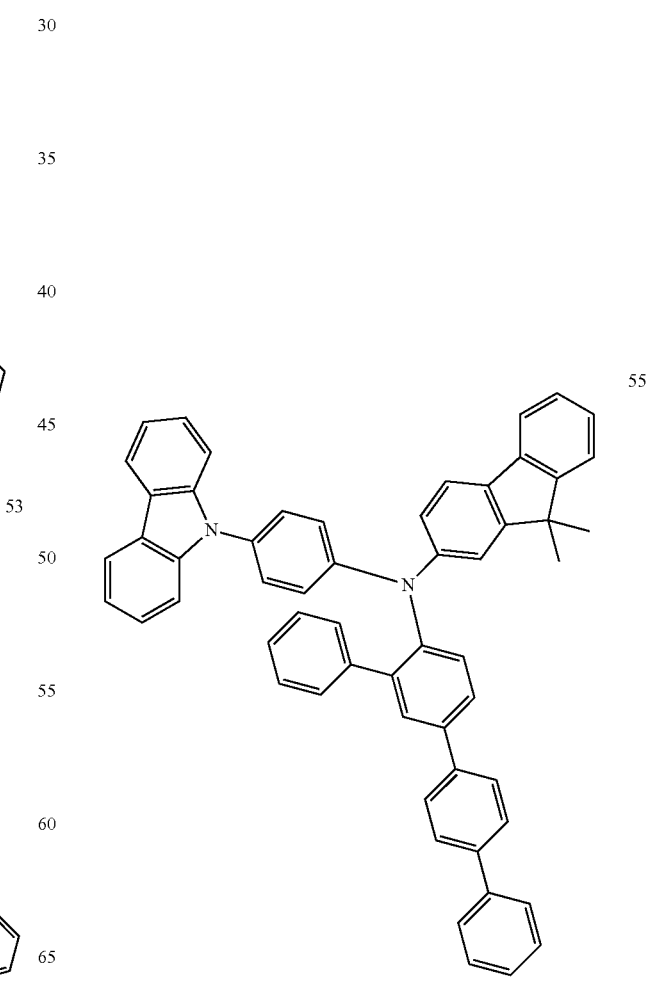

-continued
56
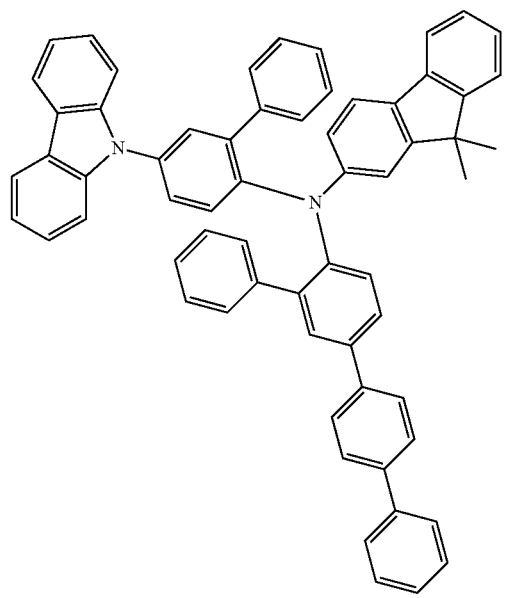
58
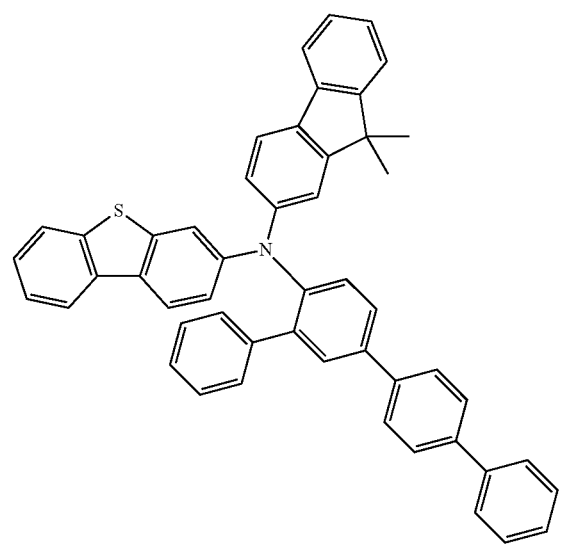
57
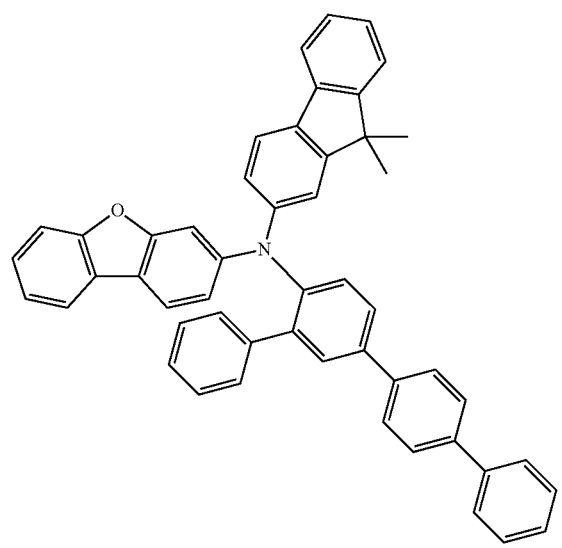
59

169
-continued
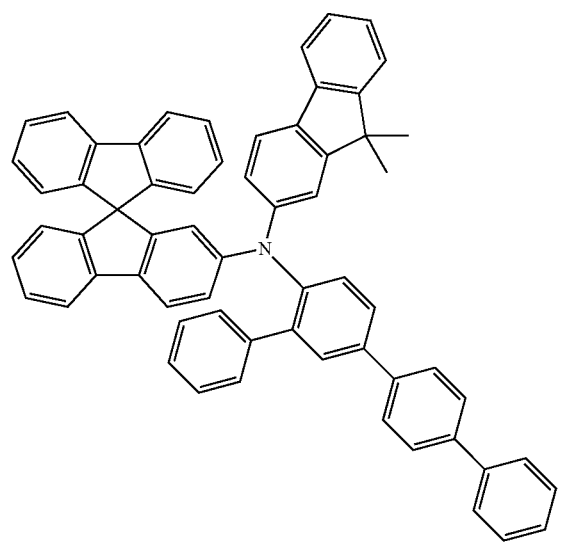
60
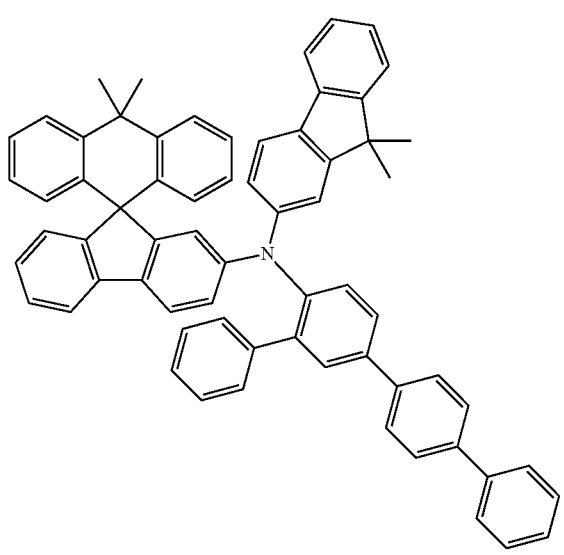
61
170
-continued
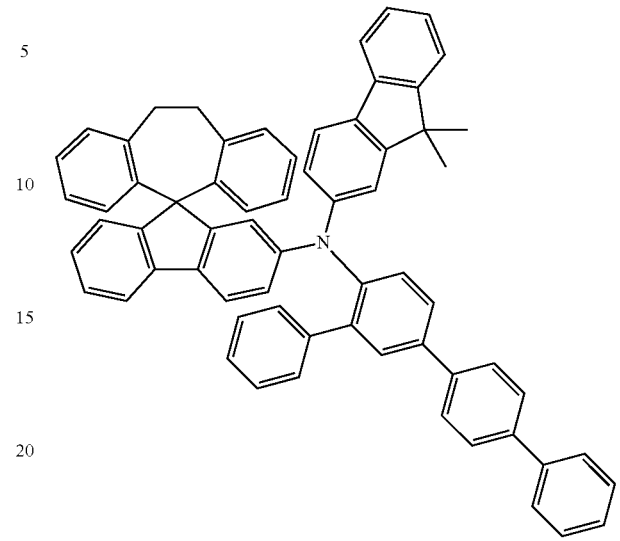

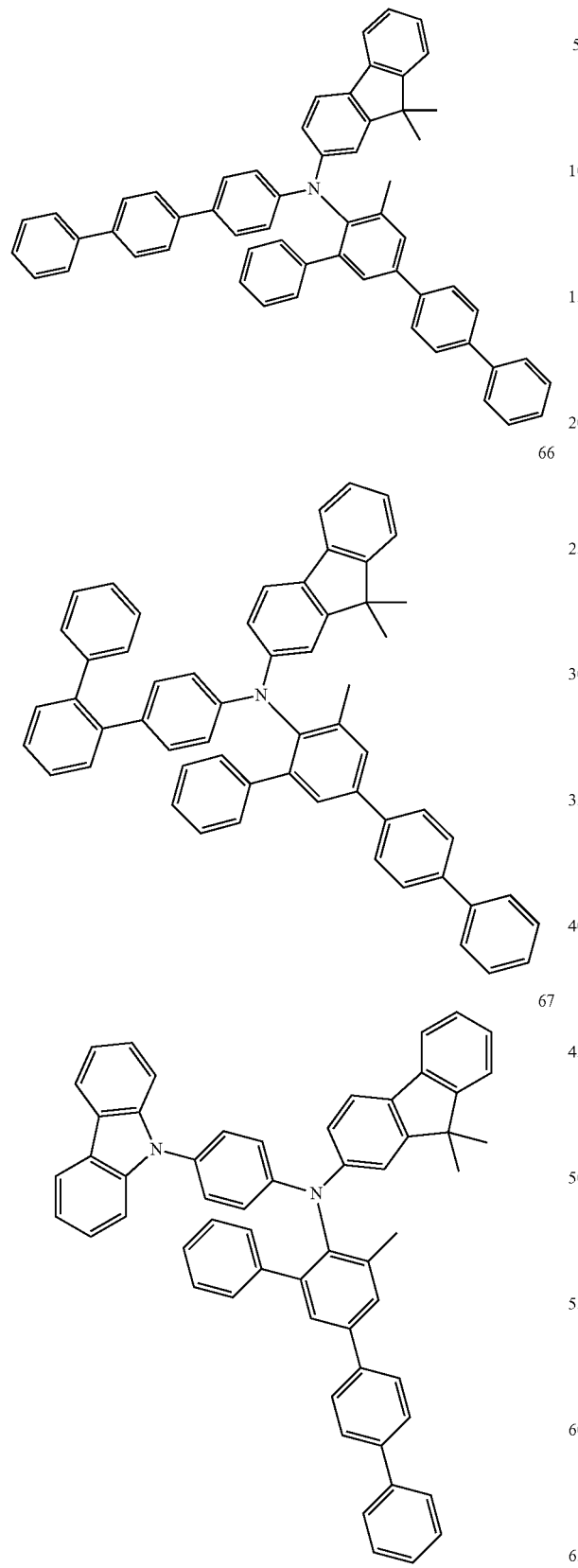
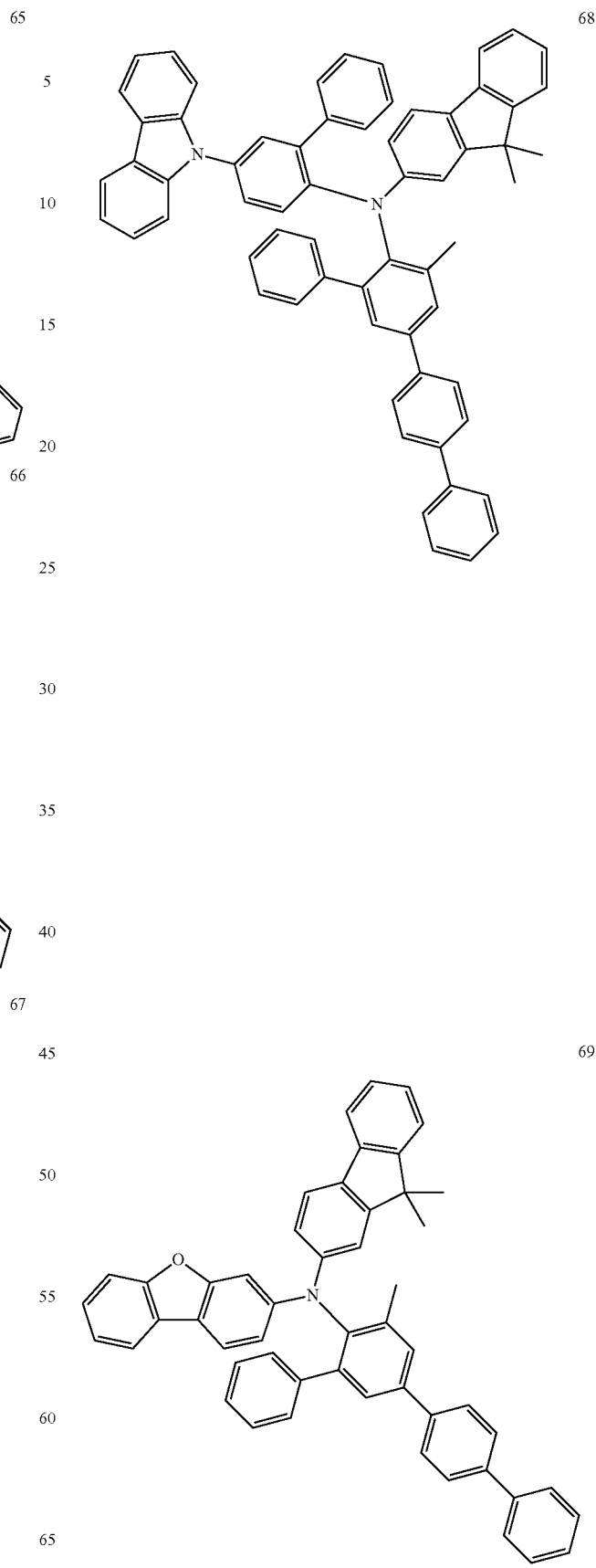

70
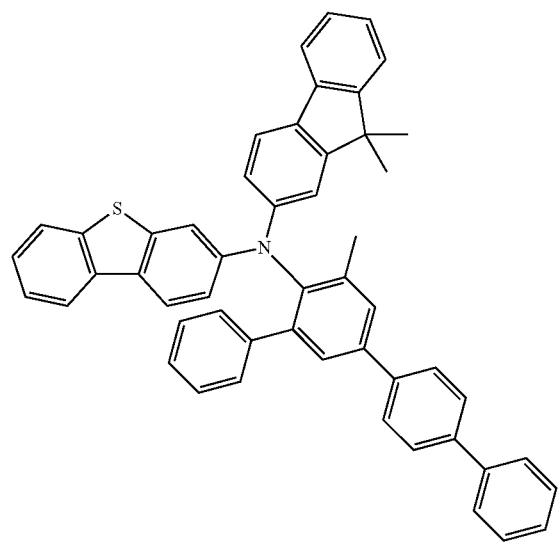
72
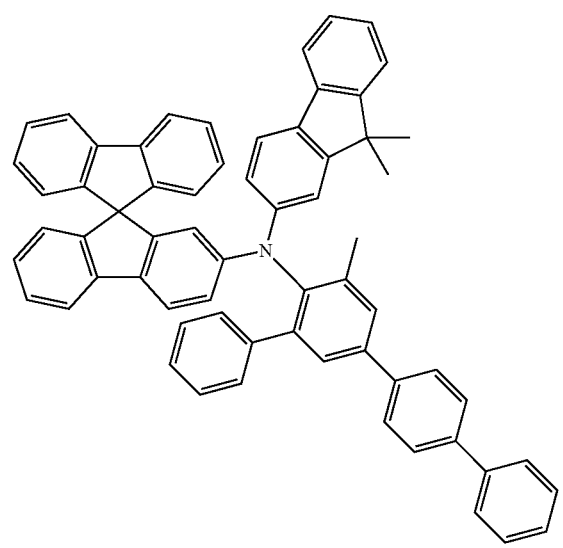
71
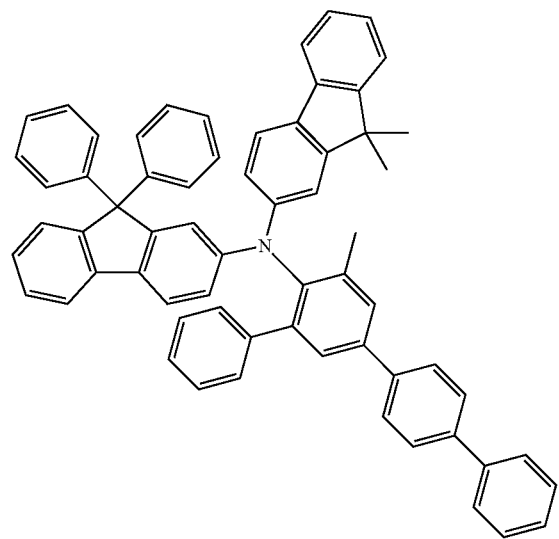
73
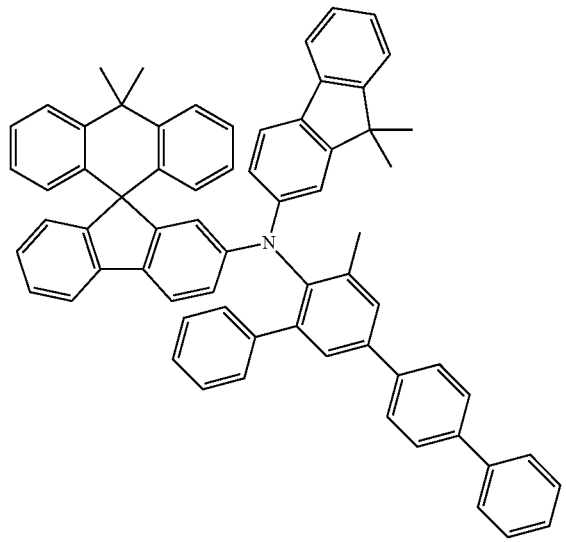

74
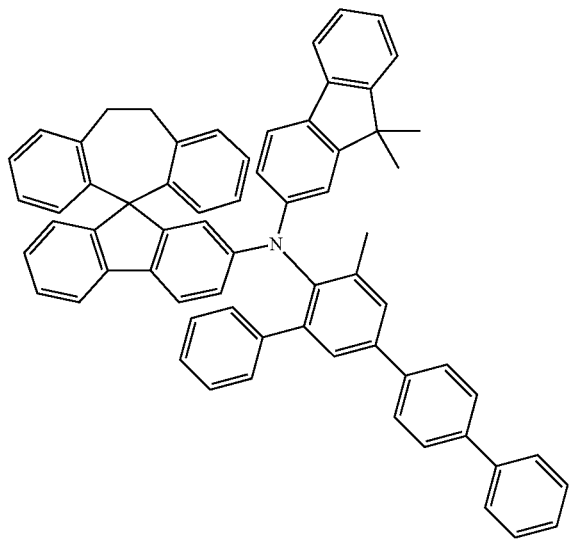
75
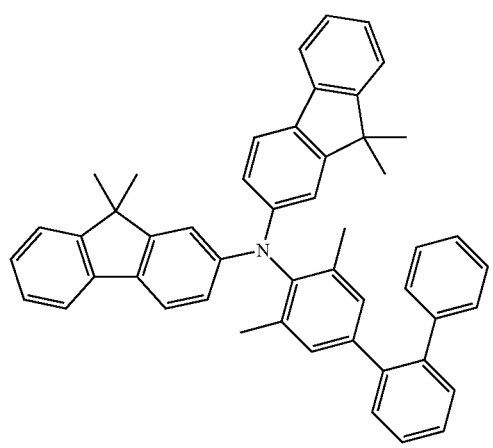
76
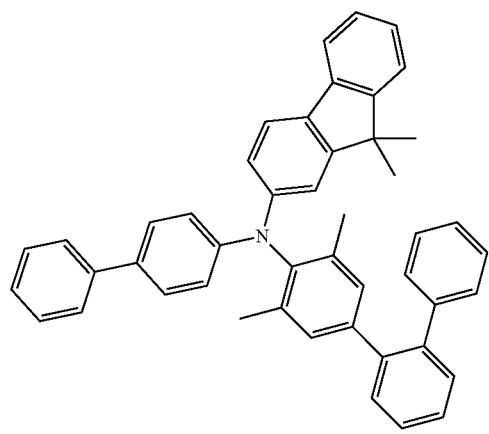
77
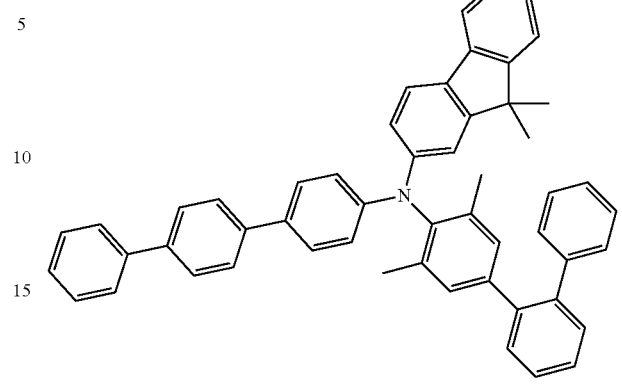
78
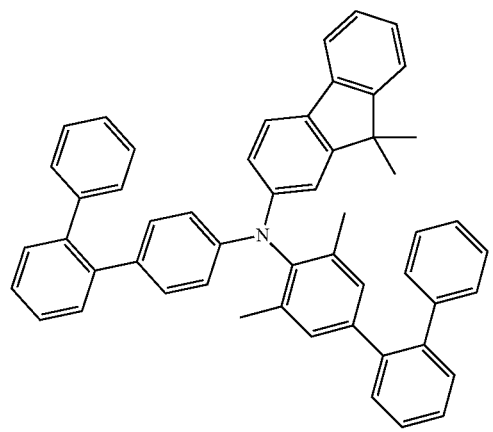
79
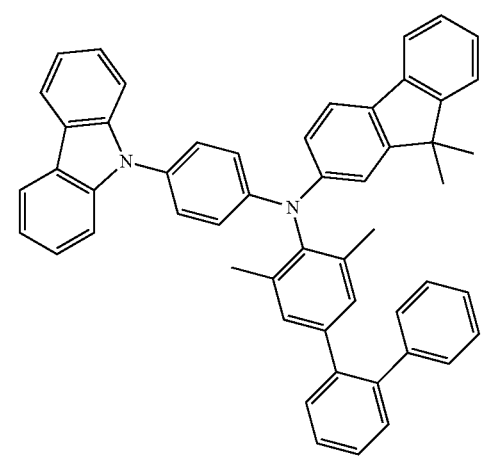

177
-continued
80
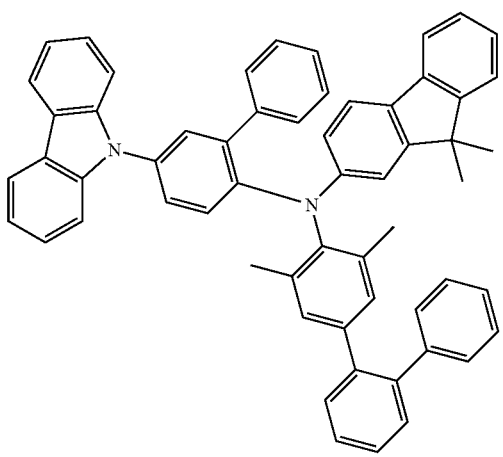
81
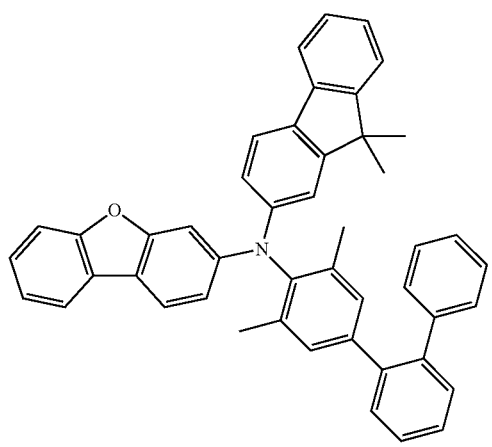
82
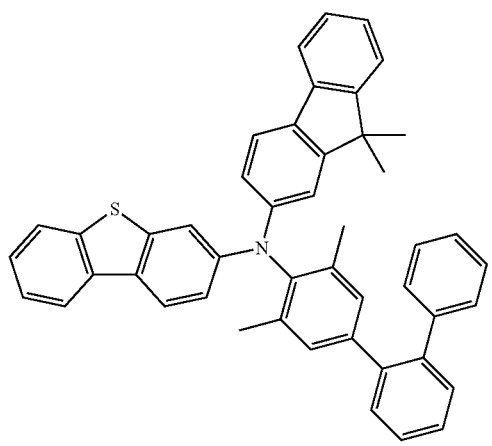
178
-continued
83
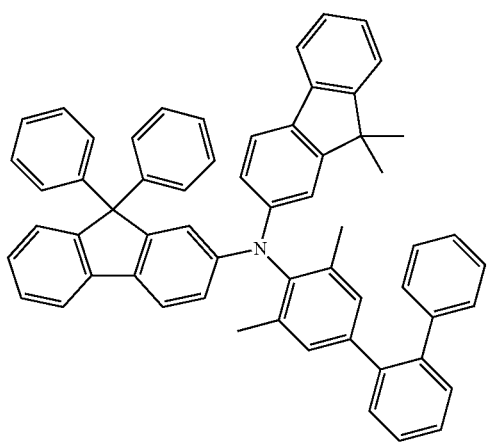
84
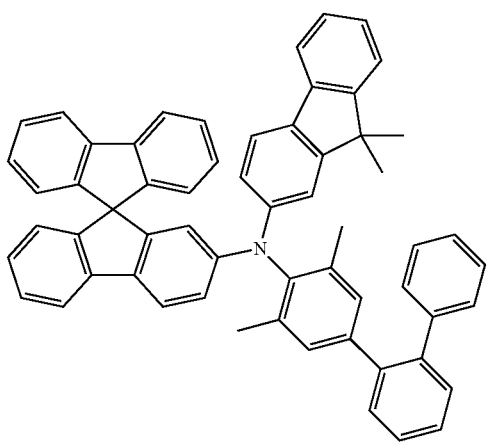
85
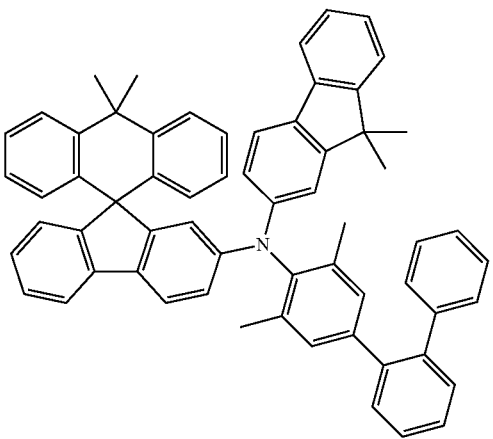

86
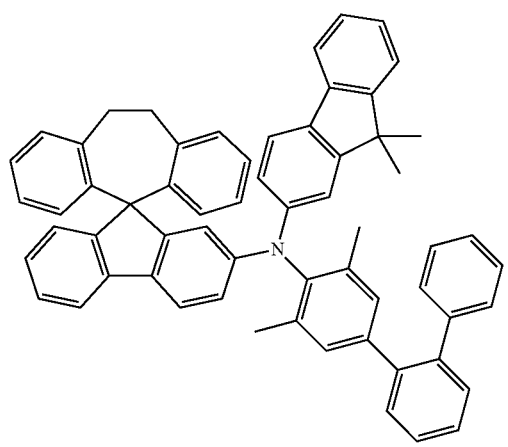
87
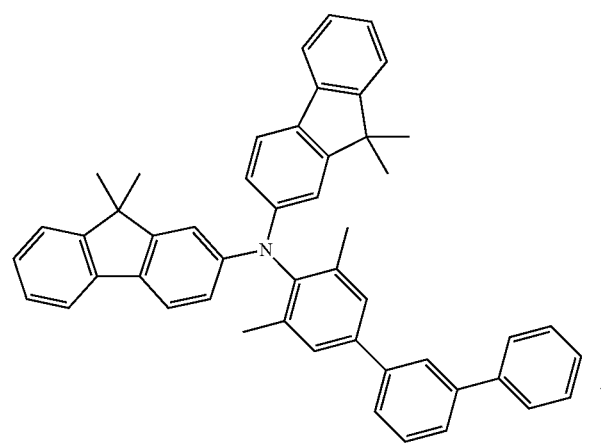
88
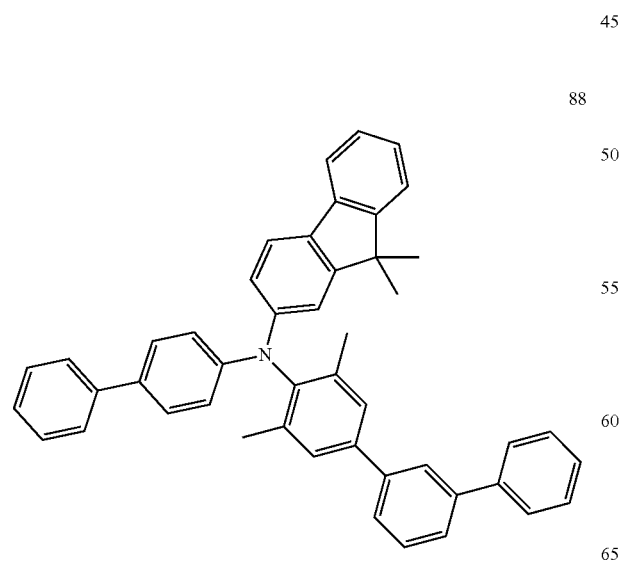
89
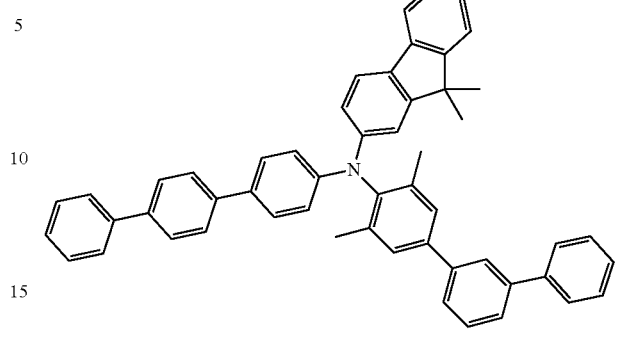
90
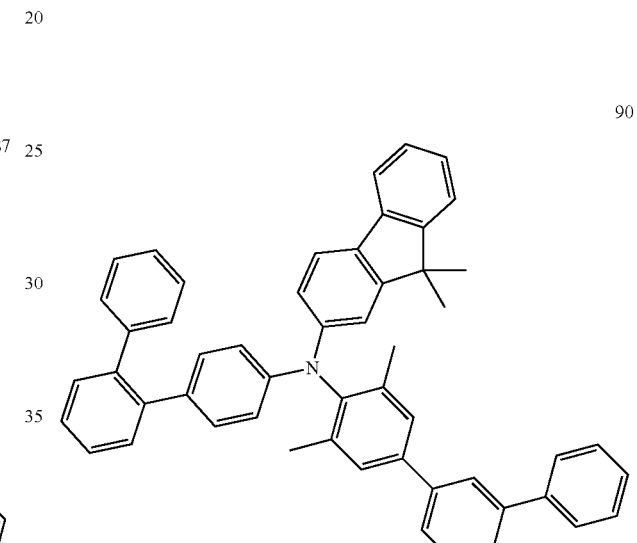
91
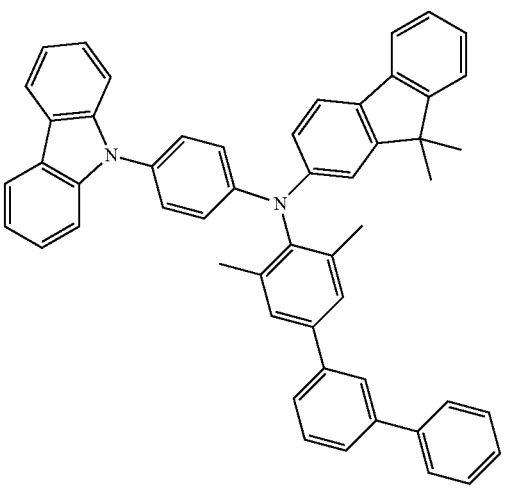

92
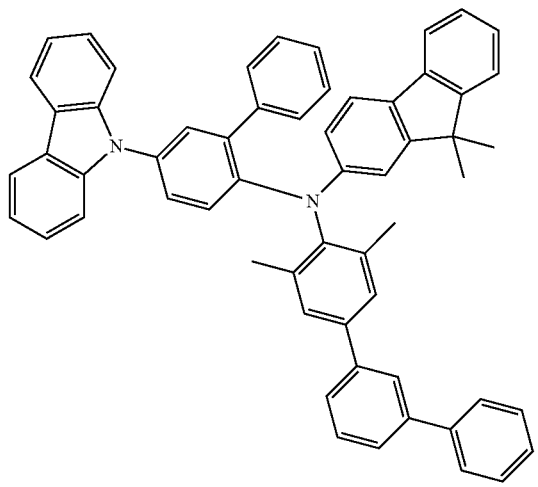
93
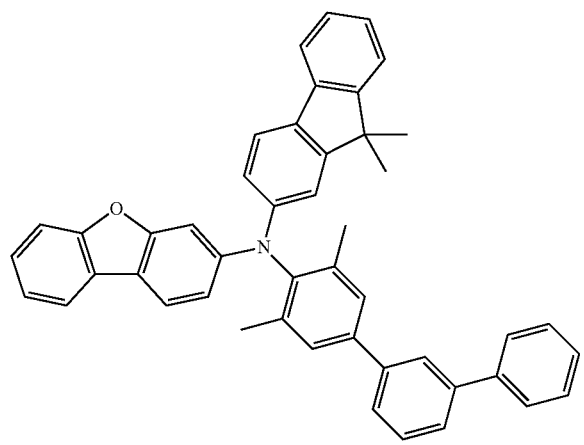
94
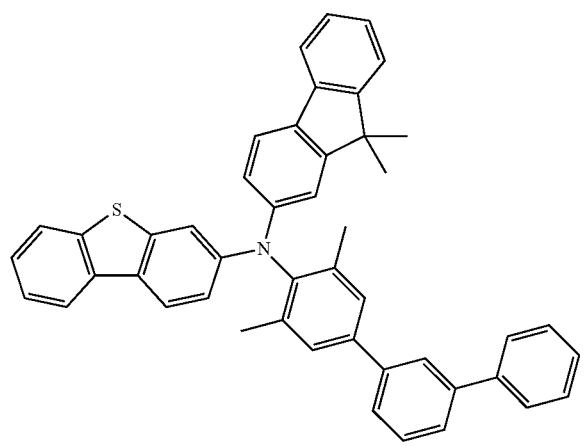
95
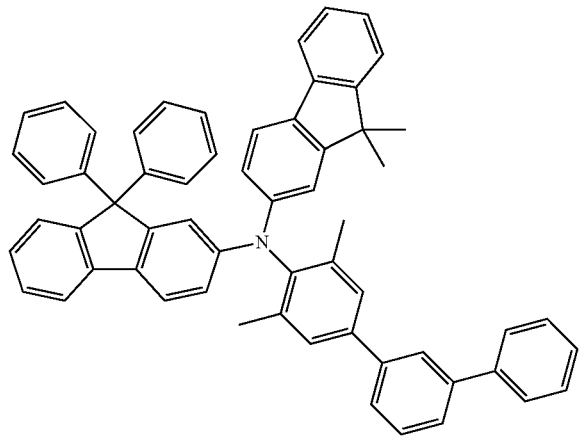
96
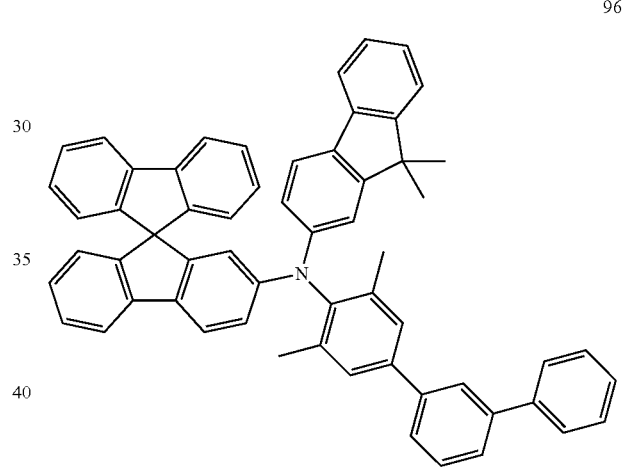
97
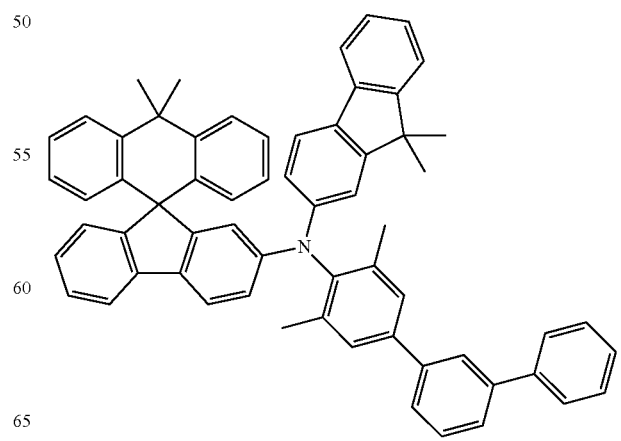

98
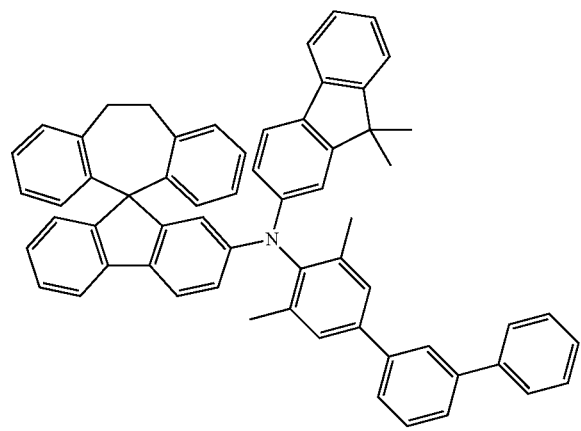
99
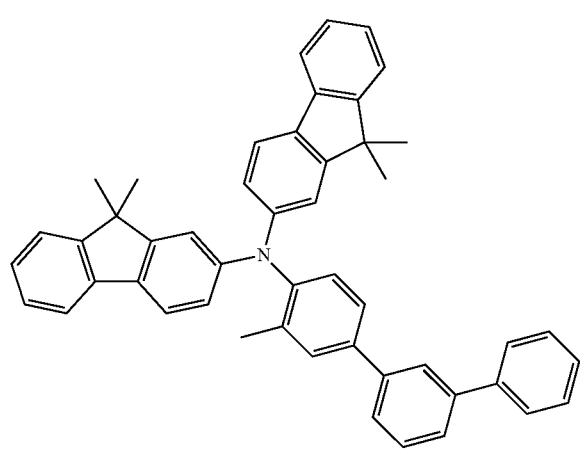
100
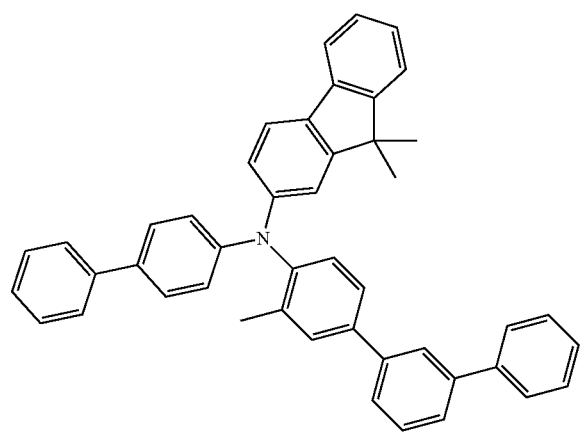
101
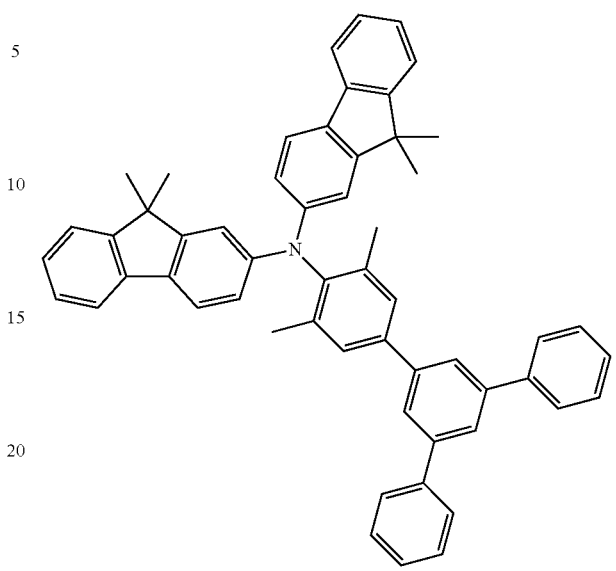
102
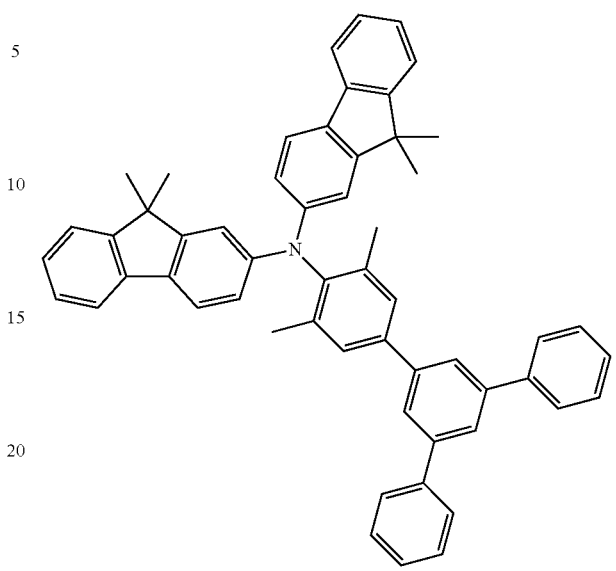
103
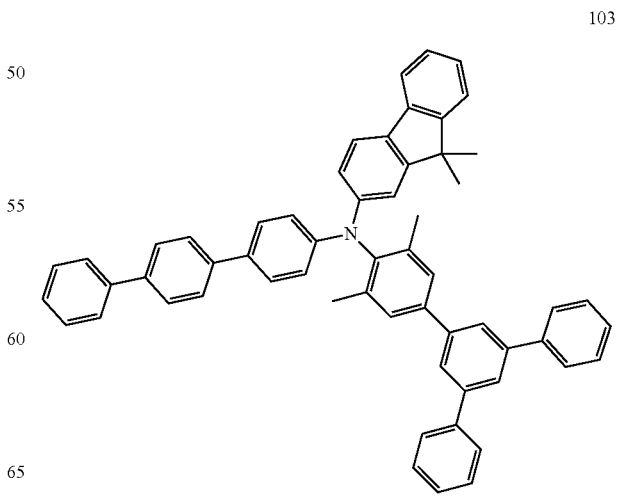

104
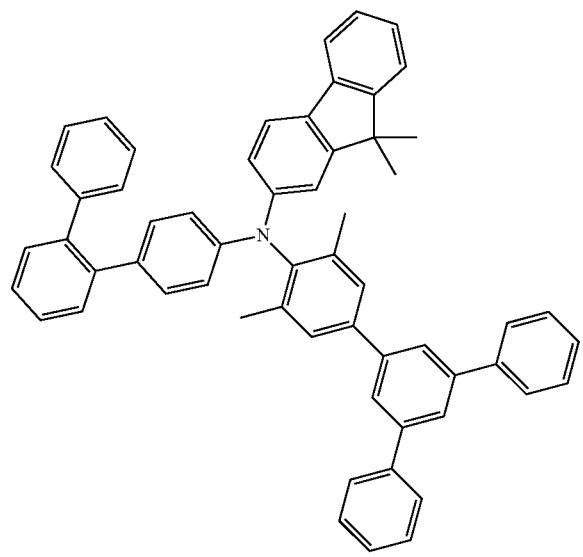
105
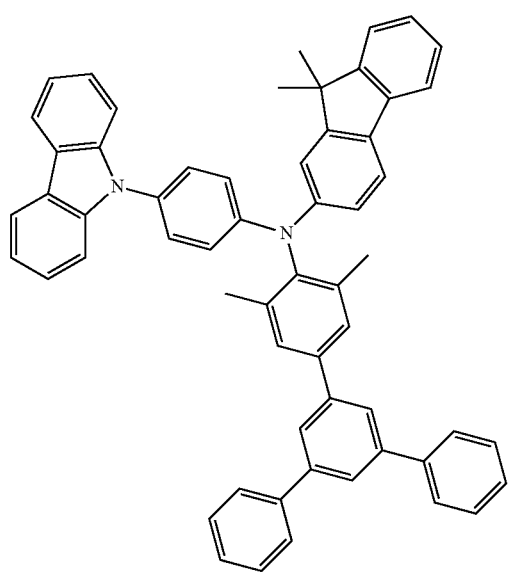
106
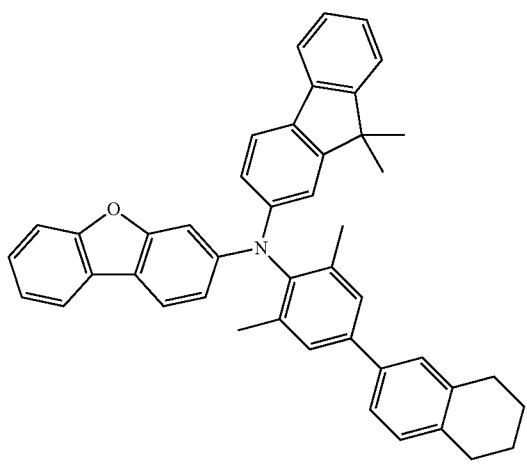
107
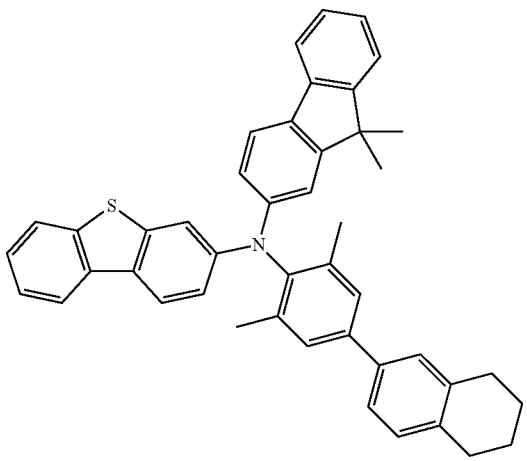
108
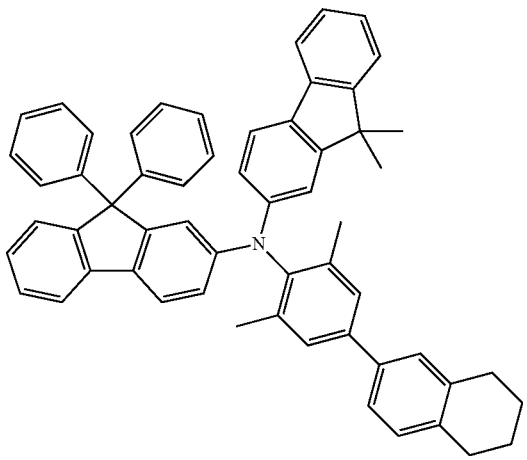
109
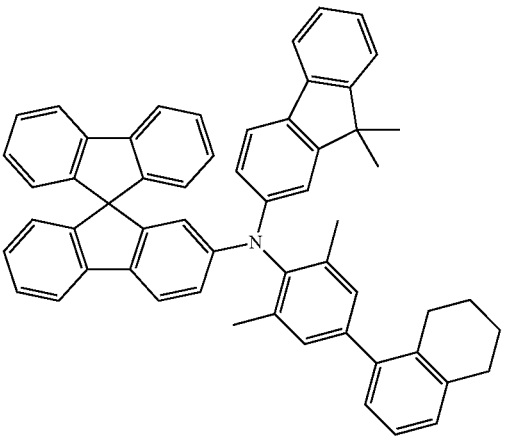

110 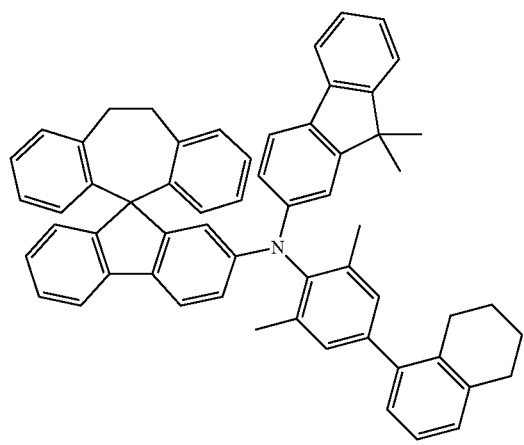
113 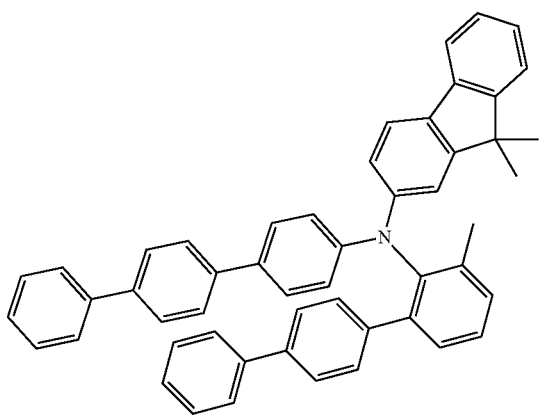
111 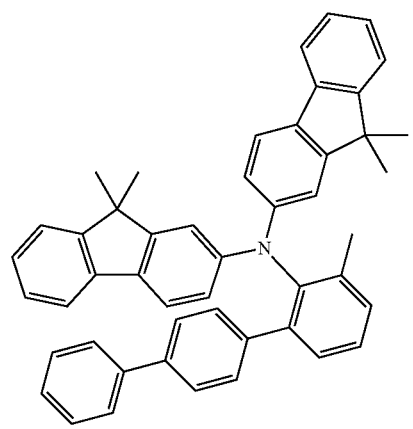
114 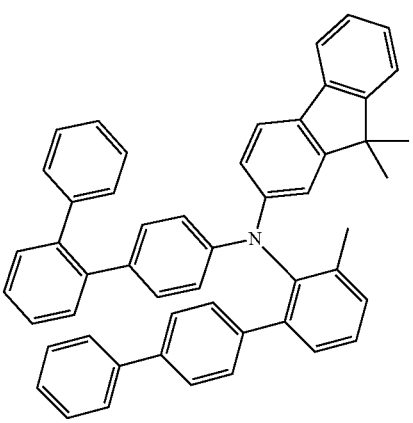
112 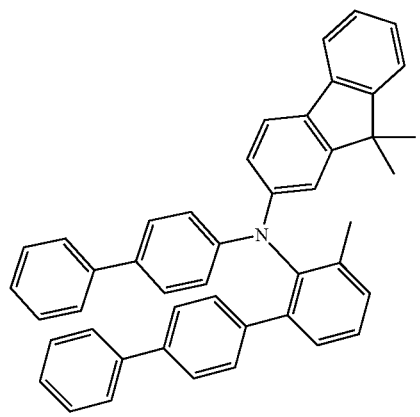
115 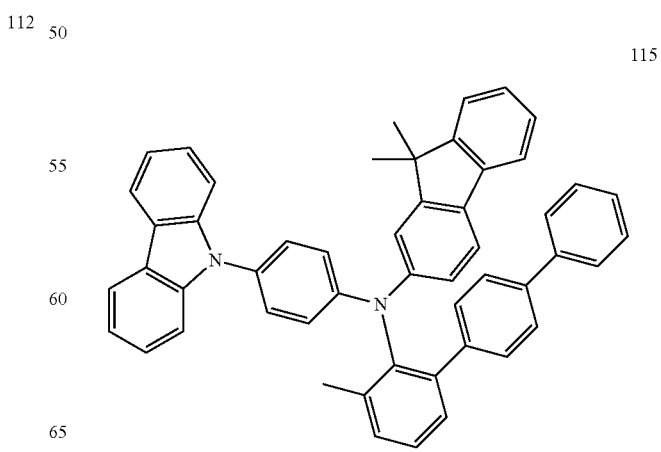

189
-continued
116
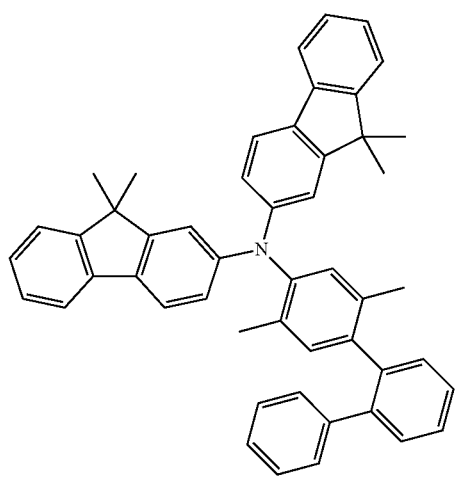
117
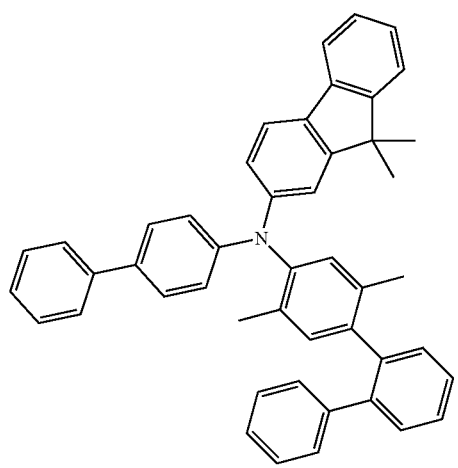
118
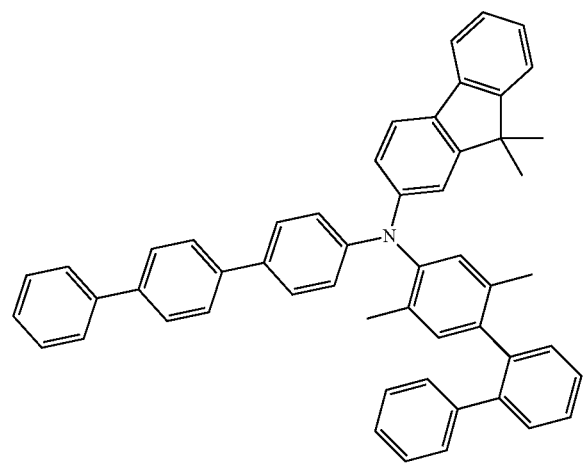
190
-continued
119
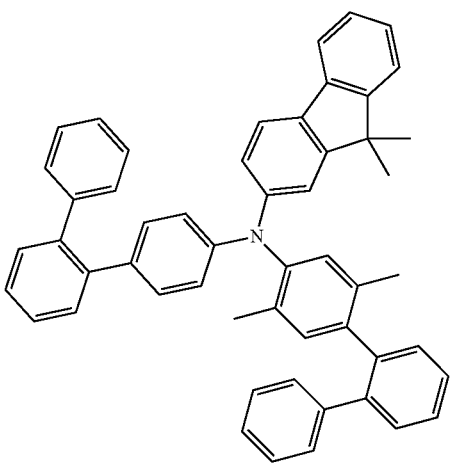
120
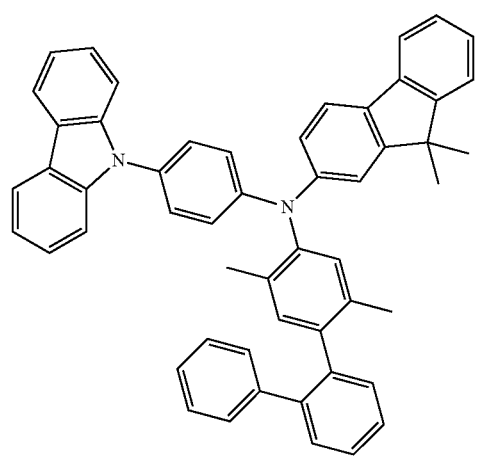
121
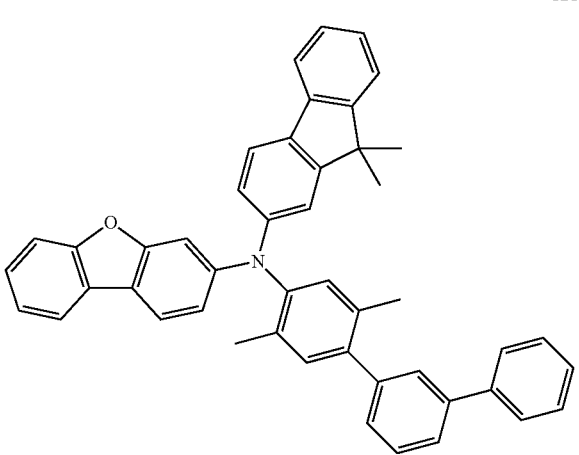

122
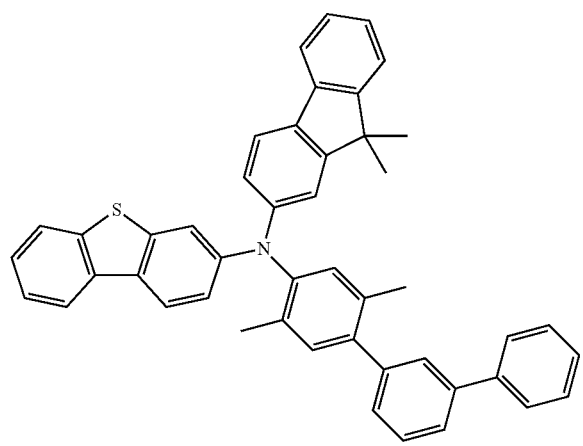
125
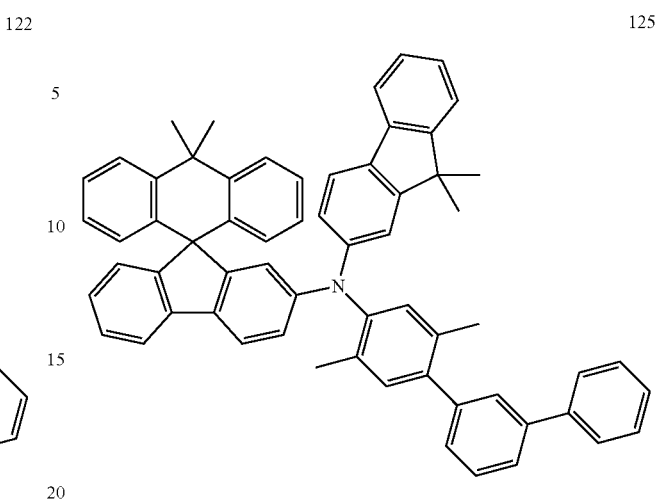
123
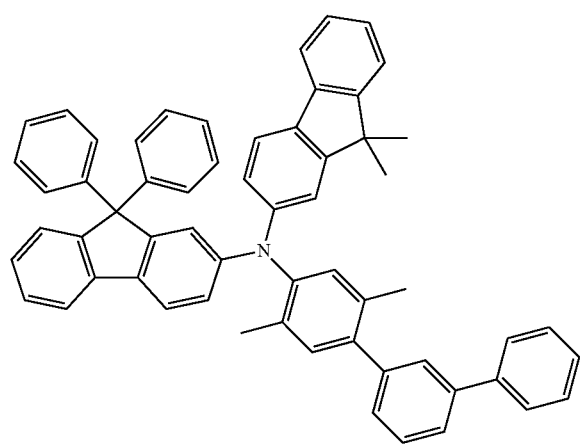
186
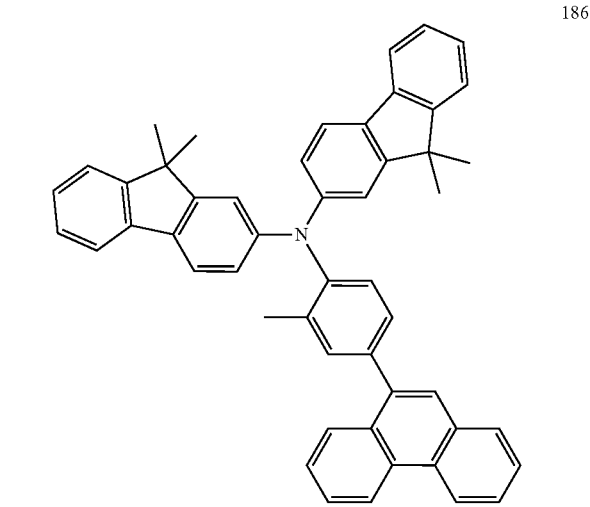 [SMILES: Cc1cc(-c2cc3ccccc3c3ccccc23)ccc1N(c1ccc2c(c1)C(C)(C)c1ccccc1-2)c1ccc2c(c1)C(C)(C)c1ccccc1-2]
124
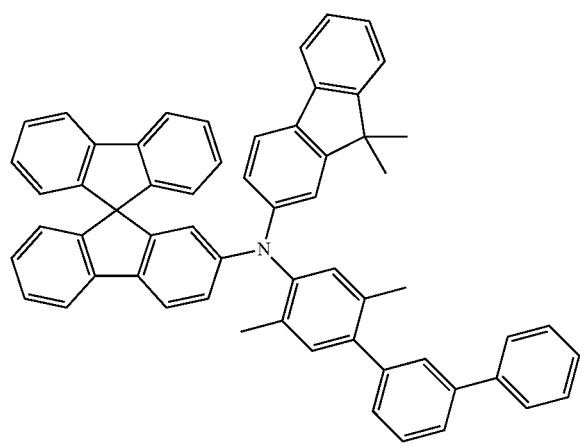
187
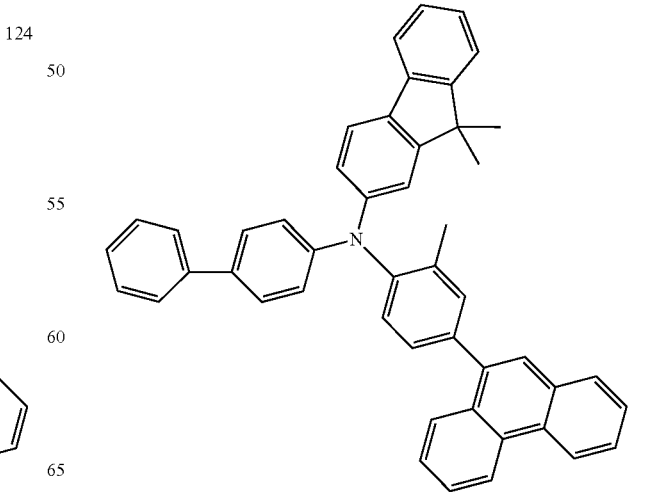

-continued
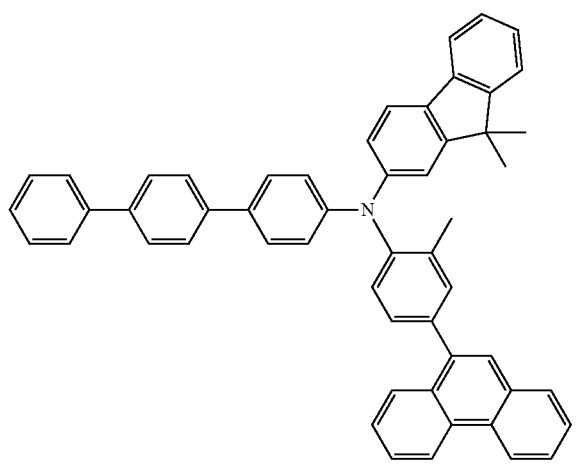
188
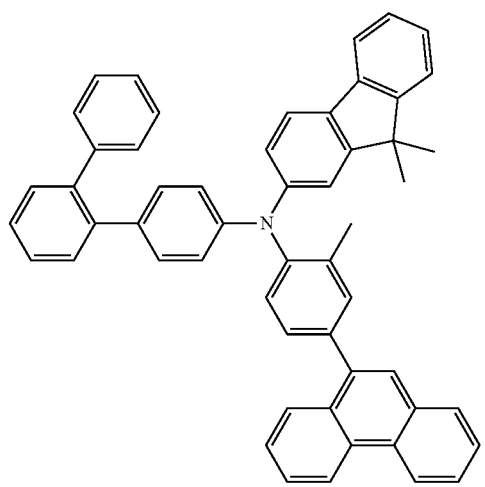
189
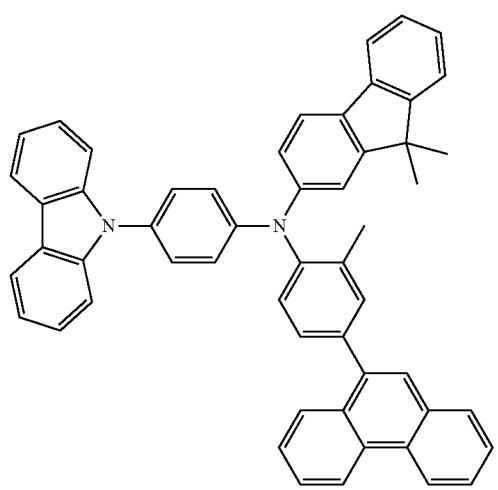
190
-continued
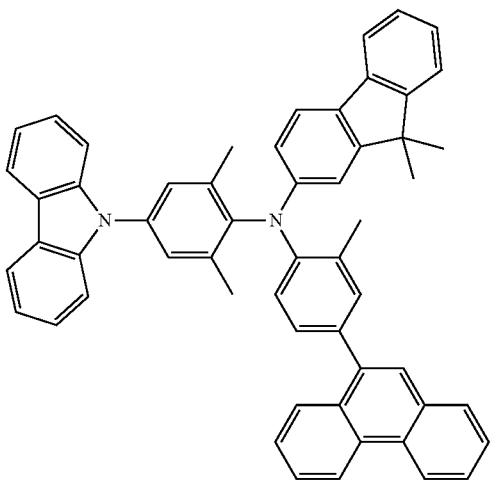
191
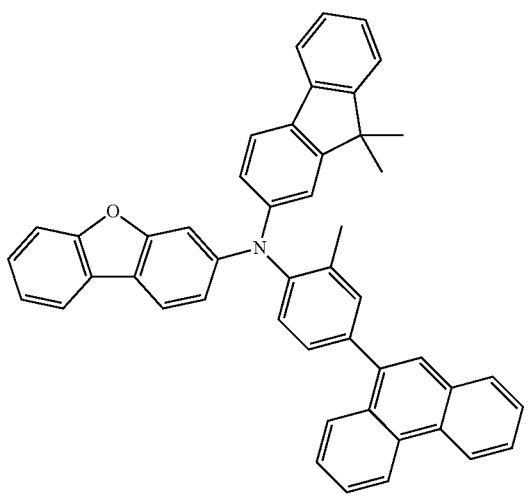
192
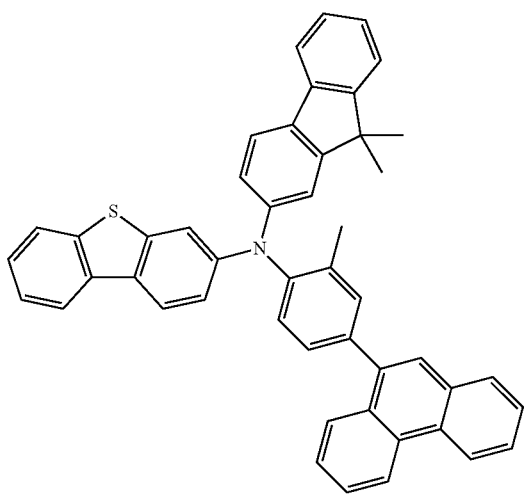
193

194 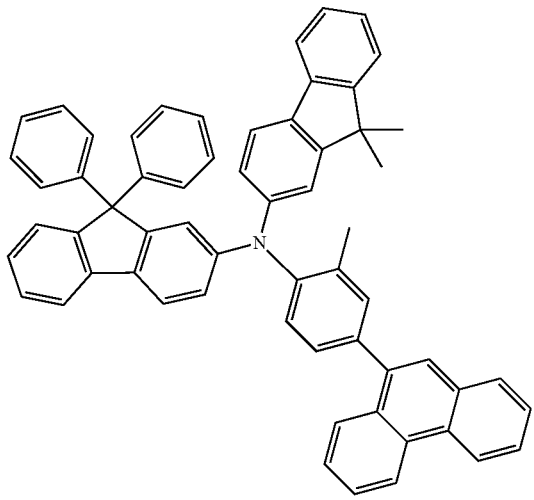
195 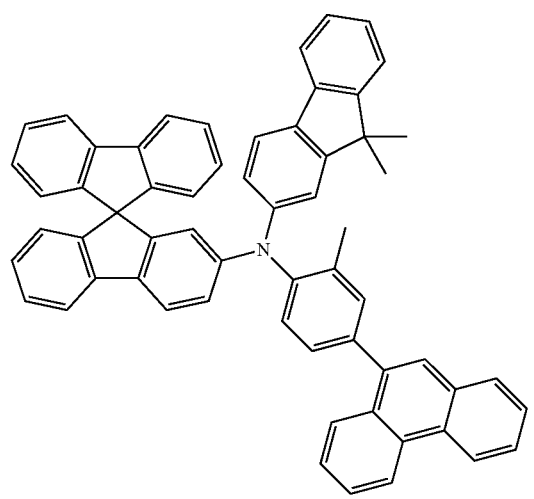
196 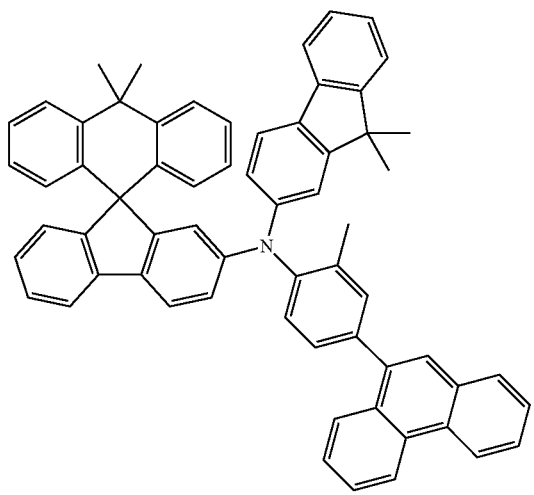
197 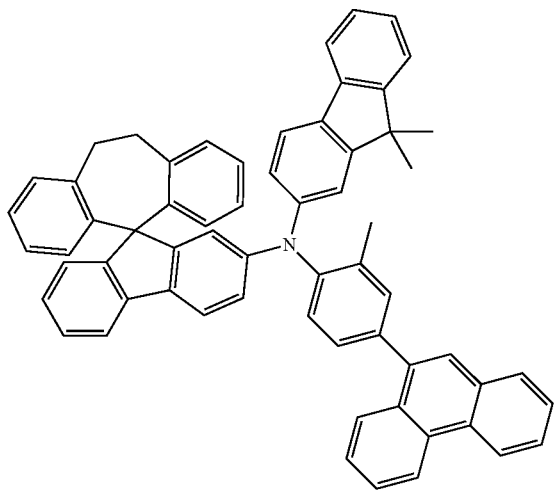
198 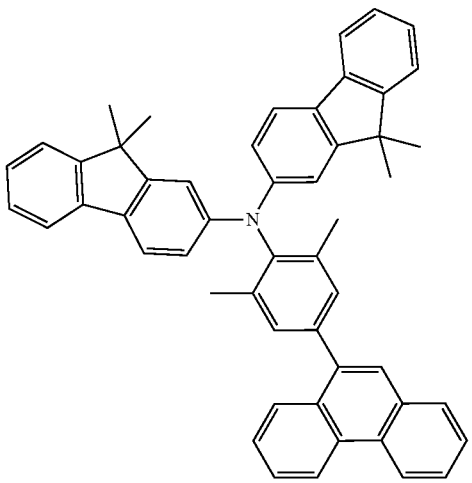
199 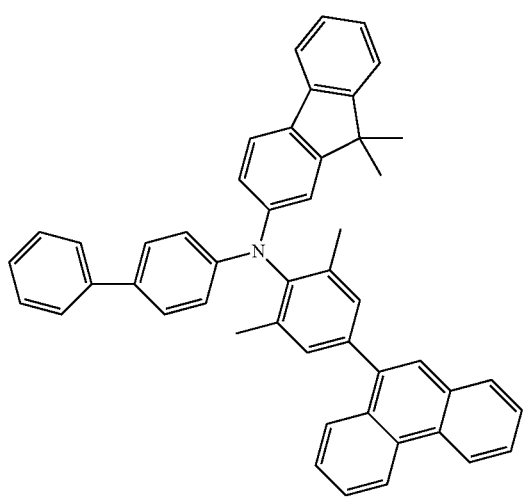

197
-continued
200
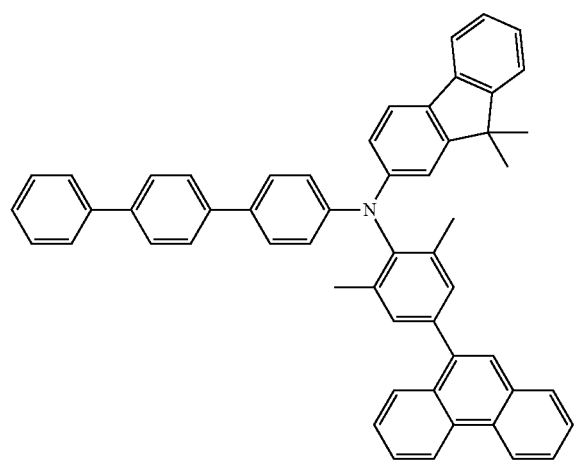
201
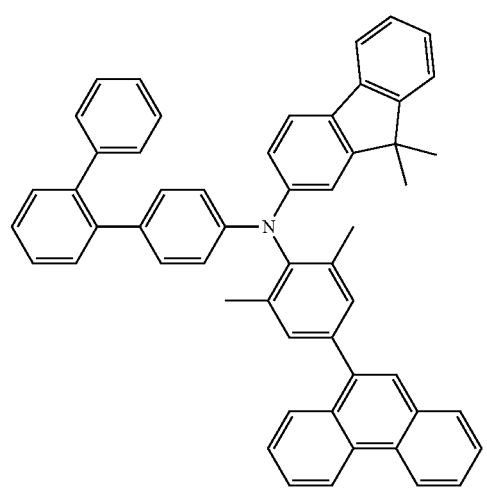
202
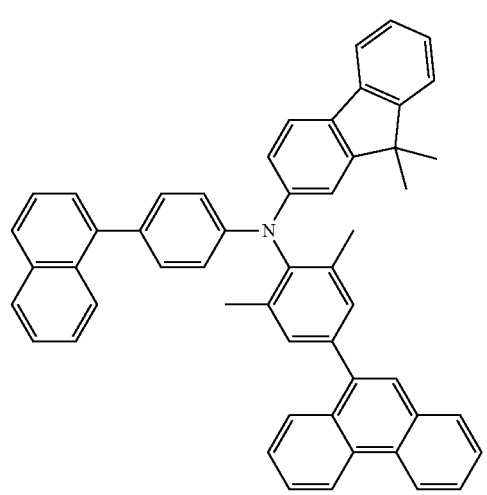
198
-continued
203
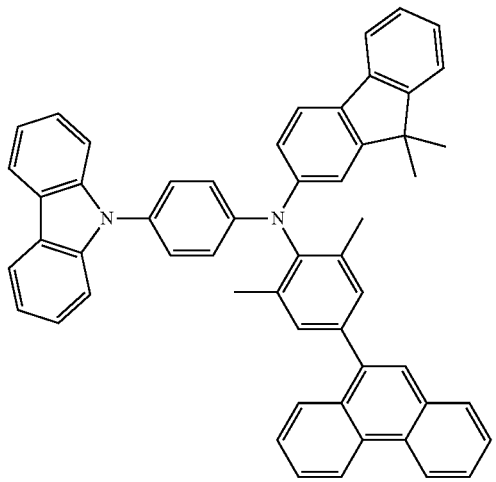
204
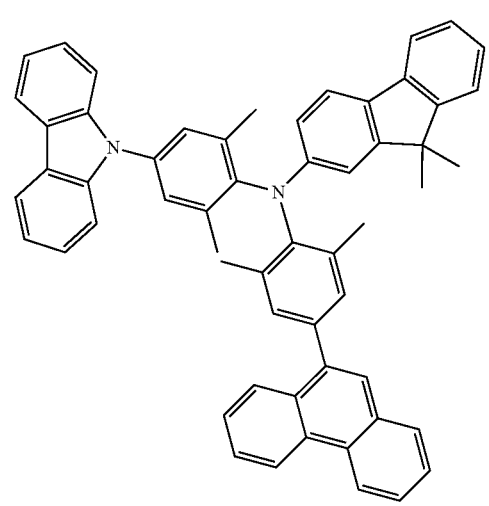
205
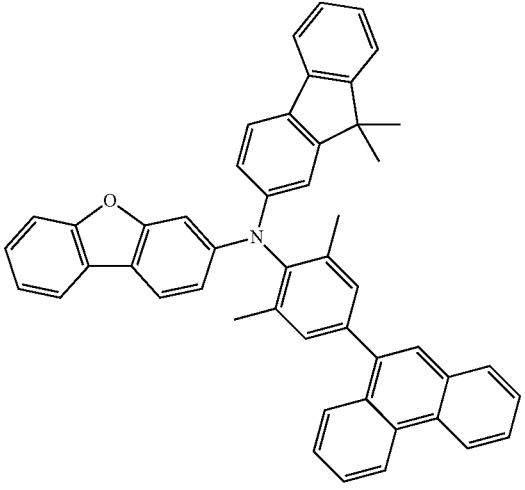

206
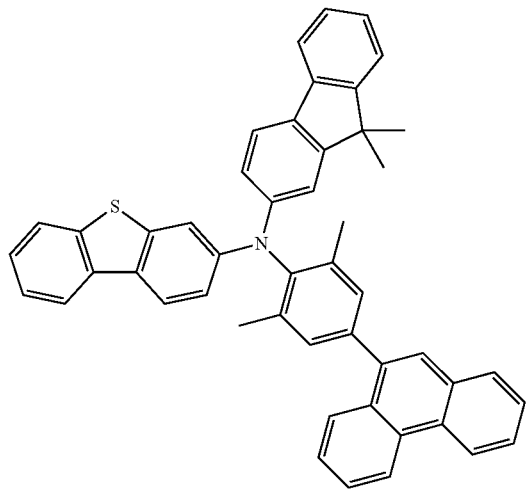
207
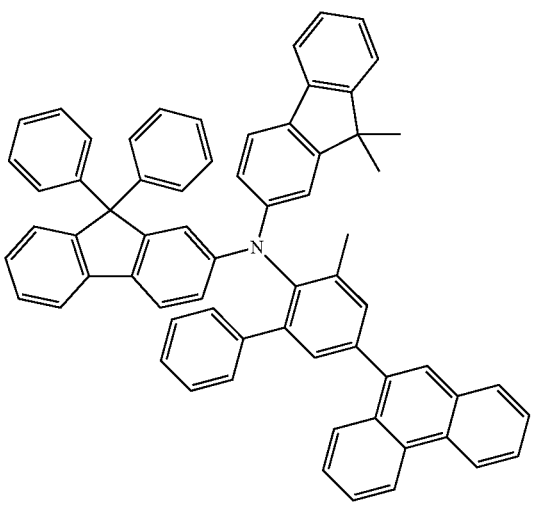
208
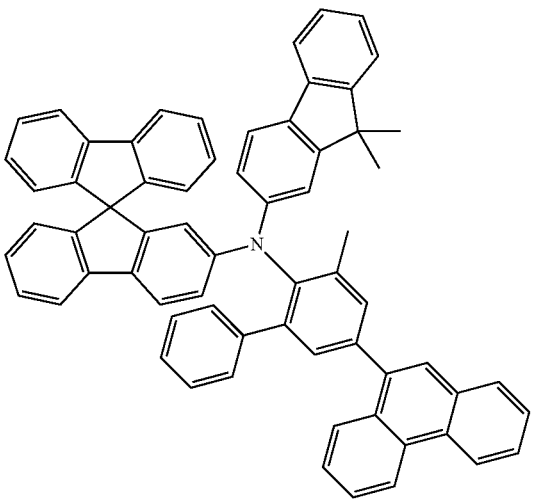
209
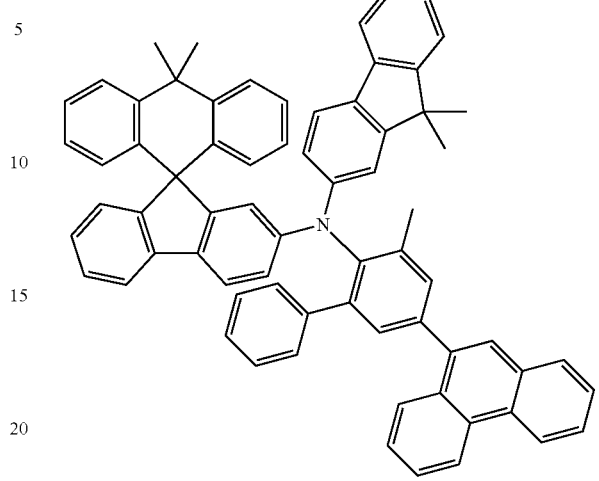
210
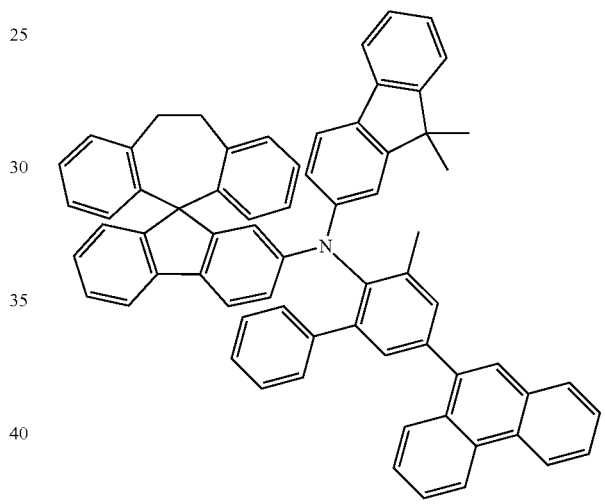
221
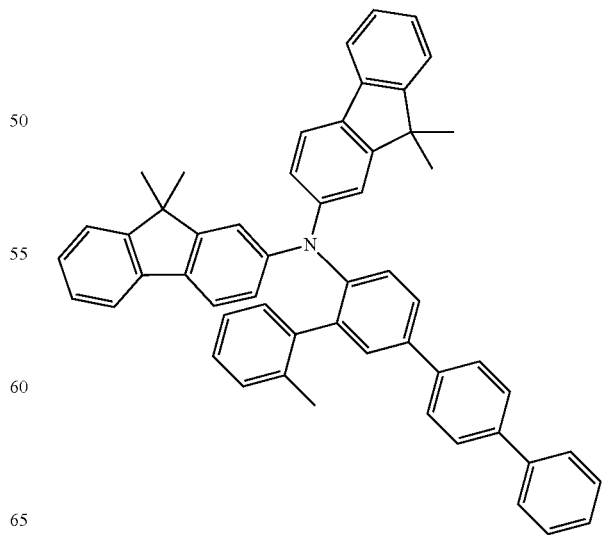

201
-continued
222
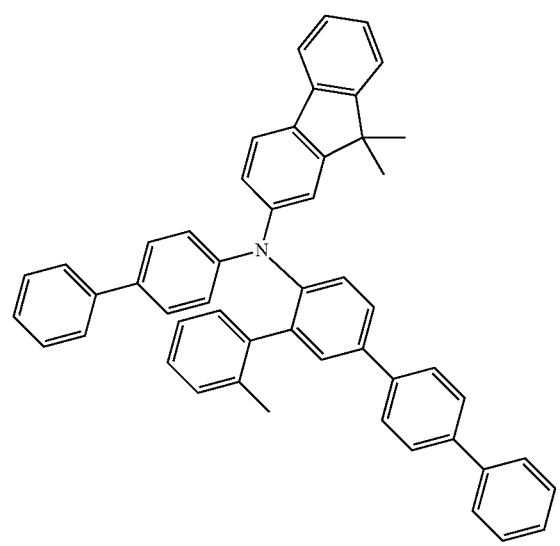
223
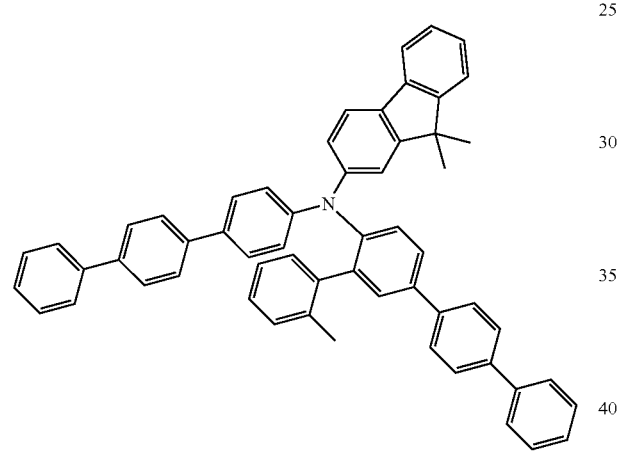
224
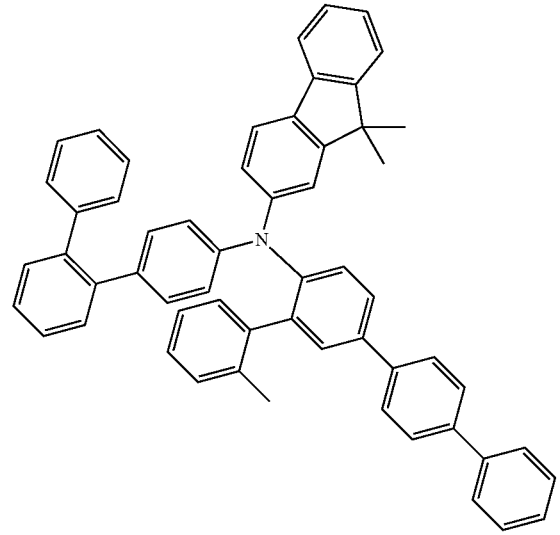
202
-continued
225
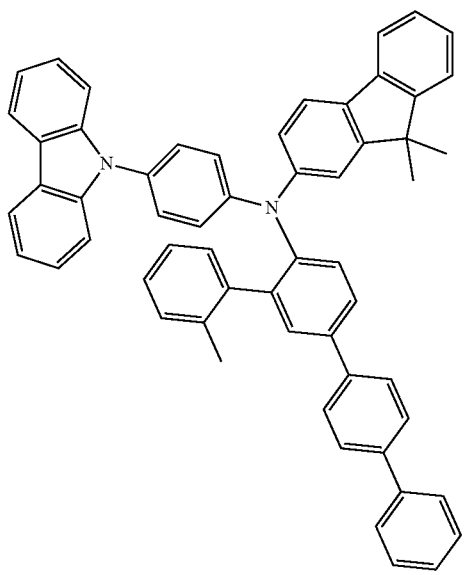
226
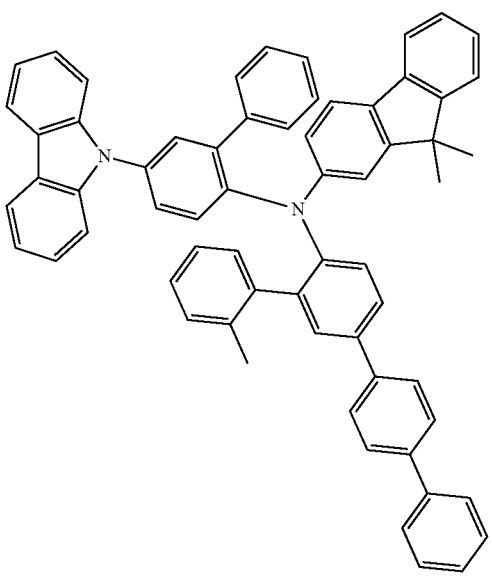

203
-continued
227
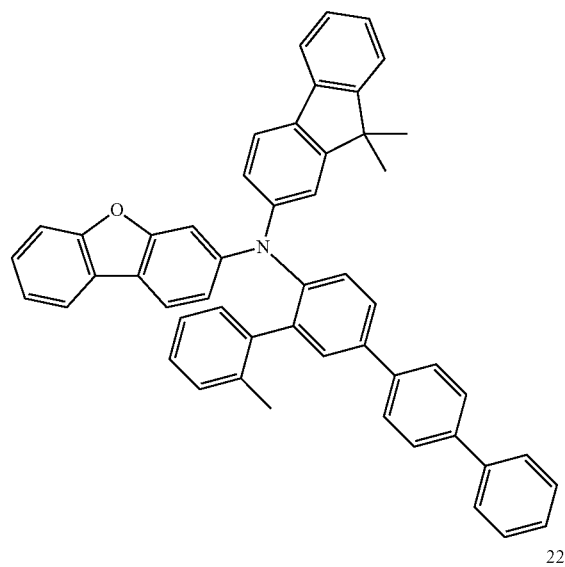
228
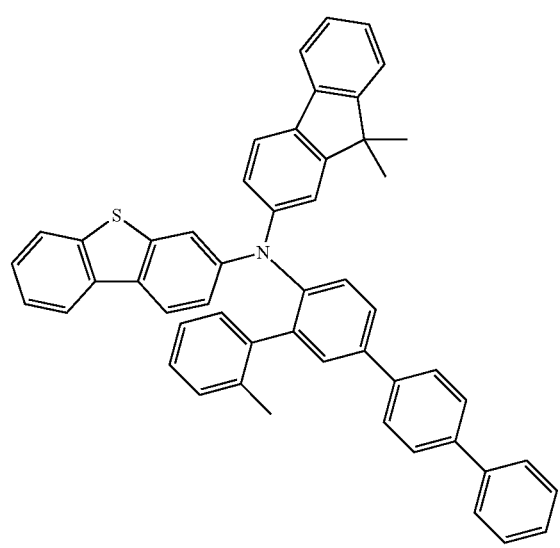
229
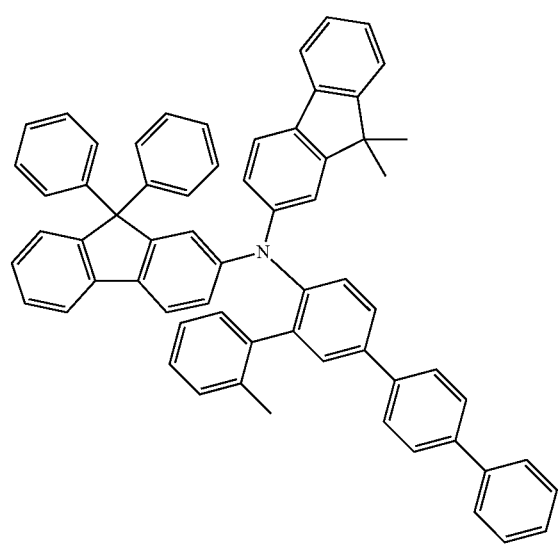
204
-continued
230
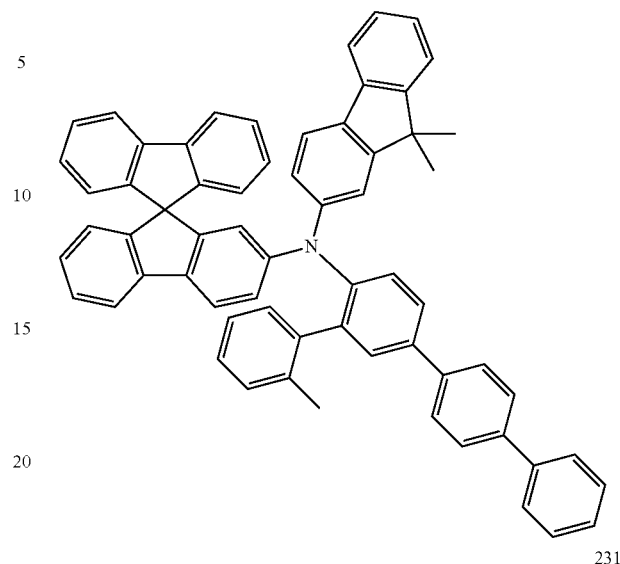
231
232
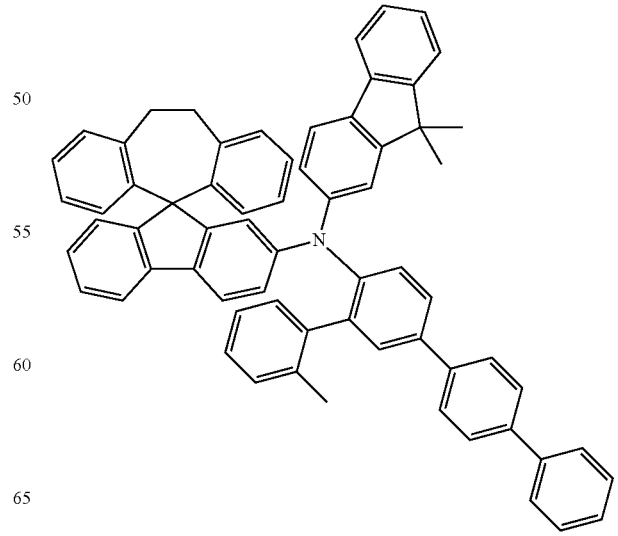

233
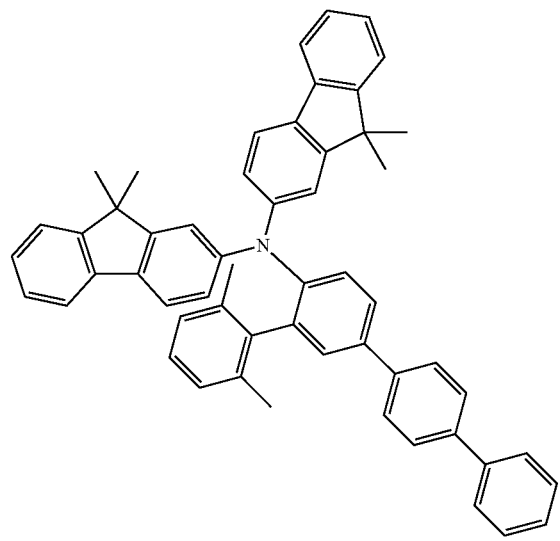
234
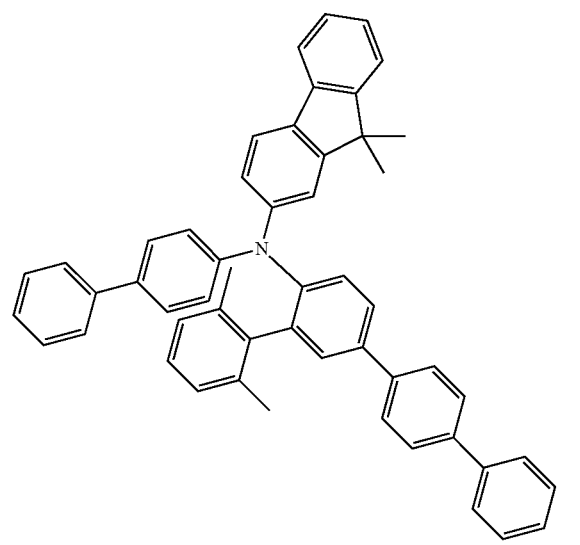
235
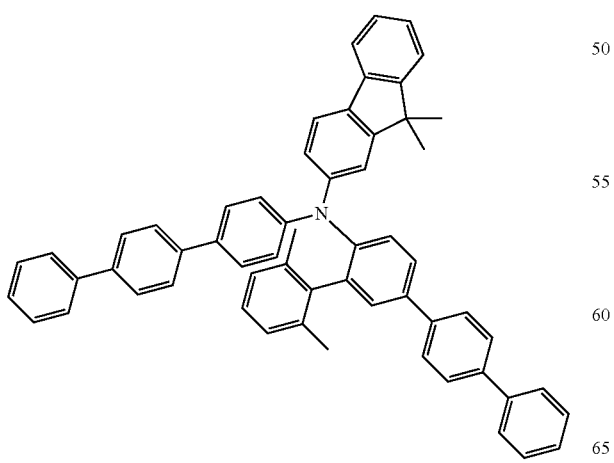
236
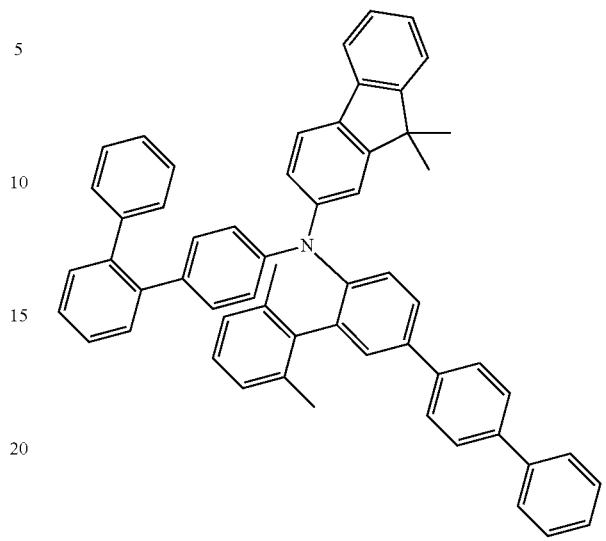
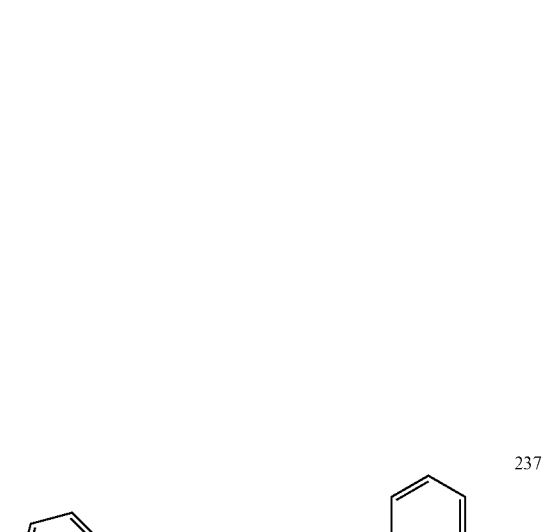
237
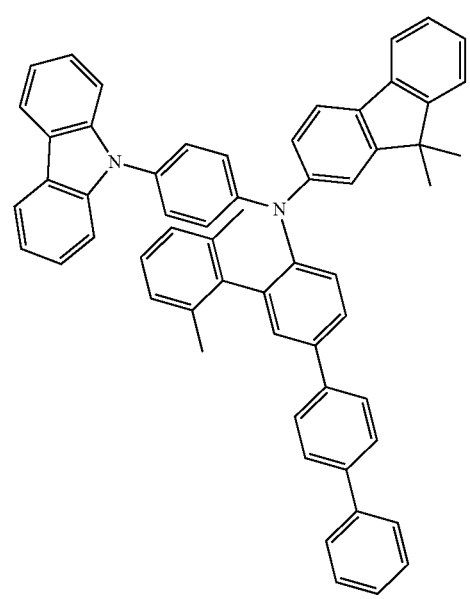

238
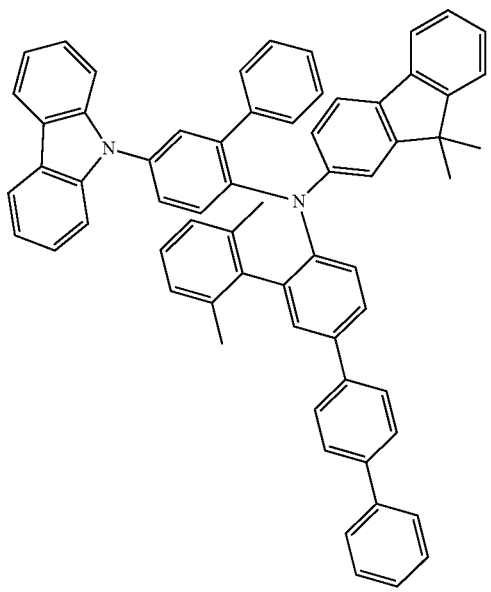
239
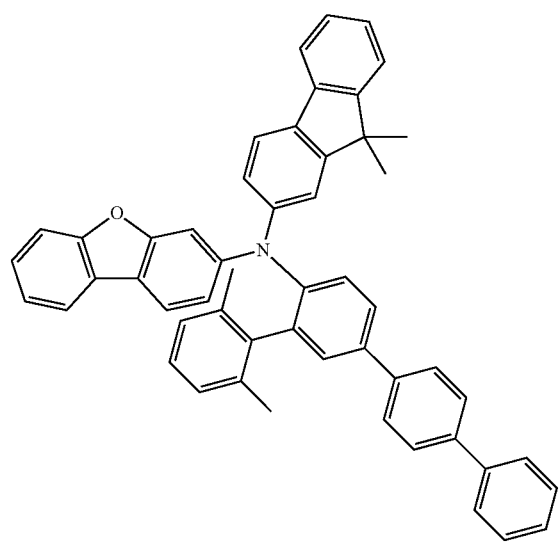
240
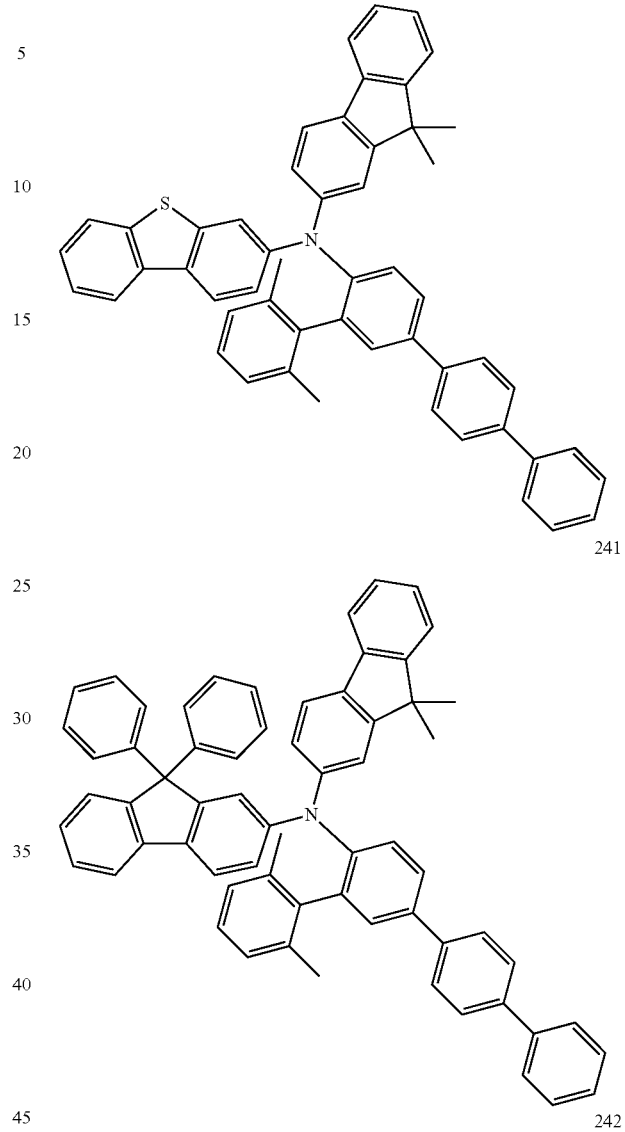
241
242

243
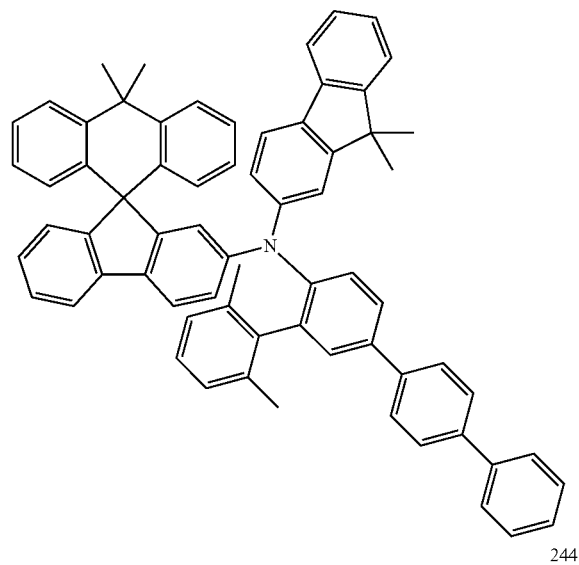
244
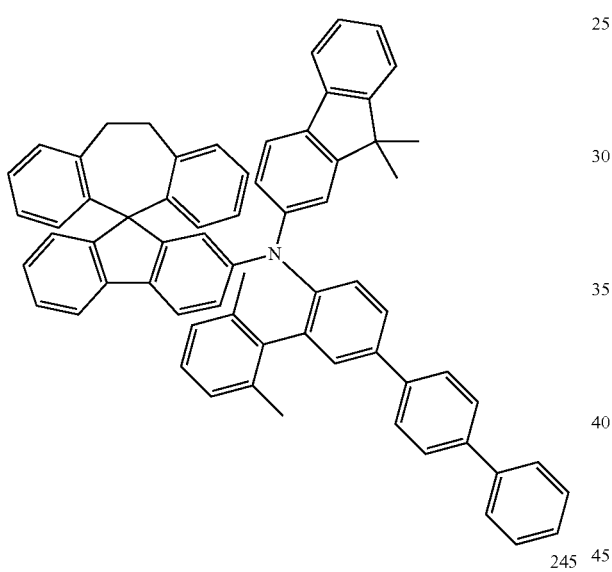
245
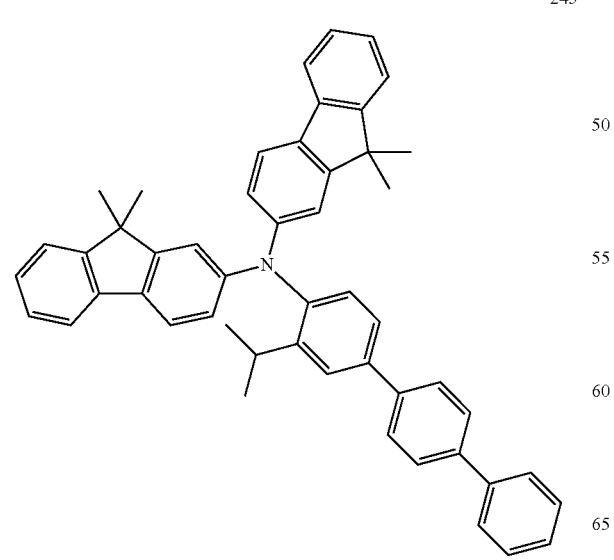
246
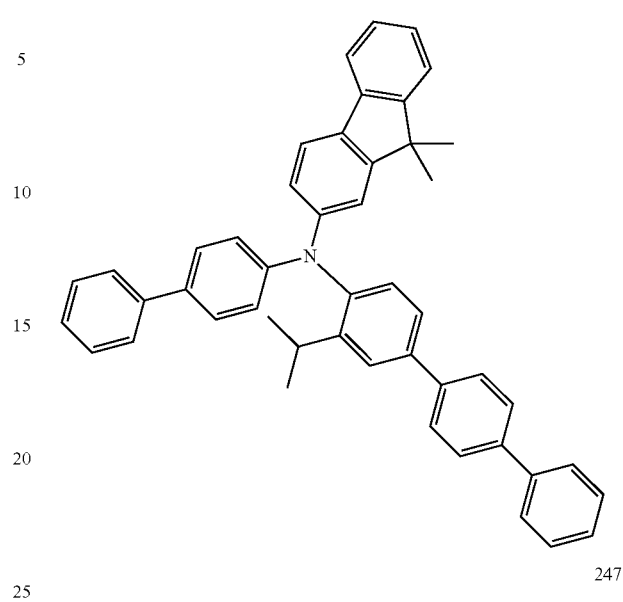
247
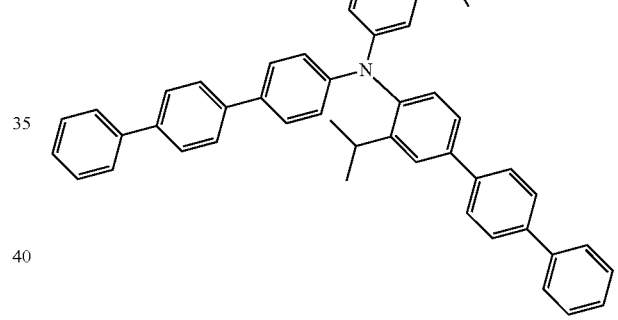
248
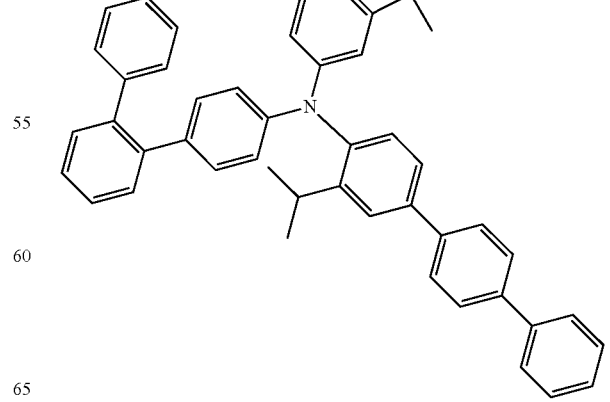

211
-continued
249
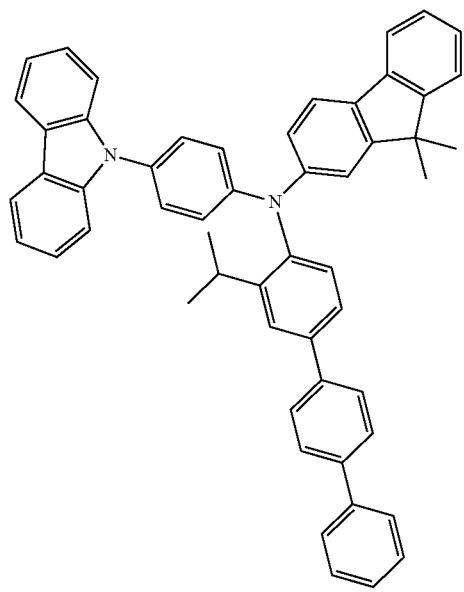
250
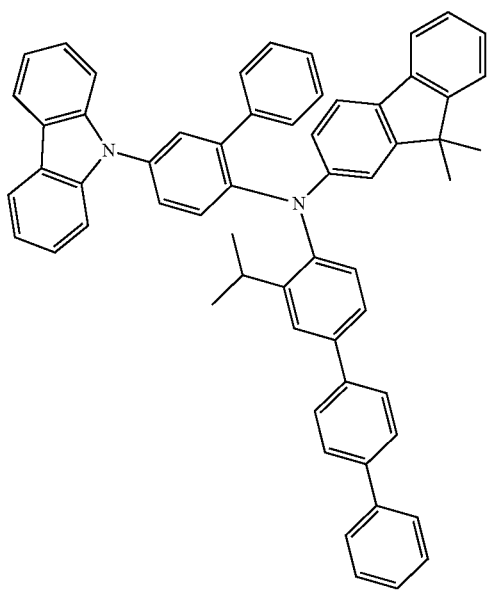
212
-continued
251
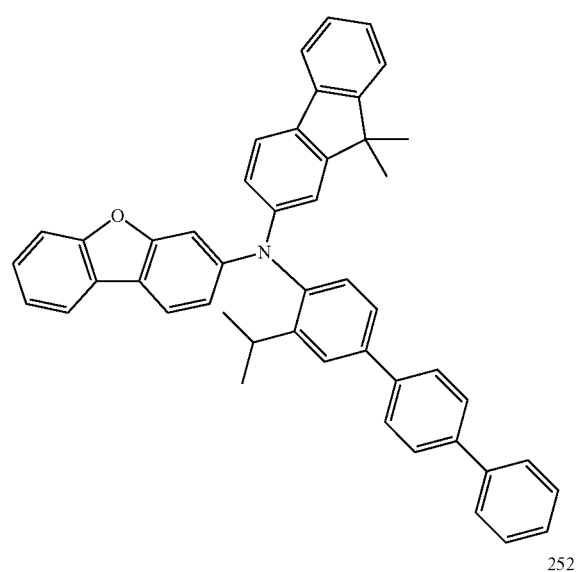
252
253
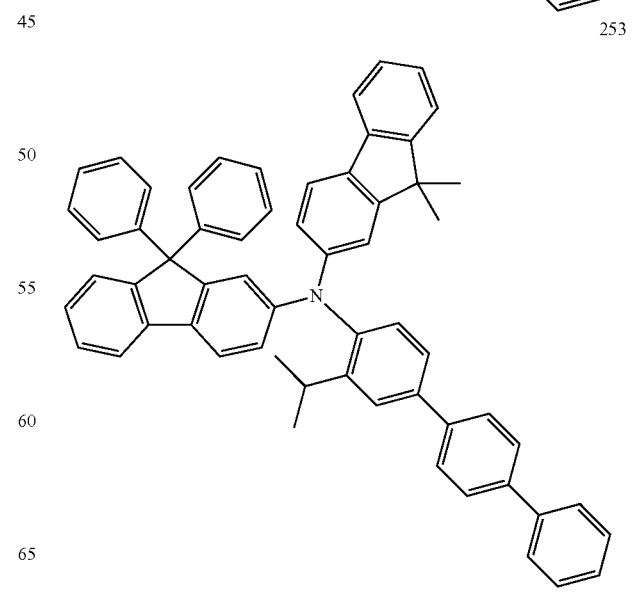

213
-continued
254
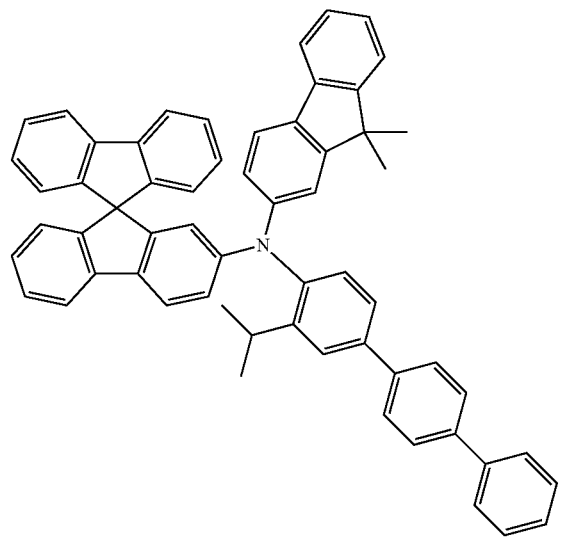
255
256
214
-continued
257
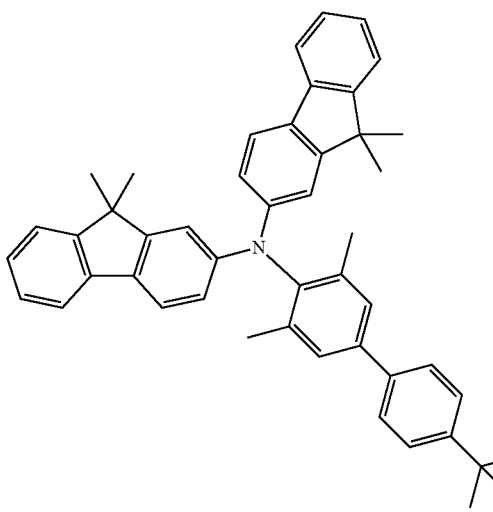
258
259

260
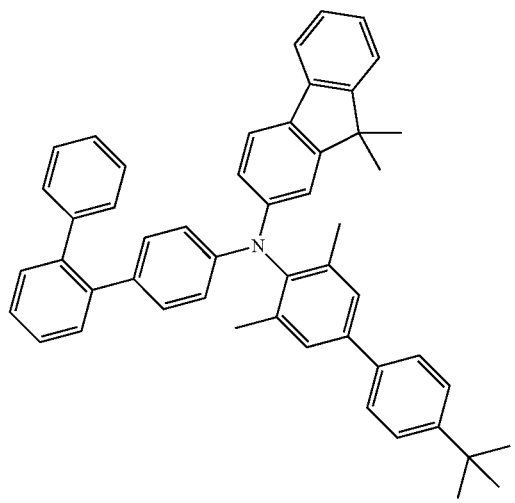
261
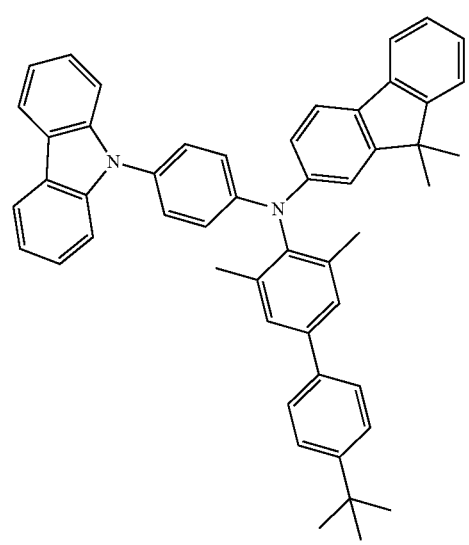
262
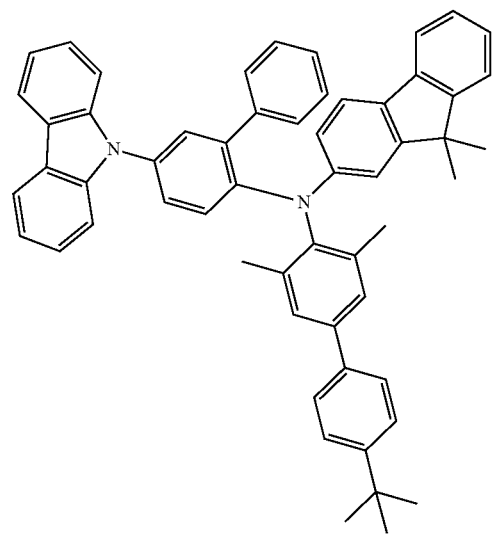
263
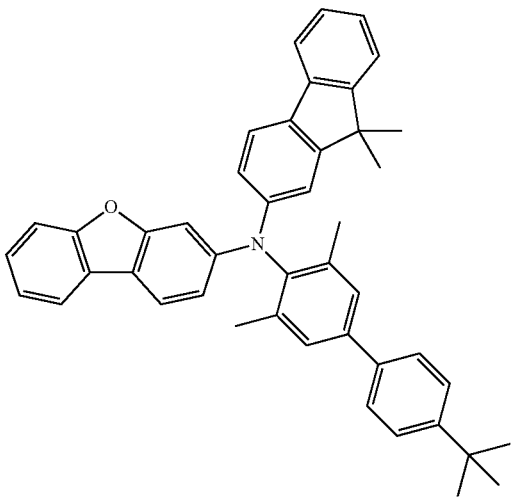
264
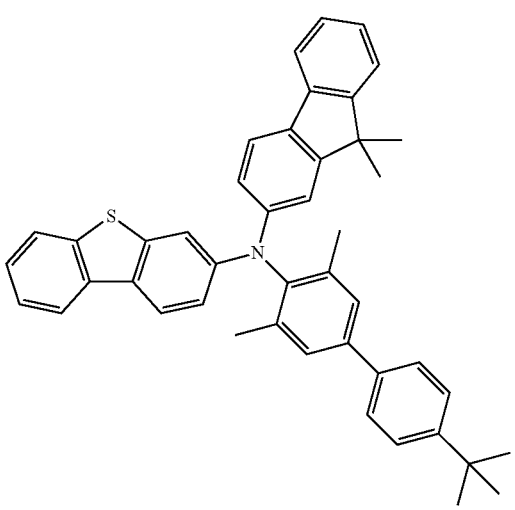
265
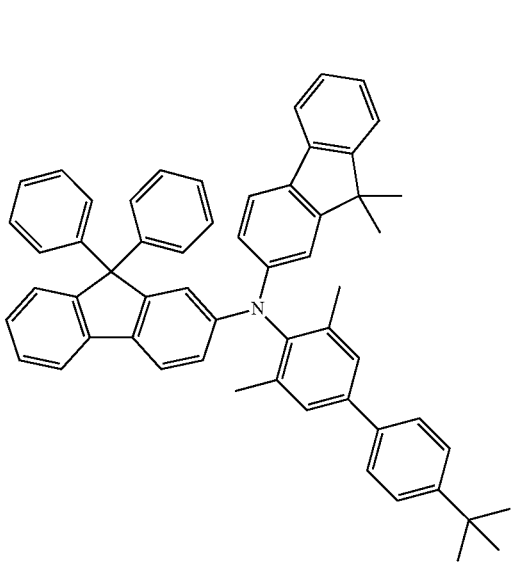

266
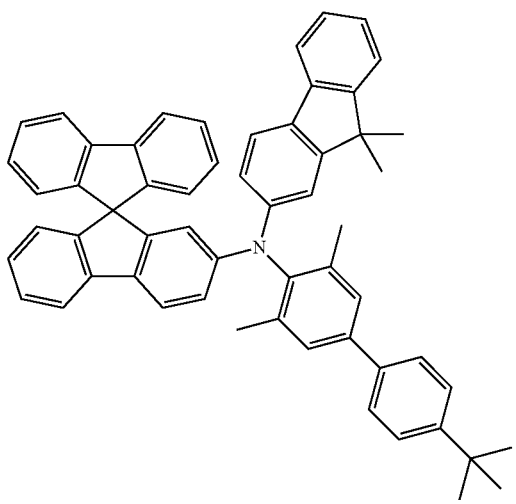
267
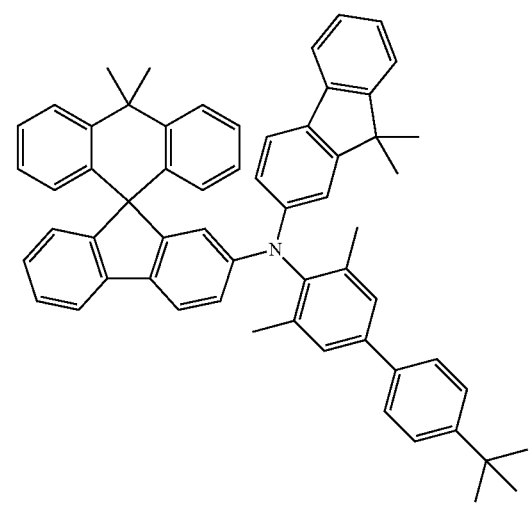
268
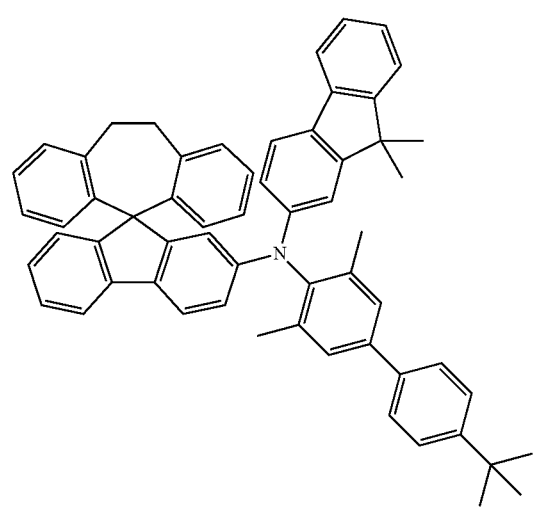
269
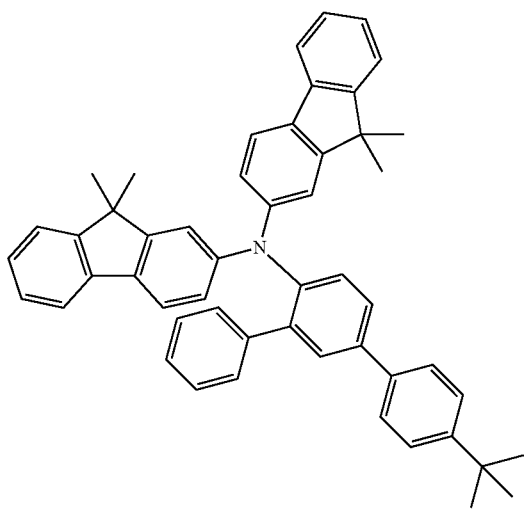
270
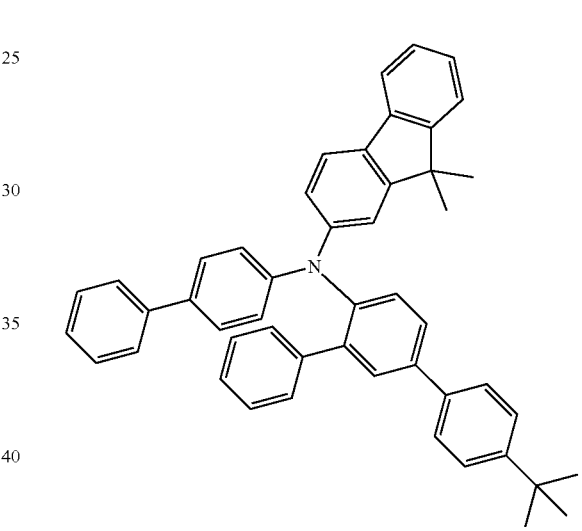
271
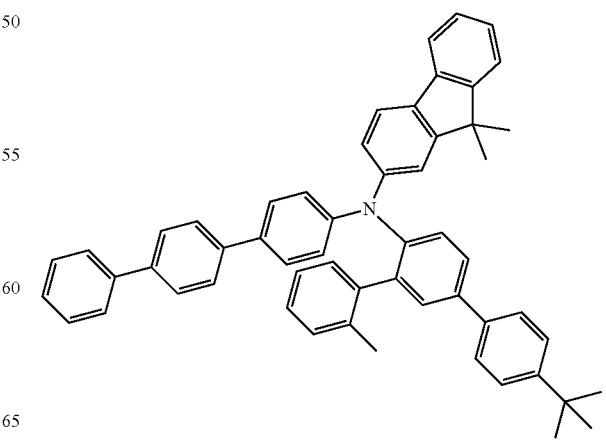

272
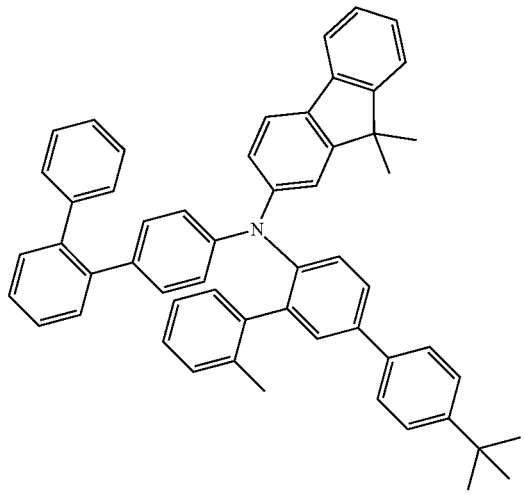
273
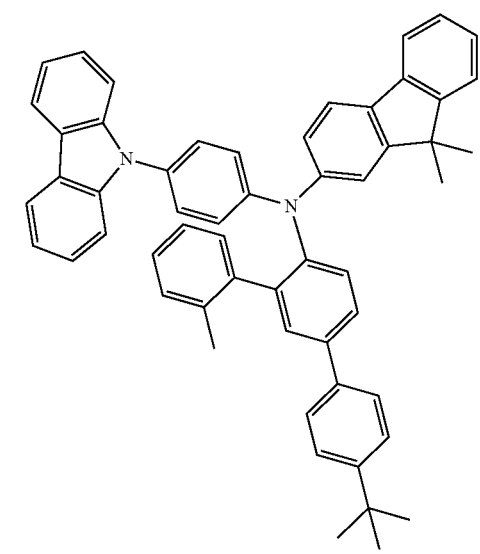
274
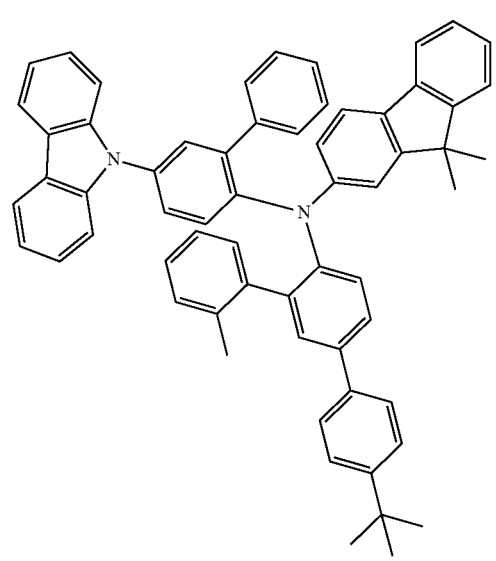
275
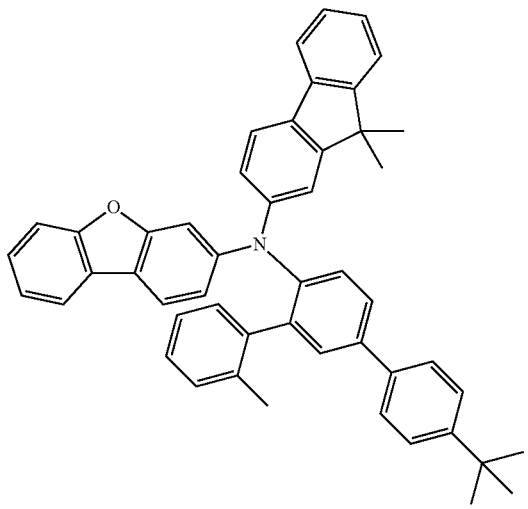
276
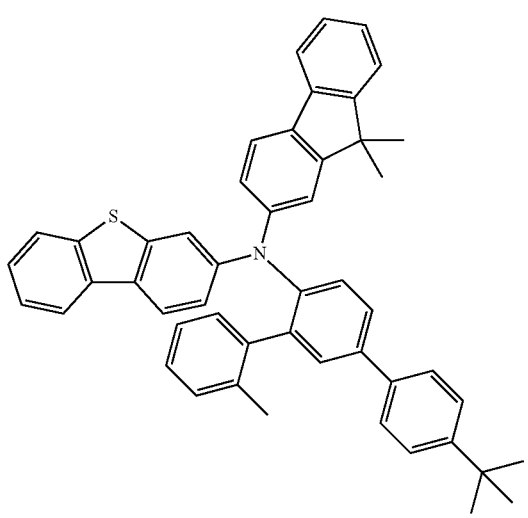
277
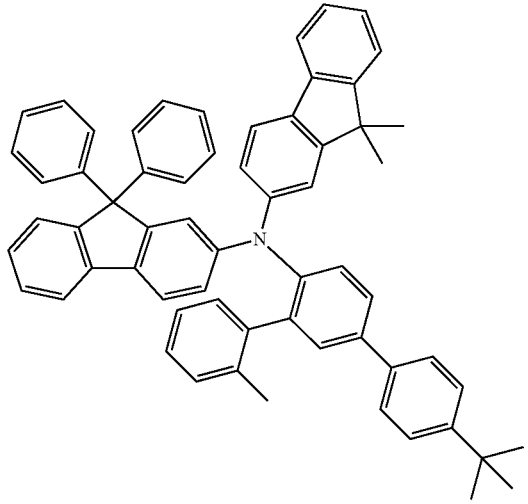

278
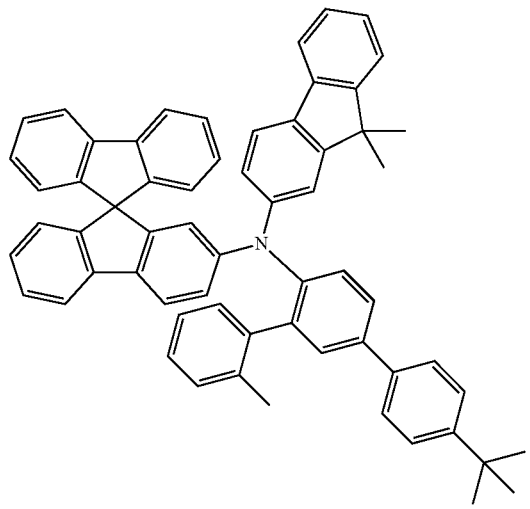
279
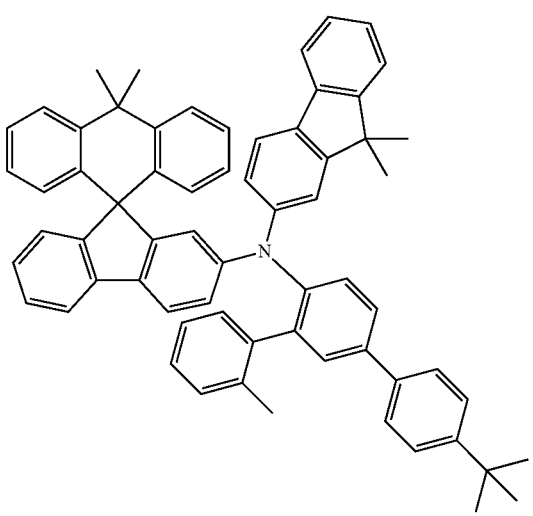
280
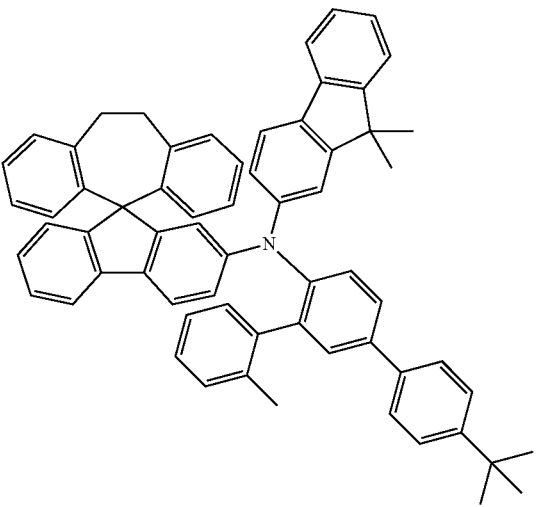
281
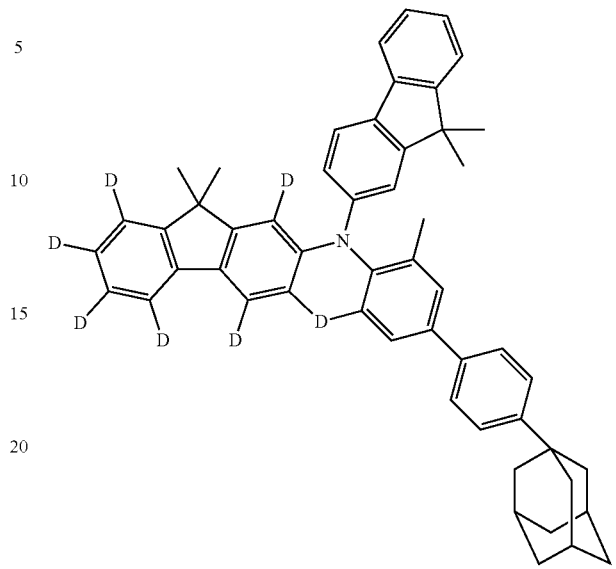
282
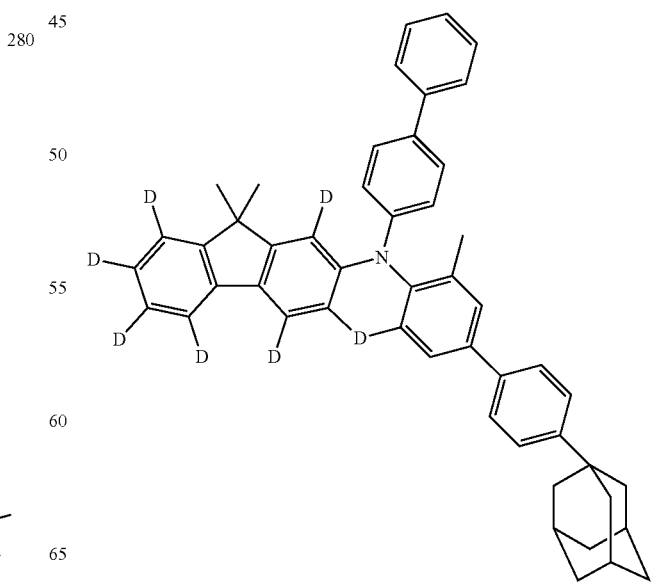

223
-continued
283
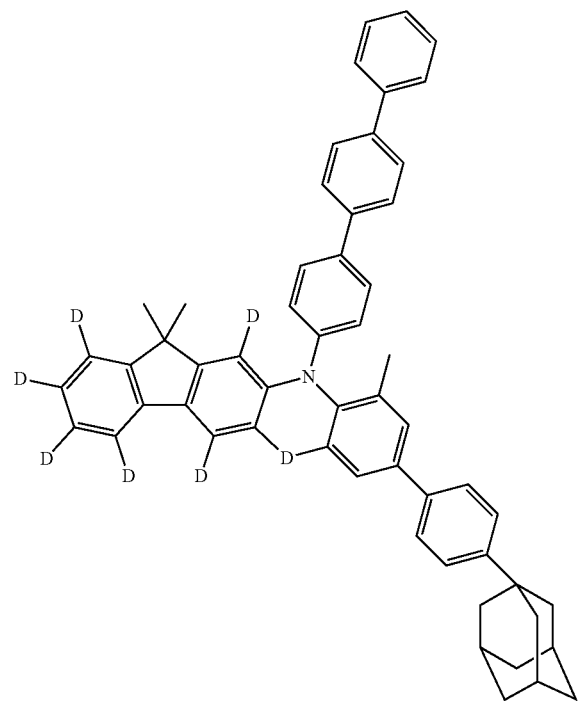
284
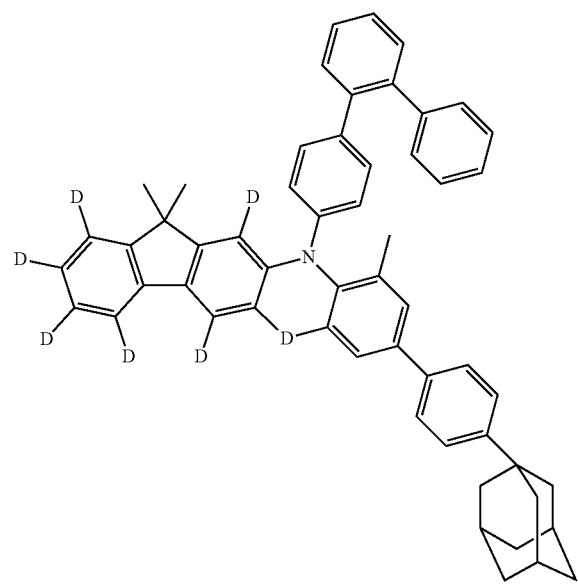
224
-continued
285
286
287
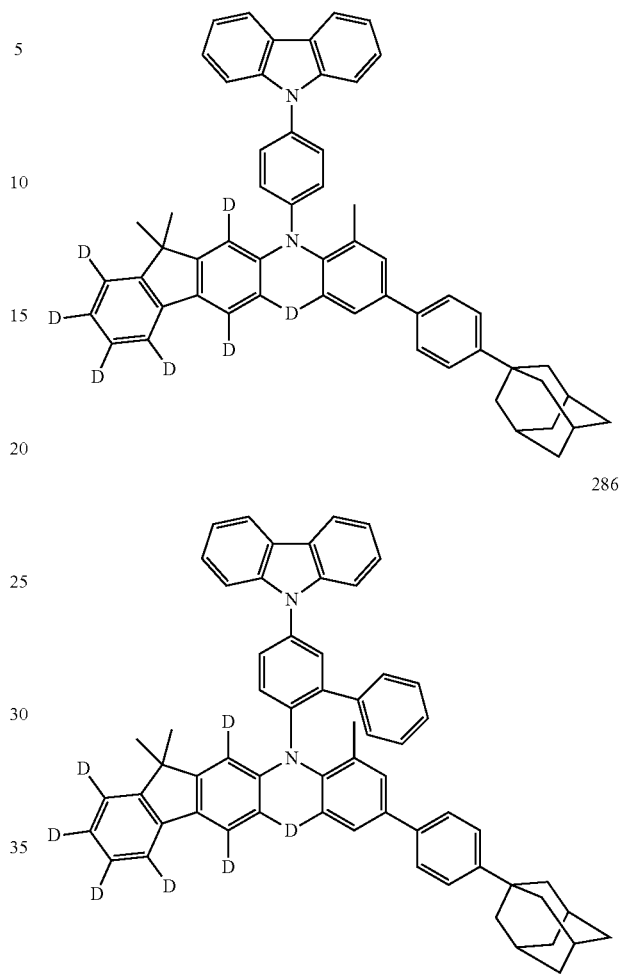

288
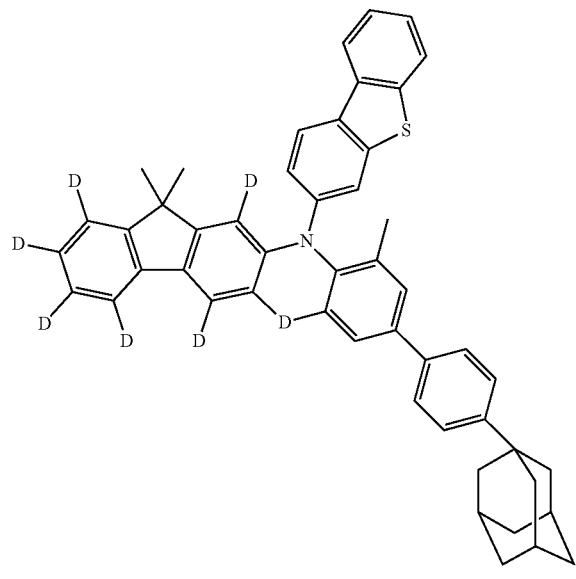
289
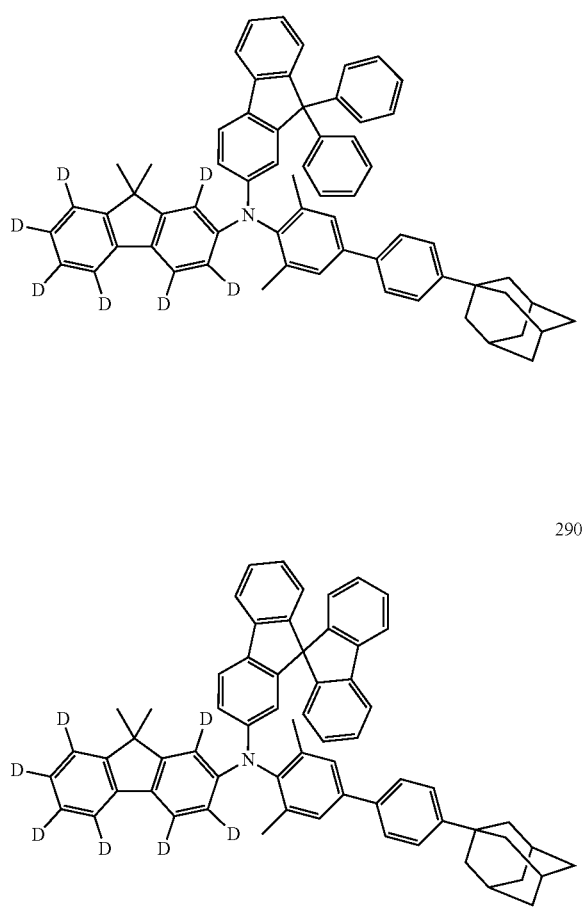
290
291
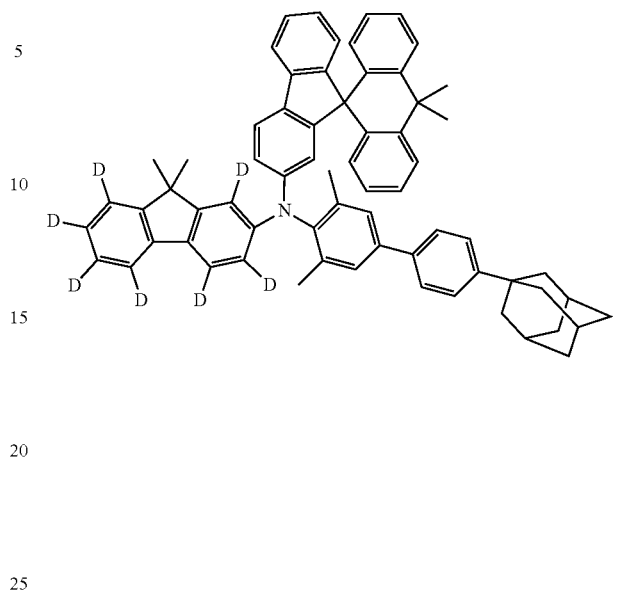
292
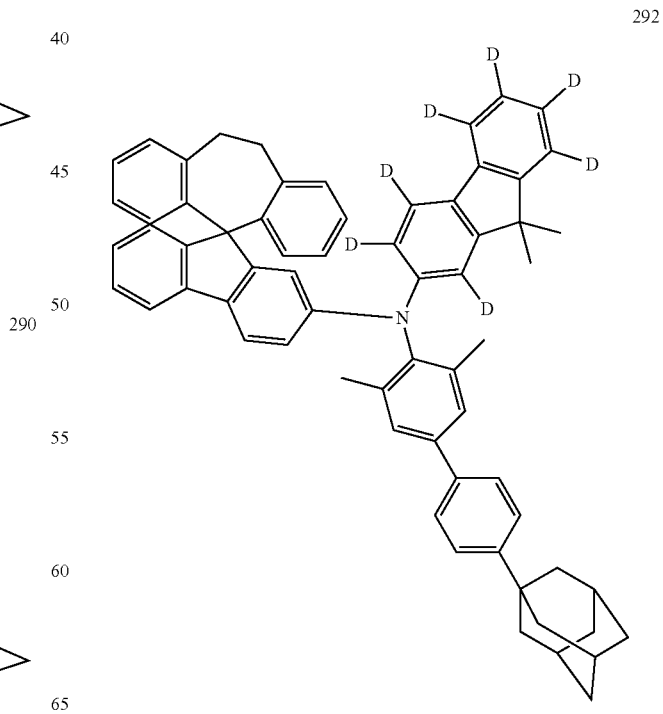

293
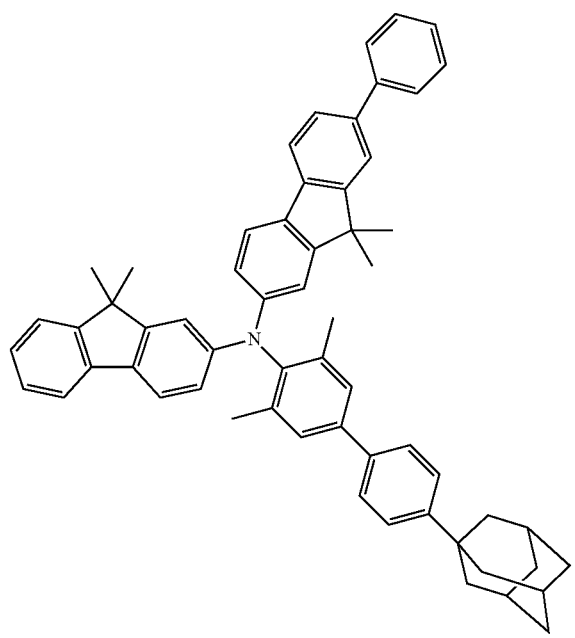
295
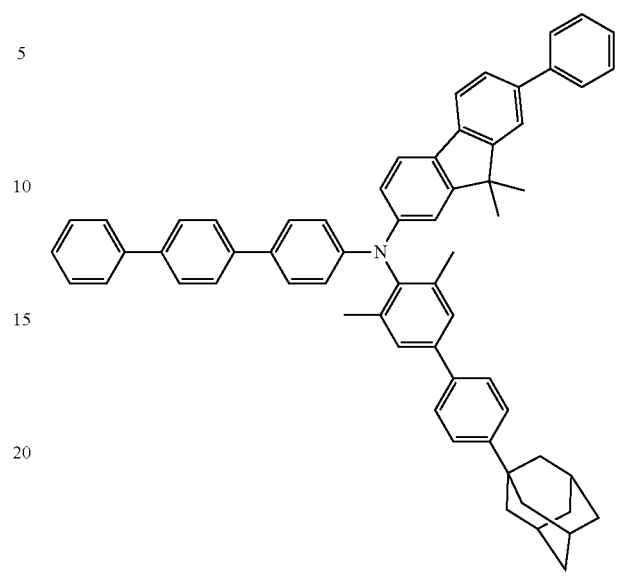
294
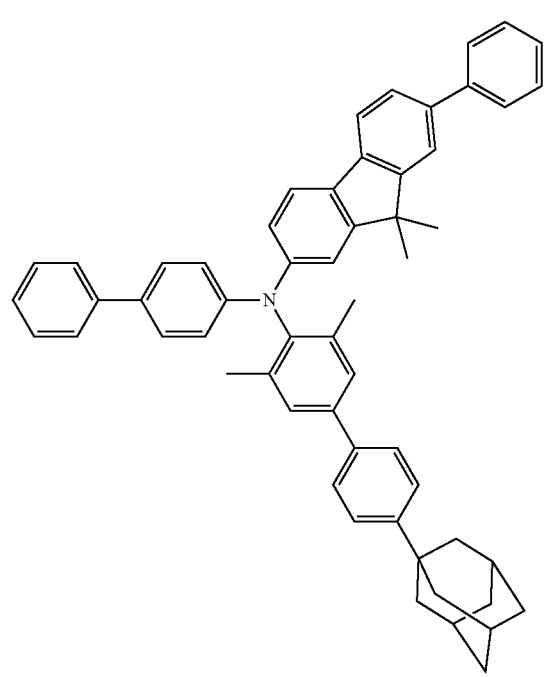
296
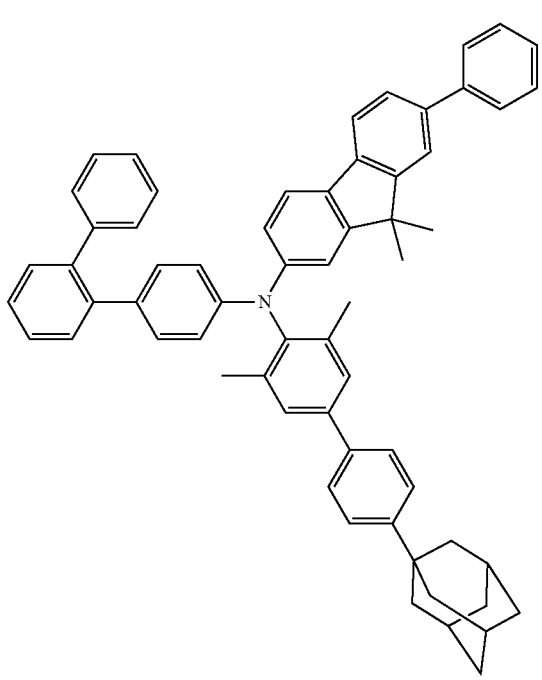

229
-continued
297
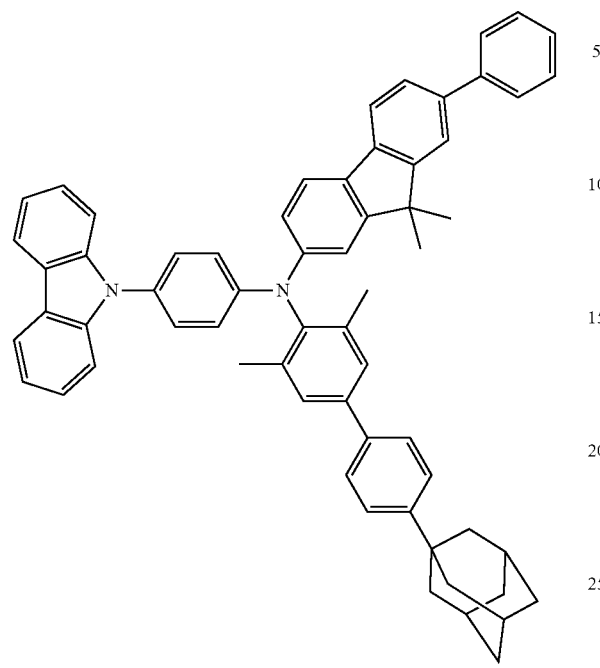
298
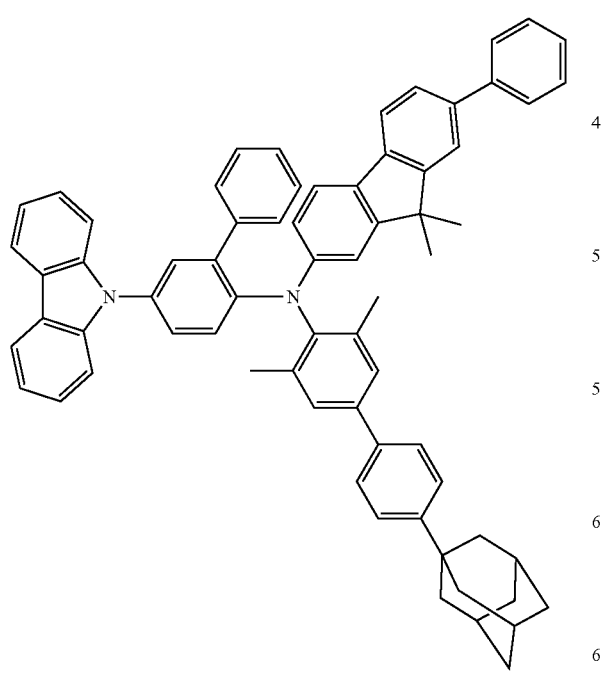
230
-continued
299
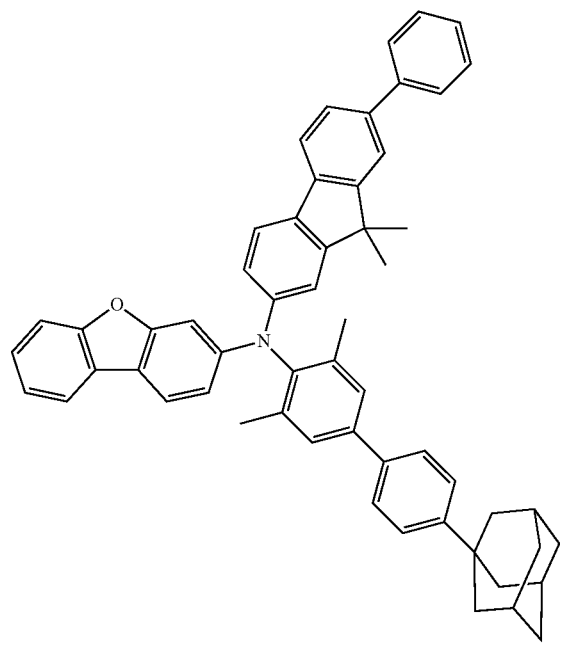
300
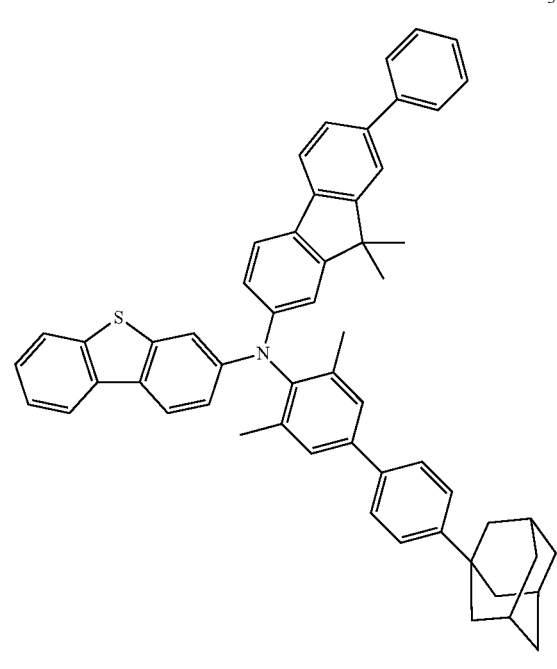

231
-continued

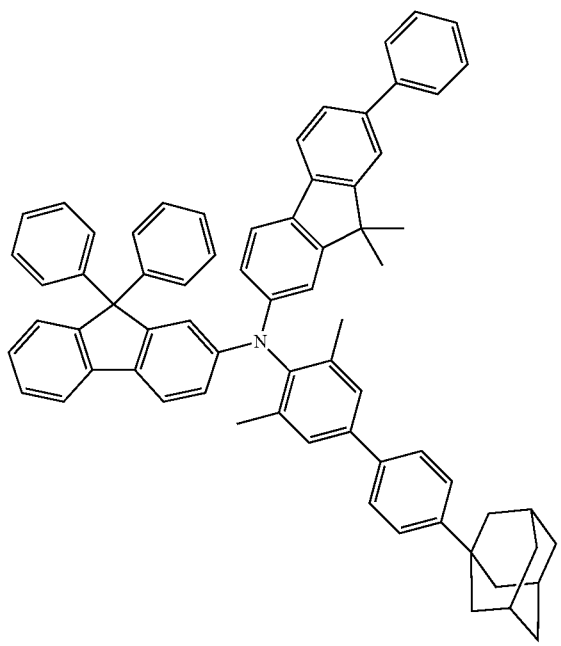
301

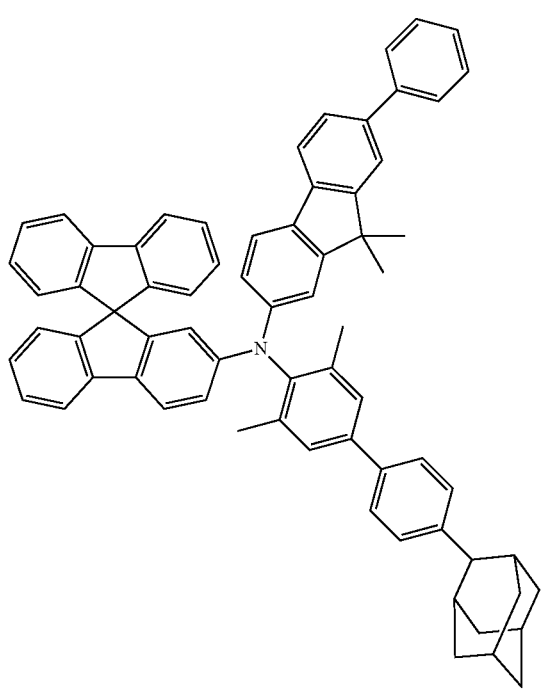
302

232
-continued

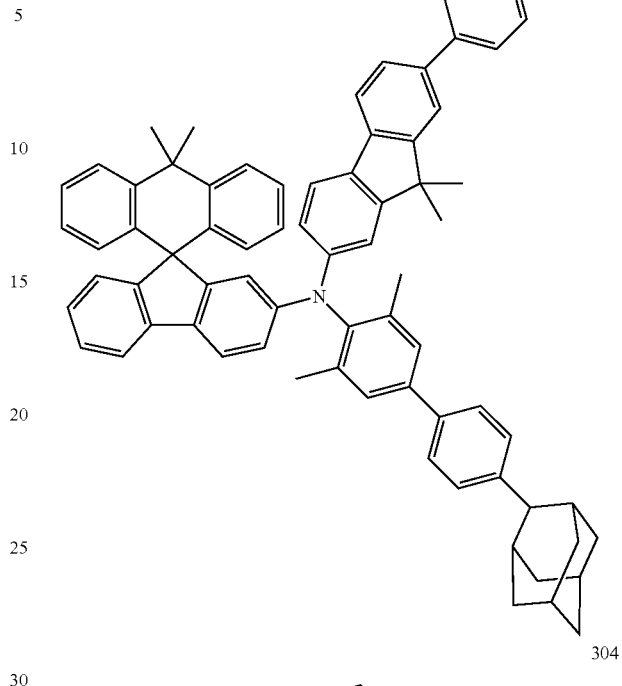
303

304

2. The organic light-emitting device of claim 1, wherein the organic material layer further includes at least one layer selected from a group consisting of a hole injection layer, an auxiliary hole transport layer, a light-emitting layer, an auxiliary electron transport layer, an electron transport layer, and an electron injection layer.

3. The organic light-emitting device of claim 2, wherein the compound of the selected at least one layer contains at least two types of compounds.

4. The organic light-emitting device of claim 1, wherein the organic light-emitting device further comprises an encapsulation layer formed on the second electrode.

5. The organic light-emitting device of claim 4, wherein the organic light-emitting device further comprises a barrier layer formed on the encapsulation layer.

6. The organic light-emitting device of claim 1, wherein the organic light-emitting device further comprises a driving thin-film transistor including an active layer electrically connected to the first electrode.

7. The organic light-emitting device of claim 6, wherein the active layer includes an oxide semiconductor layer.

8. The organic light-emitting device of claim 6, wherein the driving thin-film transistor includes a gate insulating film formed on the active layer, and a gate electrode formed on the gate insulating film.

9. An organic light-emitting display device comprising the organic light-emitting device of claim 1.

* * * * *